(12) United States Patent
Li et al.

(10) Patent No.: US 10,160,812 B2
(45) Date of Patent: Dec. 25, 2018

(54) BISPECIFIC HER2 ANTIBODIES

(71) Applicant: MedImmune, LLC, Gaithersburg, MD (US)

(72) Inventors: John Li, Gaithersburg, MD (US); Nazzareno Dimasi, Gaithersburg, MD (US); Steven Coats, Gaithersburg, MD (US); Melissa Damschroder, Gaithersburg, MD (US); Changshou Gao, Gaithersburg, MD (US); Godfrey Rainey, Gaithersburg, MD (US); Cuihua Gao, Gaithersburg, MD (US); Dorin Toader, Gaithersburg, MD (US); Lakshmaiah Gingipalli, Waltham, MA (US); Fengjiang Wang, Gaithersburg, MD (US); Ryan Fleming, Gaithersburg, MD (US); Binyam Bezabeh, Gaithersburg, MD (US); Andy Qingan Yuan, Monmouth, NJ (US); Srinath Kasturirangan, Gaithersburg, MD (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 15/302,018

(22) PCT Filed: Apr. 10, 2015

(86) PCT No.: PCT/US2015/025232
§ 371 (c)(1),
(2) Date: Oct. 5, 2016

(87) PCT Pub. No.: WO2015/157592
PCT Pub. Date: Oct. 15, 2015

(65) Prior Publication Data
US 2017/0291955 A1 Oct. 12, 2017

Related U.S. Application Data

(60) Provisional application No. 61/978,516, filed on Apr. 11, 2014, provisional application No. 62/107,050, filed on Jan. 23, 2015.

(51) Int. Cl.
C07K 16/32 (2006.01)
C07K 16/30 (2006.01)
A61K 47/48 (2006.01)
A61K 47/68 (2017.01)
A61K 39/00 (2006.01)

(52) U.S. Cl.
CPC ........ *C07K 16/32* (2013.01); *A61K 47/48484* (2013.01); *A61K 47/48584* (2013.01); *A61K 47/6829* (2017.08); *A61K 47/6855* (2017.08); *C07K 16/30* (2013.01); *A61K 2039/505* (2013.01); *C07K 2317/30* (2013.01); *C07K 2317/31* (2013.01); *C07K 2317/33* (2013.01); *C07K 2317/41* (2013.01); *C07K 2317/52* (2013.01); *C07K 2317/522* (2013.01); *C07K 2317/54* (2013.01); *C07K 2317/55* (2013.01); *C07K 2317/56* (2013.01); *C07K 2317/565* (2013.01); *C07K 2317/622* (2013.01); *C07K 2317/626* (2013.01); *C07K 2317/732* (2013.01); *C07K 2317/76* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,208,020 A | 5/1993 | Chari et al. | |
| 5,416,064 A | 5/1995 | Chari et al. | |
| 5,677,171 A | 10/1997 | Hudziak et al. | |
| 5,783,186 A | 7/1998 | Arakawa et al. | |
| 5,821,337 A | 10/1998 | Carter et al. | |
| 6,653,084 B1 | 11/2003 | King et al. | |
| 6,987,088 B2 | 1/2006 | Dennis | |
| 7,135,174 B2 | 11/2006 | Corvalan et al. | |
| 7,244,826 B1 | 7/2007 | Marks | |
| 7,306,801 B2 | 12/2007 | Caligiuri et al. | |
| 7,754,885 B2 | 7/2010 | Hoefle et al. | |
| 7,776,330 B2 | 8/2010 | Yazaki et al. | |
| 7,776,814 B2 | 8/2010 | Dömling | |
| 7,777,008 B2 | 8/2010 | Ponath et al. | |
| 7,816,377 B2 | 10/2010 | Dömling et al. | |
| 8,350,011 B2 * | 1/2013 | Cartlidge | C07K 16/32 424/133.1 |
| 2003/0228663 A1 * | 12/2003 | Lowman | C07K 16/32 435/69.1 |
| 2009/0155275 A1 * | 6/2009 | Wu | C07K 16/468 424/136.1 |
| 2010/0240701 A1 | 9/2010 | Vlahov et al. | |
| 2011/0021568 A1 | 1/2011 | Ellman et al. | |
| 2011/0263650 A1 | 10/2011 | Ellman et al. | |
| 2012/0213705 A1 * | 8/2012 | Dimasi | A61K 47/48507 424/9.1 |
| 2013/0089544 A1 | 4/2013 | Cartilage et al. | |

FOREIGN PATENT DOCUMENTS

| | | |
|---|---|---|
| EP | 0425235 | 9/1996 |
| EP | 1106183 A2 | 6/2001 |

(Continued)

OTHER PUBLICATIONS

Liu et al (Immunol Rev, 2008, 222: 9-27).*

(Continued)

*Primary Examiner* — Sean E Aeder

(57) ABSTRACT

The present invention relates to anti-HER2 binding molecules (e.g., antibodies and antigen binding fragments thereof), derived HER2-binding molecules (e.g., bispecific anti-HER2 antibodies), and antibody-drug conjugates (ADC) that bind the extracellular domain of the HER2 receptor. Also provided are pharmaceutical formulation comprising the disclosed compositions and method for the treating diseases associated with HER2-mediated signal transduction.

18 Claims, 47 Drawing Sheets

Specification includes a Sequence Listing.

(56) References Cited

FOREIGN PATENT DOCUMENTS

| WO | WO 89/06692 | 7/1989 |
|---|---|---|
| WO | WO 94/00136 | 1/1994 |
| WO | WO 96/14339 | 5/1996 |
| WO | WO 97/00271 | 1/1997 |
| WO | WO 99/55367 | 11/1999 |
| WO | WO 01/00245 | 1/2001 |
| WO | WO 03/006509 A2 | 1/2003 |
| WO | WO 03/048731 | 6/2003 |
| WO | WO 2004/005326 | 1/2004 |
| WO | WO 2004/005327 | 1/2004 |
| WO | WO 2008/019290 | 2/2008 |
| WO | WO 2008/070593 | 6/2008 |
| WO | WO 2009/055562 | 4/2009 |
| WO | WO 2009/092011 | 7/2009 |
| WO | WO 2009/134279 | 11/2009 |
| WO | WO 2011/005481 | 1/2011 |
| WO | WO 2012/019123 | 2/2012 |
| WO | WO 2012/088290 | 6/2012 |
| WO | WO 2012/143523 | 10/2012 |
| WO | WO 2013/070565 | 5/2013 |
| WO | WO 2015/157594 | 10/2015 |
| WO | WO 2015/157595 | 10/2015 |

OTHER PUBLICATIONS

Songsivilai et al (Clin Exp Immunol, 1990, 79: 315-321).*
Deyev et al (BioEssays, 2008, 30: 904-918).*
Agus, D B et al., 2003, "Clinical activity in a phase I trial of HER-2-targeted rhuMAb 2C4 (pertuzumab) in patients with advanced solid malignancies (AST)," Program/Preceedings—American Society of Clinical Oncology, vol. 22, p. 192, Abstract No. 771.
Anido et al., 2006, "Biosynthesis of tumorigenic HER2 C-terminal fragments by alternative initiation of translation," The EMBO Journal, 25:3234-3244.
Arteaga et al., 1994, "$_p185^{c\text{-}erbB\text{-}2}$ Signaling Enhances Cisplatin-induced Cytotoxicity in Human Breast Carcinoma Cells: Association Between an Oncogenic Receptor Tyrosine Kinase and Drug-induced DNA Repair," Cancer Research, 54:3758-3765.
Bacus et al., 1990, "Differentiation of cultured human breast cancer cells (AU-565 and MCF-7) associated with loss of cell surface HER-2/neu antigen", Molecular Carcinog., 3(6):350-362.
Bacus et al., 1992, "Tumor-inhibitory Monoclonal Antibodies to the HER-2/Neu Receptor Induce Differentiation of Human Breast Cancer Cells", Cacner Research, 52:2580-2589.
Baselga et al., 1996, "Phase II Study of Weekly Intravenous Recombinant Humanized Anti $p185^{HER2}$ Monoclonal Antibody in Patients With HER2/neu-Overexpressing Metastic Breast Cancer", Journal of Clinical Oncology, 14(3):737-744.
Birrane et al., 2003, "Novel Mode of Ligand Recognition by the Erbin PDZ Domain", The Journal of Biological Chemistry,278(3):1399-1402.
Bostrom et al., 2009, "Variants of the Antibody Herceptin That Interact with HER2 and VEGF at the Antigen Binding Site", Science, 323:1610-1614.
Chari et al., 1992, "Immunoconjugates Containing Novel Maytansinoids: Promising Anticancer Drugs", Cancer Research, 52:127-131.
Cho et al., 2003, "Structure of the extracellular region of HER2 alone and in complex with the Herceptin Fab", Nature, 421:756-760.
Coussens et al, 1985, "Tyrosine kinase receptor with extensive homology to EGF receptor shares chromosomal location with neu oncogene", Science, 230(4730):1132-1139.
Dimasi et al., 2009, "The Design and Characterization of Oligospecific Antibodies for Simultaneous Targeting of Multiple Disease Mediators", Journal of Molecular Biology, 393:672-692.
Paterson Trevor et al: "Variation in IgG1 heavy chain allotype does not contribute to differences in biological activity of two human anti-Rhesus (D) monoclonal antibodies", Immunotechnology (Shannon) vol. 4, No. 1, Jun. 1998 (Jun. 1998) pp. 37-40.

Dömling et al., 2005, "Myxobacterial epothilones and tubulysins as promising anticancer agents", Molecular Diversity, 9:141=147.
D'Souza et al., 1994, "Overexpression of ERBB2 in human mammary epitherlial cells signals inhibition of transcription of the E-cadherin gene", Proc. Natl. Acad. Sci. USA, 91:7202-7206.
Eigenbrot et al., 2010, "Stuctural Basis for high-affinity HER2 receptor binding by an engineered protein", PNAS, 107:15039-15044.
Fendly et al., 1990, "Characterization of Murine Monoclonal Antibodies Reactive to Either the Human Epidermal Growth Factor Receptor or HER2/neu Gene Product", Cancer Research, 50:1550-1558.
Franklin et al., 2004, "Insights into ErbB signaling from the structure of the ErbB2-pertuzumab complex", Cancer Cell, 5:317-328.
Giri et al., 2005, "Endosomal Transport of ErbB-2: Mechanism for Nuclear Entry of the Cell Surface Receptor", Molecular and Cellular Biology, 11005-11018.
Goldenberg, 1999, "Trastuzumab, a recombinant DNA-derived humanized monoclonal antibody, a novel agent for the treatment of metastatic breast cancer", Clinical Therapeutics, vol. 21, Issue 2, 309-318.
Greenman et al., 2007, "Patterns of somatic mutation in human cancer genomes", Nature, 446(7132):153-158.
Hancock et al., 1991, "A monoclonal antibody against the c-erbB-2 Protein Enhances the Cytotoxicity of cis-Diamminedichloroplatinum against Human Breast and Ovarian Tumor Cell Lines", Cancer Research, 51(17):4575-4580.
Harwerth et al., 1992, "Monoclonal Antibodies against the Extracellular Domain of the erbB-2 Receptor Function as Partial Ligand Agonists", The Journal of Biological Chemistry, 267(21):15160-15167.
Hudziak et al., 1989, "$p185^{HER2}$ Monoclonal Antibody Has Antiproliferative Effects In Vitro and Sensitizes Human Breast Tumor Cells to Tumor Necrosis Factor", Molecular and Cellular Biology, 1165-1172.
Hynes et al., 2005, "ERBB Receptors and Cancer: The Complexity of Targeted Inhibitors", Nature Reviews Cancer, 5:341-354.
International Search Report for corresponding PCT/US2007/070578 dated Jan. 23, 2008.
International Preliiminary Report for correspondnig PCT/US2015/025232 dated Aug. 7, 2015.
Ivancic et al., 2003, "Solution structure of the human Grb7-SH2 domain/erbB2 peptide complex and structural basis for Grb7 binding to ErbB2", J. Biomol. NMR, 27(3):205-219.
Junutula et al., 2010, "Engineered Thio-Trastuzumab-DM1 Conjugate with an Improved Therapeutic Index to Target Human Epidermal Growth Factor Receptor 2-Positive Breast Cancer", Clincal Cancer Research, 16:4769-4778.
Kasprzyk et al., 1992, "Therapy of an Animal Model of Human Gastric Cancer Using a Combination of Anti-erbB2 Monoclonal Antibodies," Cancer Research, 52:2771-2776.
Kaur et al., 2006, "Biological evaluation of tubulysin A: a potential anticancer and antiangiogenic natural product", Biochmeical Journal, 396:235-242.
Khalil et al., 2006, "Mechanism of Action of Tubulysin, an Antimitotic Peptide from Myxobacteria", ChemBioChem, 7:678-683.
Klapper et al., 1997, "A subclass of tumor-inhibitory monoclonal antibodies ErbB-2'HER2 blocks crosstalk with growth factor receptors", Oncogene, 14(17):2099-2109.
Kudo, Toshio et al., 1993, "Production of a Human Monoclonal Antibody to a Synthetic Peptide by Active In Vivo Immunization Using a SCID Mouse Grafted with Human Lymphocytes," Journal of Experimental Medicine, 171:327-338.
Kumar et al., 1991, "Regulation of phosphorylation of the c-erbB-2/HER2 gene product by a monoclonal antibody and serum growth factor(s) in human mammary carcinoma cells" Mol Cell Biol. 11(2): 979-986.
Lamminmaki et al., Sep. 28, 2001, "Crystal structure of a recombinant anti-estradiol Fab fragment in complex with 17Beta-estradiol," J. Biol. Chem. 276(39):36687-36694.

(56) References Cited

OTHER PUBLICATIONS

Le, Xiaogfeng et al., 2006, "HER2 antibodies pertuzumab and trastuzumab differ in their effect on cell signaling and growth inhibition in breast cancer cells," Proc. Amer. Assoc. Cancer Res., 47(1):902 Abstract #3836.

Lewis et al., 1993, "Differential responses of human tumor cell lines to anti-p185HER2 monoclonal antibodies", Cancer Immunology Immunotherapy, 37(4):255-263.

Lewis et al., 1996, "Growth Regulation of Human Breast and Ovarian Tumor Cells by Heregulin: Evidence for the Requirement of ErbB2 as a Critical Component in Mediating Heregulin Responsiveness," Cancer Research, 56:1457-1465.

Li et al., 2013, "Bispecific Antibody to ErbB2 Overcomes Trastuzumab Resistance through Comprehensive Blockade of ErbB2 Heterodimerization," Cancer Research 73(21):6471-6483.

Li et al., 2016, "A Biparatopic HER2-Targeting Antibody-Drug Conjugate Induces Tumor Regression in Primary Models Refractory to or Ineligible for HER2-Targeted Therapy," Cancer Cell 29:117-129.

Liu, et al., 1996, "Eradication of large colon tumor xenografts by targeted delivery of maytansinoids", Proc. Natl. Acad. Sci. USA, 93:8618-8623.

Lorusso et al., 2011, "Trastuzumab Emtansine: A Unique Antibody-Drug Conjugate in Development for Human Epidermal Growth Factor Receptor 2-Positive Cancer", Clinical Cancer Research, 17(20):6437-6447.

MacCallum et al., 1996, "Antibody-antigen interactions: contact analysis and binding site topography", J. Mol. Biol. 262:732-745.

McDonagh et al., 2006, "Engineered antibody-drug conjugates with defined sites and stoichiometries of drug attachment", Protein Engineering, Design & Selection, 19(7):299-307.

Maier, et al., 1991, "Requirements for the Internalization of a Murine Monoclonal Antibody Directed against the HER-2/ neu Gene Product c-erb B-2," Cancer Research, 51:5361-5369.

Dhillon, 2014, "Trastuzumab Emtansine: A Review of Its Use in Patients with HER2-Positive Advanced Breast Cancer Previously Treated with Trastuzumab-Based Therapy" Drugs, vol. 74, Issue 6, pp. 675-686.

Pietras, et al., 1999, "Monoclonal Antibody to HER-2/neuReceptor Modulates Repair of Radiation-induced DNA Damage and Enhances Radiosensitivity of Human Breast Cancer Cells Overexpressing This Oncogene", Cancer Res, 59:1347-1355.

Ross, J. S. et al., 2004, "Targeted Therapies for Cancer 2004", American Society for Clinical Pathology, 122:598-609.

Rudikoff et al., Mar. 1992, "Single amino acid substitution altering antigen-binding specificity," Proc. Natl Acad Sci USA, 79:1979-1983.

Saga et al., Feb. 1, 1991, "Scintigraphic detection of overexpressed c-erbB-2 protooncogene products by a class-switched murine anti-c-erbB2 protein monoclonal antibody," Cancer Res., 51:990-994.

Sasse et al., 2000, "Tubulysins, New Cytostatic Peptides from Myxobacteria Acting on Microtubuli Production, Isolation, Physicochemcial and Biological Properties", The Juornal of Antibotics, 53(9):879-885.

Scott et al., 1991, "p185$^{HER2}$ Signal Transduction in Breast Cancer Cells", The Journal of Biological Chemistry, 266:14300-14305.

Schaefer et al., 1997, γ-Heregulin:a novel heregulin isoform that is an autocrine growth factor for the human breast cancer cell line, MDS-MB-175, Oncogene, 15:1385-1394.

Semba et al., 1985, "Av-erbB-related protooncogene, c-erbB-2, is distinct from the c-erbB-1/epidermal growth factor-receptor gene and is amplified in a human salivary gland adenocarcinoma", Proc. Natl. Acad. Sci. USA, 82:6497-6501.

Shawver et al., 1994, "Ligand-like Effects Induced by Anti-c-erbB-2 Antibodies Do Not Correlate with and Are Not Required for Growth Inhibition of Human Carcinoma Cells," Cancer Research, 54:1367-1373.

Sliwkowski et al., 1994, "Coexpression of erbB2 and erbB3 Proteins Reconstitutes a High Affinity Receptor for Heregulin", The Journal of Biological Chemistry, 269(20):14661-14665.

Stancovski et al., 1991, "Mechanistic aspects of the opposing effects of monoclonal antibodies to the ERBB2 receptor on tumor growth", PNAS, 88:8691-8695.

Stephens et al., 2004, "Intragenic ERBB2 kinase mutations in tumours", Nature, 431:525-526.

Stimmel et al., 2000, "Site-specific Conjugation on Serine Cysteine Variant Monoclonal Antibodies," The Journal of Biological Chemistry, 275(39):30445-30450.

Tagliabue, et al., 1991, "Selection of monoclonal antibodies which induce internalization and phosphorylation of p185HER2 and growth inhibition of cells with HER2/NEU gene amplification," International Journal of Cancer, 47(6):933-937.

Tal et al., 1987, "Human HER2 (neu) Promoter: Evidence for Multiple Mechanisms for Transcriptional Initiation," Molecular and Cellular Biology, 2597-2601.

Yamamoto et al., 1986, "Similarity of protein encoded by the human c-erb-B-2 gene to epidermal growth factor receptor," Nature, 319:230-234.

Yang, X.D. et al, 2001, "Development of ABX-EGF, a fully human anti-EGF receptor monoclonal antibody, for cancer therapy," Crit. Rev. Oncol. Hematol. 38:17-23.

Xu, Fengji et al. 1993, "Antibody-Induced Growth Inhibition Is Mediated Through Immunochemically and Functionally Distinct Epitopes on the Extracellular Domain of the c-erbB-2 (HER-2/neu) Gene Product p185," Int. J. Cancer, 53:401-408.

Vitetta et al., 1994, "Monoclonal Antibodies as Agonists: An Expanded Role for Their Use in Cancer Therapy," Cancer Research, 54:5301-5309.

* cited by examiner

FIG. 1

| Construct [a] | IgG in sups (μg/ml) [b] |
|---|---|
| After LC-FR swapping | 140 |
| Before LC-FR swapping | 72 | a: All constructs have the same heavy chain as G4A (AZ1.39.1 (WT) heavy chain with DG mutated to DA in CDR3H)

b: Average from two Octet-96 quants after 7 days in culture of 293F cells transfected with corresponding IgG vectors; cv% ~10%

FIG. 2

DIQMTQSPSSLSASVGDRVTITCRASQDVNTAVAWYQQKPGKAPKLLIYSASFLYSGVPSRFSGSRSGTDFTLTISSLQPEDFA
TYYCQQHYTTPPTFGCGTKVEIKGGGSGGGGSGGGGSGGGGSEVQLVESGGGLVQPGGSLRLSCAASGFNIKDTYIHWVRQAP
GKCLEWVARIYPTNGYTRYADSVKGRFTISADTSKNTAYLQMNSLRAEDTAVYYCSRWGGDGFYAMDYWGQGTLVTVSSGGGGS
GGGGSGGGGSEVQLVESGGGLVKPGGSLRLSCAASGFTFSSYSMSWVRQAPGKGLEWVSSISSSSSYIYYADSVKGRFTISRDN
AKNSLYLQMNSLRAEDTAVYYCARGGDAYNYYFDYWGQGTLVTVSSASTKGPSVFPLAPSSKSTSGGTAALGCLVKDYFPEPV
TVSWNSGALTSGVHTFPAVLQSSGLYSLSSVVTVPSSSLGTQTYICNVNHKPSNTKVDKRVEPKSCDKTHTCPPCPAPEX1LGG
PX2\*VFLFPPKPKDTLMISRTPEVTCVVVDVSHEDPEVKFNWYVDGVEVHNAKTKPREEQYNSTYRVVSVLTVLHQDWLNGKEY
KCKVSNKALPX3PX4EKTISKAKGQPREPQVYTLPPSREEMTKNQVSLTCLVKGFYPSDIAVEWESNGQPENNYKTTPPVLDSD
GSFFLYSKLTVDKSRWQQGNVFSCSVMHEALHNHYTQKSLX5LSPGK

| EU# | | | | |
|---|---|---|---|---|
| 234 | X1 = L for WT; | L for ADCC; | F for ADC | "F", "FC", "FCC" |
| 239 | X2 = S for WT; | S or D for ADCC; | C for ADC | "FC", "FCC" |
| 239i | * = absent for WT; | absent for ADCC; | C for ADC 239-ins | "C" |
| 330 | X3 = A for WT; | L or A for ADCC; | A for ADC | |
| 332 | X4 = I for WT; | E for ADCC; | I for ADC | |
| 442 | X5 = S for WT; | S for ADCC; | C for ADC | "FCC" and "CC" |

FIG. 8A

EVQLVESGGGLVKPGGSLRLSCAASGFTFSSYSMSWVRQAPGKGLEWVSSISSSSYIYADSVKGRFTISRDNAKNSLYLQMN
SLRAEDTAVYYCARGGDAYNYYFDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCDKTHTCPPCPAPEX1LGGPX2\* VFLFPP
KPKDTLMISRTPEVTCVVVDVSHEDPEVKFNWYVDGVEVHNAKTKPREEQYNSTYRVVSVLTVLHQDWLNGKEYKCKVSNKALP
X3PX4EKTISKAKGQPREPQVYTLPPSREEMTKNQVSLTCLVKGFYPSDIAVEWESNGQPENNYKTTPPVLDSDGSFFLYSKLT
VDKSRWQQGNVFSCSVMHEALHNHYTQKSLX5LSPGKGGGGSGGGGSGGGGSDIQMTQSPSSLSASVGDRVTITCRASQDVNTA
VAWYQQKPGKAPKLLIYSASFLYSGVPSRFSGSRSGTDFTLTISSLQPEDFATYYCQQHYTTPPTFGCGTKVEIKGGGGSGGGG
SGGGGSGGGGSEVQLVESGGGLVQPGGSLRLSCAASGFNIKDTYIHWVRQAPGKCLEWVARIYPTNGYTRYADSVKGRFTISAD
TSKNTAYLQMNSLRAEDTAVYYCSRWGGDGFYAMDYWGQGTLVTVSS

```
EU#
234   X1 = L for WT;       L for ADCC;         F for ADC  "F", "FC", "FCC"
239   X2 = S for WT;       S or D for ADCC;    C for ADC  "FC", "FCC"
239i  * = absent for WT;   absent for ADCC;    C for ADC  239-ins "C"
330   X3 = A for WT;       L or A for ADCC;    A for ADC
332   X4 = I for WT;       E for ADCC;         I for ADC
442   X5 = S for WT;       S for ADCC;         C for ADC  "FCC" and "CC"
```

FIG. 8B

EVQLVESGGGLVKPGGSLRLSCAASGFTFSSYSMSWVRQAPGKGLEWVSSISSSSSYIYYADSVKGRFTISRDNAKNSLYLQMN
SLRAEDTAVYYCARGDAYNYYFDYWGQGTLVTVSSASTKGPSVFPLAPSSKSTSGGTAALGCLVKDYFPEPVTVSWNSGALT
SGVHTFPAVLQSSGLYSLSSVVTVPSSSLGTQTYICNVNHKPSNTKVDKRVEPKSCGKTGGGGSGGGGSDIQMTQSPSSLSASV
GDRVTITCRASQDVNTAVAWYQQKPGKAPKLLIYSASFLYSGVPSRFSGSRSGTDFTLTISSLQPEDFATYYCQQHYTTPPTFG
CGTKVEIKGGGGSGGGGSGGGGSEVQLVESGGGLVQPGGSLRLSCAASGFNIKDTYIHWVRQAPGKCLEWVARIYPTNG
YTRYADSVKGRFTISADTSKNTAYLQMNSLRAEDTAVYYCSRWGGDGFYAMDYWGQTLVTVSSSGGGGSGGGGSCPPCPAPE**X
1LGGPX2**VFLFPPKPKDTLMISRTPEVTCVVVDVSHEDPEVKFNWYVDGVEVHNAKTKPREEQYNSTYRVVSVLTVLHQDWLN
GKEYKCKVSNKALPX3PX4EKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLX5LSPGK

EU#
234   X1 = L for WT;           L for ADCC;              F for ADC   "F", "FC", "FCC"
239   X2 = S for WT;           S or D for ADCC;         C for ADC   "FC", "FCC"
239i  * = absent for WT;       absent for ADCC;         C for ADC   239-ins "C"
330   X3 = A for WT;           L or A for ADCC;         A for ADC
332   X4 = I for WT;           E for ADCC;              I for ADC
442   X5 = S for WT;           S for ADCC;              C for ADC   "FCC" and "CC"

FIG. 8C

**Tubulysin 1508 Payload (*compound T-32*)**

FIG. 32

BISPECIFIC HER2 ANTIBODIES

CROSS-REFERENCE TO RELATED APPLICATIONS

This application is a U.S. National Stage Application of International Application No. PCT/US2015/025232, filed on Apr. 10, 2015, said International Application No. PCT/US2015/025232 claims benefit under 35 U.S.C. § 119(e) of U.S. Provisional Patent Application No. 61/978,516, filed Apr. 11, 2014 and U.S. Provisional Patent Application No. 62/107,050, filed Jan. 23, 2015. Each of the above listed applications is incorporated by reference herein in its entirety for all purposes.

REFERENCE TO THE SEQUENCE LISTING

This application incorporates by reference a Sequence Listing submitted with this application as text file entitled ERB2-105WO1, created on Aug. 26, 2016, and having a size of 231 kilobytes.

BACKGROUND

The present invention provides compositions that specifically bind to HER2 and methods for the use of such compositions for the treatment of cancer.

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185neu), HER3 (ErbB3) and HER4 (ErbB4 or tyro2).

HER2 was originally identified as the product of the transforming gene from neuroblastomas of chemically treated rats. Amplification of the human homolog has observed in breast and ovarian cancers and correlates with a poor prognosis. Overexpression of HER2 (frequently but not uniformly due to gene amplification) has also been observed in other carcinomas including carcinomas of the stomach, endometrium, salivary gland, lung, kidney, colon, thyroid, pancreas and bladder. HER2 can also be overexpressed in prostate cancer.

The HER receptors are generally found in various combinations in cells and heterodimerization is thought to increase the diversity of cellular responses to a variety of HER ligands (Earp et al. Breast Cancer Research and Treatment 35: 115-132 (1995)). While EGF and TGFα do not bind HER2, EGF stimulates EGFR and HER2 to form a heterodimer, which activates EGFR and results in transphosphorylation of HER2 in the heterodimer. Dimerization and/or transphosphorylation appear to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., J. Biol. Chem., 269:14661-14665 (1994)).

Numerous antibodies targeting HER2 have been described in the art (see, e.g., Hudziak et al., Mol. Cell. Biol. 9:1165-1172 (1989); U.S. Pat. No. 5,677,171; Fendly et al. Cancer Research 50:1550-1558 (1990); Kotts et al. In vitro 26(3):59A (1990); Sarup et al. Growth Regulation 1:72-82 (1991); Shepard et al. J. Clin. Immunol. 11: 117-127 (1991); Kumar et al. Mol. Cell. Biol. 1:979-986 (1991); Lewis et al. Cancer Immunol. Immunother. 37:255-263 (1993); Pietras et al. Oncogene 9:1829-1838 (1994); Vitetta et al. Cancer Research 54:5301-5309 (1994); Sliwkowski et al. J. Biol. Chem. 269(20):14661-14665 (1994); Scott et al. J. Biol. Chem. 266:14300-5 (1991); D'souza et al. Proc. Natl. Acad. Sci. 91:7202-7206 (1994); Lewis et al. Cancer Research 56:1457-1465 (1996); and Schaefer et al. Oncogene 15:1385-1394 (1997).

Other HER2 antibodies with various properties have been described in Tagliabue et al. Int. J. Cancer 47:933-937 (1991); McKenzie et al. Oncogene 4:543-548 (1989); Maier et al. Cancer Res. 51:5361-5369 (1991); Bacus et al. Molecular Carcinogenesis 3:350-362 (1990); Stancovski et al. PNAS (USA) 88:8691-8695 (1991); Bacus et al. Cancer Research 52:2580-2589 (1992); Xu et al. Int. J. Cancer 53:401-408 (1993); WO94/00136; Kasprzyk et al. Cancer Research 52:2771-2776 (1992); Hancock et al. Cancer Res. 51:4575-4580 (1991); Shawver et al. Cancer Res. 54:1367-1373 (1994); Arteaga et al. Cancer Res. 54:3758-3765 (1994); Harwerth et al. J. Biol. Chem. 267:15160-15167 (1992); U.S. Pat. No. 5,783,186; and Klapper et al. Oncogene 14:2099-2109 (1997).

Trastuzumab (HERCEPTIN®; see U.S. Pat. No. 5,821,337), a recombinant humanized version of the murine HER2 antibody 4D5, is clinically active in patients with HER2-overexpressing metastatic breast cancers that have received extensive prior anti-cancer therapy (Baselga et al., J. Clin. Oncol. 14:737-744 (1996)). To target the HER signaling pathway, Pertuzumab (PERJETA™; see Patent Publication WO2001/00245) was developed as a humanized version of the murine antibody 2C4 that inhibits the dimerization of HER2 with other HER receptors, thereby inhibiting ligand-driven phosphorylation and activation, and downstream activation of the RAS and AKT pathways. Ado-trastuzumab emtansine (T-DM1; KADCYLA®) is an antibody drug conjugate of trastuzumab linked to the cytotoxic agent mertansine approved for use in patients with HER2-overexpressing metastatic breast cancers resistant to trastuzumab.

Although, the therapeutic efficacy of trastuzumab in breast carcinoma is well demonstrated, it is strictly limited and only approved for 30% of breast cancer patients whose tumor overexpress HER2. 70% of the breast cancer patients do not or insufficiently respond to trastuzumab because their individual tumor do not overexpress or do not sufficiently express HER2. In other cancers and/or individual cancers, HER2 is overexpressed in a significant percentage of cases ranging from 43 to 69%, However, as a rule, the levels of HER2 expression are in principle low in the majority of tumors. Furthermore, the-overexpression of HER2 receptors is often caused by encoding gene amplification (Hynes et al., Nat Rev Cancer 5:341 (2005)). Thus, the present day consensus is that anti-HER2 monoclonal antibody therapy is inefficient in tumors with low HER2 expression or missing overexpression. Furthermore, resistance to these anti-HER2 antibodies is a significant problem.

Given the lack of an effective anti-HER2 therapy in specific cancers expressing low levels of HER2 and resistance to the current therapies, there is a need for improved antibodies capable of effectively binding to cancer cells expressing a wider range of levels of HER2 and inhibiting their growth via, for example, (i) Antibody-Dependent Cell-Mediated Cytotoxicity (ADCC) and/or (ii) cytotoxic action due to payloads conjugated to the antibodies as Antibody Drug Conjugates (ADC) and/or (iii) inhibiting receptor mediating signaling (e.g. by inhibiting receptor dimerization and/or mediating receptor internalization).

Thus, it is an object of the present disclosure to provide improved immunotherapeutic agents that effectively inhibit HER2-mediated cell signaling that can be used for the treatment of HER2-expressing cancers, including cancers where HER2 is not expressed at high levels.

BRIEF SUMMARY

The present disclosure provides an anti-HER2 binding molecule comprising an immunoglobulin heavy chain (VH) and an immunoglobulin light chain (VL), wherein the VH comprises the amino acid sequence of SEQ ID NO:15. Also provided is an anti-HER2 binding molecule comprising a VH and a VL, wherein the VL comprises the amino acid sequence of SEQ ID NO:16. In some aspects, the VH comprises the amino acid sequence of SEQ ID NO:15 and the VL comprises the amino acid sequence of SEQ ID NO:16. In some aspects, the anti-HER2 binding molecule comprises an antibody, or antigen-binding fragment thereof.

The present disclosure also provides a bispecific anti-HER2 antibody comprising a first immunoglobulin antigen-binding domain and a second immunoglobulin antigen-binding domain, wherein (i) the first and second immunoglobulin antigen-binding domains specifically bind to distinct HER2 antibody binding sites, (ii) the first immunoglobulin antigen-binding domain binds to a first HER2 antibody binding site which comprises an epitope within domain II of HER2, and (iii) the first HER2 antibody binding site is distinct from the antibody binding site of pertuzumab. In some aspects, the second immunoglobulin antigen-binding domain binds to a second HER2 antibody binding site which comprises an epitope within domain IV of HER2. In some aspects, the second HER2 antibody binding site is identical the HER2 antibody binding site of trastuzumab. In some aspects, the second HER2 antibody binding site partially overlaps with the HER2 antibody binding site of trastuzumab. In other aspects, the second HER2 antibody binding site is distinct from the HER antibody binding site of trastuzumab.

The present disclosure also provides a bispecific anti-HER2 antibody comprising a first immunoglobulin antigen-binding domain and a second immunoglobulin antigen-binding domain, wherein the first and second immunoglobulin antigen-binding domains specifically bind to distinct HER2 epitopes; and wherein the first immunoglobulin antigen-binding domain binds HER2 at an epitope comprising one or more amino acid residues in SEQ ID NO: 52.

In some aspects, the first immunoglobulin antigen-binding domain binds HER2 at an epitope comprising one or more amino acid residues in SEQ ID NO: 52 and the second immunoglobulin antigen-binding domain specifically binds HER2 at an epitope within domain IV. In some aspects, the second immunoglobulin antigen-binding domain binds HER2 at an epitope comprising one or more amino acid residues in SEQ ID NO: 53.

In some aspects, the first immunoglobulin antigen-binding domain comprises a heavy chain variable region (VH) and a light chain variable region (VL) comprising:
(i) a variable heavy chain CDR-1 (VH-CDR1) sequence identical to SEQ ID NO: 1 or identical to SEQ ID NO: 1 except for up to 1, 2, 3, or 4 amino acid substitutions;
(ii) a variable heavy chain CDR-2 (VH-CDR2) sequence identical to SEQ ID NO: 2 or identical to SEQ ID NO: 2 except for up to 1, 2, 3, or 4 amino acid substitutions;
(iii) a variable heavy chain CDR-3 (VH-CDR3) sequence identical to SEQ ID NO: 3 or identical to SEQ ID NO: 3 except for up to 1, 2, 3, or 4 amino acid substitutions;
(iv) a variable light chain CDR-1 (VL-CDR1) sequence identical to SEQ ID NO: 4 or identical to SEQ ID NO: 4 except for up to 1, 2, 3, or 4 amino acid substitutions;
(v) a variable light chain CDR-2 (VL-CDR2) sequence identical to SEQ ID NO: 5 or identical to SEQ ID NO: 5 except for up to 1, 2, 3, or 4 amino acid substitutions; and,
(vi) a variable light chain CDR-3 (VL-CDR3) sequence identical to SEQ ID NO: 6 or identical to SEQ ID NO: 6 except for up to 1, 2, 3, or 4 amino acid substitutions.

In certain aspects, the first immunoglobulin antigen-binding domain comprises at least one heterologous variable domain framework region (FW) relative to the immunoglobulin antigen-binding domain comprising a VH comprising the amino acid sequence SEQ ID NO:43 and a VL comprising the amino acid sequence of SEQ ID NO:44.

In certain aspects, the first immunoglobulin antigen-binding domain comprises an scFv antibody fragment.

In certain aspects, the second immunoglobulin antigen-binding domain comprises an scFv antibody fragment.

In some aspects, the at least one heterologous FW region of the bispecific anti-HER2 antibody comprises a first immunoglobulin antigen-binding domain further comprising (i) a variable light chain framework 1 (VL-FW1) amino acid sequence comprising SEQ ID NO:11; (ii) a VH-FW2 amino acid sequence comprising SEQ ID NO:12; (iii) a VH-FW3 amino acid sequence comprising SEQ ID NO:13; (iv) a VH-FW4 amino acid sequence at comprising SEQ ID NO:14; or (vi) any combination thereof.

In some aspects, the bispecific anti-HER2 antibody comprises a first immunoglobulin antigen binding-domain and a second immunoglobulin antigen-binding domain, wherein the first immunoglobulin antigen-binding domain comprises a VH and a VL, wherein the VH amino acid sequence comprises SEQ ID NO:15; wherein the first or the second immunoglobulin antigen-binding domain comprises an scFv antibody fragment, and wherein the first and second immunoglobulin antigen-binding domains specifically bind to distinct HER2 epitopes.

In some aspects, the bispecific anti-HER2 antibody comprises a first immunoglobulin antigen binding-domain and a second immunoglobulin antigen-binding domain, wherein the first immunoglobulin antigen-binding domain comprises a VH and a VL, wherein the VL amino acid sequence comprises SEQ ID NO:16; wherein the first or the second immunoglobulin antigen-binding domain comprises an scFv antibody fragment, and wherein the first and second immunoglobulin antigen-binding domains specifically bind to distinct HER2 epitopes.

In some aspects, the bispecific anti-HER2 antibody comprises a VH and a VL, wherein the VH amino acid sequence comprises SEQ ID NO:15; and wherein the VL amino acid sequence comprises SEQ ID NO: 16, wherein the first or the second immunoglobulin antigen-binding domain comprises an scFv antibody fragment, and wherein the first and second immunoglobulin antigen-binding domains specifically bind to distinct HER2 epitopes.

In some aspects, the bispecific anti-HER2 antibody disclosed herein comprises a first immunoglobulin antigen binding domain comprising or consisting of (a) a VH further comprising a heavy chain constant region or a fragment thereof and a VL comprising a light chain constant region or a fragment thereof; (b) a single chain Fv ("scFv"); (c) a diabody; (d) a minibody; (e) an F(ab')$_2$; or (f) F(ab). In same aspects, the heavy chain constant region or fragment thereof is an IgG constant region. In some aspects, the IgG constant region or fragment thereof is an IgG1 constant region. In some aspects, the LC constant region is a kappa constant region.

In some aspects, the LC constant region is a lambda constant region. In some aspects, the first immunoglobulin antigen-binding domain is a monoclonal antibody. In some aspects, the first immunoglobulin antigen-binding domain is a humanized antibody. In some aspects, the first immunoglobulin antigen-binding domain is a human antibody. In some aspects, the first immunoglobulin antigen-binding domain is a chimeric antibody. In some aspects, the first immunoglobulin antigen-binding domain is an affinity optimized antibody. In some aspects, the first immunoglobulin antigen-binding domain does not compete with trastuzumab or pertuzumab for epitope binding. In some aspects, the first and second immunoglobulin antigen binding domains specifically bind to distinct non-overlapping HER2 epitopes.

In some aspects, the bispecific anti-HER2 antibody comprises a first and a second immunoglobulin antigen-binding domain, wherein (a) the second immunoglobulin antigen-binding domain specifically binds to the same epitope in domain IV of HER2 as the trastuzumab antibody; (b) the second immunoglobulin antigen-binding domain competitively inhibits HER2 binding by the trastuzumab antibody; and/or (c) the second immunoglobulin antigen-binding domain comprises at least one, at least two, at least three, at least four, at least five, or at least six complementarity determining regions (CDRs) having amino acids selected from the group consisting of SEQ ID NOs: 54 to 59.

In some aspects, the second immunoglobulin antigen-binding domain comprises an scFv comprising: (i) a VH-CDR1 comprising the amino acids of SEQ ID NO:54; (ii) a VH-CDR2 comprising the amino acids of SEQ ID NO:55; (iii) a VH-CDR3 comprising the amino acids of SEQ ID NO:56; (iv) a VL-CDR1 comprising the amino acids of SEQ ID NO:57; (v) a VL-CDR2 comprising the amino acids of SEQ ID NO:58; and (vi) a VL-CDR3 comprising the amino acids of SEQ ID NO:59. In some aspects, the scFv is a disulfide stabilized scFv. In some aspects, the scFv comprises a VH comprising the amino acids of SEQ ID NO:17, and a VL comprising the amino acids of SEQ ID NO:18.

In some aspects, the VH and VL of the scFv are covalently linked via a peptide linker. In some aspects, the peptide linker comprises the amino acid sequence of SEQ ID NO:19.

In some aspects, the second immunoglobulin antigen-binding domain of the bispecific anti-HER2 antibody is covalently linked to the carboxy-terminus of the HC of the first immunoglobulin antigen-binding domain. In some aspects, the bispecific anti-HER2 antibody comprises a linker interposed between the second immunoglobulin antigen binding domain and the carboxy-terminus of the HC of the first immunoglobulin antigen-binding domain. In other aspects, the second immunoglobulin antigen-binding domain of the bispecific anti-HER2 antibody is covalently linked to the amino-terminus of the HC of the first immunoglobulin antigen-binding domain. In some aspects, the bispecific anti-HER2 antibody comprises a linker interposed between the second immunoglobulin antigen-binding domain and the amino-terminus of the HC of the first immunoglobulin antigen-binding domain.

In some aspects, the second immunoglobulin antigen binding domain of the bispecific anti-HER2 antibody is covalently intercalated in the polypeptide chain of the HC of the first immunoglobulin antigen-binding domain. In some aspects, the second immunoglobulin antigen binding domain is covalently intercalated between the CH1 region and CH2 region of the HC of the first immunoglobulin antigen-binding domain. In some aspects, the bispecific anti-HER2 antibody comprises a linker interposed between the CH1 region of the HC of the first immunoglobulin antigen binding domain and the second immunoglobulin antigen binding domain, and a second linker interposed between the second immunoglobulin antigen binding domain and the CH2 region of the HC of the of the first immunoglobulin antigen-binding domain.

In some aspects, the first linker and the second linker are identical. In other aspects, the first linker and the second linker are different. In some aspects, one or more of the linkers comprise a peptide linker. In some aspects, the peptide linker comprises at least one, at least two, at least three, at least four, at least five, at least 10, at least 20, or at least 30 amino acids. In other aspects, the peptide linker comprises a peptide having the formula $Ser_x[(Gly)_y-Ser_4]_z$ where x is from 0 to 1, y is from 1 to 4, and z is from 1 to 10 (SEQ ID NO: 60). In some aspects, the peptide linker comprises SEQ ID NOS:19, 20, 21, or 22.

In some aspects, the bispecific anti-HER2 antibody comprises a heavy chain which can include an Fc domain comprising a CH2 and a CH3 region. In some aspects, the Fc domain is an IgG1 Fc domain. In other aspects, the IgG1 Fc domain is a native IgG1 Fc domain. In some aspects, the native IgG1 Fc domain comprises the amino acid sequence of SEQ ID NO: 23.

In some aspects, the Fc domain is a mutant IgG1 Fc domain. In other aspects, the mutant IgG1 Fc domain comprises at least one mutation capable of reducing the ADCC activity of the bispecific antibody. In some aspects, at least one mutation capable of reducing the ADCC activity of the bispecific antibody is an amino acid substitution. In some aspects, at least one amino acid substitution comprises L234F, S239A, S239C, or any combination thereof.

In some aspects, the mutant IgG1 Fc domain comprises at least one amino acid substitution introducing a derivatizable group. In some aspects, the derivatizable group in a sulfhydryl group. In some aspects, the at least one amino acid substitution comprises S239C, 248C, 254C, 273C, 279C, 282C, 284C, 286C, 287C, 289C, 297C, 298C, 312C, 324C, 326C, 330C, 335C, 337C, 339C, 350C, 355C, 356C, 359C, 360C, 361C, 375C, 383C, 384C, 389C, 398C, 400C, 413C, 415C, 418C, 422C, 440C, 441C, S442C, 443C and 446C, or any combination thereof. In some aspects, the mutant Fc domain comprises the amino acids of SEQ ID NO: 24 or SEQ ID NO:25.

Also provided is a bispecific anti-HER2 antibody comprising a first and a second polypeptide chain associated with each other, wherein the first polypeptide chain comprises a sequence selected from:

 (1)

 (2)

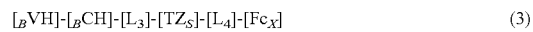 (3)

wherein
TZs is an scFv that binds the same epitope as trastuzumab;
$L_1$, $L_2$, $L_3$, and $L_4$ are peptide linkers;
Fcx is an Fc domain;
$_B$VH and $_B$CH are the VH and CH1 regions, respectively, of an antibody capable of binding to an HER2 epitope distinct from the epitope recognized by the trastuzumab antibody. In certain aspects the distinct epitope comprises one or more amino acid residues in SEQ ID NO: 52.

In some aspects a hinge polypeptide links [$_B$CH] and [Fc$_X$]. In a specific aspect the hinge polypeptide comprises or alternatively consists of the amino acids of SEQ ID NO: 26.

In some aspects, the second chain of the bispecific anti-HER2 antibody comprises the sequence [$_B$VL]-[CL] wherein $_B$VL is the VL region of an antibody capable of binding to an HER2 epitope distinct from the epitope recognized by the trastuzumab antibody, and CL is an IgG light chain constant region. In some aspects, CL is selected from the group consisting of a human kappa constant region and a human lambda constant region. In some aspects the $_B$VL comprises (i) a variable light chain CDR-1 (VL-CDR1) identical to SEQ ID NO: 4 or identical to SEQ ID NO: 4 except for up to 1, 2, 3, or 4 amino acid substitutions; (ii) a variable light chain CDR-2 (VL-CDR2) identical to SEQ ID NO: 5 or identical to SEQ ID NO: 5 except for up to 1, 2, 3, or 4 amino acid substitutions; and, (iii) a variable light chain CDR-3 (VL-CDR3) identical to SEQ ID NO: 6 or identical to SEQ ID NO: 6 except for up to 1, 2, 3, or 4 amino acid substitutions. In some aspects, $_B$VL comprises the amino acids of SEQ ID NO:16 or SEQ ID NO:44.

In other aspects, CL is a kappa light chain comprising the amino acid sequence of SEQ ID NO:27.

In other aspects, CL is a lambda light chain comprising the amino acid sequence of SEQ ID NO:66.

In some aspects, [TZ$_S$] comprises (i) a VH-CDR1 comprising the amino acids of SEQ ID NO:54; (ii) a VH-CDR2 comprising the amino acids of SEQ ID NO:55; (iii) a VH-CDR3 comprising the amino acids of SEQ ID NO:56; (iv) a VL-CDR1 comprising the amino acids of SEQ ID NO:57; (v) a VL-CDR2 comprising the amino acids of SEQ ID NO:58; and (vi) a VL-CDR3 comprising the amino acids of SEQ ID NO:59. In some aspects, [TZ$_S$] is a disulfide stabilized scFv. In some aspects, [TZ$_S$] comprises a VH comprising the amino acid sequence of SEQ ID NO:17 and a VL comprising the amino acid sequence of SEQ ID NO:18, covalently linked by a peptide linker. In some aspects, the peptide linker comprises the amino acid sequence of SEQ ID NO:19. In some aspects, [TZ$_S$] comprises of the amino acid sequence of SEQ ID NO:28.

In some aspects, the amino acid sequence of [Fc$_X$] is selected from the group consisting of SEQ ID NOs: 23, 24, 62, 63, 25, 64 and 65. In some aspects, the amino acids of [L$_1$], [L$_2$], [L$_3$], and [L$_4$] is independently selected from the group consisting of SEQ ID NOs: 19, 20, 21, and 22. In other aspects (i) [L$_1$] comprises the amino acids of SEQ ID NO:20; (ii) [L$_2$] comprises the amino acids of SEQ ID NO:20; (iii) [L$_3$] comprises the amino acids of SEQ ID NO:21; and, (iv) [L$_4$] comprises the amino acids of SEQ ID NO:22.

In some aspects, [$_B$VH] comprises (i) a variable heavy chain CDR-1 (VH-CDR1) identical to SEQ ID NO: 1 or identical to SEQ ID NO: 1 except for up to 1, 2, 3, or 4 amino acid substitutions; (ii) a variable heavy chain CDR-2 (VH-CDR2) identical to SEQ ID NO: 2 or identical to SEQ ID NO: 2 except for up to 1, 2, 3, or 4 amino acid substitutions; and (iii) a variable heavy chain CDR-3 (VH-CDR3) identical to SEQ ID NO: 3 or identical to SEQ ID NO: 3 except for up to 1, 2, 3, or 4 amino acid substitutions. In some aspects, [$_B$VH] comprises SEQ ID NO:15 or SEQ ID NO:43. In other aspects, [$_B$CH] comprises the amino acid sequence of SEQ ID NO: 29.

In some aspects, [$_B$VL] comprises (i) a variable light chain CDR-1 (VL-CDR1) identical to SEQ ID NO: 4 or identical to SEQ ID NO: 4 except for up to 1, 2, 3, or 4 amino acid substitutions; (ii) a variable light chain CDR-2 (VL-CDR2) identical to SEQ ID NO: 5 or identical to SEQ ID NO: 5 except for up to 1, 2, 3, or 4 amino acid substitutions; and (iii) a variable light chain CDR-3 (VL-CDR3) identical to SEQ ID NO: 6 or identical to SEQ ID NO: 6 except for up to 1, 2, 3, or 4 amino acid substitutions. In other aspects, [$_B$VL] comprises the amino acids of SEQ ID NO:16.

In some aspects, the first polypeptide chain of the bispecific anti-HER2 antibody comprises an amino acid sequence selected from the group consisting of SEQ ID NO: 30, 31, 67, 32, 68, 69 33, 70, 71, 34, 35, 72, 36, 73, 74, 37, 75, 76, 38, 39, 77, 40, 78, 79, 41, 80 and 81, and the second polypeptide chain of the bispecific anti-HER2 antibody comprises the amino acids of SEQ ID NO:42 or 82.

In some aspects, the second immunoglobulin antigen-binding domain of the bispecific anti-HER2 antibody induces internalization upon binding to the HER2 target. In some aspects, the second immunoglobulin antigen-binding domain of the bispecific HER2 antibody promotes effective lysosomal trafficking following internalization. In some aspects, the second immunoglobulin antigen-binding domain of the bispecific HER2 antibody induces HER2 target degradation. In some aspects, the second immunoglobulin antigen-binding domain of the bispecific HER2 antibody blocks ligand-induced AKT phosphorylation in low HER2-expressing cancer cells. In some aspects, the first immunoglobulin antigen-binding domain of the bispecific HER2 antibody disrupts ligand-induced HER2:HER3 dimerization.

The present disclosure also provides an ADC comprising an anti-HER2 binding molecule disclosed herein, or an anti-HER2 bispecific antibody disclosed herein, further comprising at least one therapeutic moiety. In some aspects, the ADC further comprises at least one optional spacer. In some aspects, the at least one spacer is a peptidic spacer. In some aspects, the at least one spacer is a nonpeptidic spacer.

Conventional conjugation strategies for ADCs rely on randomly conjugating the payload (e.g., therapeutic moiety) to the antibody through lysines or cysteines. Accordingly, in some aspects the ADC is randomly conjugated to a therapeutic moiety. In particular aspects, site-specific conjugation of therapeutic moieties to antibodies using reactive amino acid residues at specific positions yields homogeneous ADC preparations with uniform stoichiometry. In some aspects, the ADC comprises two, three, or four or more therapeutic moieties. In some aspects, all therapeutic moieties are the same. In some aspects, each therapeutic moiety is chemically conjugated to the side chain of an amino acid at a specific Kabat position in the Fc region of the bispecific antibody. In some aspects, the specific Kabat positions are 239, 442, or both. In some aspects, the specific positions are Kabat position 442, an amino acid insertion between Kabat positions 239 and 240, or both. In some aspects, the amino acid side chain is a sulfhydryl side chain. In some aspects, the therapeutic moiety comprises a cytotoxin, a radioisotope, an auristatin, a maytansinoid or a pyrrolobenzodiazepine (PBD), or combinations thereof. In certain aspects, the cytotoxin is tubulysin. In certain aspects, the tubulysin is Compound T32 (also referred to herein as "tubulysin 1508" or simply "1508").

The present disclosure also provides an ADC comprising a bispecific anti-HER2 antibody, wherein said antibody comprises:
(i) a first polypeptide chain comprising the amino acids of SEQ ID NO: 32 and a second polypeptide chain comprising the amino acids of SEQ ID NO:42, wherein the first polypeptide chain comprises a tubulysin molecule covalently linked to a cysteine amino acid at Kabat position 239.

(ii) a first polypeptide chain comprising the amino acids of SEQ ID NO:33 and a second polypeptide chain comprising the amino acids of SEQ ID NO:42, wherein the first polypeptide chain comprises two tubulysin molecules covalently linked to cysteine amino acids respectively located at Kabat positions 239 and 442.

(iii) a first polypeptide chain comprising the amino acids of SEQ ID NO:40 and a second polypeptide chain comprising the amino acids of SEQ ID NO:42, wherein the first polypeptide chain comprises a tubulysin molecule covalently linked to a cysteine amino acid at Kabat position 239.

(iv) a first polypeptide chain comprising the amino acids of SEQ ID NO:41 and a second polypeptide chain comprising the amino acids of SEQ ID NO:42, wherein the first polypeptide chain comprises two tubulysin molecules covalently linked to cysteine amino acids respectively located at Kabat positions 239 and 442.

The instant disclosure also provides an isolated nucleic acid molecule or a set of nucleic acid molecules encoding an anti-HER2 binding molecule (e.g., a bispecific anti-HER2 antibody disclosed herein), or a complement thereof. Also provided is a vector or a set of vectors comprising such nucleic acid molecule or set of the nucleic acid molecules, or a complement thereof. Also provided is a host cell comprising the isolated nucleic acid molecule or a set of nucleic acid molecules, or the vector or set of vectors. Also provided is a host cell expressing an anti-HER2 binding molecule or bispecific anti-HER2 antibody disclosed herein. Also provided is a method for producing an anti-HER2 binding molecule or bispecific anti-HER2 antibody comprising culturing the host cell and recovering the antibody from the culture medium.

The instant disclosure also provides a pharmaceutical composition comprising an anti-HER2 binding molecule or anti-HER2 bispecific antibody, and a pharmaceutically acceptable carrier. Also provided is a method of treating a HER2-expressing cancer comprising administering an anti-HER2 binding molecule disclosed herein, an anti-HER2 bispecific antibody disclosed herein, an ADC disclosed herein, or a pharmaceutical composition disclosed herein to a subject in need thereof. In some aspects, the cancer is a low HER2-expressing cancer. In some aspects, the method further comprises administering at least one additional therapeutic agent. In some aspects, the at least one additional therapeutic agent is a radionuclide or a chemotherapeutic agent. Also provided is a method to target a therapeutic or prophylactic agent to the surface of cells expressing HER2 comprising conjugating the agent to an anti-HER2 binding molecule disclosed herein, or an anti-HER2 bispecific antibody disclosed herein. Also provided is a method to increase the activity of a therapeutic moiety comprising conjugating the agent to an anti-HER2 binding molecule disclosed herein, or an anti-HER2 bispecific antibody disclosed herein. Also provided is a method to improve the pharmacokinetic properties of a therapeutic or prophylactic agent comprising conjugating the agent to an anti-HER2 binding molecule disclosed herein, or an anti-HER2 bispecific antibody disclosed herein. In some aspects, the therapeutic moiety is a cytotoxin. In some aspects, the cytotoxin is tubulysin. In some aspects, the tubulysin is Compound T32, also referred to herein as "tubulysin 1508" or simply "1508".

Also provided is a method to treat resistance to a HER2-targeting therapeutic agent comprising administering a bispecific HER2 antibody disclosed herein, an anti-HER2 binding molecule disclosed herein, or an ADC disclosed herein to a patient in need thereof. In some aspects, the patient is resistant to a HER2-targeting therapeutic agent comprising trastuzumab and/or the maytansinoid DM1.

BRIEF DESCRIPTION OF THE DRAWINGS/FIGURES

FIG. 1 shows a sequence alignment corresponding to the amino acid sequences of the VL and VH regions of the lead optimized 39S antibody (LO) (SEQ ID NOS 16 and 15, respectively) and the parent AZ 1.39.1 antibody (WT) (SEQ ID NOS 44 and 43, respectively). The location of CDR1, CDR2, and CDR3 is indicated. Amino acid residues which differ with respect to the parent antibody are highlighted. Replaced framework regions in VL region are also highlighted.

FIG. 2. shows that changing the light chain frameworks to germline IGKV2D resulted in a doubling of expression.

FIG. 3. Shows a ribbon representation of the structure of the extracellular domain of HER2 (SEQ ID NO: 52). The binding sites of the 39S, pertuzumab and the domain IV scFv are indicated with arrows. The binding site of 39S includes amino acids within domain II that are distinct from those of pertuzumab.

FIG. 4 shows FACS competition assays using DL-680-labeled 39S (2 µg/ml) and varying concentrations of unlabeled monoclonal antibodies (R347 control, trastuzumab, pertuzumab, AZ 1.39.1, and 39S).

FIG. 5 shows ligand-dependent proliferation assays using different antibody combinations and the cell line MCF-7, demonstrating that 39S synergistically inhibits the growth of the assayed cell lines when administered in combination with trastuzumab and/or pertuzumab. For each experiment, the antibody samples plotted are: R347 control, trastuzumab, pertuzumab plus trastuzumab, 39S, 39S plus trastuzumab, and 39S plus pertuzumab.

FIG. 6 shows ligand-dependent proliferation assays using different antibody combinations and the cell line NCI-N87 demonstrating that 39S synergistically inhibits the growth of the assayed cell lines when administered in combination with trastuzumab and/or pertuzumab. For each experiment, the antibody samples plotted are: R347 control, trastuzumab, pertuzumab plus trastuzumab, 39S, 39S plus trastuzumab, and 39S plus pertuzumab.

FIG. 7 depicts bispecific constructs in which an HER2-binding moiety (a cysteine-stabilized scFv that binds within domain IV) has been genetically fused to different locations within the structure of the 39S antibody. The scFv was fused to the carboxy-terminus of each one of the heavy chains of the 39S antibody (referred to as "Bs3Ab-39SH") (FIG. 7B), fused to the amino-terminus of each one of the heavy chains of the 39S antibody (referred to as "Bs2Ab-39SH") (FIG. 7A), or intercalated between the CH1 and CH2 regions of each one of the heavy chains of the 39S antibody (referred to as "Bs4Ab-39SH") (FIG. 7C).

FIG. 8A shows the sequences of the heavy chains of Bs2 antibodies, indicating the amino acids at Kabat locations 234, 239, 239-ins, 330, 332 and 442 in wild-type heavy chains and heavy chains which may be optimized for ADCC activity or for the production of ADCs that have reduced ADCC activity and/or site specific conjugation. FIG. 8A discloses the consensus sequence as SEQ ID NO: 84.

FIG. 8B shows the sequences of the heavy chains of Bs3 antibodies, indicating the amino acids at Kabat locations 234, 239, 239-ins, 330, 332 and 442 in wild-type heavy chains and heavy chains which may be optimized for ADCC activity or for the production of ADCs that have reduced ADCC activity and/or site specific conjugation. FIG. 8B discloses the consensus sequence as SEQ ID NO: 85.

FIG. 8C shows the sequences of the heavy chains of Bs4 antibodies, indicating the amino acids at Kabat locations 234, 239, 239-ins, 330, 332 and 442 in wild-type heavy chains and heavy chains which may be optimized for ADCC activity or for the production of ADCs that have reduced ADCC activity and/or site specific conjugation. FIG. 8C discloses the consensus sequence as SEQ ID NO: 86.

Figure 9A:
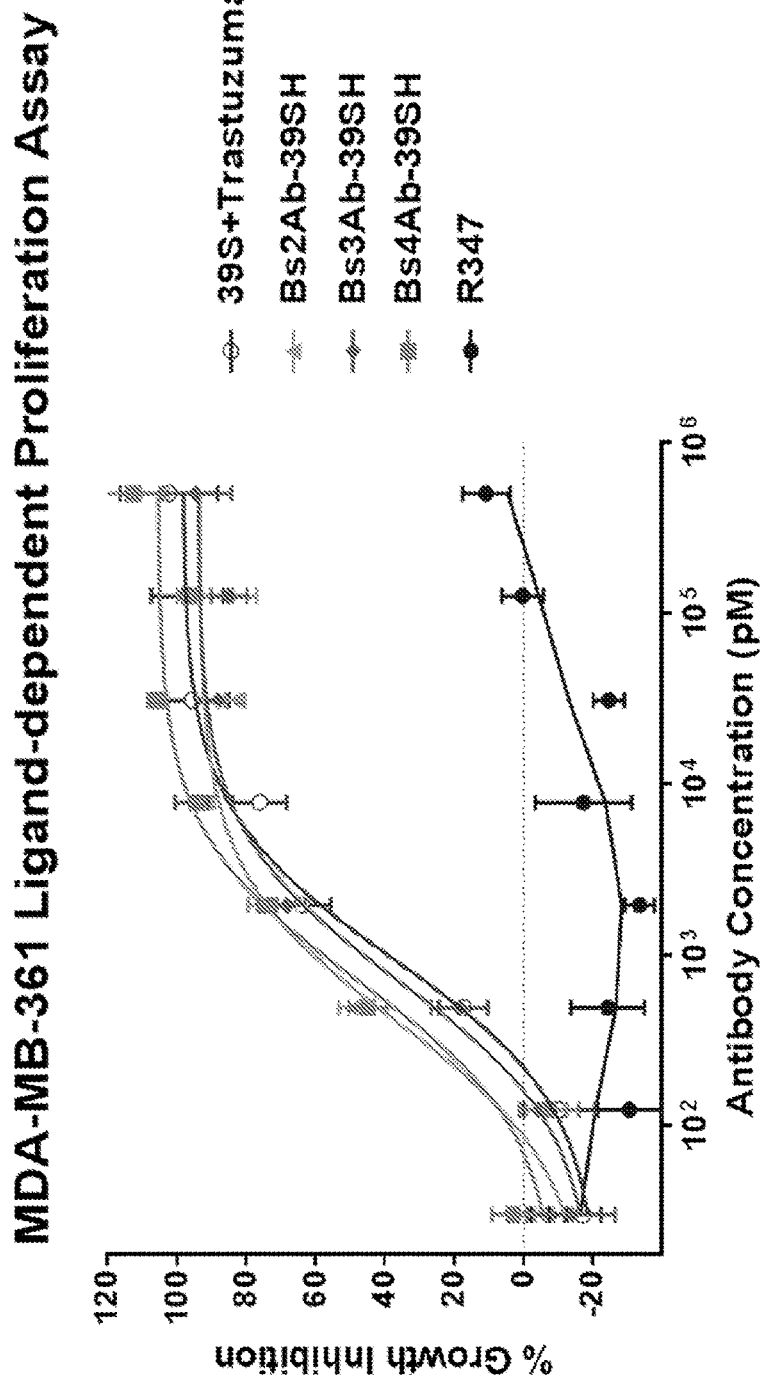

FIG. 9A shows ligand-dependent proliferation assays using different bispecific antibody constructs and MDA-MB-361 cells demonstrating that Bs2Ab-39SH, Bs3Ab-39SH and Bs4Ab-39SH have similar potency in MDA-MB-361 and MCF-7 cells (FIGS. 9A and 9B, respectively), which is also comparable to the activity of parental antibody combination (39S plus trastuzumab). For each experiment, the antibody samples plotted are: R347 control, Bs2Ab-39SH, Bs3Ab-39SH, Bs4Ab-39SH, and 39S plus trastuzumab.

Figure 9B:
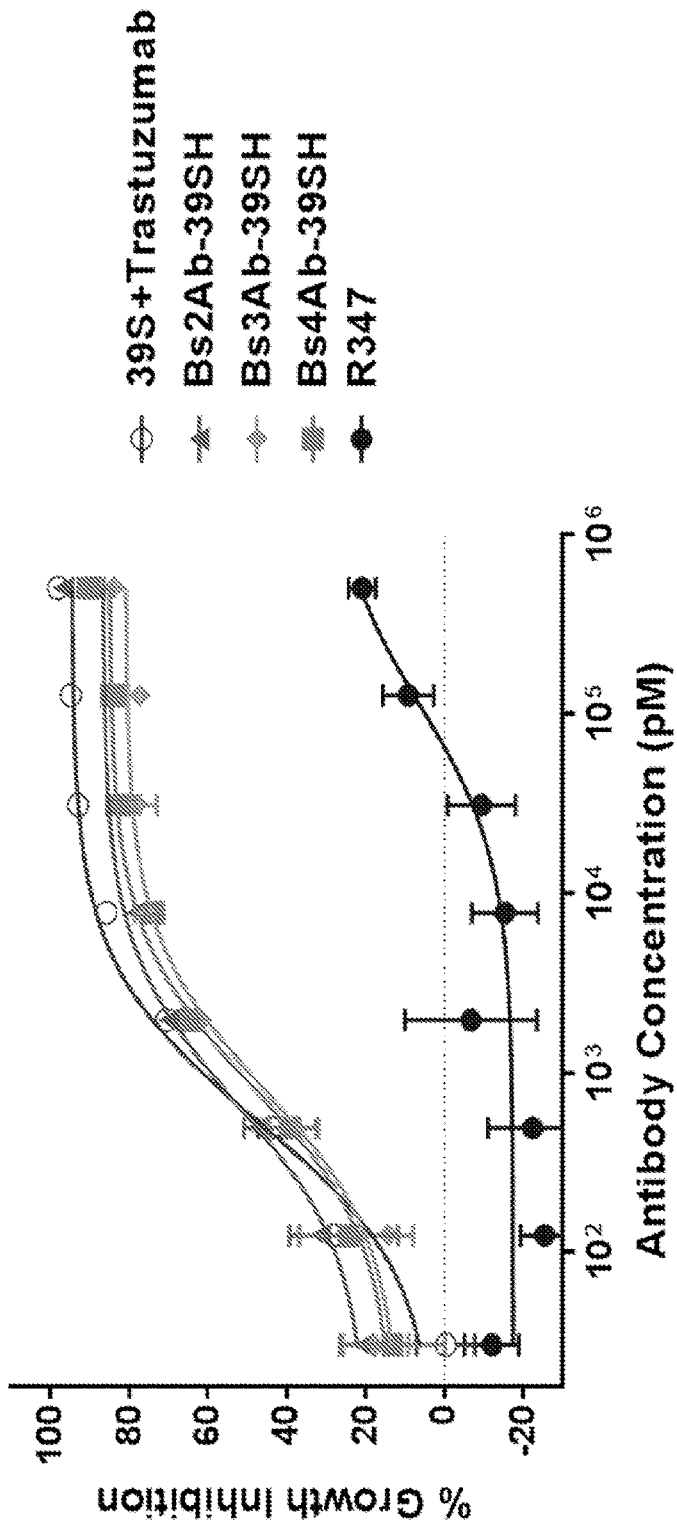

FIG. 9B shows ligand-dependent proliferation assays using different bispecific antibody constructs and MCF-7 cells demonstrating that Bs2Ab-39SH, Bs3Ab-39SH and Bs4Ab-39SH have similar potency in MDA-MB-361 and MCF-7 cells (FIGS. 9A and 9B, respectively), which is also comparable to the activity of parental antibody combination (39S plus trastuzumab). For each experiment, the antibody samples plotted are: R347 control, Bs2Ab-39SH, Bs3Ab-39SH, Bs4Ab-39SH, and 39S plus trastuzumab.

Figure 10:
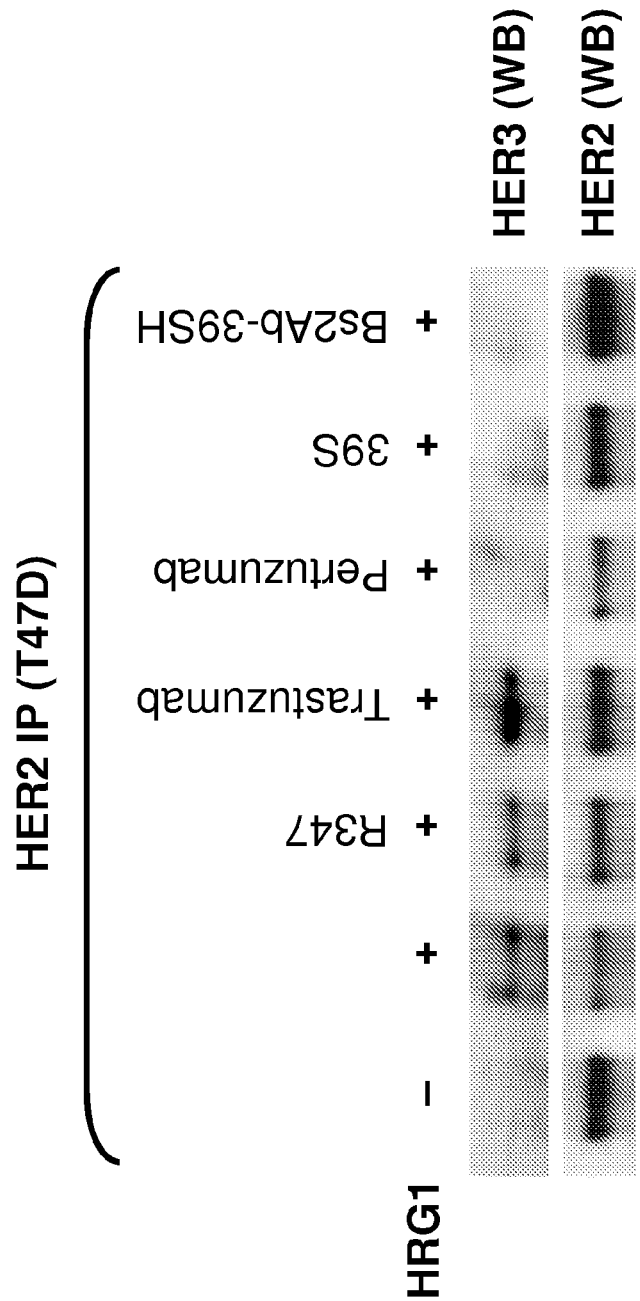

FIG. 10 shows immunoprecipitation (IP) of HER2 from T47D cells followed by Western (WB) detection of HER2 and HER3 to measure the disruption of HER2:HER3 dimerization induced by heregulin (HRG1), in the presence or absence of anti-HER2 antibodies. T47D cells were incubated under control conditions (with no antibody and with no HRG1; with no antibody but with HRG1; or, with control antibody R347 and with HRG1), and after incubation with HRG1 plus (i) trastuzumab, (ii) pertuzumab, (iii) 39S antibody, or (iv) the Bs2Ab-39SH bispecific construct.

Figure 11:
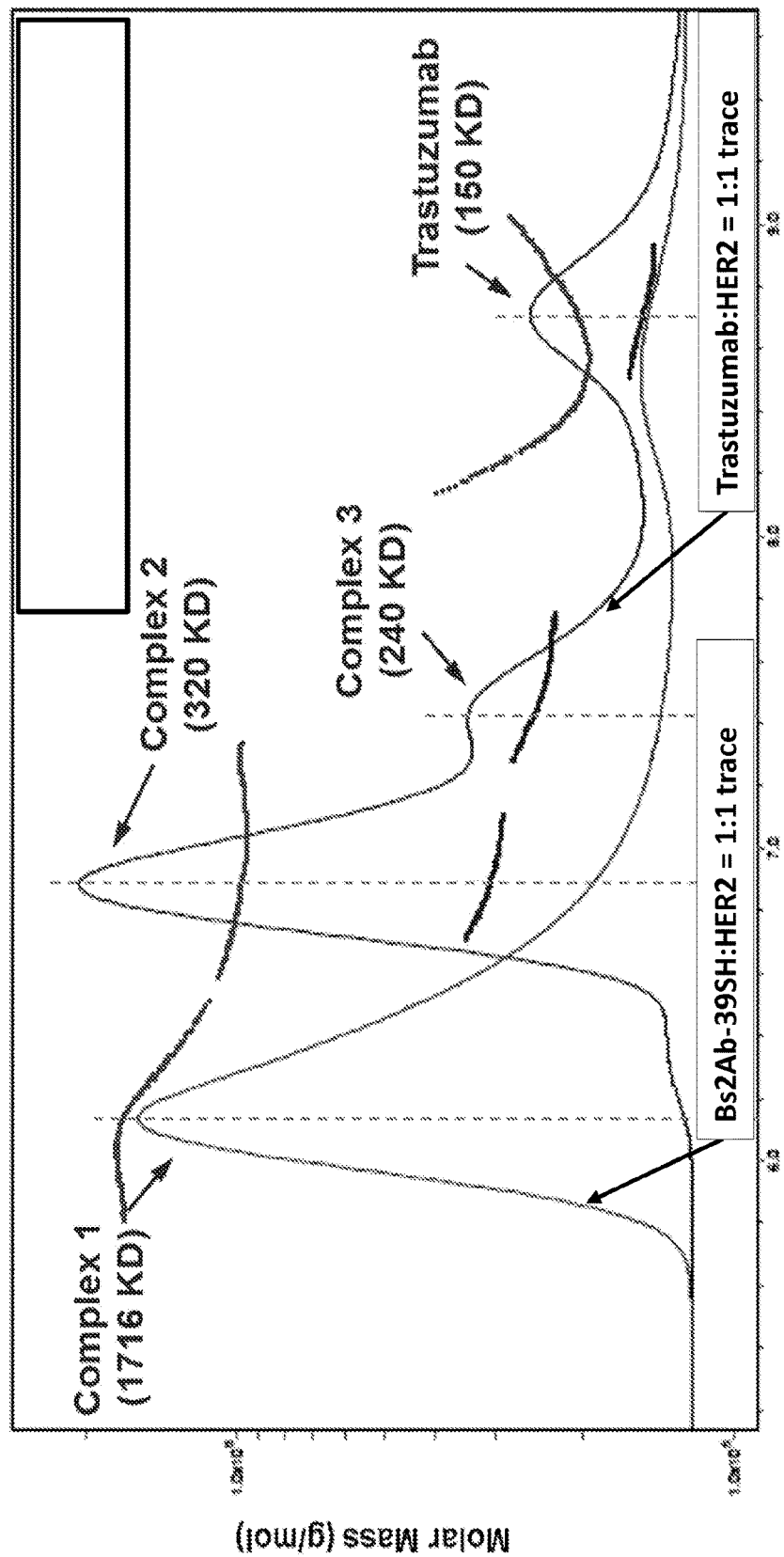

FIG. 11 shows the representative HPLC size-exclusion chromatography profiles showing the size separation of immune complexes derived from antibody:HER2 molar ratio of 1:1. Bs2Ab-39SH can cross-link many HER2 molecules to form complexes as large as 1716 kDa in size, while trastuzumab can only bind to two HER2 molecules in maximal to form a 320 kDa complex.

Figure 6:
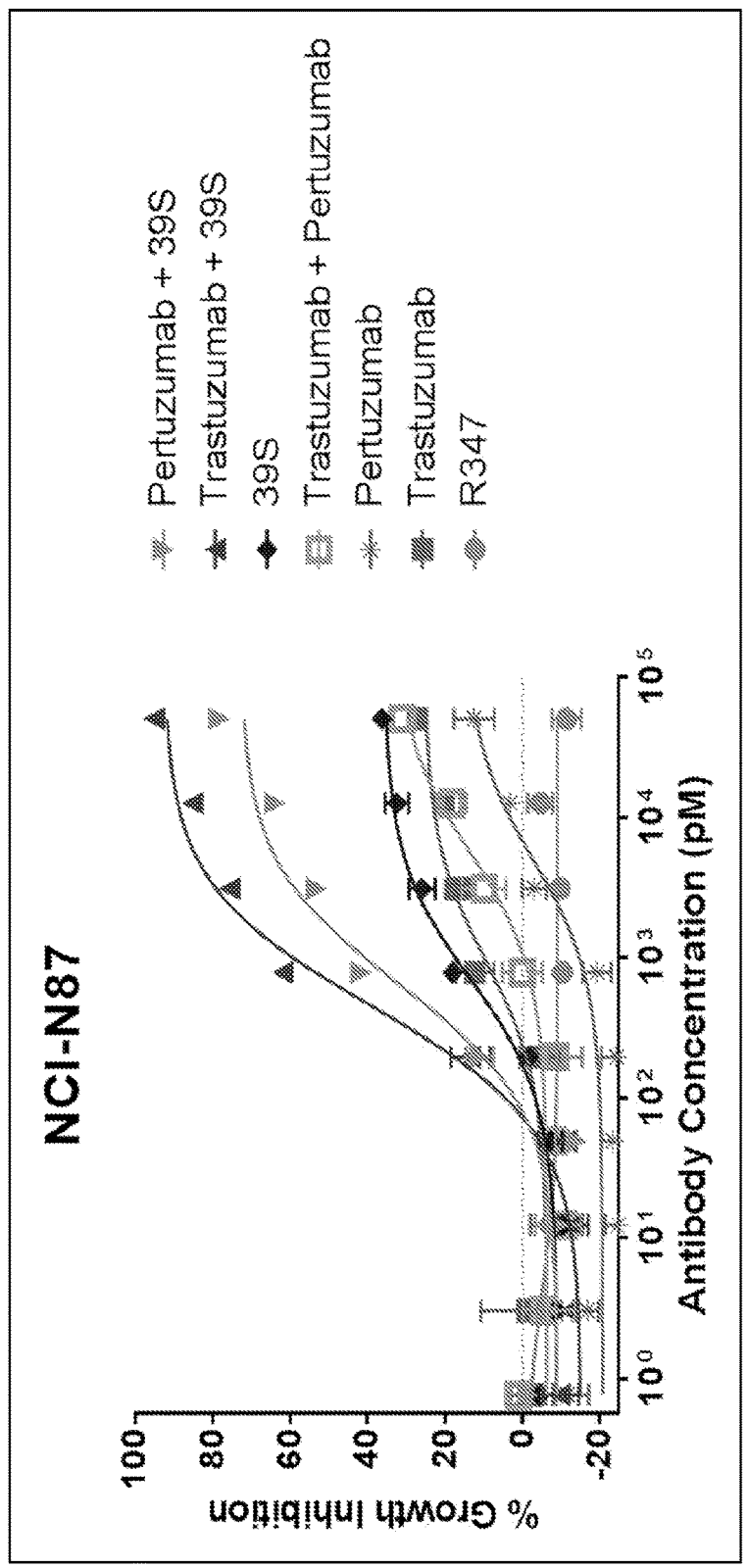
Figure 12:
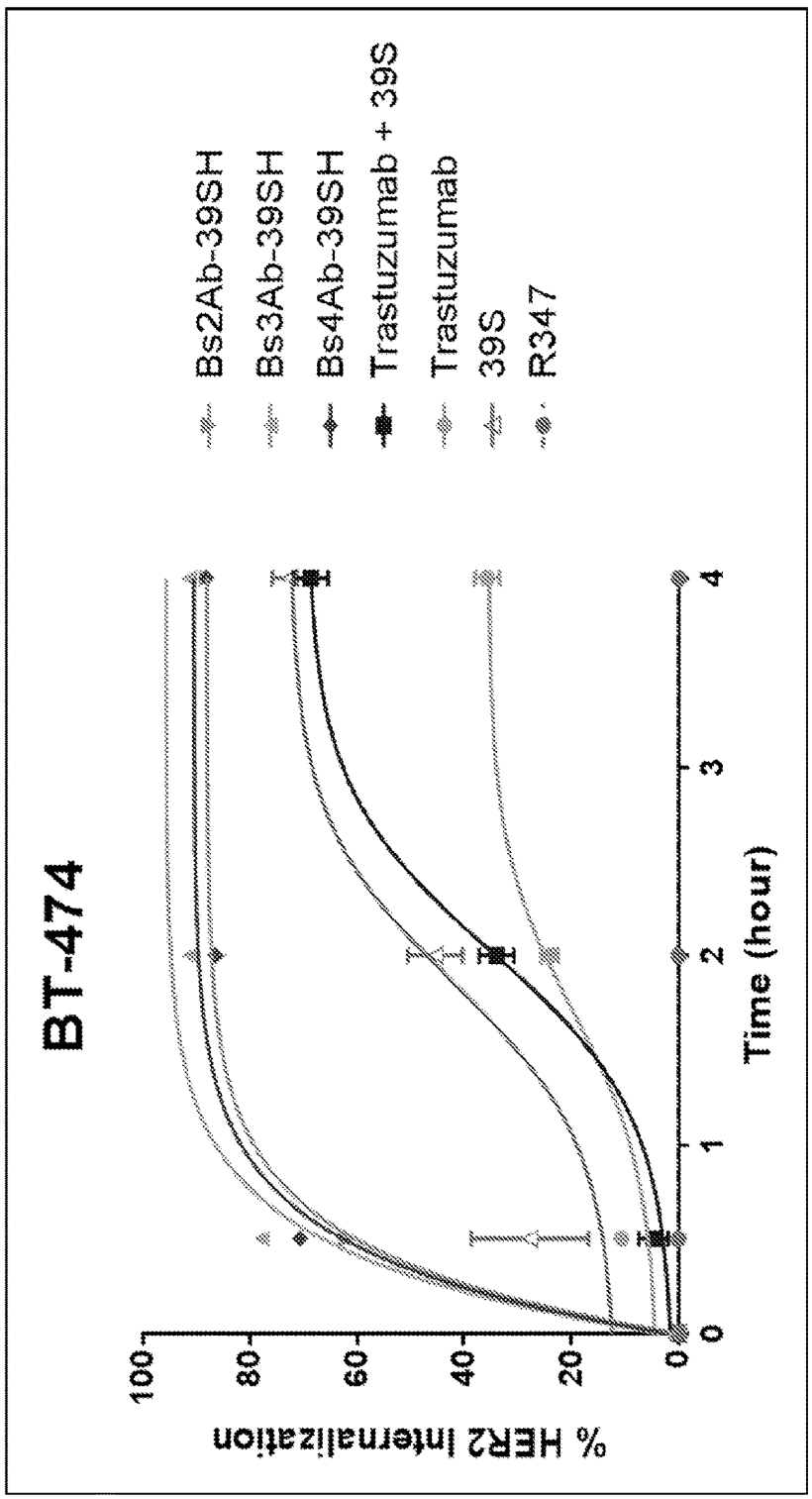

FIG. 12 presents FACS-based receptor internalization assays showing that the three formats of HER2 bispecific antibodies presented in FIG. 6 internalized rapidly in the cell line BT-474. Plotted on the graph are: R347 control, trastuzumab, 39S, trastuzumab plus 39S, Bs2Ab-39SH, Bs3Ab-39SH, and BsAb-39SH. Similar results were seen in MCF-7, T47D, RT-112, MDA-MB-361, and NCI-N87 cell lines (data not shown).

Figure 13:
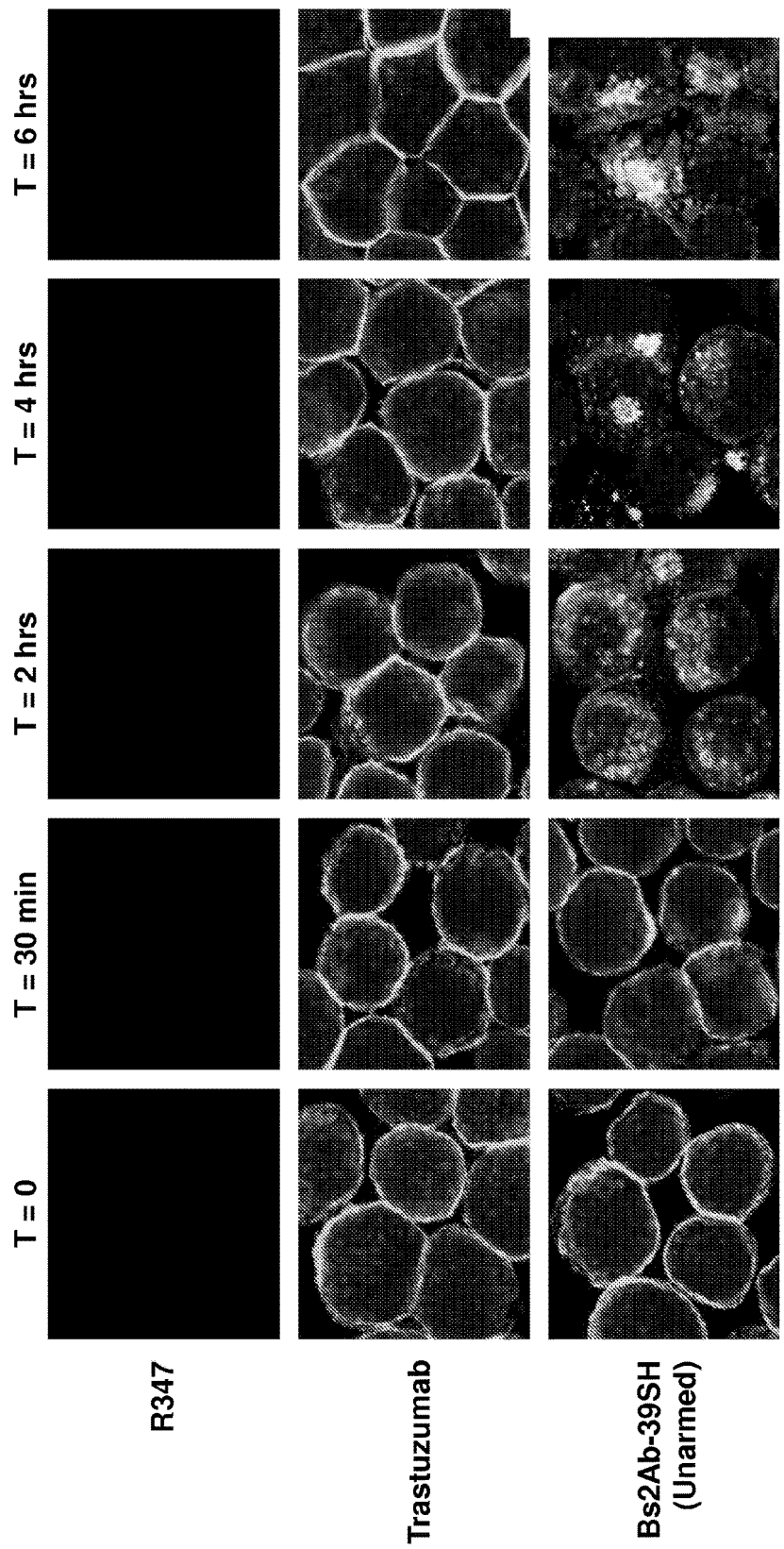

FIG. 13 shows the kinetics of Bs2Ab-39SH internalization by BT-474 cells. Microscopy images were taken at 0, 30, 60, 120, and 360 minutes after addition of the Bs2Ab-39SH construct, trastuzumab or the R347 control. The cytoplasm of the BT-474 cells was stained with CELL-TRACKER™ Green (Life Technologies Corp.), and the antibodies were labeled with ALEXA FLUOR® 647 (Life Technologies Corp.).

Figure 14:
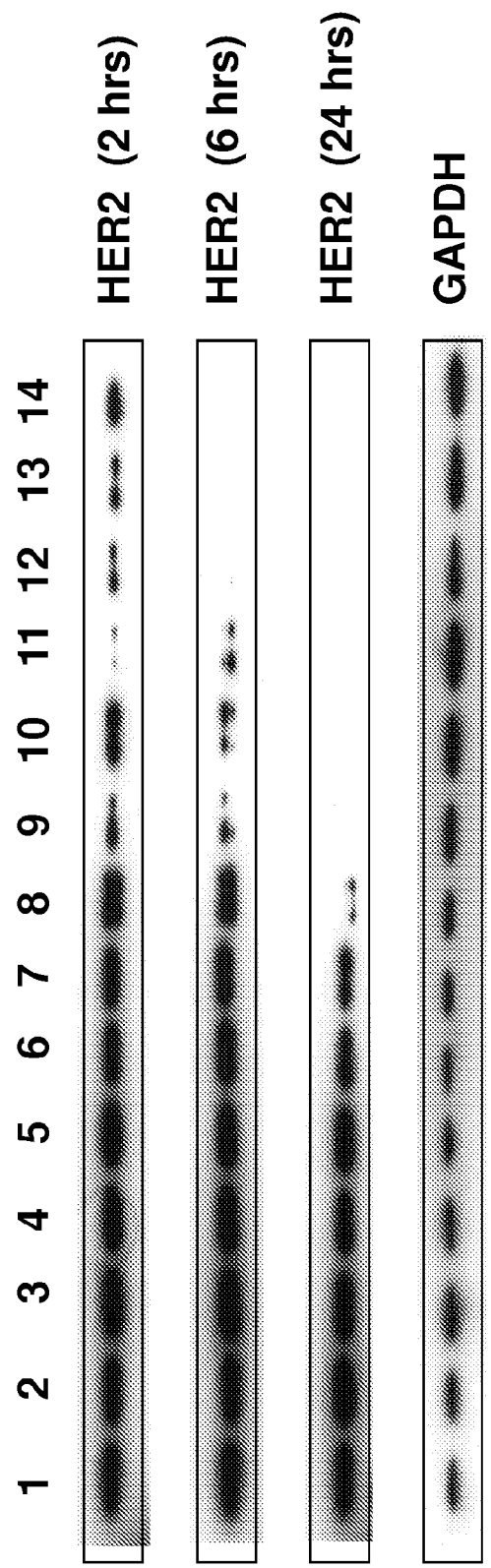

FIG. 14 is a Western immunoblot showing the degree of degradation of HER2, or lack thereof, 2 hours, 6 hours, and 24 hours after incubation of BT-474 cells with antibody samples. GAPDH was used as control. The tested antibody samples were: (lane 1) R347 control antibody, (lane 2) trastuzumab, (lane 3) pertuzumab, (lane 4) trastuzumab and pertuzumab, (lane 5) 39S, (lane 6) trastuzumab and 39S, (lane 7) pertuzumab and 39S, (lane 8) trastuzumab, pertuzumab and 39S, (lane 9) Bs2Ab-39SH, (lane 10) Bs2Ab-39SH_aFuc (homogenously afucosylated Bs2Ab-39SH), (lane 11) Bs3Ab-39SH, (lane 12) Bs3Ab-39SH_aFuc (homogenously afucosylated Bs3Ab-39SH_aFuc), (lane 13) Bs4Ab-39SH, and (lane 14) Bs4Ab-39SH_aFuc (homogenously afucosylated Bs4Ab-39SH).

Figure 15:
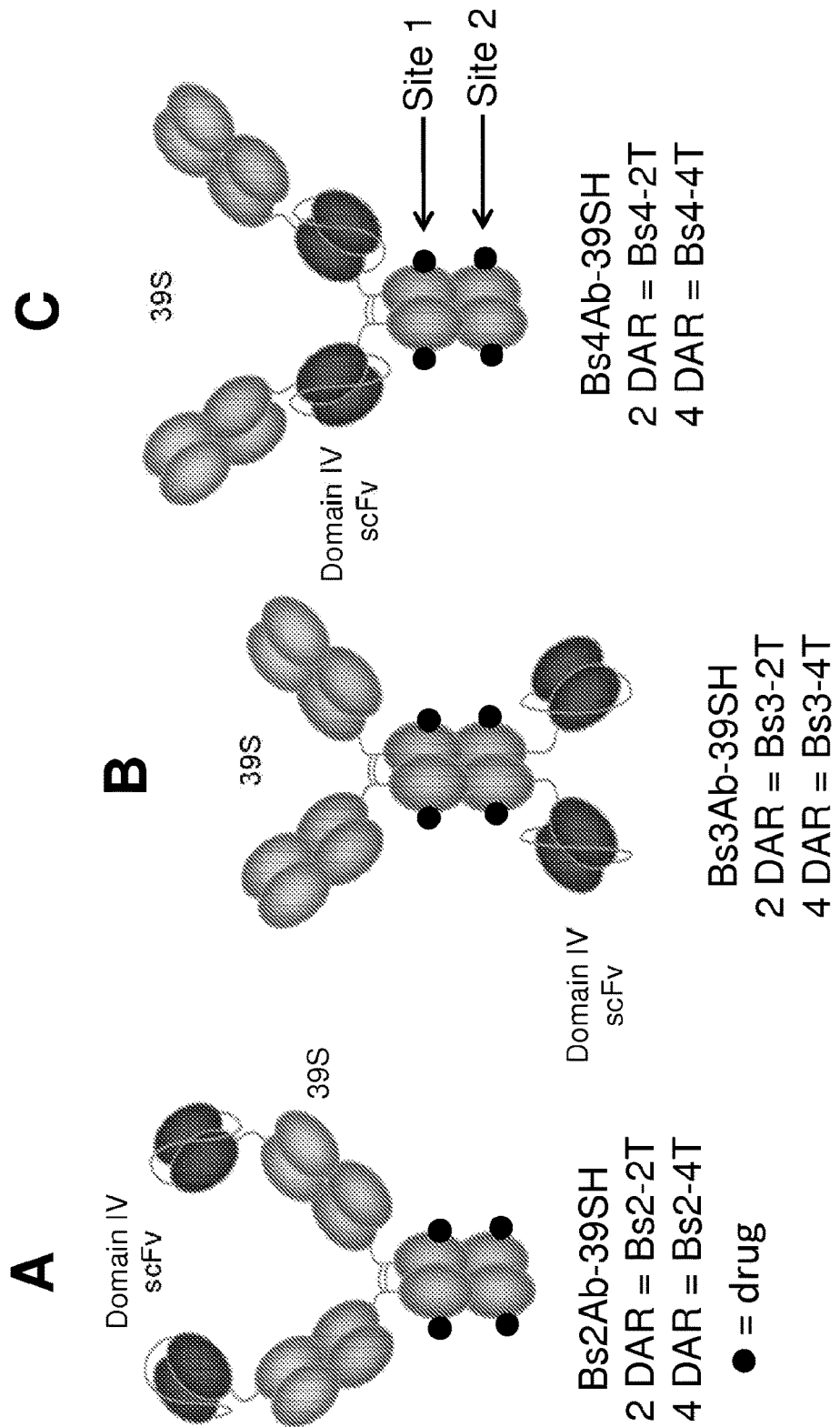

FIG. 15 is a detailed cartoon representations of exemplary ADCs derived from the Bs2Ab-39SH (panel A), the Bs3Ab-39SH (panel B) and the Bs4Ab-39SH (panel C) anti-HER2 constructs. Two potential engineered cytotoxic agent conjugation sites in the CH2 and CH3 domains of the ADC constructs are indicated by circles. Where the desired drug-to-antibody ratio (DAR) is 2 to 1 either site 1 or site 2 may be used. Where a DAR of 4 is desirable both sites 1 and 2 are utilized. Alternative and/or additional sites may be engineered. The bispecific anti-HER2 ADCs are abbreviated herein as "Bs2Ab-2T", "Bs3Ab-2T" and "Bs4Ab-2T" (or simply as "Bs2-2T", "Bs3-2T" and "Bs4-2T") for the ADCs having a DAR of ~2 and as "Bs2Ab-4T", "Bs3Ab-4T" and "Bs4Ab-4T" (or simply as "Bs2-4T", "Bs3-4T" and "Bs4-4T") for the ADCs having a DAR of ~4. The bispecific constructs lacking any cytotoxic agent are referred by the designations provided in FIG. 7 and may be identified as "unarmed." As provided herein (see, e.g., FIG. 8) the engineered conjugate sites may be selected to reduce or ablate ADCC functions. Alternatively or additionally Fc portion of the antibody may further comprise additional mutations which reduce or ablate ADCC activity. Alternatively, an ADC may be generated using a classic conjugation method such as conjugating to antibodies through the often-numerous lysine residues or native cysteine residues of an antibody, generating a heterogeneous antibody-drug conjugate mixture.

Figure 16A:
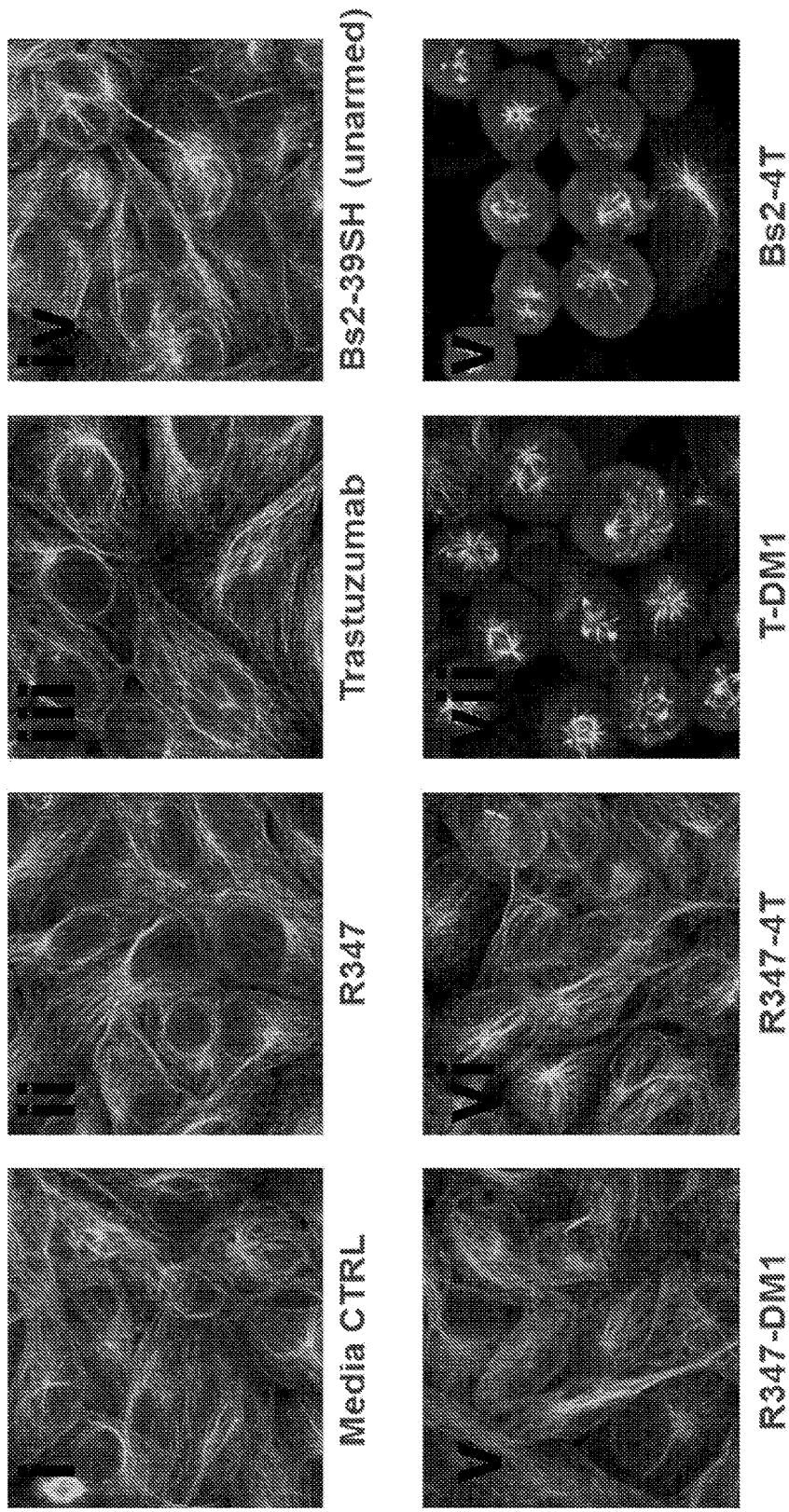

FIG. 16A presents immunofluorescence images of SKOV-3 cells treated with 1 µg/ml of the antibody indicated under each image, showing the disruption of the intracellular microtubule network or lack thereof. Microtubule staining is shown. The following samples were tested: media control without any antibody (image i), R347 control antibody (image ii), trastuzumab (image iii), Bs2Ab-39SH (image iv), R347-DM1 (R347 control antibody conjugated to the cytotoxic agent maytansinoid DM1) (image v), R347-4T (R347 control antibody conjugated to 4 molecules of the cytotoxic agent tubulysin) (image vi), T-DM1 (trastuzumab conjugated to maytansinoid DM1) (image vii), and Bs2-4T (Bs2Ab-39SH conjugated to 4 molecules of the cytotoxic agent tubulysin) (image viii).

Figure 16B:
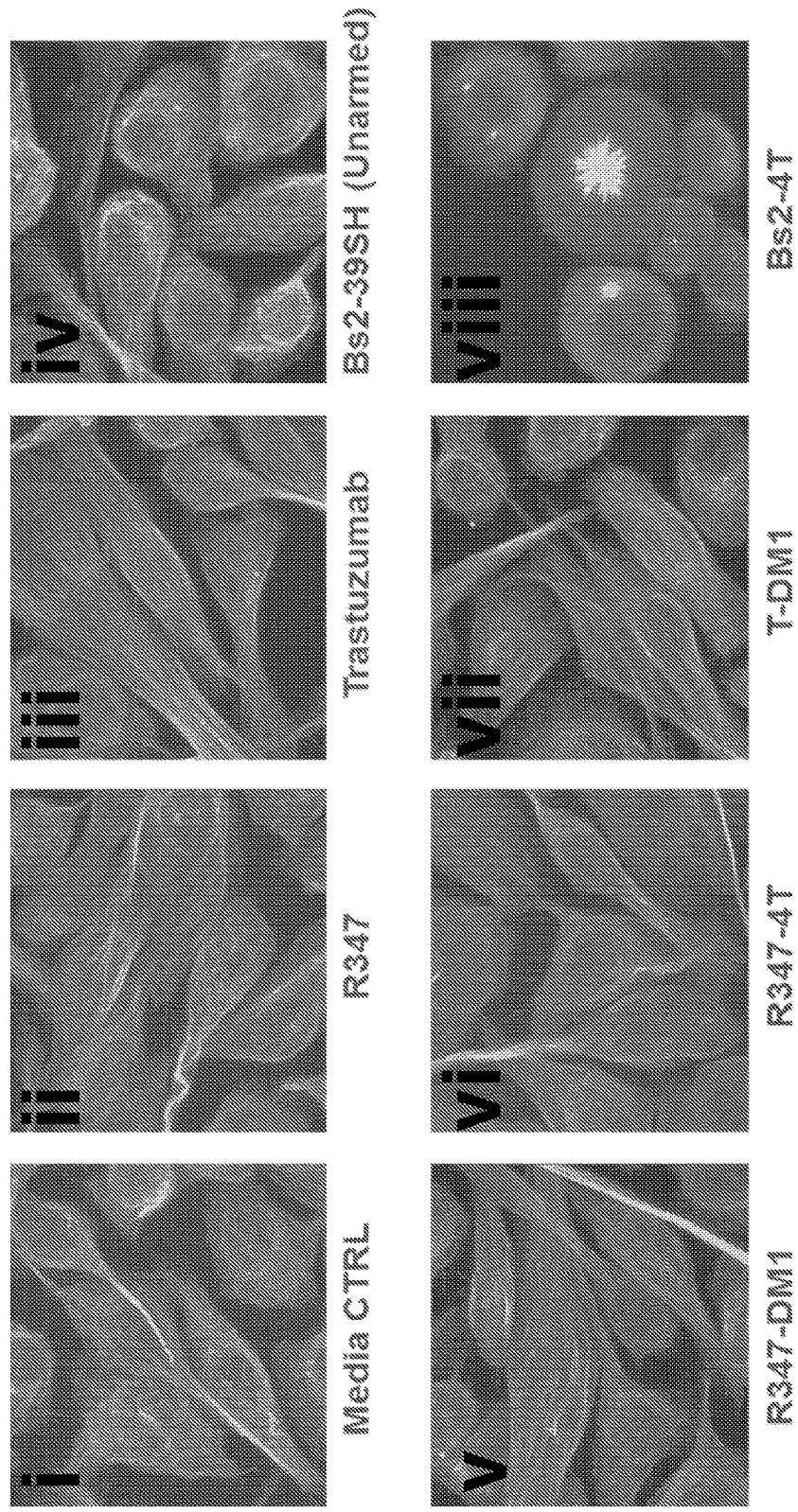

FIG. 16B presents immunofluorescence images of JIMT-1 cells treated with 1 µg/ml of the antibody indicated under each image, showing the disruption of the intracellular microtubule network or lack thereof. Microtubule staining is shown. The following samples were tested: media control without any antibody (image i), R347 control antibody (image ii), trastuzumab (image iii), Bs2Ab-39SH (image iv), R347-DM1 (R347 control antibody conjugated to the cytotoxic agent maytansinoid DM1) (image v), R347-4T (R347 control antibody conjugated to 4 molecules of the cytotoxic agent tubulysin) (image vi), T-DM1 (trastuzumab conjugated to maytansinoid DM1) (image vii), and Bs2-4T (Bs2Ab-39SH conjugated to 4 molecules of the cytotoxic agent tubulysin) (image viii).

Figure 16C:
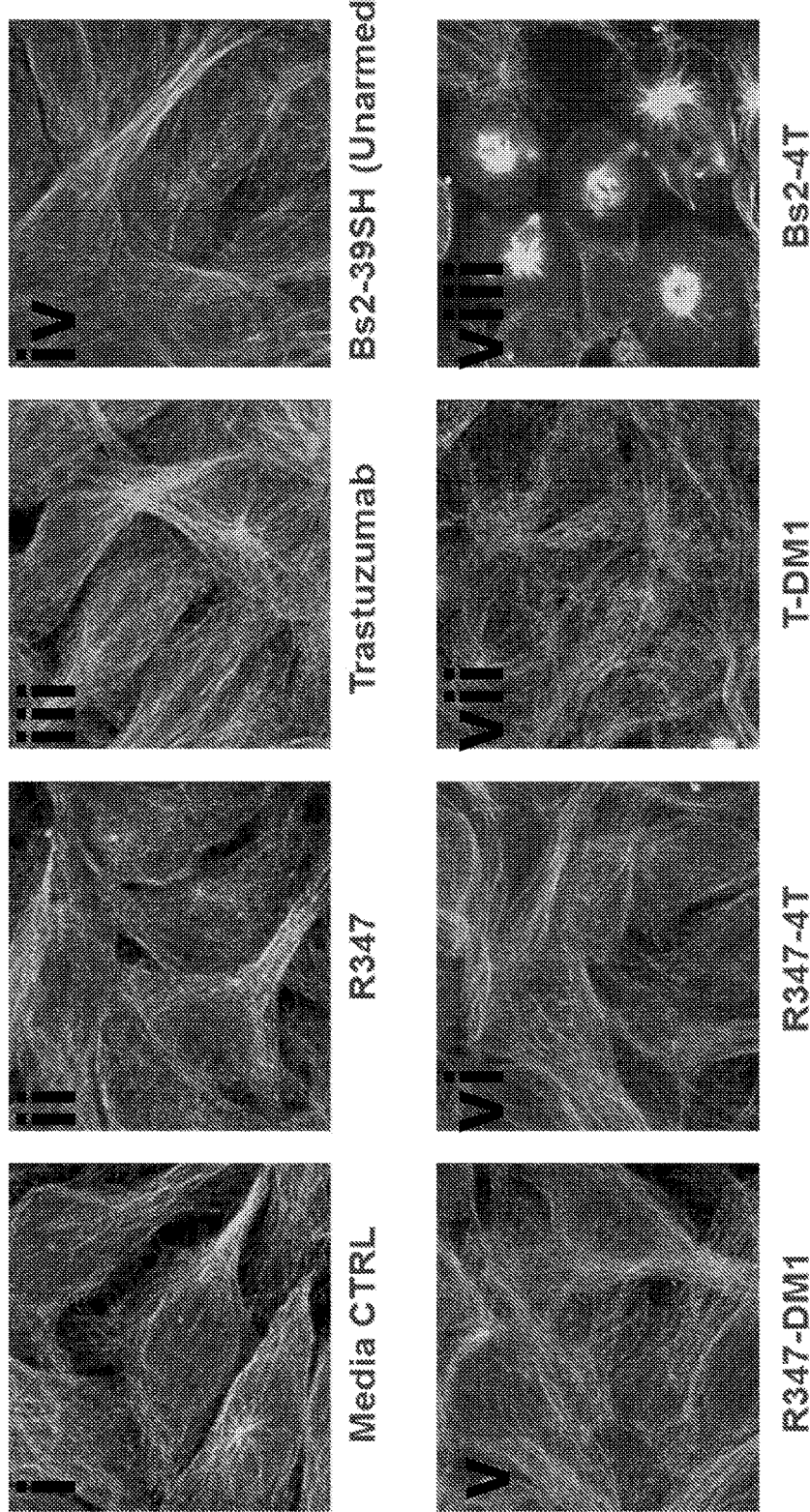

FIG. 16C presents immunofluorescence images of RT-112 cells treated with 1 µg/ml of the antibody indicated under each image, showing the disruption of the intracellular microtubule network or lack thereof. Microtubule staining is shown. The following samples were tested: media control without any antibody (image i), R347 control antibody (image ii), trastuzumab (image iii), Bs2Ab-39SH (image iv), R347-DM1 (R347 control antibody conjugated to the cytotoxic agent maytansinoid DM1) (image v), R347-4T (R347 control antibody conjugated to 4 molecules of the cytotoxic agent tubulysin) (image vi), T-DM1 (trastuzumab conjugated to maytansinoid DM1) (image vii), and Bs2-4T (Bs2Ab-39SH conjugated to 4 molecules of the cytotoxic agent tubulysin) (image viii).

Figure 17A:
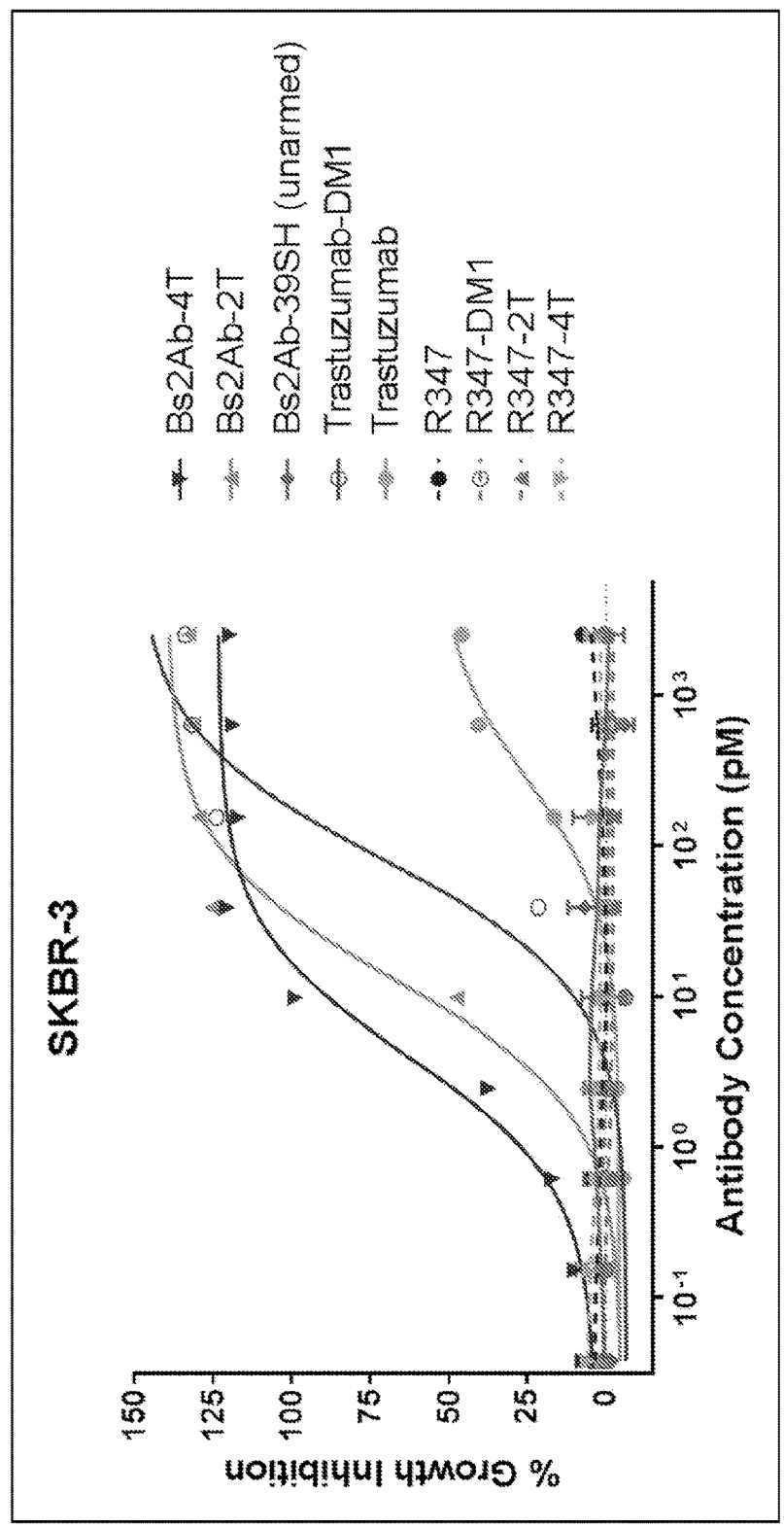

FIG. 17A shows the cytotoxic activity of the Bs2Ab format with a DAR of 2 or 4 relative to the T-DM1, non conjugated (unarmed) Bs2Ab-39SH and trastuzumab on the SKBR-3 human breast cancer cell line. Also shown are the curves for R347 (R347 control antibody), R347 conjugated with 2 or 4 tubulysins (R347-2T and R3474T respectively) R347 conjugated to DM1. Both Bs2-2T and Bs2-4T are more potent than T-DM1.

Figure 17B:
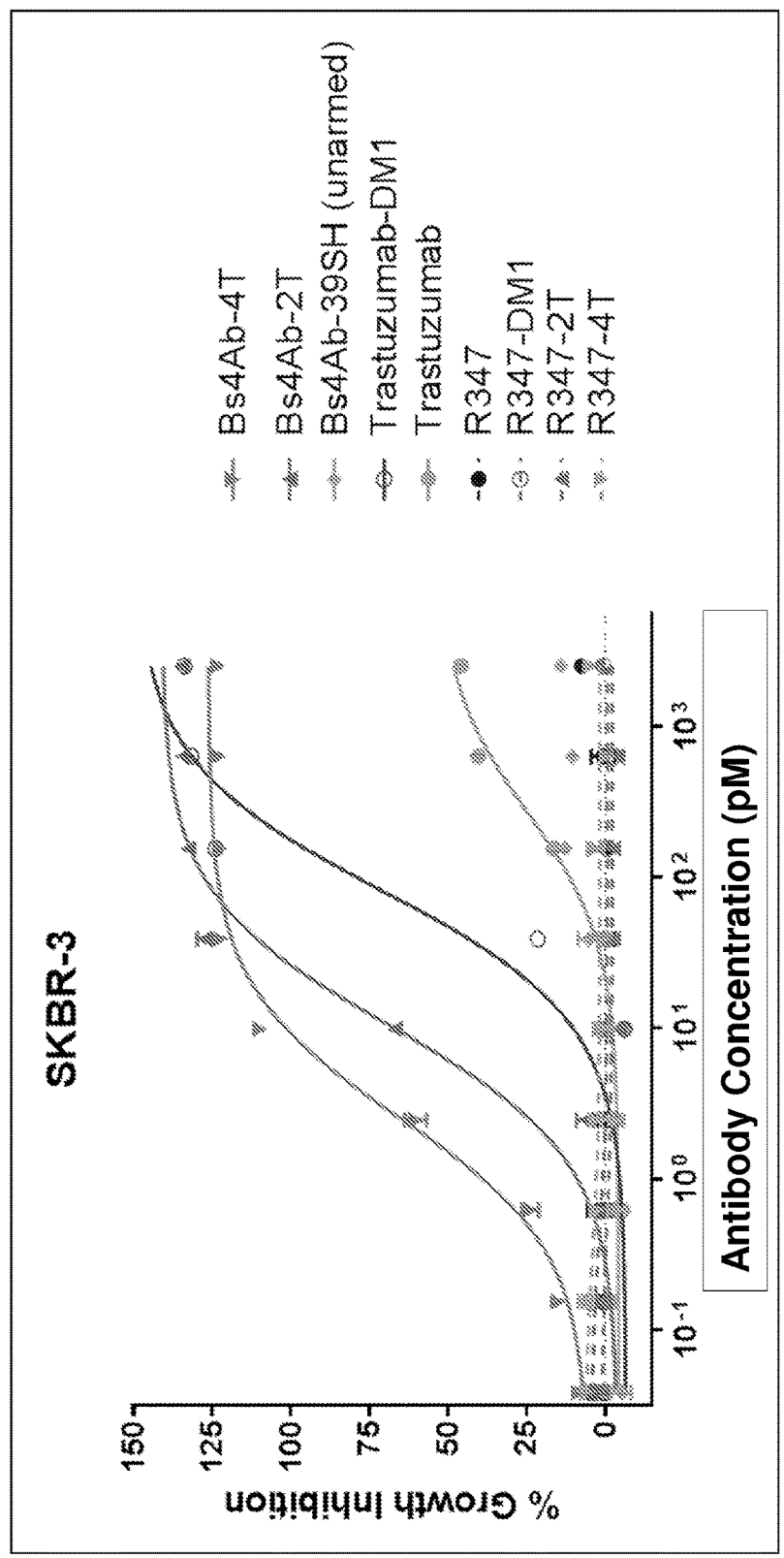

FIG. 17B shows the cytotoxic activity the Bs4Ab format with a DAR of 2 or 4 (Panel B) relative to the T-DM1, non conjugated (unarmed) Bs4Ab-39SH and trastuzumab on the SKBR-3 human breast cancer cell line. Also shown are the curves for R347 (R347 control antibody), R347 conjugated with 2 or 4 tubulysins (R347-2T and R3474T respectively) R347 conjugated to DM1. Both Bs4-2T and Bs4-4T are more potent than T-DM1.

Figure 18A:
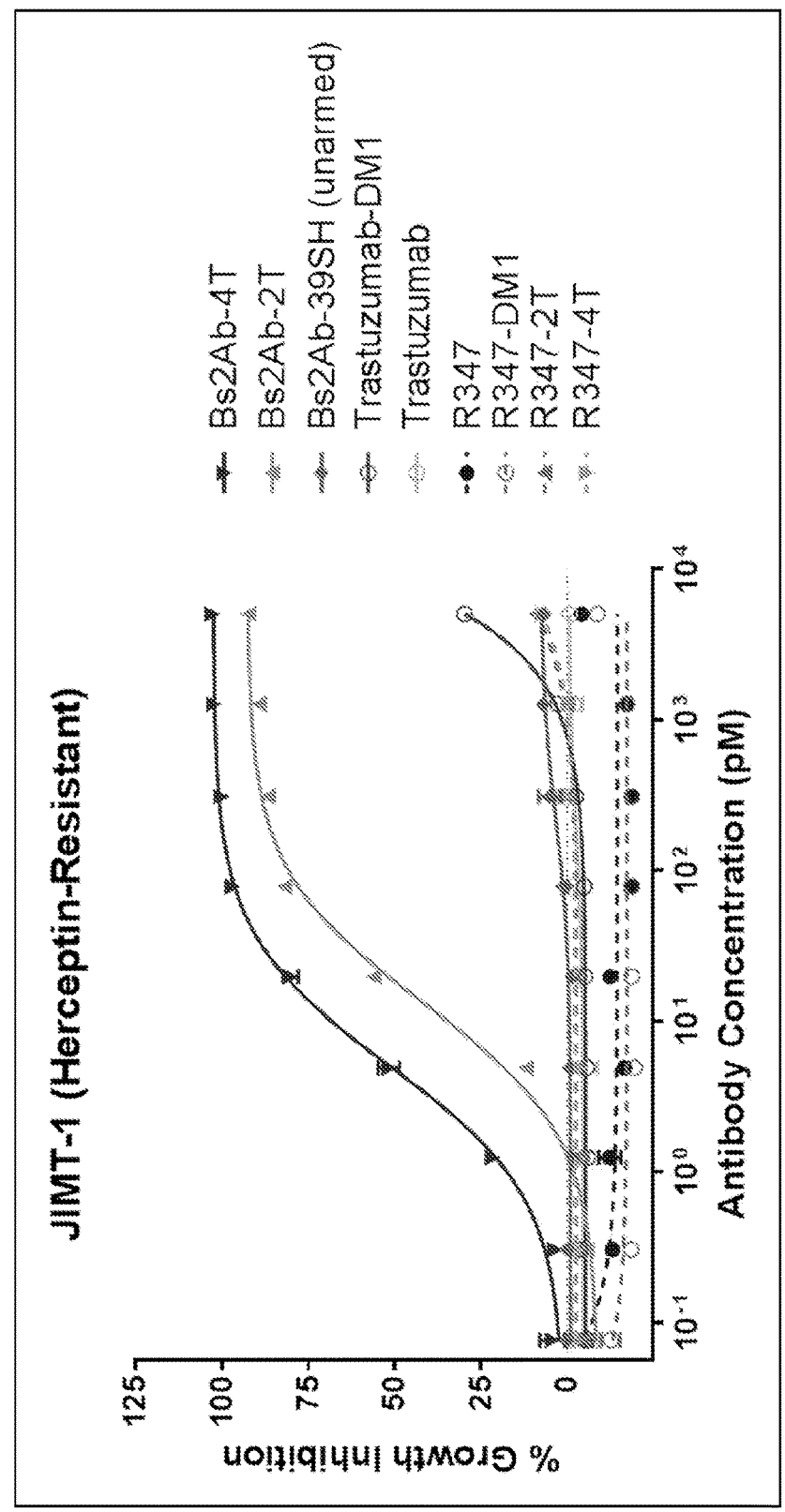

FIG. 18A shows the cytotoxic activity of the Bs2Ab format with a DAR of 2 or 4 relative to the T-DM1, non conjugated (unarmed) Bs2Ab-39SH and trastuzumab on the JIMT-1 human breast cancer cell line. Also shown are the curves for R347 (R347 control antibody), R347 conjugated with 2 or 4 tubulysins (R347-2T and R3474T respectively) R347 conjugated to DM1. Both Bs2-2T and Bs2-4T are very potent in killing JIMT-1 cells, while T-DM1 shows no activity.

Figure 18B:
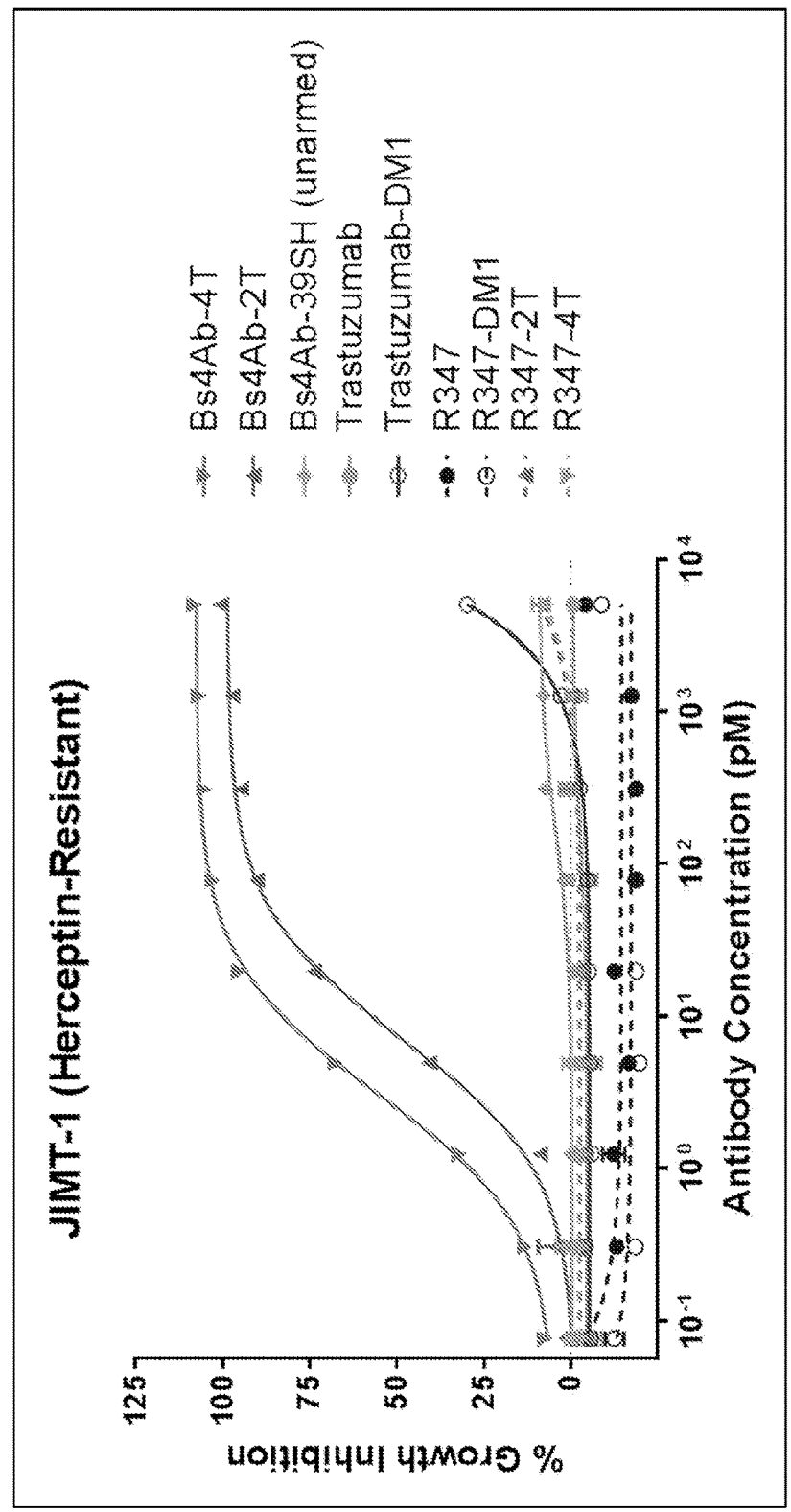

FIG. 18B shows the cytotoxic activity of the Bs4Ab format with a DAR of 2 or 4 (Panel B) relative to the T-DM1, non conjugated (unarmed) Bs4Ab-39SH and trastuzumab on the JIMT-1 human breast cancer cell line. Also shown are the curves for R347 (R347 control antibody), R347 conjugated with 2 or 4 tubulysins (R347-2T and R3474T respectively) R347 conjugated to DM1. Both Bs4-2T and Bs4-4T are very potent in killing JIMT-1 cells, while T-DM1 shows no activity.

Figure 19A:
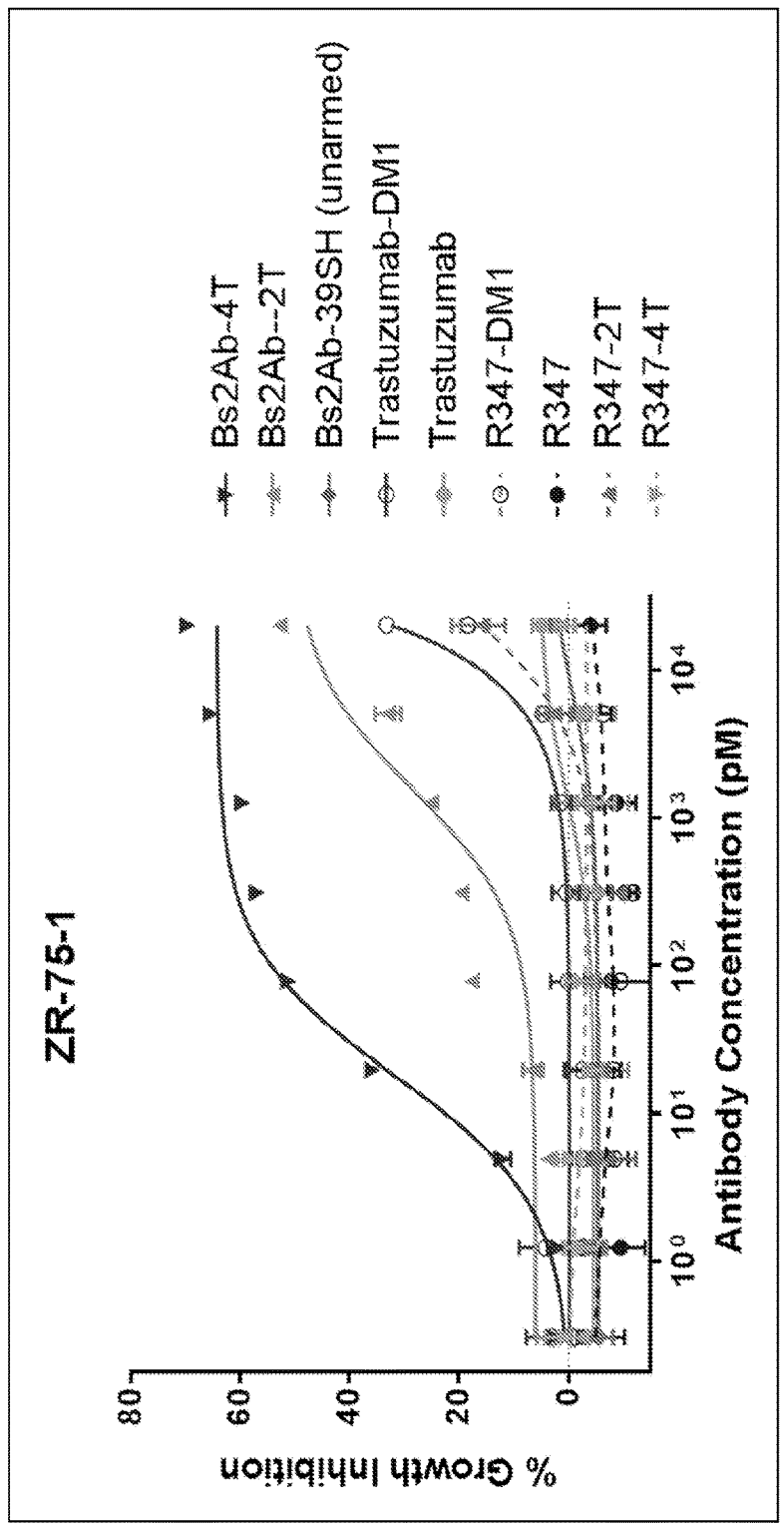

FIG. 19A shows the cytotoxic activity of the Bs2Ab format with a DAR of 2 or 4 relative to the T-DM1, non conjugated (unarmed) Bs2Ab-39SH and trastuzumab on the ZR-75-1 human breast cancer cell line. Also shown are the curves for R347 (R347 control antibody), R347 conjugated with 2 or 4 tubulysins (R347-2T and R3474T respectively) R347 conjugated to DM1. Bs2-4T is the most active in killing ZR-75-1 cells, while Bs2-2T has a lower level of activity and T-DM1 shows no or limited cytotoxic activity.

Figure 19B:
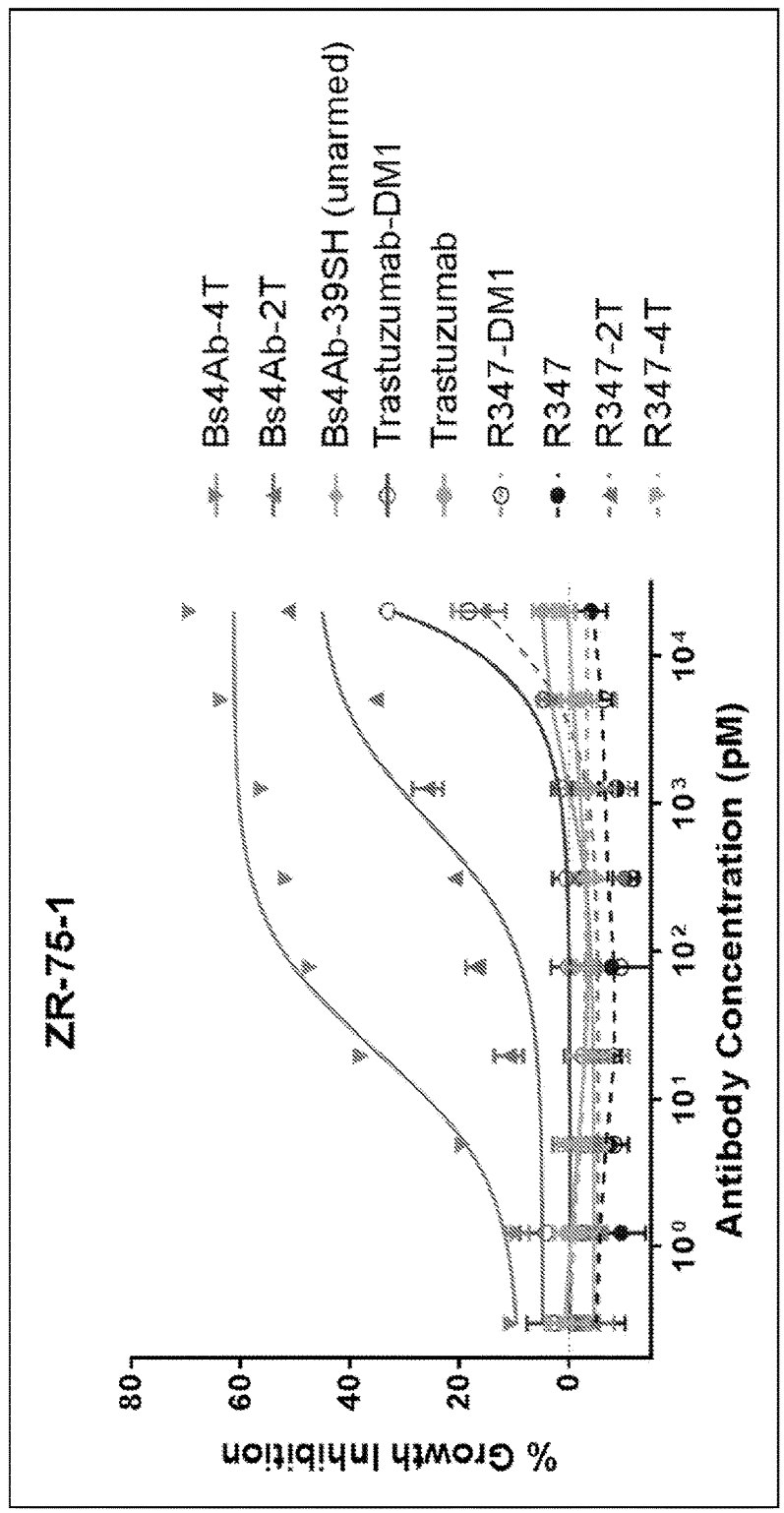

FIG. 19B shows the cytotoxic activity of the Bs4Ab format with a DAR of 2 or 4 (Panel B) relative to the T-DM1, non conjugated (unarmed) Bs4Ab-39SH and trastuzumab on the ZR-75-1 human breast cancer cell line. Also shown are the curves for R347 (R347 control antibody), R347 conjugated with 2 or 4 tubulysins (R347-2T and R3474T respectively) R347 conjugated to DM1. Bs4-4T is the most active in killing ZR-75-1 cells, while Bs4-2T has a lower level of activity and T-DM1 shows no or limited cytotoxic activity.

Figure 20:
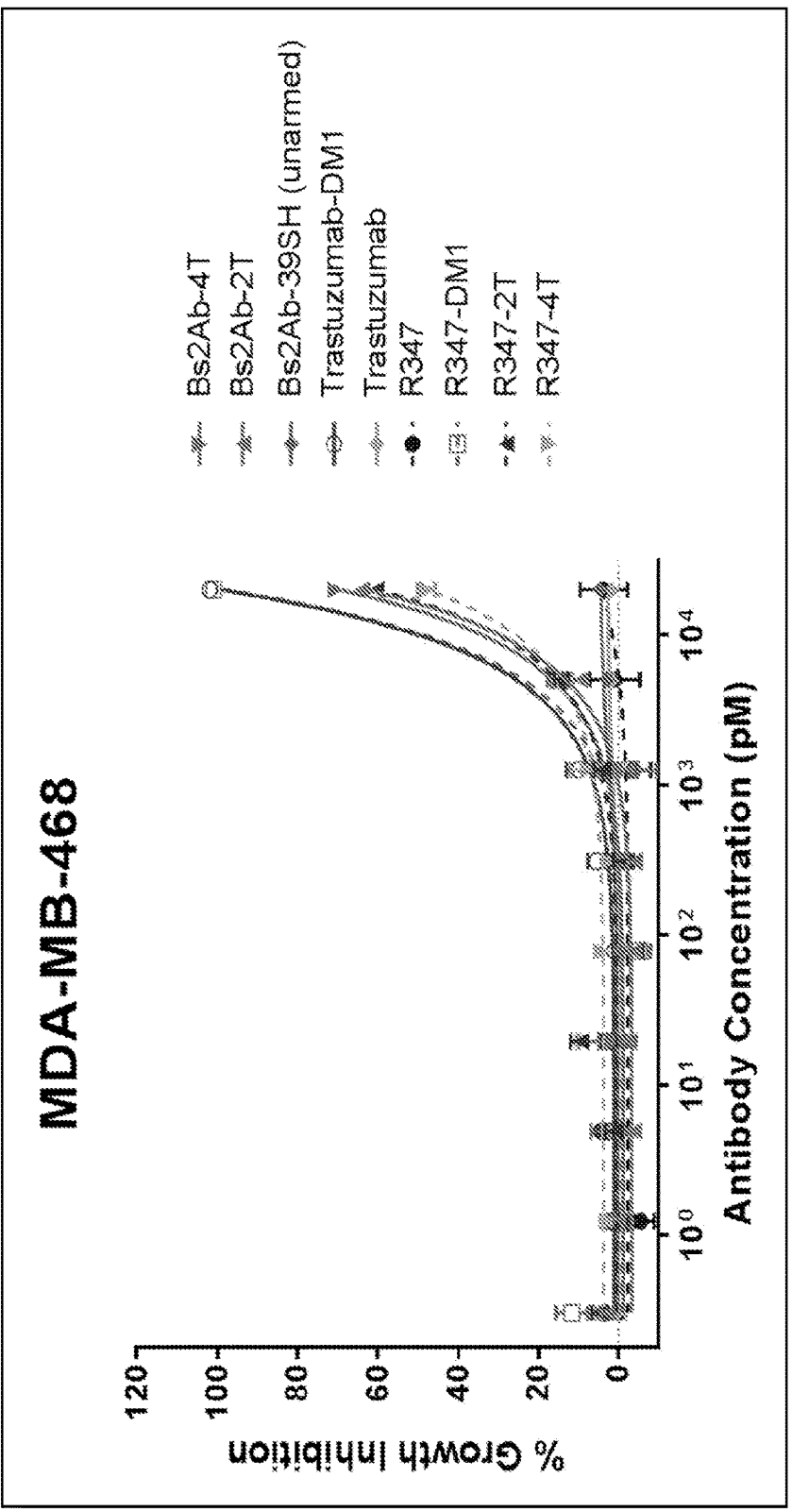

FIG. 20 shows the cytotoxic activity of the Bs2Ab format with a DAR of 2 or 4 (Panel A) relative to the T-DM1, non conjugated (unarmed) Bs2Ab-39SH and trastuzumab on the MDA-MB-468 human breast cancer cell line. Also shown are the curves for R347 (R347 control antibody), R347 conjugated with 2 or 4 tubulysins (R347-2T and R3474T respectively) R347 conjugated to DM1. Data indicate that neither Bs2-2T nor Bs2-4T is active in MDA-MB-468 cells, indicating that the cytotoxic activity of Bs2-2T and Bs2-4T is target (HER2)-dependent. Similar results were observed with Bs4-2T and Bs4-4T (data not shown)

Figure 21A:
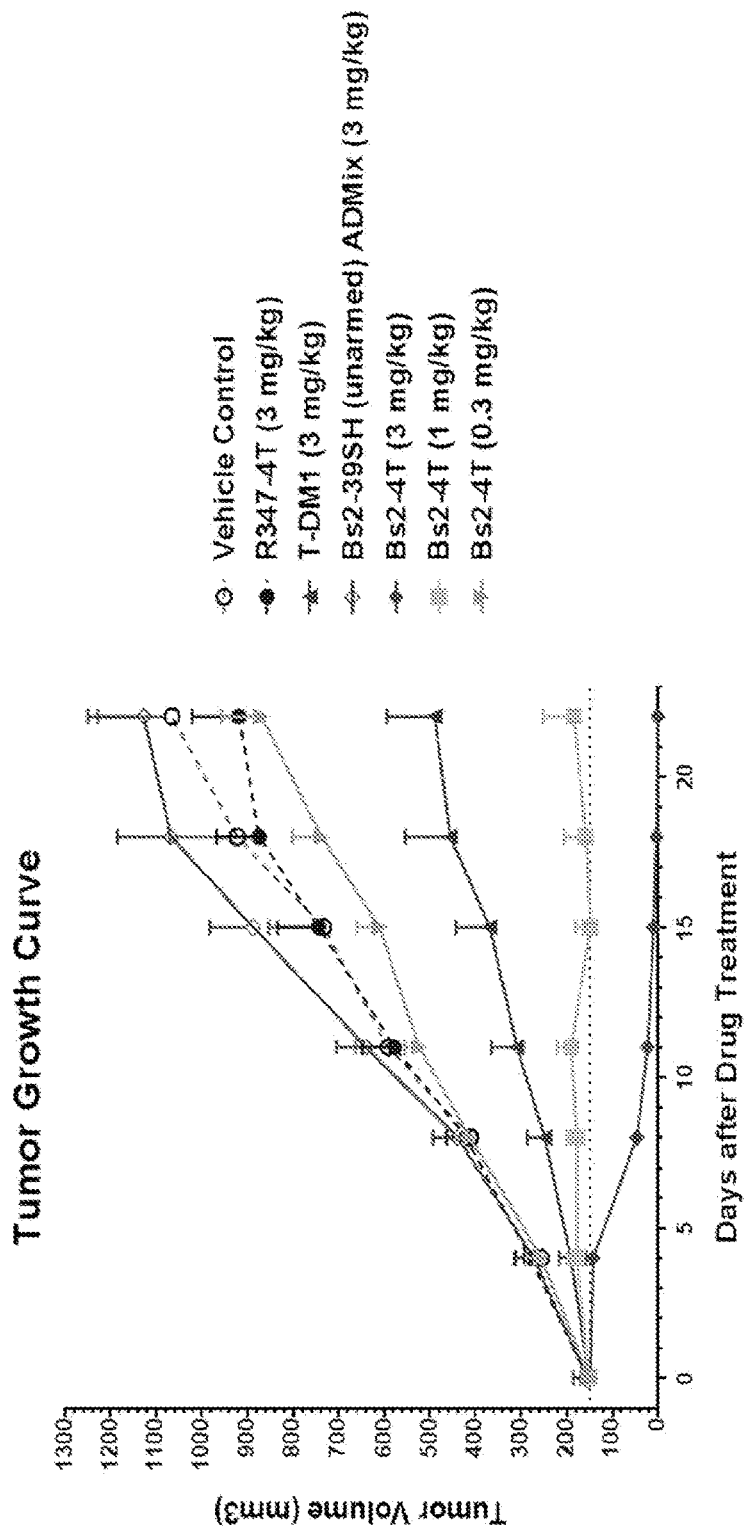

FIG. 21A shows the activity of anti-HER2 ADC activity in the MDA-MB-361 tumor model. Shown are the tumor growth curves corresponding to mice treated with (1) vehicle control, (2) R347-4T (R347 control antibody conjugated to 4 tubulysin molecules) at 3 mg/kg, (3) T-DM1 (trastuzumab-DM1 ADC) at 3 mg/kg, (4) Bs2 ADMix (Bs2Ab-39SH-(FCC) construct mixed with tubulysin) at 3 mg/kg, and (5) Bs2-4T (Bs2Ab-39SH-(FCC) construct conjugated to 4 tubulysins) at 0.3, 1 and 3 mg/kg. Concentrations are indicated between parenthesis.

Figure 21B:
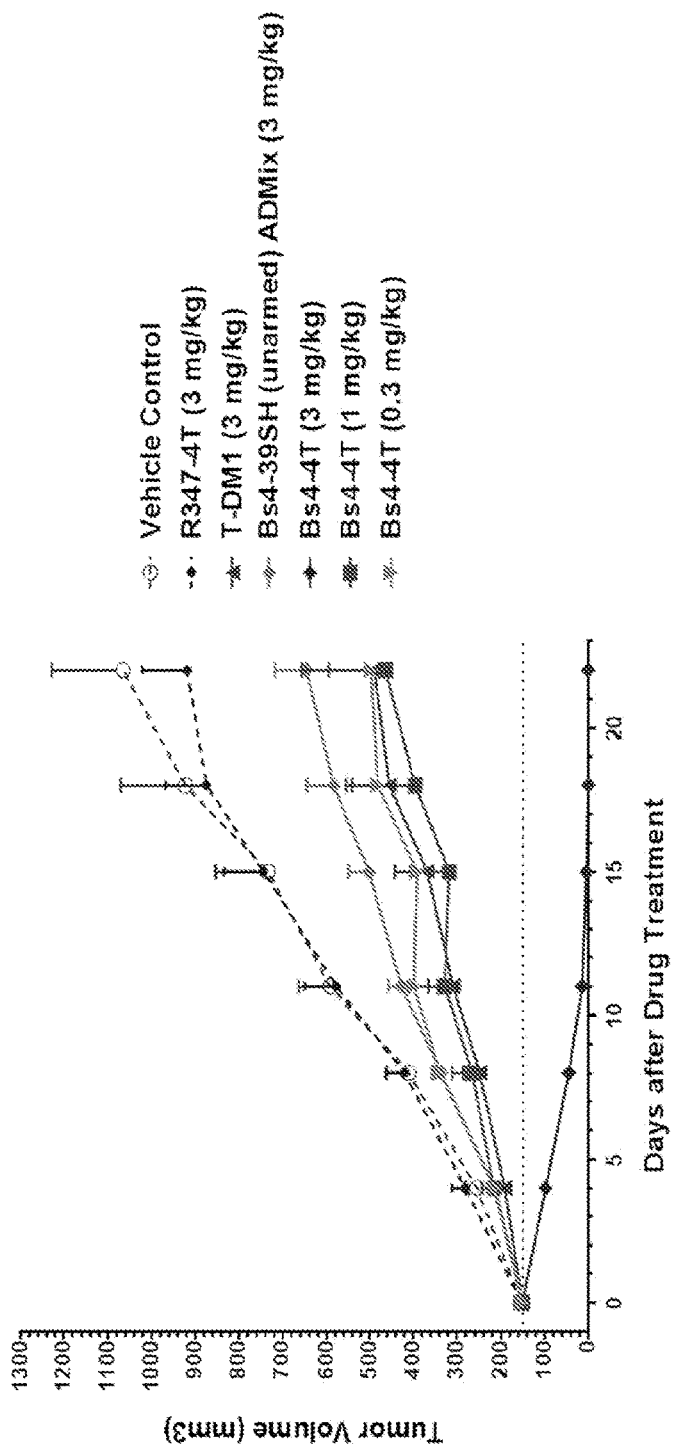

FIG. 21B shows the activity of anti-HER2 ADC activity in the MDA-MB-361 tumor model. Shown are the tumor growth curves corresponding to mice treated with (1) vehicle control, (2) R347-4T (R347 control antibody conjugated to 4 tubulysin molecules) at 3 mg/kg, (3) T-DM1 (trastuzumab-DM1 ADC) at 3 mg/kg, (4) Bs4 ADMix (Bs4Ab-39SH-(FCC) construct mixed with tubulysin) at 3 mg/kg, and (5) Bs4-4T (Bs4Ab-39SH-(FCC) conjugated to 4 tubulysins) at 0.3, 1 and 3 mg/kg. Concentrations are indicated between parenthesis.

Figure 22:
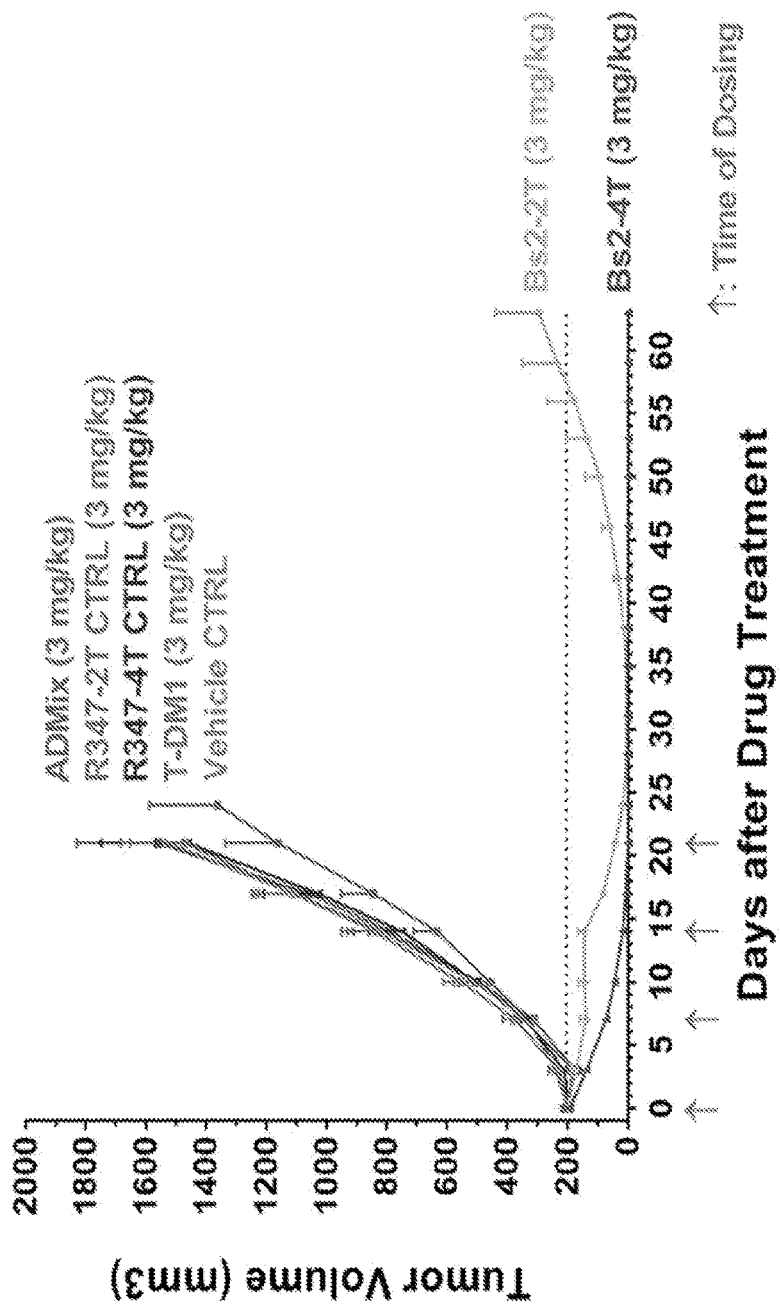

FIG. 22 shows the activity of anti-HER2 ADC in the ST996 triple-negative (ER−/PR−/HER2-1+) PDX tumor model. Shown are the tumor growth curves corresponding to mice treated with (1) vehicle control (CTRL), (2) isotype R347-2T CTRL (R347 control antibody conjugated to 2 tubulysin molecules), (3) isotype R347-4T CTRL (R347 control antibody conjugated to 4 tubulysin molecules), (4) T-DM1 (trastuzumab-DM1 ADC), (5) ADMix (construct mixed with tubulysin), (6) Bs2-2T, i.e., Bs2Ab-39SH-(FCC) construct conjugated to 2 tubulysins, or (7) Bs2-4T, i.e., Bs2Ab-39SH-(FCC) construct conjugated to 4 tubulysins. Concentrations are indicated between parenthesis. Time of dosing is also indicated by arrows. Tumor growth curves in response to the various treatments are presented as the mean tumor volume (mm$^3$)±SEM.

Figure 23:
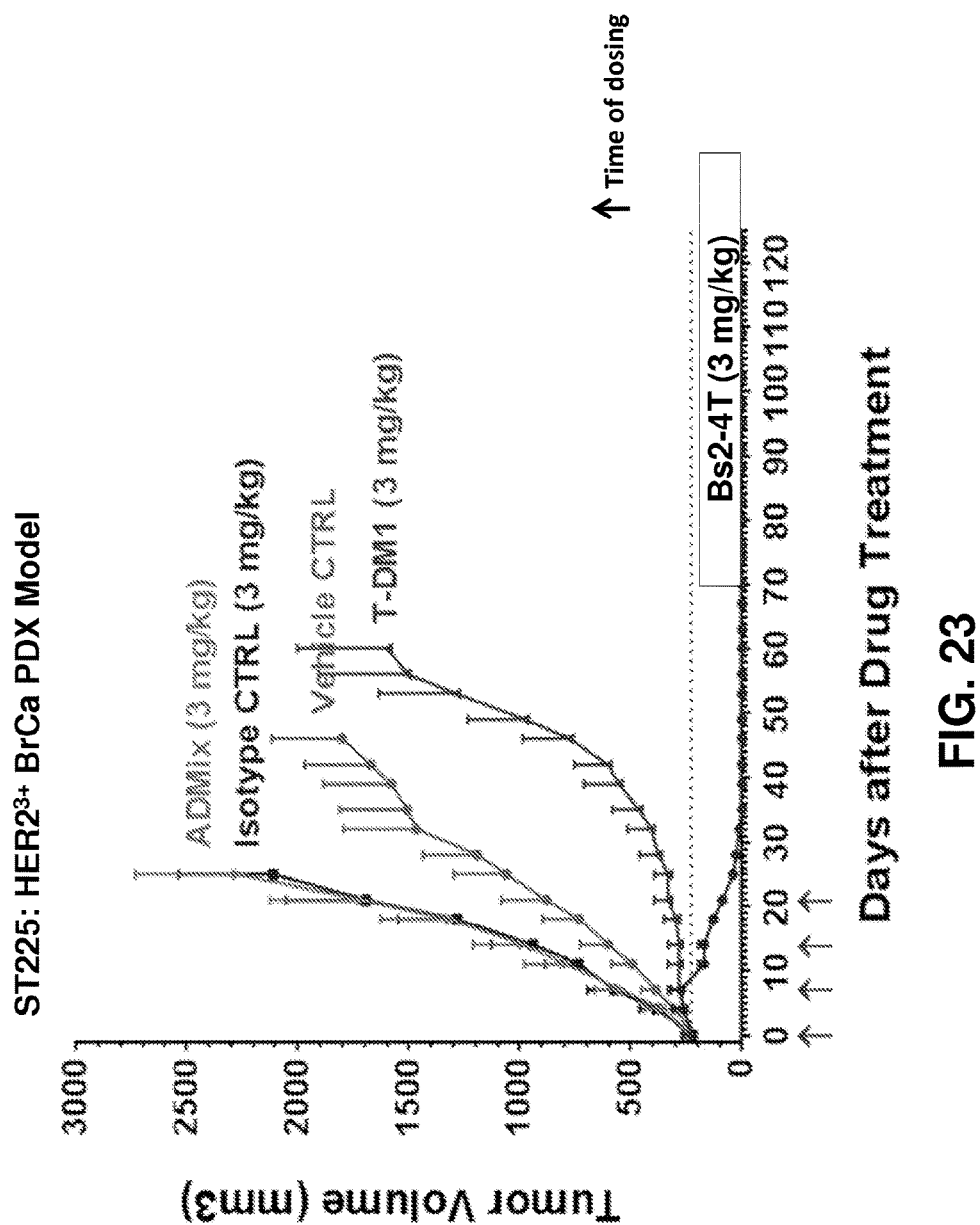

FIG. 23 shows the activity of anti-HER2 ADC activity in the ST225 (HER2-3+) BrCa PDX tumor model. Shown are the tumor growth curves corresponding to mice treated with (1) vehicle control, (2) R347-4T (R347 control antibody conjugated to 4 tubulysin molecules), (3) T-DM1 (trastuzumab-DM1 ADC), (4) BS2 ADMix (Bs2Ab-39SH-(FCC) construct mixed with tubulysin), and (5) Bs2-4T (Bs2Ab-39SH-(FCC) construct conjugated to 4 tubulysins. Concentrations are indicated between parenthesis.

Figure 24:
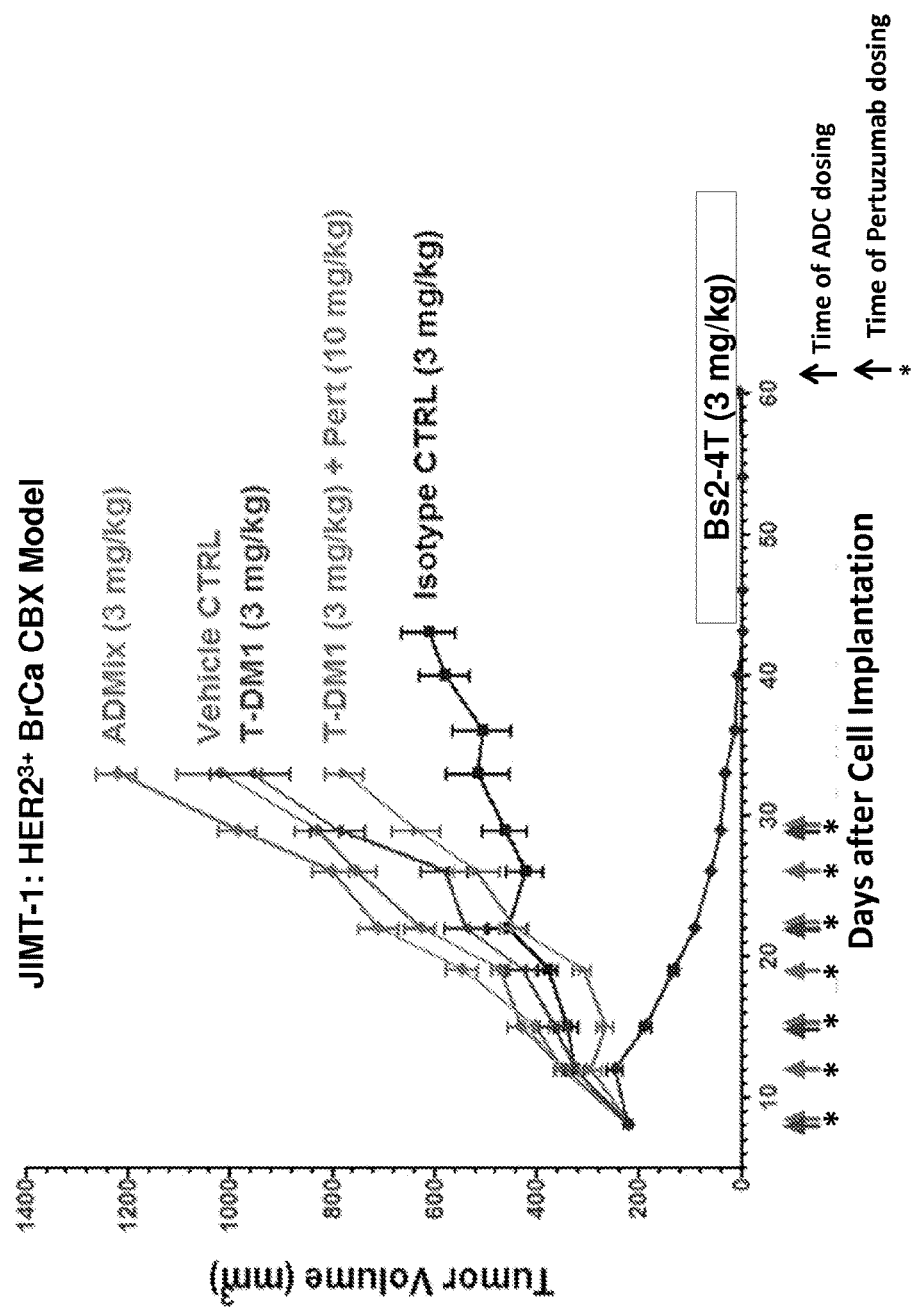

FIG. 24 shows the activity of anti-HER2 ADC activity in the T-DM-1 non-responder JIMT-1 (HER2-3+) BrCa CBX tumor model. Shown are the tumor growth curves corresponding to mice treated with (1) vehicle control, (2) R347-4T (R347 control antibody conjugated to 4 tubulysin molecules), (3) T-DM1 (trastuzumab-DM1 ADC), (4) BS2 ADMix (Bs2Ab-39SH-(FCC) construct mixed with tubulysin), and (5) Bs2-4T (Bs2Ab-39SH-(FCC) construct conjugated to 4 tubulysins. Concentrations are indicated between parenthesis.

Figure 25:
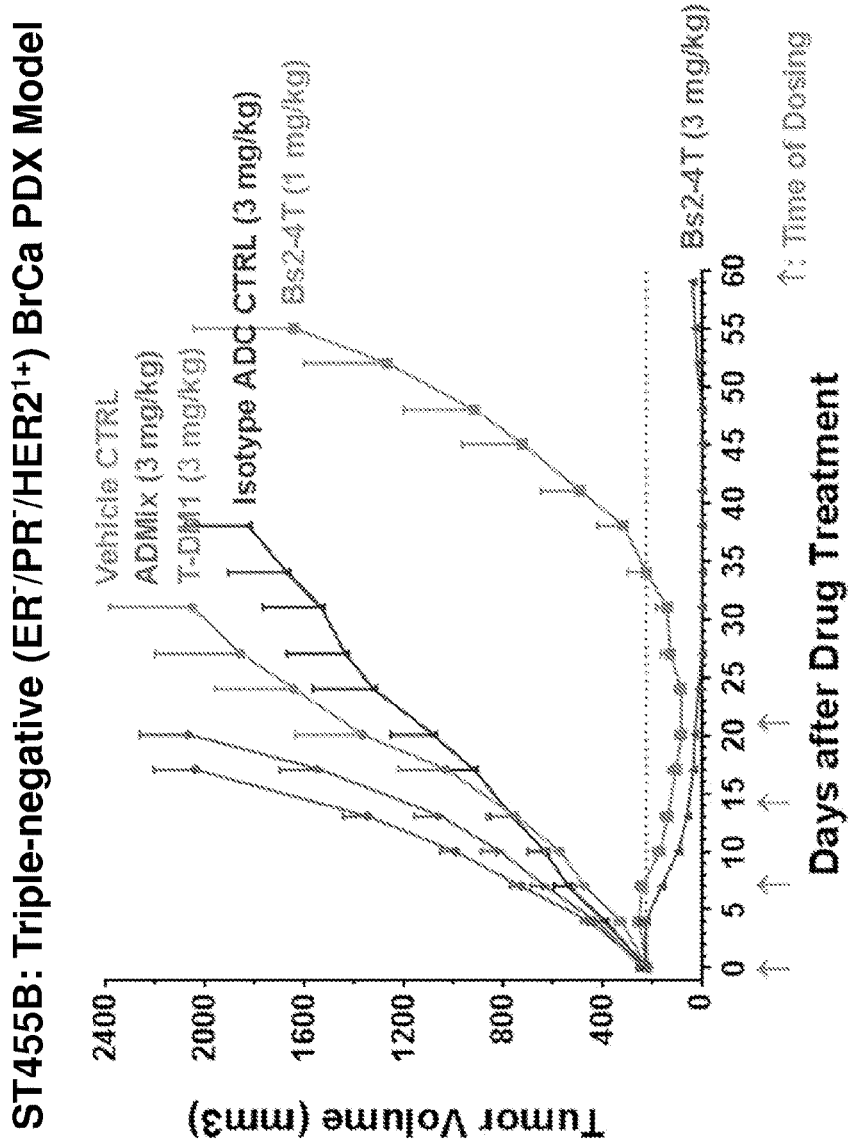

FIG. 25 shows the activity of anti-HER2 ADC activity in the ST455B triple-negative (ER−/PR−/HER2-1+) BrCa PDX tumor model. Shown are the tumor growth curves corresponding to mice treated with (1) vehicle control (CTRL), (2) isotype CTRL (R347 control antibody conjugated to 4 tubulysin molecules), (3) T-DM1 (trastuzumab- DM1 ADC), (4) BS2 ADMix (Bs2Ab-39SH-(FCC) construct mixed with tubulysin), and (5) Bs2-4T (Bs2Ab-39SH-(FCC) construct conjugated to 4 tubulysins. Concentrations are indicated between parenthesis.

Figure 26A:
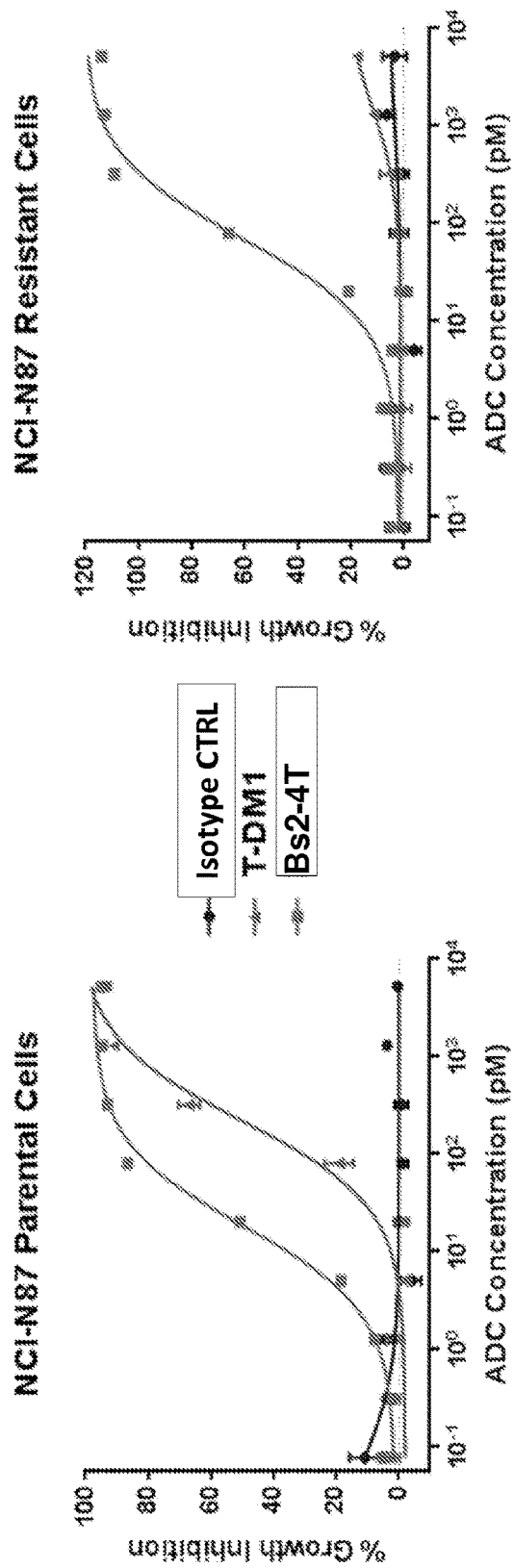

FIG. 26A shows the cytotoxic activity Bs2-4T and T-DM1 on a parental NCI-N87 cell line (left panel) and an NCI-N87 cell line with acquired resistance to T-DM1 (right panel). Bs2-4T has more potent activity in the parent cell line and is still active in killing the T-DM1 resistant cells.

Figure 26B:
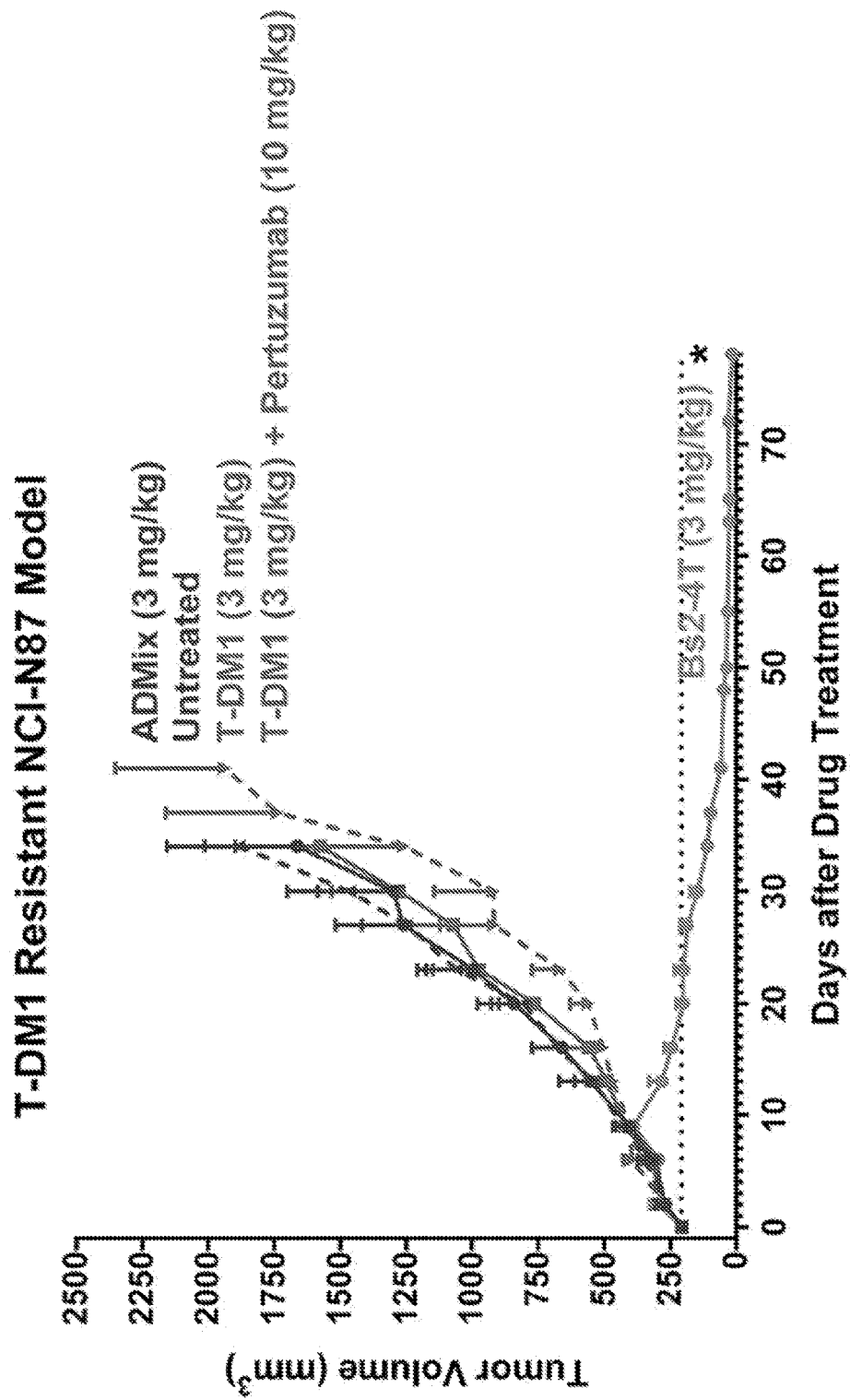

FIG. 26B shows the activity of anti-HER2 ADC in the T-DM1 resistant NCI-N87 tumor model. Shown are the tumor growth curves corresponding to untreated mice and mice treated with (1) ADMix (construct mixed with tubulysin), (2) T-DM1 (trastuzumab-DM1 ADC), (3) T-DM1 (trastuzumab-DM1 ADC) plus pertuzumab, or (4) Bs2-4T, i.e., Bs2Ab-39SH-(FCC) construct conjugated to 4 tubulysins. Concentrations are indicated between parenthesis. Tumor growth curves in response to the various treatments are presented as the mean tumor volume (mm$^3$)±SEM (n=7). *P<0.001 by Student's t test as compared to the untreated control group.

Figure 27:
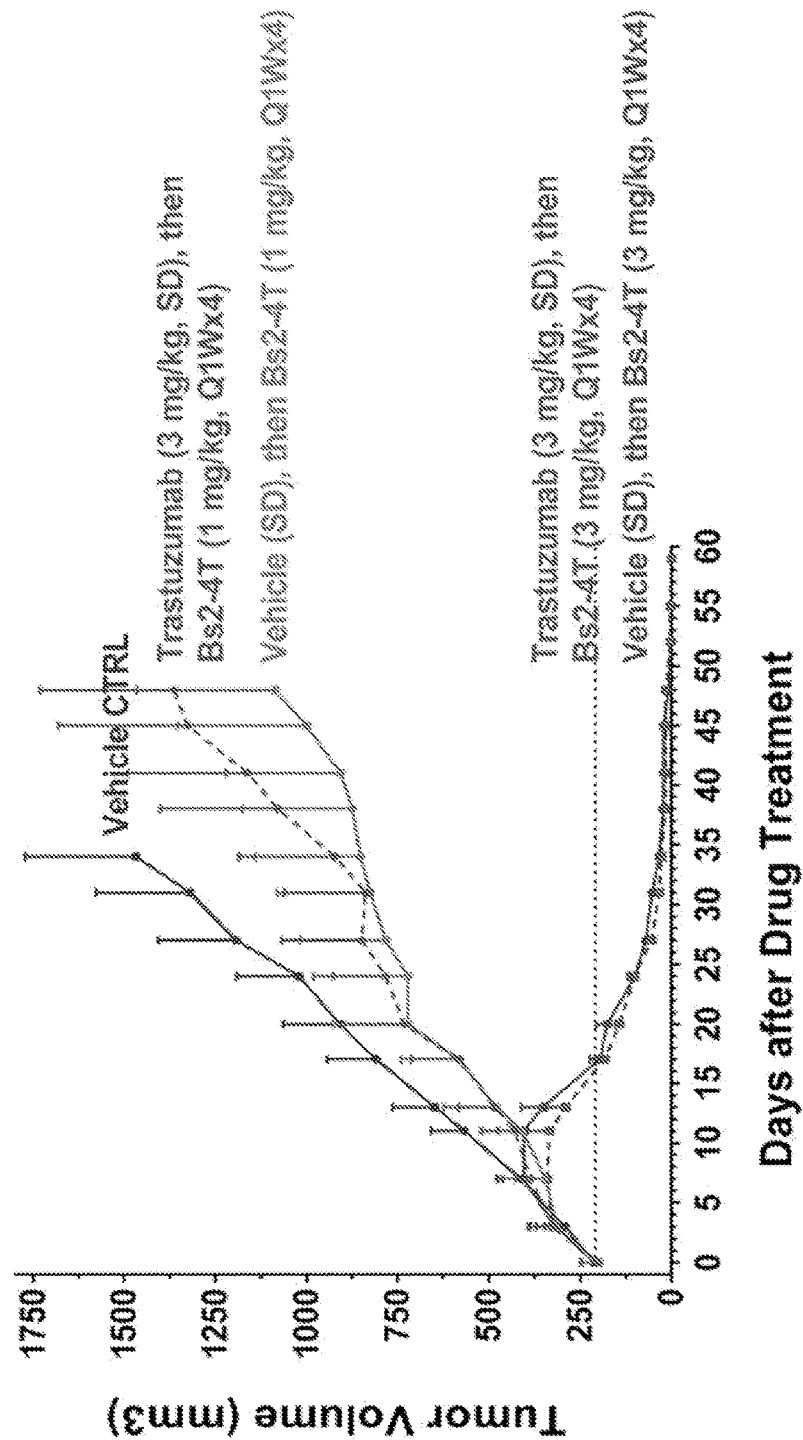

FIG. 27 shows the activity of anti-HER2 ADC after pretreatment with trastuzumab. Shown are the tumor growth curves corresponding to mice treated with (1) vehice CTRL (control), (2) trastuzumab followed by Bs2-4T, (3) vehicle followed by Bs2-4T, (4) trastuzumab followed by Bs2-4T, or (5) vehicle followed by Bs2-4T. Concentrations and dosage regimens are indicated between parentheses. Tumor growth curves in response to the various treatments are presented as the mean tumor volume (mm$^3$)+/−SEM (n=10).

Figure 28A:
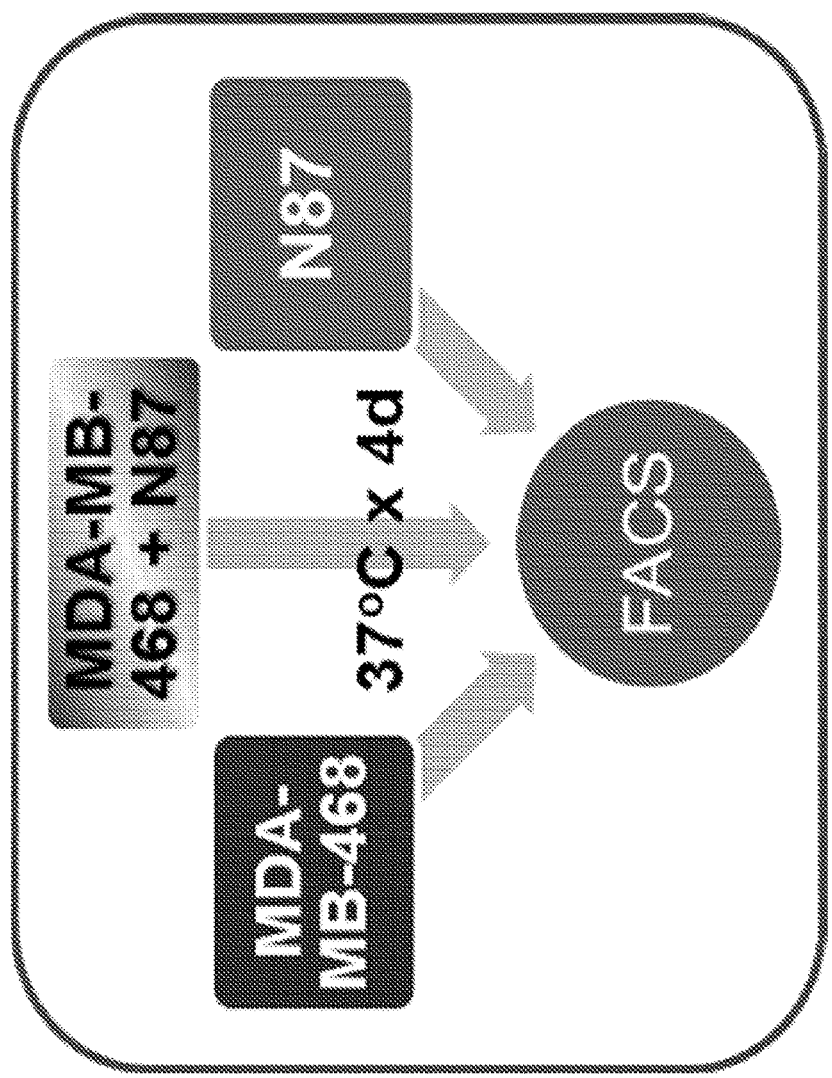

FIG. 28A shows a schematic for an assay to evaluate the bystander effect of the Bispecific ADCs.

Figure 28B:
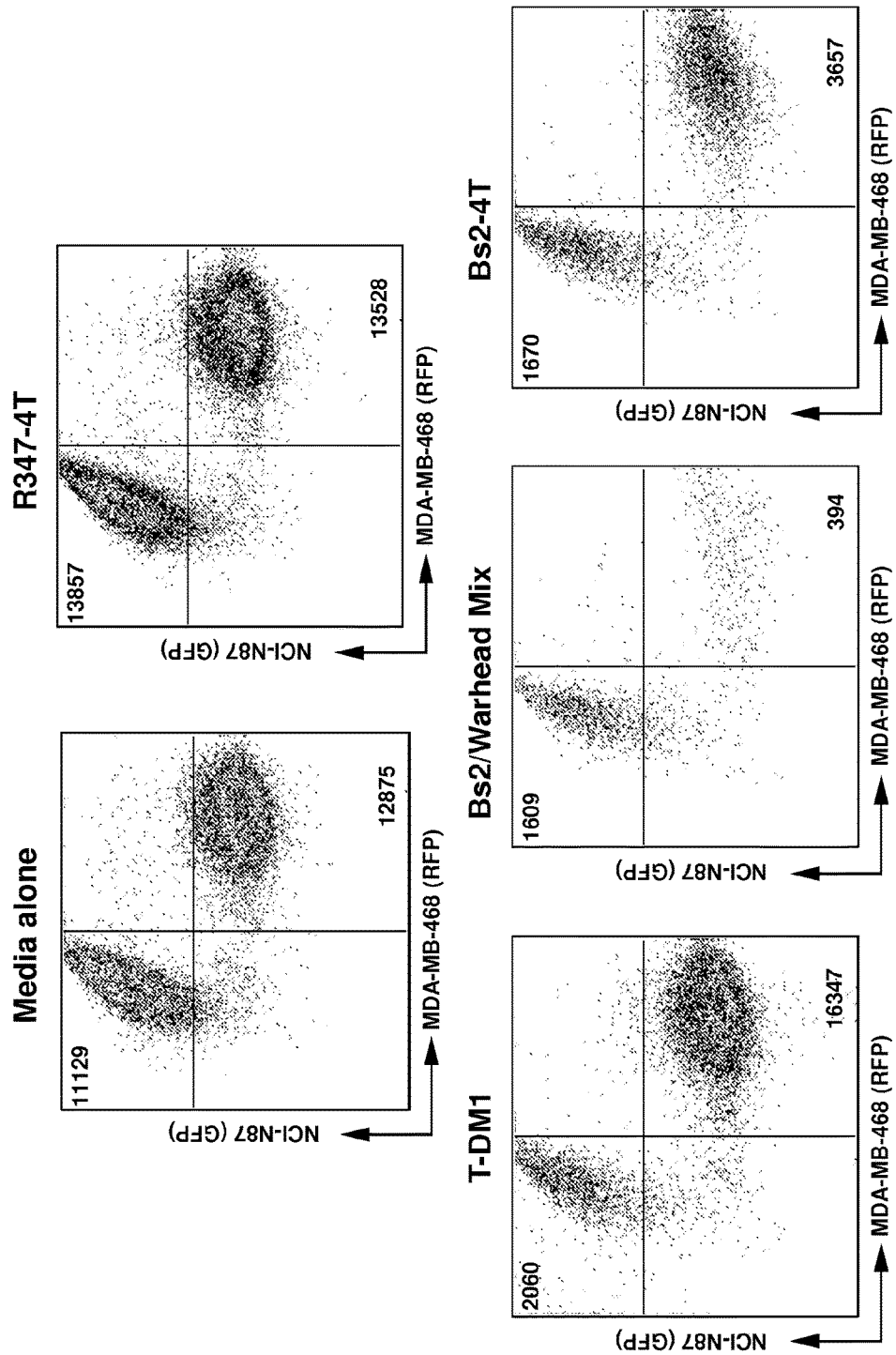

FIG. 28B shows FACS analysis results of cells treated with (i) media alone; (ii) R347-T4 control; (iii) T-DM1; (iv) Bs2Ab-39SH admix; and (v) Bs2-4T. The reduction in cell numbers in both quadrants indicates that Bs2-4T can kill both HER2-expressing and HER2-null cells in a co-culture, suggesting Bs2-4T has bystander effect. In contrast, T-DM1 cannot kill HER2-null cells in a co-culture, suggesting it does not have bystander effect.

Figure 29:
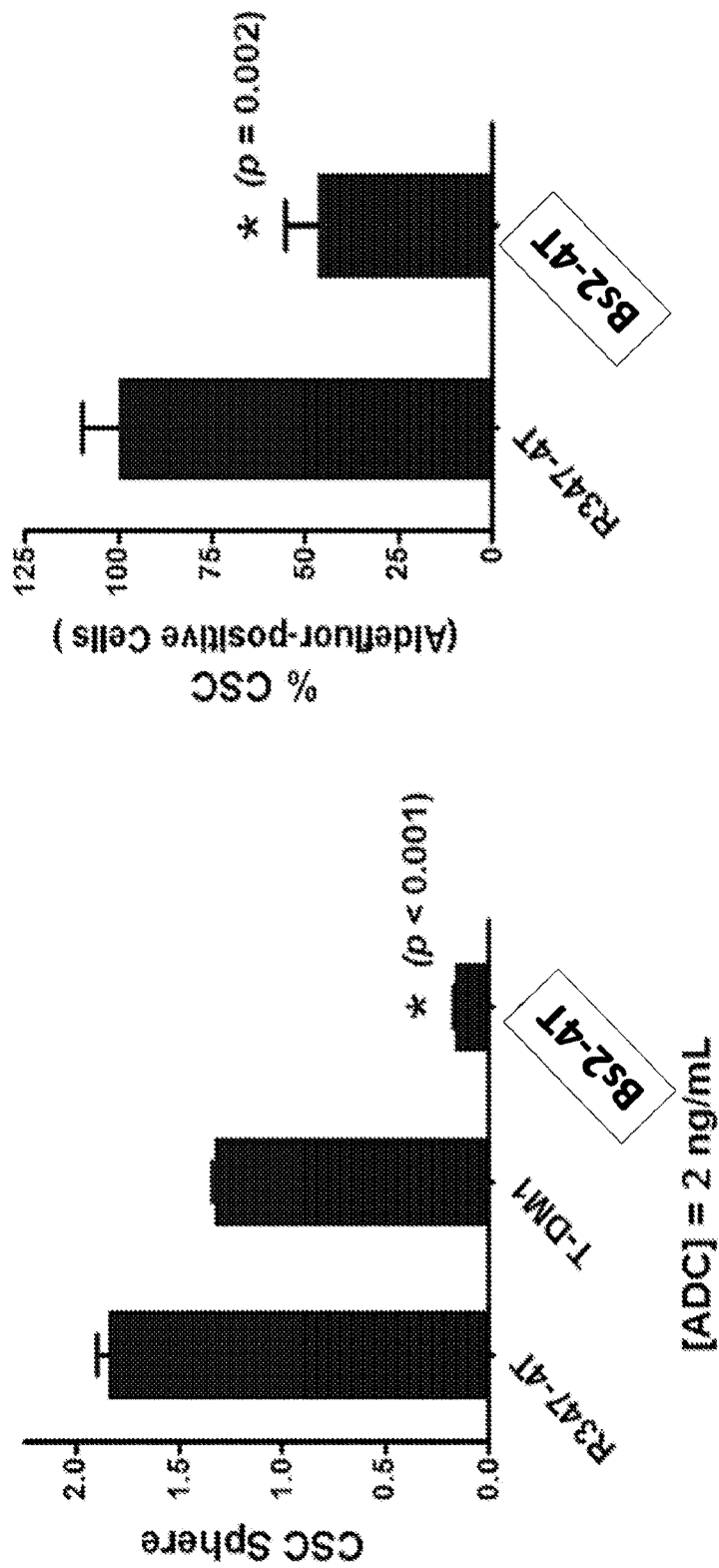

FIG. 29 shows the activity of Bs2-4T on cancer stem cell (CSC) sphere formation (left panel) relative to T-DM1 and R347-4T (R347 control antibody conjugated to 4 tubulysin molecules); and on CSC in xenograft tumors (right panel) relative to R34-4T (R234 control antibody conjugated to 4 tubulysin molecules).

Figure 30A:
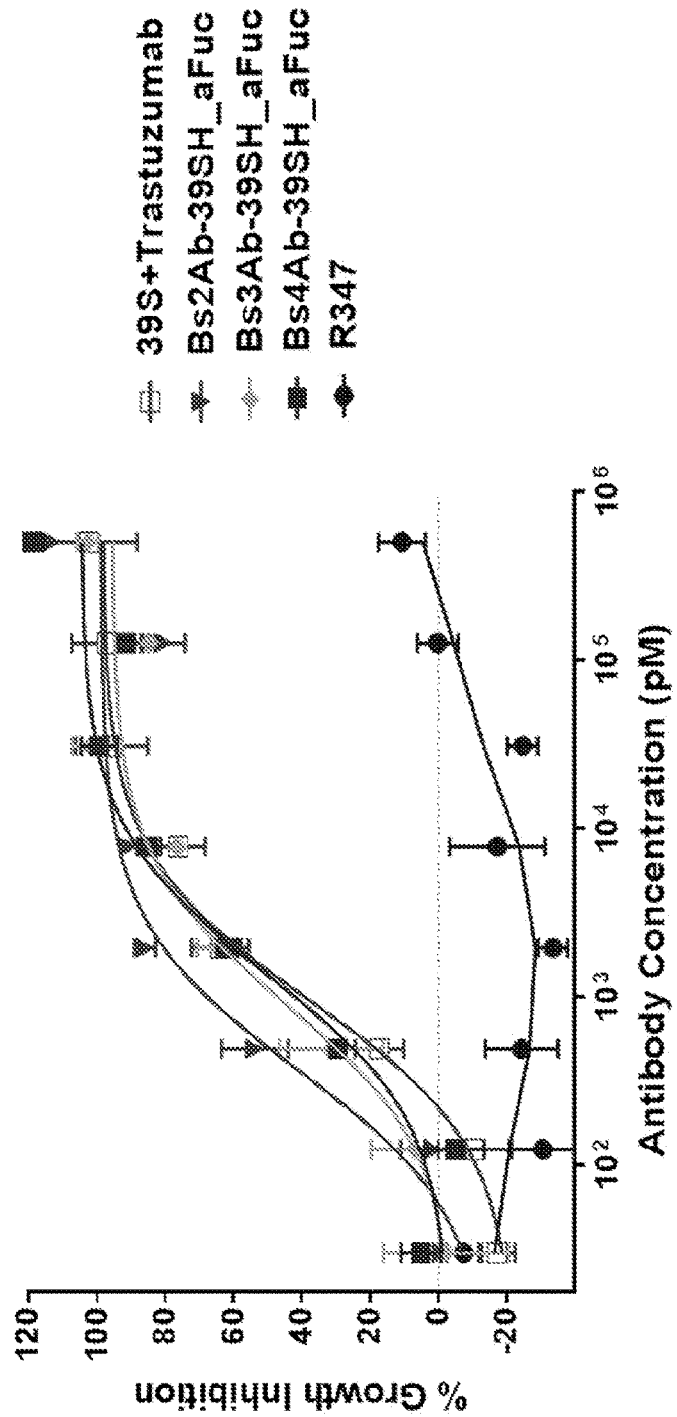

FIG. 30A shows ligand-dependent proliferation assays using the cell line MDA-MB-361 (human ductal breast epithelial adenocarcinoma derived from brain metastasis), which showed that all of the ADCC enhanced afucosylated bispecific antibodies retain in vitro anti-proliferative activity. In each experiment, the antibody samples used were: R347 control, 39S plus trastuzumab, Bs2Ab-39SH_aFuc, Bs3Ab-39SH_aFuc, and Bs4Ab-39SH_aFuc.

Figure 30B:
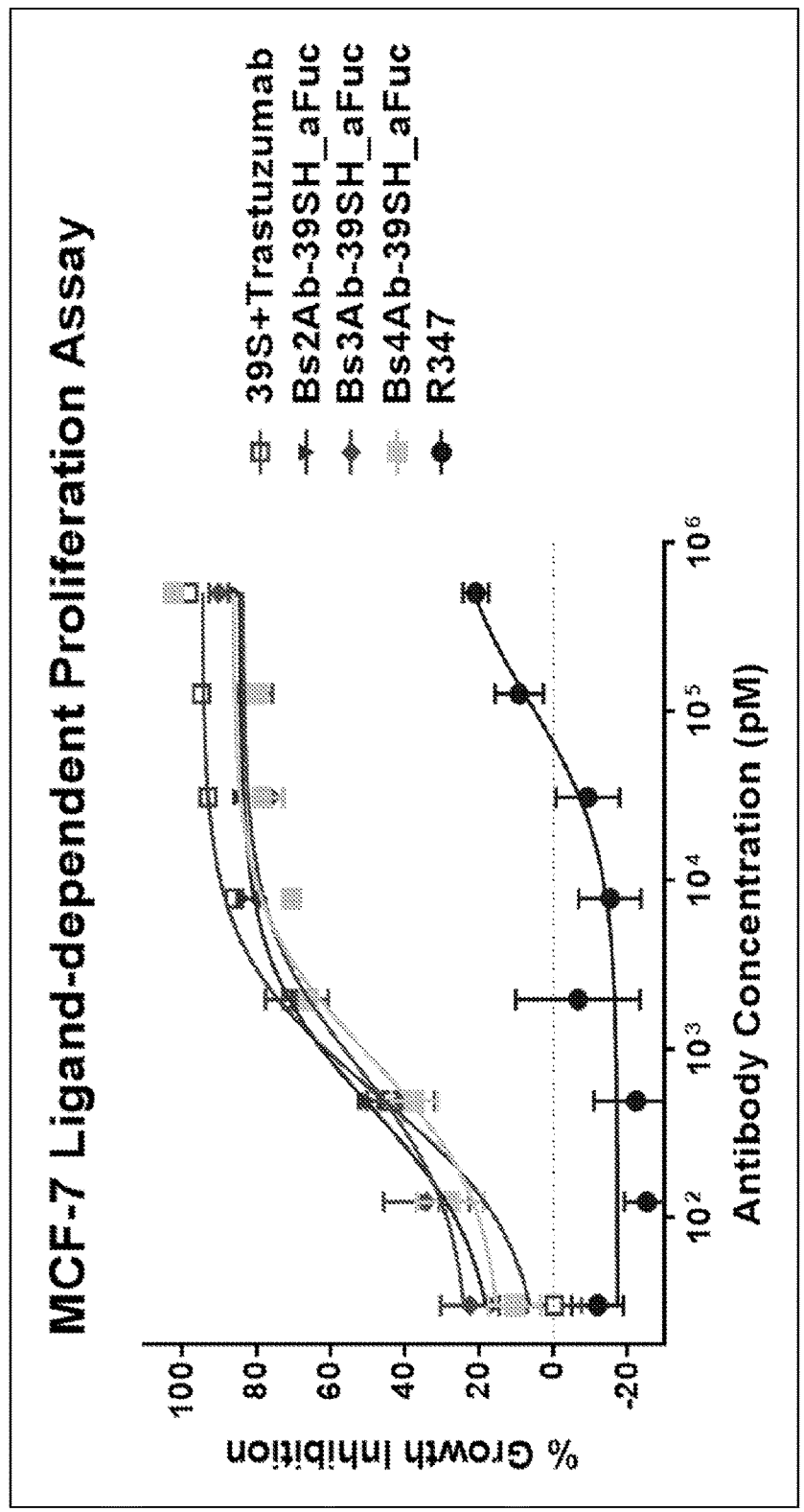

FIG. 30B shows ligand-dependent proliferation assays using the cell line MCF-7 (human invasive breast ductal adenocarcinoma), which showed that all of the ADCC enhanced afucosylated bispecific antibodies retain in vitro anti-proliferative activity. In each experiment, the antibody samples used were: R347 control, 39S plus trastuzumab, Bs2Ab-39SH_aFuc, Bs3Ab-39SH_aFuc, and Bs4Ab-39SH_aFuc.

Figure 31A:
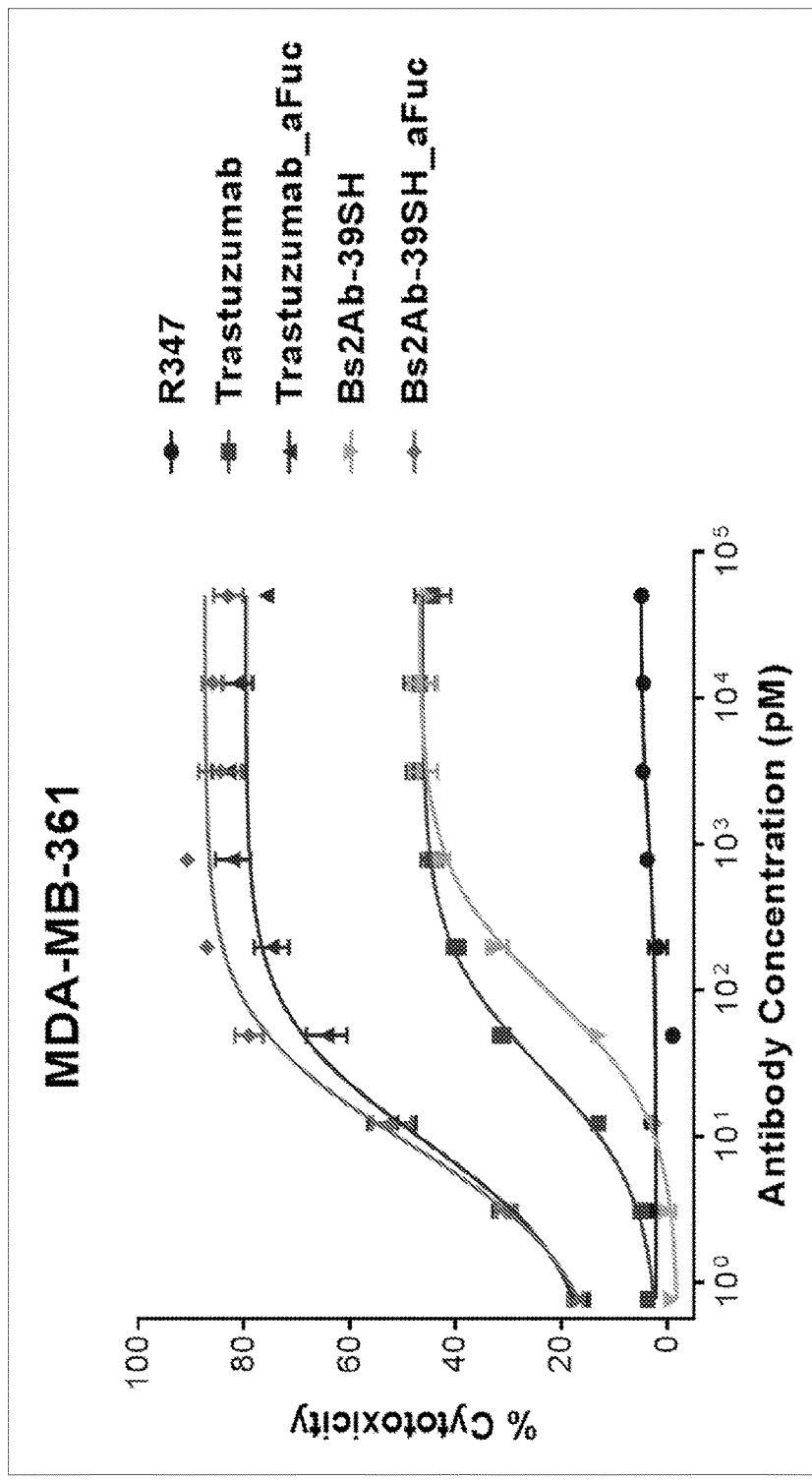
Figure 31B:
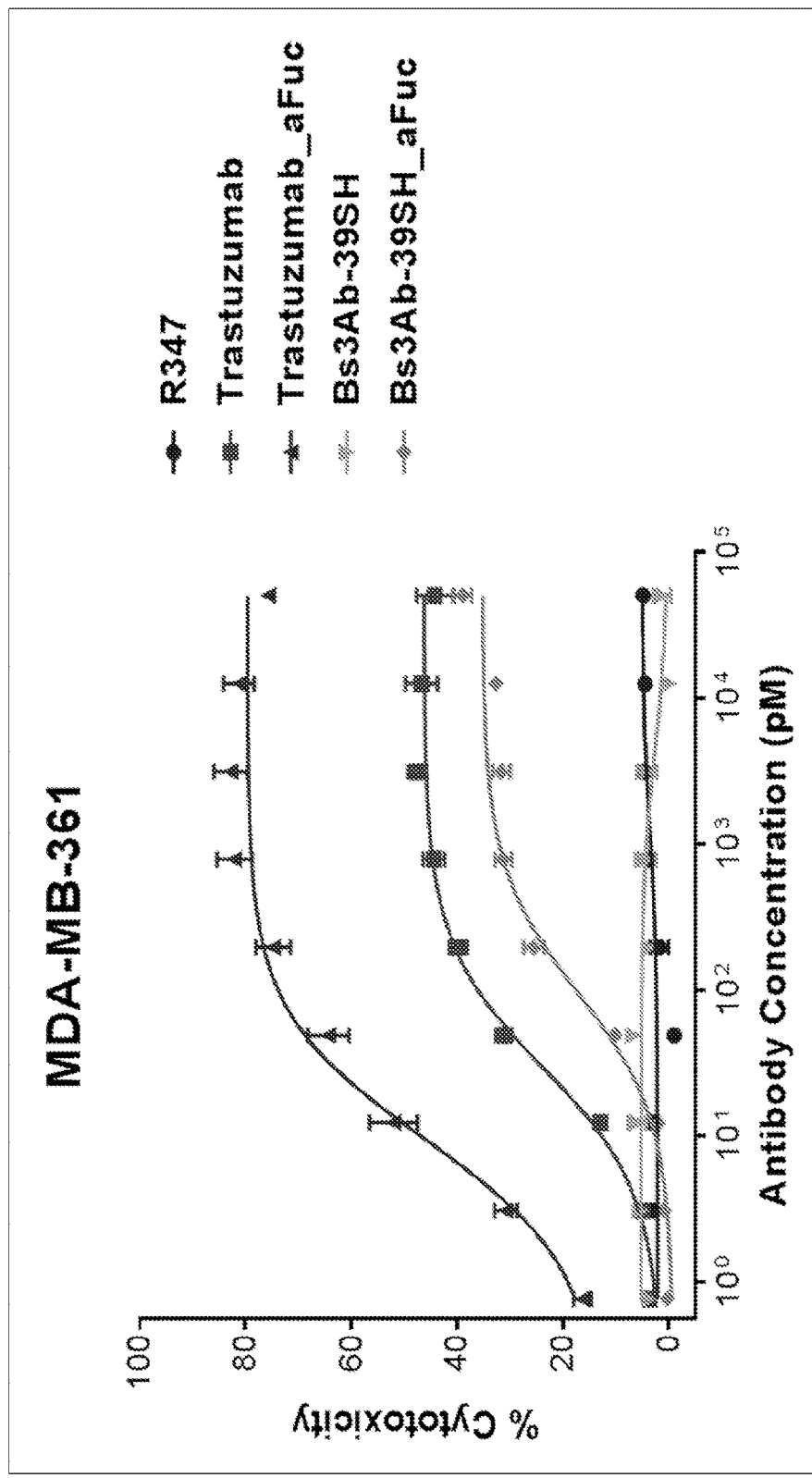

FIG. 31A shows ADCC cytotoxicity assays using the MDA-MB-361 cells as the target and engineered NK effector cells (stably expressing CD16), which showed that each of the afucosylated bispecific antibodies has more potent ADCC activity as compared to the same construct having fucosylated glycoforms. The antibody samples used were: (1) R347 control, (2) trastuzumab, (3) trastuzumab_aFuc, (4) Bs2Ab-39SH, and (5) Bs2Ab-39SH_aFuc, FIG. 31B shows ADCC cytotoxicity assays using the MDA-MB-361 cells as the target and engineered NK effector cells (stably expressing CD16), which showed that each of the afucosylated bispecific antibodies has more potent ADCC activity as compared to the same construct having fucosylated glycoforms. The antibody samples used were: (1) R347 control, (2) trastuzumab, (3) trastuzumab_aFuc, (4) Bs3Ab-39SH, and (5) Bs3Ab-39SH_aFuc.

Figure 31C:
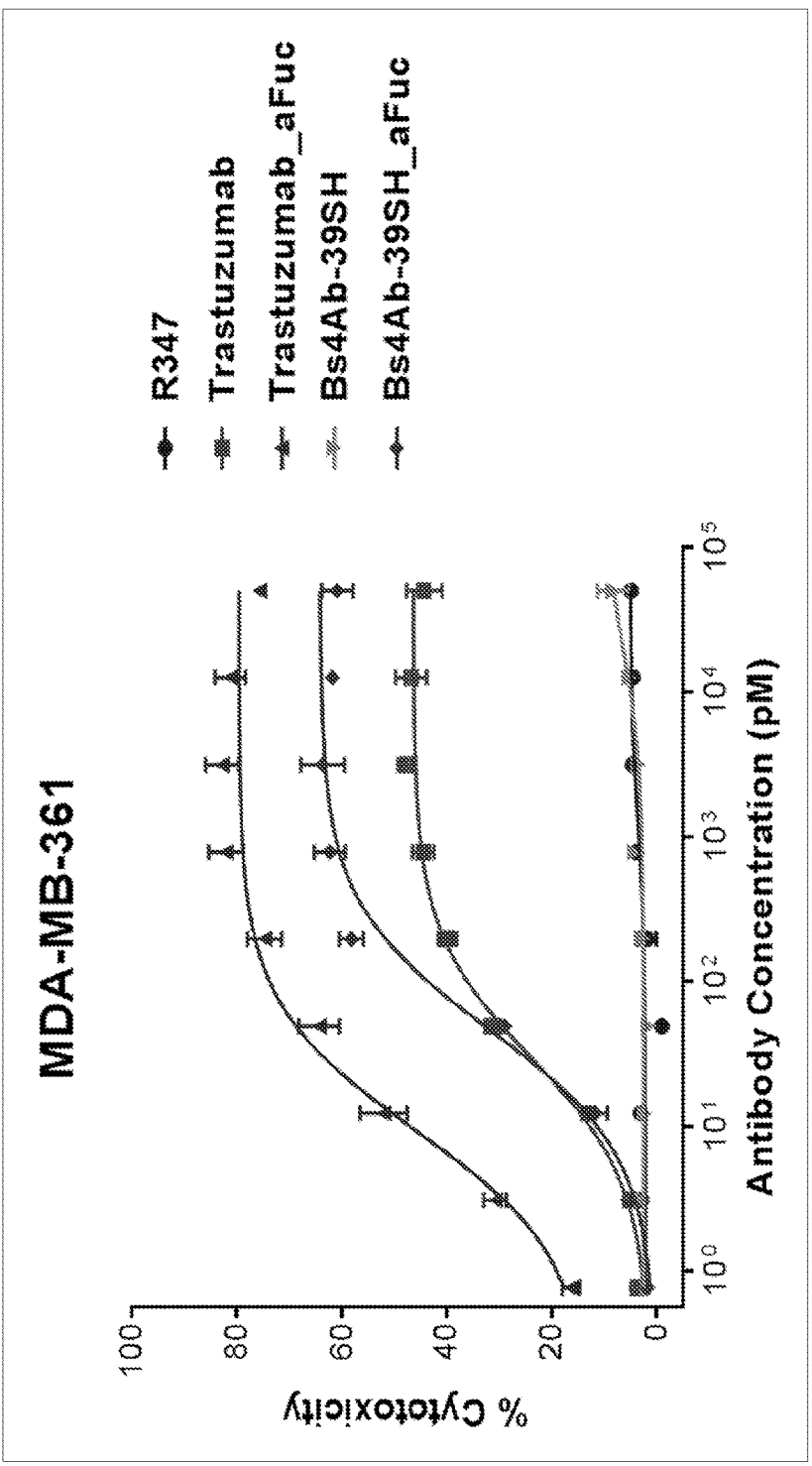

FIG. 31C shows ADCC cytotoxicity assays using the MDA-MB-361 cells as the target and engineered NK effector cells (stably expressing CD16), which showed that each of the afucosylated bispecific antibodies has more potent ADCC activity as compared to the same construct having fucosylated glycoforms. The antibody samples used were: (1) R347 control, (2) trastuzumab, (3) trastuzumab_aFuc, (4) Bs4Ab-39SH, and (5) Bs4Ab-39SH_aFuc.

Figure 32:
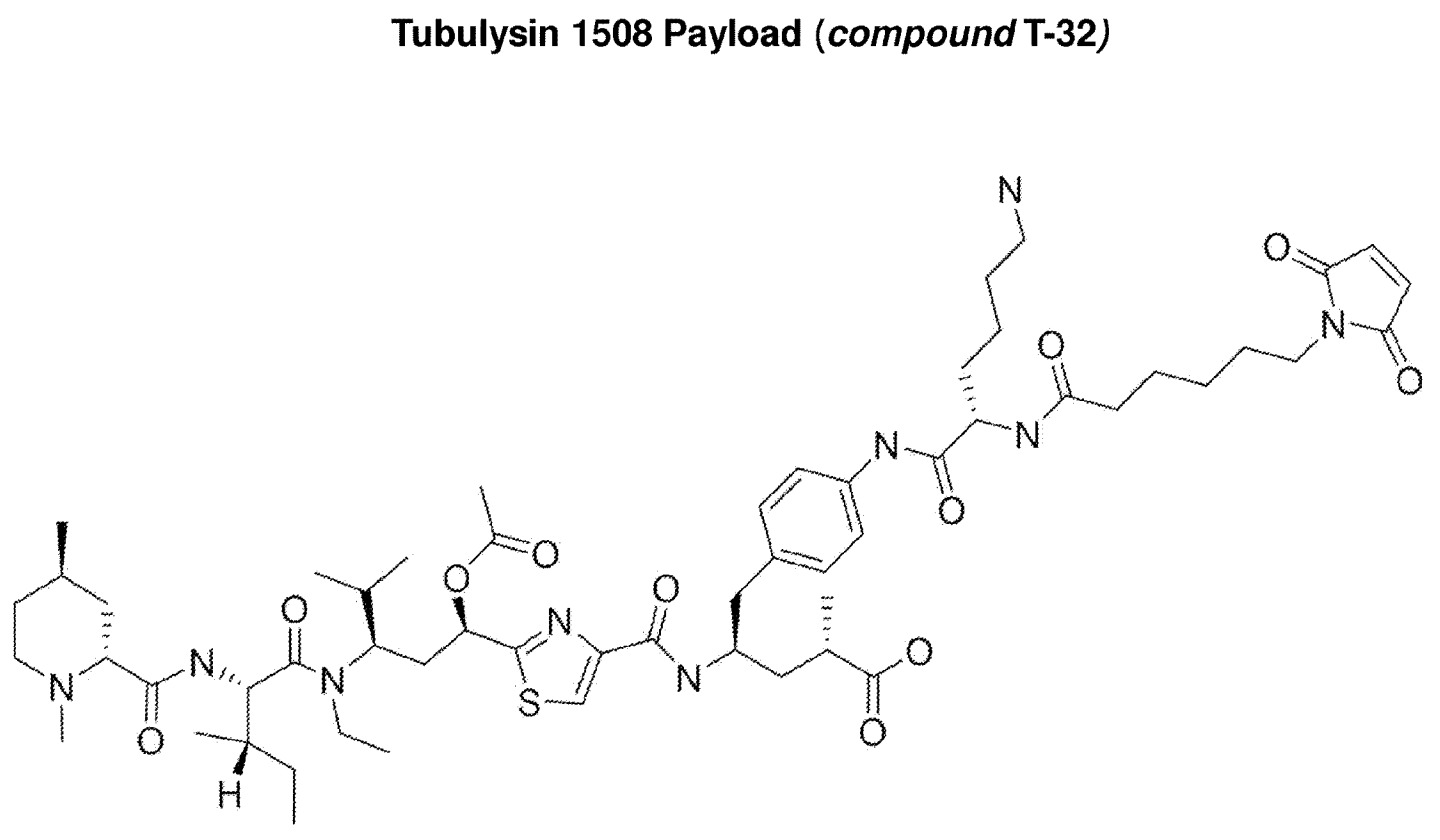

FIG. 32 shows the structure of the tubulysin 1508 payload. The double bond of the maleimide group at the far right readily reacts with the thiol group found on cysteine to form a stable carbon-sulfur bond.

Figure 33:
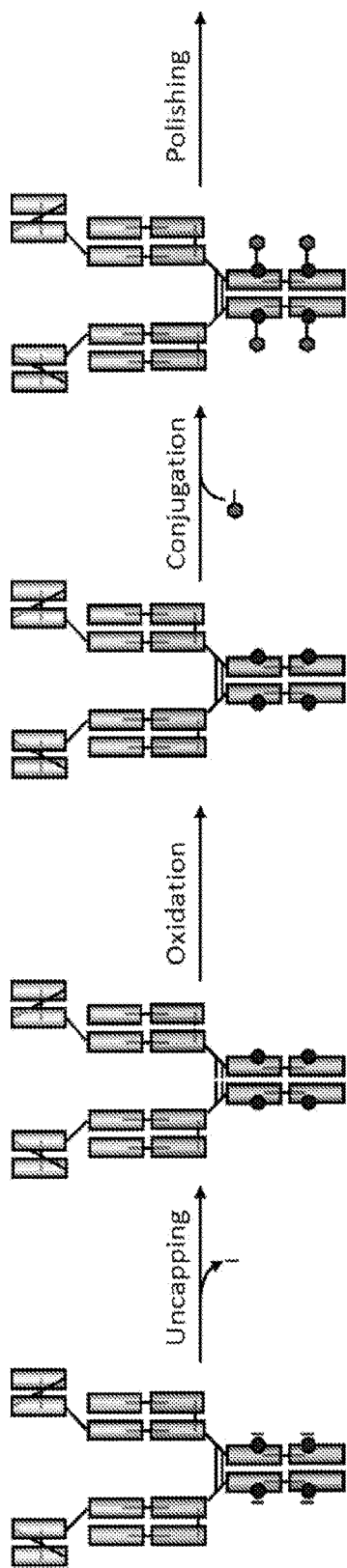

FIG. 33 shows an exemplary site-specific antibody drug conjugation process, using the Bs2Ab-FCC construct as the derivatizable platform. The process comprises the steps of (a) uncapping the size chains of the derivatizable amino acids (e.g., cysteines), (b) oxidizing, (c) conjugating a payload (e.g., a cytotoxic agent such as tubulysin), and (d) polishing by removing conjugation reagents and non-reacted payload.

DETAILED DESCRIPTION OF THE INVENTION

The present disclosure provides optimized anti-HER2 antibodies, and bispecific antibodies derived from such optimized anti-HER2 antibodies. Related polynucleotides, vectors, cells, and pharmaceutical compositions comprising such optimized anti-HER2 antibodies or bispecific anti-HER2 antibodies are also provided. Also provided are methods of making such optimized anti-HER2 antibodies or bispecific antibodies. In addition, the disclosure provides are methods of using the optimized anti-HER2 antibodies or bispecific anti-HER2 antibodies, for example, methods of treating cancer in a subject in need thereof.

The present disclosure also provides antibody-drug conjugates (ADC) derived from optimized anti-HER2 antibodies and bispecific antibodies derived from such optimized anti-HER2 antibodies. Also provided are methods of making ADC derived from such optimized antibodies and bispecific antibodies. Also provided are methods of using the ADC derived from optimized anti-HER2 antibodies and bispecific antibodies, for example, methods of treating cancer in a subject in need thereof. Also provided are methods to treat patients with cancers resistant to chemotherapy (e.g., tumors in T-DM1 non-responder or poor-responder patients); to treat patients that are relapsed, refractory, on non-eligible to be treated with other therapies, in particular mono-specific ADC therapies (e.g. T-DM1); or to treat patients after pretreatment with other therapies (e.g. T-DM1).

In particular, the instant disclosure provides anti-HER2 binding molecules that are suitable for treating cancer expressing low levels of HER2.

In order that the present invention can be more readily understood, certain terms are first defined. Additional definitions are set forth throughout the detailed description.

I. Definitions

Before describing the present invention in detail, it is to be understood that this invention is not limited to specific compositions or process steps, as such can vary. As used in this specification and the appended claims, the singular forms "a", "an" and "the" include plural referents unless the context clearly dictates otherwise. The terms "a" (or "an"), as well as the terms "one or more," and "at least one" can be used interchangeably herein.

Furthermore, "and/or" where used herein is to be taken as specific disclosure of each of the two specified features or components with or without the other. Thus, the term and/or as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects, which can be had by reference to the specification as a whole. Accordingly, the terms defined immediately below are more fully defined by reference to the specification in its entirety.

It is understood that wherever aspects are described herein with the language "comprising," otherwise analogous aspects described in terms of "consisting of" and/or "consisting essentially of" are also provided.

Amino acids are referred to herein by either their commonly known three letter symbols or by the one-letter symbols recommended by the IUPAC-IUB Biochemical Nomenclature Commission. Nucleotides, likewise, are referred to by their commonly accepted single-letter codes.

The terms "HER2" and "HER2 receptor" are used interchangeably herein, and refer to the ErbB2 protein (also referred to as HER2/neu in the literature). As used herein, the terms are intended to include variants (e.g., splice variants), isoforms, and homologs of HER2 (both orthologs and paralogs). In some aspects, binding of an anti-HER2 binding molecule disclosed herein to HER2 inhibits the growth of cells expressing HER2 (i.e. typically tumor cells, and in particular cancer cells expressing low levels of HER2) by inhibiting formation of heteromeric complexes between HER2 and other ErbB family members, e.g. inhibiting heterodimerization with EGFR or HER3.

HER2 is a receptor tyrosine kinase and is composed of an extracellular domain (ECD), which consists of (i) two leucine-rich domains (domain I/L1 and domain III/L2) responsible for ligand binding, and (ii) two cysteine-rich domains (domain II/CR1 and domain IV/CR2) responsible for receptor dimerization; a transmembrane domain; and an intracellular tyrosine kinase domain. Alternative splice variants of HER2 exist. Examples of alternative splice variants of HER2 include p100 and herstatin (two soluble forms), as well as 611-CTF, 687-CTF, 648-CTF, and Δ16HER2. The soluble forms of HER2 can interact of with full-length receptors (p185) and inhibit receptor dimerization; 687-CTF is inactive; 611-CTF and 648-CTF can activate several intracellular signal transduction pathways; and Δ16HER2 lacks the amino acids 634-649 in domain IV, which induce a conformational change that promotes the formation of constitutively activated HER2 homodimers. The extracellular portion of mature HER2, without the signal sequence, corresponds to positions 23-652 of canonical Isoform 1 (see Uniprot P04626; see also "Structure of the extracellular region of HER2 alone and in complex with the Herceptin Fab." Cho et al., Nature 421:756-760 (2003), incorporated herein by reference in its entirety). The pertuzumab antibody binds to an epitope within domain II of HER2. Antibodies that do not bind to the pertuzumab binding epitope within domain II include trastuzumab, which binds to an epitope within domain IV.

The terms "inhibit," "block," and "suppress" are used interchangeably herein and refer to any statistically significant decrease in biological activity, including full blocking of the activity. For example, "inhibition" can refer to a decrease of about 10%, 20%, 30%, 40%, 50%, 60%, 70%, 80%, 90% or 100% in biological activity. Accordingly, when the terms "inhibition" or "suppression" are applied to describe, e.g., an effect on ligand-mediated HER2 phosphorylation, the term refers to the ability of an anti-HER2 antibody or a HER2-binding molecule comprising an antigen binding fragment thereof, to statistically significantly decrease the phosphorylation of HER2 induced by an EGF-like ligand, relative to the phosphorylation in an untreated (control) cell.

The cell which expresses HER2 can be a naturally occurring cell or cell line (e.g., a cancer cell) or can be recombinantly produced by introducing a nucleic acid encoding HER2 into a host cell. In one aspect, the anti-HER2 binding molecule, e.g., an anti-HER2 antibody or a HER2-binding molecule comprising an antigen binding fragment thereof, inhibits ligand mediated phosphorylation of HER2 by at least 10%, or at least 20%, or at least 30%, or at least 40%, or at least 50%, or at least 60%, or at least 70%, or at least 80%, or at least 905, or about 100%, as determined, for example, by Western blotting followed by probing with an anti-phosphotyrosine antibody or by ELISA.

The terms "growth suppression" or "growth inhibition" of a cell expressing HER2, as used herein, refer to the ability of anti-HER2 binding molecule, e.g., an anti-HER2 antibody or a HER2-binding molecule comprising an antigen-binding fragment thereof, to statistically significantly decrease proliferation of cells expressing HER2 relative to the proliferation in the absence of the anti-HER2 binding molecule. In one aspect, the proliferation of cells expressing HER2 (e.g., cancer cells) can be decreased by at least 10%, or at least 20%, or at least 30%, or at least 40%, or at least 50%, or at least 60%, or at least 70%, or at least 80%, or at least 90%, or about 100% when cells are contacted with an anti-HER2 binding molecule, e.g., an anti-HER2 antibody or a HER2-binding molecule comprising an antigen-binding fragment thereof, relative to the proliferation measured in the absence of the anti-HER2 binding molecule (control conditions).

Cell proliferation can be measured according to various methods known in the art, e.g., by counting the number of viable cells, identifying the presence of markers of growth markers, measuring the incorporation of molecules (e.g., radioactively labelled molecules such a $^3$H-thymidine), by measuring the size of a tumor (e.g, by volume or by weight), etc. In certain aspects, growth suppression refers to reduction in the number, size, or distribution of metastases.

As used throughout the instant specification, the phrase "anti-HER2 binding molecule" refers, for example, to (i) antibodies and antigen-binding fragments thereof which bind the same epitope as or are derived from the 1.39.1 antibody (see PCT Publ. No. WO 2008/019290) disclosed in the instant application, e.g., the 39S antibody and antigen-binding fragments thereof, and in general molecules comprising such antibodies and antigen-binding fragments thereof; (ii) anti-HER2 antibodies and other HER2-binding molecules which bind the same epitope as or are derived from the 39S antibody which incorporate additional antigen-binding moieties, e.g., bispecific antibodies; (iii) antibody-drug conjugates (ADC) comprising at least one of the molecules according to (i) or (ii) conjugated to a cytotoxic moiety (e.g., a small molecule anticancer agent, a radionuclide, etc.), and (iv) anti-HER2 molecules according to (i) or (ii) having enhanced ADCC. As used herein, the term "39S antibody" refers to a lead optimized monoclonal antibody derived from the 1.39.1 antibody disclosed in PCT Publ. No. WO 2008/019290, wherein said optimized antibody comprises a VH comprising the amino acids of SEQ ID NO:15 and a VL comprising the amino acids of SEQ ID NO:16.

As used herein, the term "tubulysin" refers both collectively and individually to the naturally occurring tubulysins, and analogs and derivatives of tubulysins. Illustrative examples of tubulysins are disclosed, for example, in WO2004005326A2, WO2012019123A1, WO2009134279A1, WO2009055562A1, WO2004005327A1, U.S. Pat. No. 7,754,885, US20100240701, U.S. Pat. No. 7,816,377, US20110021568, and US20110263650 and in the Examples provided herein. It is to be understood that such derivatives include, for example, tubulysin prodrugs or tubulysins that include one or more protection or protecting groups, one or more linking moieties.

Cellular proliferation can be assayed using art recognized techniques which measure rate of cell division, and/or the fraction of cells within a cell population undergoing cell division, and/or rate of cell loss from a cell population due to terminal differentiation or cell death (e.g., thymidine incorporation).

The terms "antibody" or "immunoglobulin," as used interchangeably herein, include whole antibodies and any antigen binding fragment or single chains thereof and combinations thereof (e.g., bispecific antibodies).

A typical antibody comprises at least two heavy (H) chains and two light (L) chains interconnected by disulfide bonds. Each heavy chain is comprised of a heavy chain variable region (abbreviated herein as VH) and a heavy chain constant region (abbreviated herein as CH). The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include typical antibodies, scFvs, and combinations thereof where, for example, an scFv is covalently linked (for example, via peptidic bonds or via a chemical linker) to the N-terminus of either the heavy chain and/or the light chain of a typical antibody, or intercalated in the heavy chain and/or the light chain of a typical antibody.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain variable fragment (scFv), disulfide stabilized scFvs, multispecific antibodies such as bispecific antibodies generated from at least two intact antibodies and/or antigen binding fragments thereof, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

A "blocking" antibody or an "antagonist" antibody is one which inhibits or reduces biological activity of the antigen it binds, such as HER2. In a certain aspect, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The terms "anti-HER2 antibody" or "anti-HER2" refers to an antibody that is capable of binding HER2 with sufficient affinity such that the antibody is useful as a therapeutic agent or diagnostic reagent in targeting HER2. The extent of binding of an anti-HER2 antibody to an unrelated, non-HER2 protein is less than about 10% of the binding of the antibody to HER2 as measured, e.g., by a radioimmunoassay (RIA), or BIACORE™ (using recombinant HER2 as the analyte and antibody as the ligand, or vice versa), or other binding assays known in the art. In certain aspects, an antibody that binds to HER2 has a dissociation constant ($K_D$) of ≤1 μM, ≤100 nM, ≤10 nM, ≤1 nM, ≤0.1 nM, ≤10 pM, ≤1 pM, or ≤0.1 pM.

The terms "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDRs of a non-human species (e.g., mouse, rat, rabbit, or hamster) that have the desired specificity, affinity, and capability (Jones et al., 1986, *Nature*, 321:522-525; Riechmann et al., 1988, *Nature*, 332:323-327; Verhoeyen et al., 1988, *Science*, 239:1534-1536). In some instances, the FW residues of a human immunoglobulin are replaced with the corresponding residues in an antibody from a non-human species that has the desired specificity, and/or affinity, and/or capability.

The humanized antibody can be further modified by the substitution of additional residues either in the FW regions and/or within the replaced non-human residues to refine and optimize antibody specificity, and/or affinity, and/or capability. In general, the humanized antibody will comprise substantially all of at least one, and typically two or three, variable domains containing all or substantially all of the CDR regions that correspond to the non-human immunoglobulin whereas all or substantially all of the FW regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. Nos. 5,225,539 or 5,639,641.

A "variable region" of an antibody refers to the variable region of the antibody light chain or the variable region of the antibody heavy chain, either alone or in combination. The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) *J. Molec. Biol.* 273:927-948)). In addition, combinations of these two approaches are sometimes used in the art to determine CDRs. The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The phrases "amino acid position numbering as in Kabat," "Kabat position," and grammatical variants thereof refer to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence can contain fewer or additional amino acids corresponding to a shortening of, or insertion into, a FW or CDR of the variable domain. For example, a heavy chain variable domain can include a single amino acid insert (residue 52a according to Kabat) after residue 52 of H2 and inserted residues (e.g., residues 82a, 82b, and 82c, etc. according to Kabat) after heavy chain FW residue 82.

TABLE 1

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The Kabat numbering of residues can be determined for a given antibody by alignment at regions of homology of the sequence of the antibody with a "standard" Kabat numbered sequence. Chothia refers instead to the location of the structural loops (Chothia and Lesk, J. Mol. Biol. 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

IMGT (ImMunoGeneTics) also provides a numbering system for the immunoglobulin variable regions, including the CDRs. See e.g., Lefranc, M. P. et al., Dev. Comp. Immunol. 27: 55-77 (2003), which is herein incorporated by reference. The IMGT numbering system was based on an alignment of more than 5,000 sequences, structural data, and characterization of hypervariable loops and allows for easy comparison of the variable and CDR regions for all species. According to the IMGT numbering schema VH-CDR1 is at positions 26 to 35, VH-CDR2 is at positions 51 to 57, VH-CDR3 is at positions 93 to 102, VL-CDR1 is at positions 27 to 32, VL-CDR2 is at positions 50 to 52, and VL-CDR3 is at positions 89 to 97.

For all heavy chain constant region amino acid positions discussed in the present invention, numbering is according to the EU index first described in Edelman et al., 1969, Proc. Natl. Acad. Sci. USA 63(1):78-85, describing the amino acid sequence of myeloma protein Eu, which is the first human IgG1 sequenced. The Eu index of Edelman et al. is also set forth in Kabat et al., 1991, Sequences of Proteins of Immunological Interest, 5th Ed., United States Public Health Service, National Institutes of Health, Bethesda. Thus, the phrases "EU index as set forth in Kabat" or "EU index of Kabat" and "position . . . according to the EU index as set forth in Kabat," and grammatical variants thereof refer to the residue numbering system based on the human IgG1 Eu antibody of Edelman et al. as set forth in Kabat 1991.

The numbering system used for the variable domains (both heavy chain and light chain) and light chain constant region amino acid sequence is that set forth in Kabat 1991.

As used herein the Fc region includes the polypeptides comprising the constant region of an antibody excluding the first constant region immunoglobulin domain. Thus Fc refers to the last two constant region immunoglobulin domains of IgA, IgD, and IgG, and the last three constant region immunoglobulin domains of IgE and IgM, and the flexible hinge N-terminal to these domains. For IgA and IgM Fc can include the J chain. For IgG, Fc comprises immunoglobulin domains Cgamma2 and Cgamma3 (Cγ2 and Cγ3) and the hinge between Cgamma1 (Cγ1) and Cgamma2 (Cγ2).

Although the boundaries of the Fc region can vary, the human IgG heavy chain Fc region is usually defined to comprise residues C226 or P230 to its carboxyl-terminus, wherein the numbering is according to the EU index as set forth in Kabat. Fc can refer to this region in isolation, or this region in the context of an antibody, antibody fragment, or Fc fusion protein.

Polymorphisms have been observed at a number of different positions within antibody constant regions (e.g., Fc positions, including but not limited to positions 270, 272, 312, 315, 356, and 358 as numbered by the EU index as set forth in Kabat), and thus slight differences between the presented sequence and sequences in the prior art can exist. Polymorphic forms of human immunoglobulins have been well-characterized. At present, 18 Gm allotypes are known: G1m (1, 2, 3, 17) or G1m (a, x, f, z), G2m (23) or G2m (n), G3m (5, 6, 10, 11, 13, 14, 15, 16, 21, 24, 26, 27, 28) or G3m (b1, c3, b3, b0, b3, b4, s, t, g1, c5, u, v, g5) (Lefranc, et al., The human IgG subclasses: molecular analysis of structure, function and regulation. Pergamon, Oxford, pp. 43-78 (1990); Lefranc, G. et al., 1979, Hum. Genet.: 50, 199-211). It is specifically contemplated that the antibodies of the present invention may be incorporate any allotype, isoallotype, or haplotype of any immunoglobulin gene, and are not limited to the allotype, isoallotype or haplotype of the sequences provided herein.

The term "human antibody" means an antibody produced by a human or an antibody having an amino acid sequence corresponding to an antibody produced by a human made using any technique known in the art (e.g., recombinant expression in cultures cells, or expression in transgenic animals). Thus, the term human antibody also encompasses an antibody having an amino acid sequence corresponding to an antibody originally produced by a human (or an engineered variant or derivative thereof) but expressed in a non-human system (e.g., produced by chemical synthesis; recombinantly expressed in microbial, mammal, or insect cells; or expressed in an animal subject). Accordingly, an antibody obtained from a human subject or from human cells (e.g., hybridoma or cell line expressing a recombinant antibody or fragment thereof) and subsequently expressed in an animal, e.g., mice, is considered a human antibody. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another species (usually human) to avoid eliciting an immune response in that species.

The term "epitope" as used herein refers to an antigenic protein determinant capable of binding to an HER2 antibody or HER2 binding molecule disclosed herein. Epitopes usually consist of chemically active surface groupings of molecules such as amino acids or sugar side chains and usually have specific three dimensional structural characteristics, as well as specific charge characteristics. The part of an antibody or binding molecule that recognizes the epitope is called a paratope. The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

The term "antibody binding site" refers to a region in the antigen (e.g., HER2) comprising a continuous or discontinuous site (i.e., an epitope) to which a complementary antibody specifically binds. Thus, the antibody binding site can contain additional areas in the antigen which are beyond the epitope and which can determine properties such as binding affinity and/or stability, or affect properties such as antigen enzymatic activity or dimerization. Accordingly, even if two antibodies bind to the same epitope within an antigen, if the antibody molecules establish distinct intermolecular contacts with amino acids outside of the epitope, such antibodies are considered to bind to distinct antibody binding sites.

"Binding affinity" generally refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($K_D$). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present disclosure.

"Potency" is normally expressed as an $IC_{50}$ value, in nM unless otherwise stated. $IC_{50}$ is the median inhibitory concentration of an antigen-binding molecule. In functional assays, $IC_{50}$ is the concentration that reduces a biological response by 50% of its maximum. In ligand-binding studies, $IC_{50}$ is the concentration that reduces receptor binding by 50% of maximal specific binding level. $IC_{50}$ can be calculated by any number of means known in the art. Improvement in potency can be determined by measuring, e.g., against the 39S parent antibody.

The fold improvement in potency for the anti-HER2 binding molecule disclosed herein (for example, as compared to the 39S parent antibody, trastuzumab, or combinations thereof) can be at least about 2-fold, at least about 4-fold, at least about 6-fold, at least about 8-fold, at least about 10-fold, at least about 20-fold, at least about 30-fold, at least about 40-fold, at least about 50-fold, at least about 60-fold, at least about 70-fold, at least about 80-fold, at least about 90-fold, at least about 100-fold, at least about 110-fold, at least about 120-fold, at least about 130-fold, at least about 140-fold, at least about 150-fold, at least about 160-fold, at least about 170-fold, or at least about 180-fold or more.

"Antibody-dependent cell-mediated cytotoxicity" or "ADCC" refers to a form of cytotoxicity in which secreted immunoglobulins bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient (e.g., an anti-HER2 binding molecule disclosed herein) to be effective, and which contains no additional components which are unacceptably toxic to a subject to which the composition would be administered. Such composition can be sterile.

An "effective amount" of an anti-HER2 binding molecule as disclosed herein is an amount sufficient to carry out a specifically stated purpose. An "effective amount" can be determined empirically and in a routine manner, in relation to the stated purpose.

The term "therapeutically effective amount" refers to an amount of an anti-HER2 binding molecule disclosed herein or other drug effective to "treat" a disease or disorder in a subject or mammal.

The word "label" when used herein refers to a detectable compound or composition which is conjugated directly or indirectly to an anti-HER2 binding molecule disclosed herein so as to generate a "labeled" anti-HER2 binding molecule. The label can be detectable by itself (e.g., radioisotope labels or fluorescent labels) or, in the case of an enzymatic label, can catalyze chemical alteration of a substrate compound or composition which is detectable.

Terms such as "derivatizable group" and "derivatizable functional group" are used interchangeably and refer to a functional group that is capable of reacting to permit the formation of a covalent bond between an anti-HER2 binding molecule disclosed herein (e.g., a HER2 antibody) and another substance. In some aspects, such substance is a therapeutic moiety (e.g., a cytotoxin), a detectable label, a polymer (e.g., PEG), etc. Exemplary derivatizable groups include thiol, hydroxyl, amino, carboxy, and amide, as well as modified forms thereof, such as activated or protected forms.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In some aspects, the term cancer as used herein specifically refers to cancer expressing HER2. In some specific aspects, the term cancer refers to cancers expression low levels of HER2.

A "low level of HER2" as used herein, refers to a cancer cell, subject, or patient exhibiting a score of less than 2+(e.g., 1+) when using a HercepTest® (DakoCytomation California Inc., Carpenteria, Calif.) classification, or a cancer, cancer cell, subject or patient that has been identified as such, for example, by FISH.

To determine HER2 expression in the cancer, various diagnostic/prognostic assays are available. In one aspect, HER2 overexpression can be analyzed by IHC, e.g., by using HERCEPTEST® (Dako). Paraffin embedded tissue sections from a tumor biopsy can be subjected to the IHC assay and accorded a HER2 protein staining intensity criteria as follows/Alternatively, or additionally, FISH assays such as the INFORM™ (sold by Ventana, Ariz.) or PATHVISION™ (Vysis, Ill.) can be carried out on formalin-fixed, paraffin-embedded tumor tissue to determine the extent (if any) of HER2 overexpression in the tumor.

"Low" is a term that refers to a measure that is less than normal, less than a standard such as a predetermined measure or a subgroup measure that is relatively less than another subgroup measure. For example, low HER2 means a measure of HER2 that is less than a normal HER2 measure in a particular set of samples of patients that is HER2 positive. A normal HER2 measure can be determined according to any method available to one skilled in the art. Low HER2 can also mean a measure of HER2 that is less than a predetermined measure, such as a predetermined cutoff Low HER2 can also mean a measure wherein a low HER2 subgroup is relatively lower than another subgroup. For example, without limitation, according to the present specification, two distinct patient subgroups can be created by dividing samples around a mathematically determined point, such as, without limitation, a median, thus creating a group whose measure is low (i.e., less than the median) with respect to another group whose measure is high. HER2 can be measured by any method known to one skilled in the art such as, for example, without limitation, using the eTag method or using any standard IHC method such as HERCEPTEST®. As another example, low level of HER2 refers to a low level of HER2 homodimers, which means a measure of HER2 homodimers that is less than a normal measure of HER2 homodimers in a particular set of samples or patients that is HER2 positive. Low HER2 homodimers can also mean a measure that is less than a predetermined measure, such as a predetermined cutoff. Low HER2 homodimers can also mean a measure wherein a low HER2 homodimer subgroup is relatively less than another subgroup. HER2 homodimers can be measured by any method known in the art such as Fluorescence resonance energy transfer (FRET), Bioluminescent resonance energy transfer (BRET), proximity ligation assay (PLA), dimer-specific antibodies or eTag or any other method that is well known to one skilled in the art.

As used herein, the term "carcinomas" refers to cancers of epithelial cells, which are cells that cover the surface of the body, produce hormones, and make up glands. Examples of carcinomas are cancers of the skin, lung, colon, stomach, breast, prostate and thyroid gland.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly produced polypeptides and proteins expressed in engineered host cells are considered isolated for the purpose of the invention, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

Unless otherwise specified, the term "substituted" as used herein in the context of modifications to the chemical structure of the cytotoxic agents, i.e. tubulysins pertains to a parent group which bears one or more substituents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known. Examples of chemical substituents are described in more detail below.

The phrase "optionally substituted" as used herein in the context of modifications to the chemical structure of cytotoxic agents, pertains to a parent group which may be unsubstituted or which may be substituted.

The terms "substituted," "amino acid substitution" and the like as used herein in the context of polypeptides refers to replacing an amino acid residue present in a parent polypeptide with another amino acid residue. An amino acid can be substituted in a parent polypeptide, for example, via chemical peptide synthesis or through recombinant methods known in the art. Accordingly, references to a "substitution at position X" or "substitution at position X" refer to the substitution of an amino acid present at position X with an alternative amino acid residue. In some aspects, substitution patterns can described according to the schema AXY, wherein A is the single letter code corresponding to the amino acid naturally present at position X, and Y is the substituting amino acid residue. Accordingly, L234F would refer to the substitution of the leucine amino acid (L) at position 234 with a phenylalanine (F). In other aspects, substitution patterns can described according to the schema XY, wherein Y is the single letter code corresponding to the amino acid residue substituting the amino acid naturally present at position X. Accordingly, 239C would refer to the substitution of the native amino acid at position 239 with a cysteine (C).

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

Non-conservative amino acid substitutions include those in which (i) a residue having an electropositive side chain (e.g., Arg, His or Lys) is substituted for, or by, an electronegative residue (e.g., Glu or Asp), (ii) a hydrophilic residue (e.g., Ser or Thr) is substituted for, or by, a hydrophobic residue (e.g., Ala, Leu, Ile, Phe or Val), (iii) a cysteine or proline is substituted for, or by, any other residue, or (iv) a residue having a bulky hydrophobic or aromatic side chain (e.g., Val, His, Ile or Trp) is substituted for, or by, one having a smaller side chain (e.g., Ala, Ser) or no side chain (e.g., Gly).

Other amino acid substitutions can be readily identified by workers of ordinary skill. For example, for the amino acid alanine, a substitution can be taken from any one of D-alanine, glycine, beta-alanine, L-cysteine and D-cysteine. For lysine, a replacement can be any one of D-lysine, arginine, D-arginine, homo-arginine, methionine, D-methionine, ornithine, or D-ornithine. Generally, substitutions in functionally important regions that can be expected to induce changes in the properties of isolated polypeptides are those in which (i) a polar residue, e.g., serine or threonine, is substituted for (or by) a hydrophobic residue, e.g., leucine, isoleucine, phenylalanine, or alanine; (ii) a cysteine residue is substituted for (or by) any other residue; (iii) a residue having an electropositive side chain, e.g., lysine, arginine or histidine, is substituted for (or by) a residue having an electronegative side chain, e.g., glutamic acid or aspartic acid; or (iv) a residue having a bulky side chain, e.g., phenylalanine, is substituted for (or by) one not having such a side chain, e.g., glycine. The likelihood that one of the foregoing non-conservative substitutions may alter functional properties of the protein is also correlated to the position of the substitution with respect to functionally important regions of the protein: some non-conservative substitutions may accordingly have little or no effect on biological properties.

The term "amino acid insertion" refers to introducing a new amino acid residue between two amino acid residues present in the parent sequence. An amino acid can be inserted in a parent sequence, for example, via chemical peptide synthesis or through recombinant methods known in the art. Accordingly as used herein, the phrases "insertion between positions X and Y" or "insertion between Kabat positions X and Y," wherein X and Y correspond to amino acid positions (e.g., a cysteine amino acid insertion between positions 239 and 240), refers to the insertion of an amino acid between the X and Y positions, and also to the insertion in a nucleic acid sequence of a codon encoding an amino acid between the codons encoding the amino acids at positions X and Y. Insertion patterns can be described according to the schema AXins, wherein A is the single letter code corresponding to the amino acid being inserted, and X is the position preceding the insertion. Accordingly, C239ins would refer to the insertion of a cysteine amino acid (C) after position 239 (i.e., an insertion between position 239 and 240).

The term "percent sequence identity" between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence.

The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download. Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI) at www.ebi.ac.uk/Tools/psa.

Different regions within a single polynucleotide or polypeptide target sequence that aligns with a polynucleotide or polypeptide reference sequence can each have their own percent sequence identity. It is noted that the percent sequence identity value is rounded to the nearest tenth. For example, 80.11, 80.12, 80.13, and 80.14 are rounded down to 80.1, while 80.15, 80.16, 80.17, 80.18, and 80.19 are rounded up to 80.2. It also is noted that the length value will always be an integer.

In certain aspects, the percentage identity "X" of a first amino acid sequence to a second sequence amino acid is calculated as $100 \times (Y/Z)$, where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be higher than the percent identity of the second sequence to the first sequence.

One skilled in the art will appreciate that the generation of a sequence alignment for the calculation of a percent sequence identity is not limited to binary sequence-sequence comparisons exclusively driven by primary sequence data. Sequence alignments can be derived from multiple sequence alignments. One suitable program to generate multiple sequence alignments is ClustalW2, available from www.clustal.org. Another suitable program is MUSCLE, available from www.drive5.com/muscle/. ClustalW2 and MUSCLE are alternatively available, e.g., from the EBI.

It will also be appreciated that sequence alignments can be generated by integrating sequence data with data from heterogeneous sources such as structural data (e.g., crystallographic protein structures), functional data (e.g., location of mutations), or phylogenetic data. A suitable program that integrates heterogeneous data to generate a multiple sequence alignment is T-Coffee, available at www.tcoffee.org, and alternatively available, e.g., from the EBI. It will also be appreciated that the final alignment used to calculate percent sequence identity can be curated either automatically or manually.

II. Anti-HER2-Binding Molecules

The present disclosure provides anti-HER2 binding molecules, e.g., anti-HER2 antibodies or molecules comprising HER2-binding fragments thereof, that specifically bind HER2.

The full-length amino acid (aa) and nucleotide (nt) sequences for HER2 are known in the art (see, e.g., UniProt Acc. No. P04626 for human HER2). See, e.g., Yamamoto et al., Nature 319:230-234 (1986); Coussens et al., Science 230:1132-1139 (1985); Tal et al., Mol. Cell. Biol. 7:2597-2601 (1987); Semba et al., Proc. Natl. Acad. Sci. U.S.A. 82:6497-6501 (1985); King et al., Science 229:974-976 (1985); Sarkar et al., DNA Cell Biol. 12:611-615 (1993); Giri et al., Mol. Cell. Biol. 25:11005-11018 (2005); Anido et al., EMBO J. 25:3234-3244 (2006); Birrane et al., J. Biol. Chem. 278:1399-1402 (2003); Ivancic et al., J. Biomol. NMR 27:205-219 (2003); Cho et al., Nature 421:756-760 (2003); Franklin et al., Cancer Cell 5:317-328 (2004); Bostrom et al., Science 323:1610-1614 (2009); Eigenbrot et al., Proc. Natl. Acad. Sci. U.S.A. 107:15039-15044 (2010); Stephens et al., Nature 431:525-526 (2004); Greenman et al., Nature 446:153-158 (2007); all of which are herein incorporated by reference in their entireties.

In certain aspects, the anti-HER2 binding molecules are antibodies or antigen-binding fragments thereof. In some aspects, the anti-HER2 binding molecules, e.g., anti-HER2 antibodies or molecules comprising HER2-binding fragments thereof, comprise a Fab, a Fab', a F(ab')$_2$, a Fd, a single chain Fv, scFv, disulfide stabilized scFv, a disulfide linked Fv, a V-NAR domain, an IgNar, an intrabody, an IgGΔCH2, a minibody, a F(ab')$_3$, a tetrabody, a triabody, a diabody, a single-domain antibody, DVD-Ig, Fcab, mAb$^2$, a (scFv)$_2$, or a scFv-Fc. In some aspects, the antibody is of the IgG type, for example of the IgG1 type.

In some aspects, the anti-HER2 binding molecules are monospecific. In other aspects, the anti-HER2 binding molecules are bispecific, trispecific, tetraspecific, etc. In other aspects, the anti-HER2 binding molecules are multispecific. In some aspects, the anti-HER2 binding molecules are monovalent, bivalent, trivalent, tetravalent, etc. In yet other aspects, the anti-HER2 binding molecules are multivalent. In specific aspects, the anti-HER2 binding molecules are bivalent, e.g., an antibody comprising two HER2 specific antigen binding sites. In specific aspects, the anti-HER2 binding molecules are bispecific, i.e., the molecule can specifically bind to two different antigens (e.g., two different epitopes on the same or different molecules). In some specific aspects, the anti-HER2 binding molecules are bivalent and tetravalent, e.g., an antibody comprising four antigen-binding sites that are capable of binding to two different antigens (e.g., two different epitopes on the same or different molecules).

In certain aspects, the anti-HER2 binding molecules comprise antibodies or antigen-binding fragments thereof have a binding site that is substantially the same as the binding site of the 1.39.1 antibody (see PCT Publ. No. WO 2008/019290, which is herein incorporated by reference in its entirety). In a specific aspect, the anti-HER2 binding molecules comprise antibodies or antigen-binding fragments thereof bind one or more amino acid residues of SEQ ID NO: 52. In certain aspects, the anti-HER2 binding molecules comprise antibodies or antigen-binding fragments thereof have a binding site that overlaps the binding site of the 1.39.1 antibody.

In certain aspects, the anti-HER2 binding molecules comprise antibodies or antigen-binding fragments thereof comprising a VH and/or a VL that have been modified compared to the VH (SEQ ID NO:43) and/or the VL (SEQ ID NO:44) of the parent 1.39.1 antibody (see PCT Publ. No. WO 2008/019290). The modifications introduced in the parent antibody can include mutations (e.g., point mutations or replacement of an entire subsequence) in the CDR regions and/or in the FW regions of the VH and VL as compared to the parent 1.39.1 antibody.

In some aspects, the VH-CDR1 (SEQ ID NO:45) of the parent 1.39.1 antibody has been replaced with a VH-CDR1 comprising the amino acids of SEQ ID NO: 1. In some aspects, VH-CDR1 (SEQ ID NO:45) of the parent 1.39.1 antibody has been replaced with a VH-CDR1 consisting of the amino acids of SEQ ID NO: 1.

In other aspects, VH-CDR3 (SEQ ID NO:46) of the parent 1.39.1 antibody has been replaced with a VH-CDR3 comprising the amino acids of SEQ ID NO: 3. In other aspects, VH-CDR3 (SEQ ID NO:46) of the parent 1.39.1 antibody has been replaced with a VH-CDR3 consisting of the amino acids of SEQ ID NO: 3.

In some aspects, VH-CDR1 (SEQ ID NO:45) and VH-CDR3 (SEQ ID NO:46) of the parent 1.39.1 antibody have been replaced with a VH-CDR1 and a VH-CDR3 comprising or consisting of the amino acids of SEQ ID NO: 1 and the amino acids of SEQ ID NO:3, respectively.

In some aspects, the VL-CDR1 (SEQ ID NO:47) of the parent 1.39.1 antibody has been replaced with a VL-CDR1 comprising the amino acids of SEQ ID NO:4. In some aspects, VL-CDR1 (SEQ ID NO:3) of the parent 1.39.1 antibody has been replaced with a VH-CDR1 consisting of the amino acids of SEQ ID NO: 4.

In some aspects, the VL FW1 region (SEQ ID NO:48) of the parent 1.39.1 antibody has been replaced with a VL FW1 comprising the amino acids of SEQ ID NO: 11. In some aspects, the VL FW1 region (SEQ ID NO:48) of the parent 1.39.1 antibody has been replaced with a FW1 consisting of the amino acids of SEQ ID NO: 11.

In other aspects, the VL FW2 region (SEQ ID NO:49) of the parent 1.39.1 antibody has been replaced with a FW2 comprising the amino acids of SEQ ID NO: 12. In other aspects, the VL FW2 region (SEQ ID NO:49) of the parent 1.39.1 antibody has been replaced with a FW2 consisting of the amino acids of SEQ ID NO: 12.

In other aspects, the VL FW3 region (SEQ ID NO:50) of the parent 1.39.1 antibody has been replaced with a FW3 comprising the amino acids of SEQ ID NO: 13. In other aspects, the VL FW3 region (SEQ ID NO:50) of the parent 1.39.1 antibody has been replaced with a VL FW2 consisting of the amino acids of SEQ ID NO: 13.

In some aspects, the VL FW1 region (SEQ ID NO:48) and/or the FW2 region (SEQ ID NO:49) and/or the FW3 region (SEQ ID NO:50) of the parent 1.39.1 antibody have been replaced with a FW1 and/or a FW2 and/or a FW3 independently comprising or consisting of the amino acids of SEQ ID NOS: 11, 12, or 13, respectively.

In some aspects the present disclosure provides an anti-HER2 binding molecule comprising an immunoglobulin heavy chain variable region (VH) and an immunoglobulin light chain variable region (VL), wherein the VH comprises the amino acids of SEQ ID NO:15. In some aspects, the present disclosure provides an anti-HER2 binding molecule comprising a VH and a VL, wherein the VL comprises the amino acids of SEQ ID NO:16. In some aspects, the VH comprises the amino acids of SEQ ID NO:15 and the VL comprises the amino acids of SEQ ID NO:16. In some aspect, an anti-HER2 binding molecule disclosed herein comprises an antibody, or a HER2-binding fragment thereof.

In certain aspects, an anti-HER2 binding molecule of the instant disclosure comprises an immunoglobulin heavy chain (VH) and an immunoglobulin light chain (VL), wherein the binding molecule comprises:
(i) VH-CDR1 comprising the amino acids of SEQ ID NO: 1;
(ii) VH-CDR2 comprising the amino acids of SEQ ID NO: 2;
(iii) VH-CDR3 comprising the amino acids of SEQ ID NO: 3;
(iv) VL-CDR1 comprising the amino acids of SEQ ID NO: 4;
(v) VL-CDR2 comprising the amino acids of SEQ ID NO: 5; and,
(vi) VL-CDR3 comprising the amino acids of SEQ ID NO: 6.

In certain aspects, an anti-HER2 binding molecule of the instant disclosure (e.g., an anti-HER2 antibody or HER2-binding fragment thereof, or a bispecific anti-HER2 antibody) comprises an antibody VL and an antibody VH, wherein the VL comprises an amino acid sequence at least about 80%, about 85%, about 90%, about 95%, about 96%, about 97%, about 98%, about 99%, or about 100% identical to a reference VL comprising or consisting of the amino acids of SEQ ID NO: 16.

In other aspects, an anti-HER2 binding molecule of the instant disclosure (e.g., an anti-HER2 antibody or HER2-binding fragment thereof, or a bispecific anti-HER2 antibody) comprises an antibody VL and an antibody VH, wherein the VH comprises an amino acid sequence at least about 80%, about 85%, about 90%, about 95%, about 96%, about 97%, about 98%, about 99%, or about 100% identical to a reference VH comprising or consisting of the amino acids of SEQ ID NO:15.

In other aspects, an anti-HER2 binding molecule of the instant disclosure (e.g., an anti-HER2 antibody or HER2-binding fragment thereof, or a bispecific anti-HER2 antibody) comprises a VL comprising a sequence at least about 80%, about 85%, about 90%, about 95%, about 96%, about 97%, about 98%, about 99%, or about 100% identical to a reference VL comprising or consisting of the amino acids of SEQ ID NO:16, and further comprises a VH comprising a sequence at least about 80%, about 85%, about 90%, about 95%, about 96%, about 97%, about 98%, about 99%, or about 100% identical to a reference VH comprising or consisting of the amino acids of SEQ ID NO:15.

In some aspects, the anti-HER2 binding molecule of the instant disclosure (e.g., an anti-HER2 antibody or HER2-binding fragment thereof, or a bispecific anti-HER2 antibody) comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In certain aspects, an anti-HER2 binding molecule of the instant disclosure (e.g., an anti-HER2 antibody or HER2-binding fragment thereof, or a bispecific anti-HER2 antibody) can bind HER2 with substantially the same or better affinity as the 1.39.1 parent antibody. Thus, in one aspect, an anti-HER2 binding molecule of the instant disclosure (e.g., an anti-HER2 antibody or HER2-binding fragment thereof, or a bispecific anti-HER2 antibody) specifically binds HER2 and antigenic fragments thereof with a dissociation constant or $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

In another aspect, an anti-HER2 binding molecule of the instant disclosure (e.g., an anti-HER2 antibody or HER2-binding fragment thereof, or a bispecific anti-HER2 antibody) binds to HER2 and/or antigenic fragments thereof with a $k_{off}$ of less than $1 \times 10^{-3}$ s$^{-1}$, or less than $2 \times 10^{-3}$ s$^{-1}$. In other aspects, an anti-HER2 binding molecule of the instant disclosure (e.g., an anti-HER2 antibody or HER2-binding fragment thereof, or a bispecific anti-HER2 antibody) binds to HER2 and antigenic fragments thereof with a $k_{off}$ of less than $10^{-3}$ s$^{-1}$, less than $5 \times 10^{-3}$ s$^{-1}$, less than $10^{-4}$ s$^{-1}$, less than $5 \times 10^{-4}$ s$^{-1}$, less than $10^{-5}$ s$^{-1}$, less than $5 \times 10^{-5}$ s$^{-1}$, less than $10^{-6}$ s$^{-1}$, less than $5 \times 10^{-6}$ s$^{-1}$, less than less than $5 \times 10^{-7}$ s$^{-1}$, less than $10^{-8}$s$^{-1}$, less than $5 \times 10^{-8}$s$^{-1}$, less than $10^{-9}$ s$^{-1}$, less than $5 \times 10^{-9}$ s$^{-1}$, or less than $10^{-10}$ s$^{-1}$.

In another aspect, an anti-HER2 binding molecule of the instant disclosure (e.g., an anti-HER2 antibody or HER2-binding fragment thereof, or a bispecific anti-HER2 antibody) binds to HER2 and/or antigenic fragments thereof with an association rate constant or $k_{on}$ rate of at least $10^5$ M$^{-1}$ s$^{-1}$, at least $5 \times 10^5$ M$^{-1}$ s$^{-1}$, at least $10^6$ M$^{-1}$ s$^{-1}$, at least $5 \times 10^6$ M$^{-1}$ s$^{-1}$, at least $10^7$ M$^{-1}$ s$^{-1}$, at least $5 \times 10^7$ M$^{-1}$ s$^{-1}$, or at least $10^8$ M$^{-1}$ s$^{-1}$, or at least $10^9$ M$^{-1}$ s$^{-1}$.

In other aspects, the VH and/or VL amino acid sequences can be 85%, 90%, 95%, 96%, 97%, 98% or 99% similar to the sequences set forth above, and comprise 1, 2, 3, 4, 5 or more conservative substitutions. An anti-HER2 binding molecule disclosed herein having VH and VL regions having high (i.e., 80% or greater) similarity to the VH region of SEQ ID NOs:16 and/or VL region of SEQ ID NOs:15, respectively, can be obtained by mutagenesis (e.g., site-directed or PCR-mediated mutagenesis) of their respective encoding nucleic acid molecules, followed by testing of the altered antibody for retained function using the functional assays described herein.

The affinity and/or avidity of an anti-HER2 binding molecule disclosed herein for an antigen can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can also be readily employed. See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein.

The measured affinity of the interaction of a particular anti-HER2 binding molecule disclosed herein with a HER2 antigen can vary if measured under different conditions (e.g., salt concentration, pH, temperature). Thus, measurements of affinity and other antigen-binding parameters (e.g., $K_D$ or Kd, $k_{on}$, $k_{off}$) are made with standardized solutions of anti-HER2 binding molecule and antigen, and a standardized buffer, as known in the art and such as the buffer described herein.

It also known in the art that affinities measured using BIACORE™ analysis can vary depending on which one of the reactants is bound to the chip. In this respect, affinity can be measured using a format in which the targeting anti-HER2 binding molecule is immobilized onto the chip (referred to as an "IgG down" format) or using a format in which the target protein (e.g., HER2) is immobilized onto the chip (referred to as, e.g., a "HER2 down" format).

III. Bispecific Anti-HER2 Binding Molecules

The present disclosure also provides bispecific anti-HER2 antibodies comprising a first immunoglobulin antigen-binding domain and a second immunoglobulin antigen-binding domain, wherein:
(i) the first and second immunoglobulin antigen-binding domains specifically bind to distinct HER2 antibody binding sites;
(ii) the first immunoglobulin antigen-binding domain binds to a first HER2 antibody binding site which comprises an epitope within domain II of HER2; and,
(iii) the first HER2 antibody binding site is distinct from the antibody binding site of pertuzumab.

In some aspects, the first immunoglobulin antigen-binding domain binds to a
HER2 antibody binding site which comprises an epitope within domain II of HER2. In some aspects, the first HER2 antibody binding site is identical the HER2 antibody binding site of the 1.39.1 or 39S antibodies. In some aspects, the first HER2 antibody binding site partially overlaps with the HER2 antibody binding site of the 1.39.1 or 39S antibodies. In other aspects, the first HER2 antibody binding site is distinct from the HER antibody binding site of the 1.39.1 or 39S antibodies.

In some aspects, the second immunoglobulin antigen-binding domain binds to a second HER2 antibody binding site which comprises an epitope within domain IV of HER2. In some aspects, the second HER2 antibody binding site is identical the HER2 antibody binding site of trastuzumab. In some aspects, the second HER2 antibody binding site partially overlaps with the HER2 antibody binding site of trastuzumab. In other aspects, the second HER2 antibody binding site is distinct from the HER antibody binding site of trastuzumab.

In some aspects, the bispecific anti-HER2 antibody comprises a comprising a first immunoglobulin antigen-binding domain and a second immunoglobulin antigen-binding domain, wherein (i) the first and second immunoglobulin antigen-binding domains specifically bind to distinct HER2 antibody binding sites, (ii) the first immunoglobulin antigen-binding domain binds to a first HER2 antibody binding site which comprises an epitope within domain II of HER2 and is distinct from the antibody binding site of pertuzumab, and (iii) the second immunoglobulin antigen-binding domain competes with HERCEPTIN® for binding to domain IV of HER2.

The present disclosure also provides bispecific anti-HER2 molecules which bind the same epitope as or are derived from the anti-HER2 binding molecules disclosed above (i.e., lead optimized antibodies derived from the 1.39.1 parent antibody, for example, the 39S antibody). In some aspects, such bispecific anti-HER2 molecules are bispecific anti-HER2 antibodies and molecules derived from such bispecific antibodies. In some aspects, such molecules derived from the bispecific anti-HER2 molecules described herein are antibody-drug conjugates (ADC). In certain aspects, the ADCs provided herein have reduced ADCC activity. In some aspects, such molecules derived from the bispecific anti-HER2 molecules described herein have enhanced ADCC activity.

The present disclosure also provides a bispecific HER antibody comprising a first immunoglobulin and a second immunoglobulin antigen-binding domain wherein (i) the first and second immunoglobulin antigen-binding domains specifically bind to distinct HER2 epitopes; and (ii) wherein the first immunoglobulin antigen-binding domain binds HER2 to one or more amino acid residues in SEQ ID NO: 52. In some aspects, the second immunoglobulin antigen-binding domain binds HER2 at an epitope within domain IV. In other aspects, the second immunoglobulin antigen-binding domain binds HER2 to one or more amino acid residues in SEQ ID NO: 53.

Accordingly, in one aspect, the instant disclosure provides bispecific anti-HER2 antibodies comprising a first immunoglobulin antigen-binding domain and a second immunoglobulin antigen-binding domain, wherein the first immunoglobulin antigen-binding domain comprises a heavy chain (HC) variable region (VH), and a light chain (LC) variable region (VL) comprising:
  (i) a variable heavy chain CDR-1 (VH-CDR1) sequence identical to SEQ ID NO: 1 or identical to SEQ ID NO: 1 except for up to 1, 2, 3, or 4 amino acid substitutions;
  (ii) a variable heavy chain CDR-2 (VH-CDR2) sequence identical to SEQ ID NO: 2 or identical to SEQ ID NO: 2 except for up to 1, 2, 3, or 4 amino acid substitutions;
  (iii) a variable heavy chain CDR-3 (VH-CDR3) sequence identical to SEQ ID NO: 3 or identical to SEQ ID NO: 3 except for up to 1, 2, 3, or 4 amino acid substitutions;
  (iv) a variable light chain CDR-1 (VL-CDR1) sequence identical to SEQ ID NO: 4 or identical to SEQ ID NO: 4 except for up to 1, 2, 3, or 4 amino acid substitutions;
  (v) a variable light chain CDR-2 (VL-CDR2) sequence identical to SEQ ID NO: 5 or identical to SEQ ID NO: 5 except for up to 1, 2, 3, or 4 amino acid substitutions; and,
  (vi) a variable light chain CDR-3 (VL-CDR3) sequence identical to SEQ ID NO: 6 or identical to SEQ ID NO: 6 except for up to 1, 2, 3, or 4 amino acid substitutions;
wherein the second immunoglobulin antigen-binding domain comprises an scFv antibody fragment; and, wherein the first and second immunoglobulin antigen-binding domains specifically bind to distinct HER2 epitopes.

In some aspects, the first immunoglobulin antigen-binding domain of the bispecific anti-HER2 antibody comprises at least one heterologous variable domain framework region (FW) different relative to the FW regions of an immunoglobulin antigen-binding domain comprising a VH comprising the amino acids of SEQ ID NO:43 and a VL comprising the amino acids of SEQ ID NO:44;

In some aspects, the first immunoglobulin antigen-binding domain of the bispecific anti-HER2 antibody comprises (i) a variable light chain framework 1 (VL-FW1) comprising the amino acids of SEQ ID NO:11; (ii) a variable light chain framework 2 (VL-FW2) comprising the amino acids of SEQ ID NO:12; (iii) a VL-variable light chain framework 3 (VL-FW3) comprising the amino acids of SEQ ID NO:13; (iv) a variable light chain framework 4 (VL-FW4) comprising the amino acids of SEQ ID NO:14; or (v) any combination thereof.

In some aspects, the first immunoglobulin antigen-binding domain of the bispecific HER2 antibody comprises (i) a VL-FW1 consisting of the amino acids of SEQ ID NO:11; (ii) a VL-FW2 consisting of the amino acids of SEQ ID NO:12; (iii) a VL-FW3 consisting of the amino acids of SEQ ID NO:13; (iv) a VL-FW4 consisting of the amino acids of SEQ ID NO:14; or (v) any combination thereof.

In other aspects, the bispecific anti-HER2 antibody disclosed herein comprises a first immunoglobulin antigen binding-domain and a second immunoglobulin antigen-binding domain, wherein:
(i) the first immunoglobulin antigen-binding domain comprises a VH and a VL, wherein the VH comprises the amino acids of SEQ ID NO:15 or SEQ ID NO:43;
(ii) the second immunoglobulin antigen-binding domain comprises an scFv antibody fragment; and,
(iii) the first and second immunoglobulin antigen-binding domains specifically bind to distinct HER2 epitopes.

In other aspects, the bispecific anti-HER2 antibody comprises a first immunoglobulin antigen binding-domain and a second immunoglobulin antigen-binding domain, wherein:
(i) the first immunoglobulin antigen-binding domain comprises a VH and a VL, wherein the VH consists of the amino acids of SEQ ID NO:15 or SEQ ID NO:43;
(ii) the second immunoglobulin antigen-binding domain comprises an scFv antibody fragment; and,
(iii) the first and second immunoglobulin antigen-binding domains specifically bind to distinct HER2 epitopes.

In some aspects, the bispecific anti-HER2 antibody comprises a first immunoglobulin antigen binding-domain and a second immunoglobulin antigen-binding domain, wherein:
(i) the first immunoglobulin antigen-binding domain comprises a VH and a VL, wherein the VL comprises the amino acids of SEQ ID NO:16 or SEQ ID NO:44;
(ii) the second immunoglobulin antigen-binding domain comprises an scFv antibody fragment; and,
(iii) the first and second immunoglobulin antigen-binding domains specifically bind to distinct HER2 epitopes.

In some aspects, the bispecific anti-HER2 antibody comprises a first immunoglobulin antigen binding-domain and a second immunoglobulin antigen-binding domain, wherein:
(i) the first immunoglobulin antigen-binding domain comprises a VH and a VL, wherein the VL consists of the amino acids of SEQ ID NO:16 or SEQ ID NO:44;
(ii) the second immunoglobulin antigen-binding domain comprises an scFv antibody fragment; and,
(iii) the first and second immunoglobulin antigen-binding domains specifically bind to distinct HER2 epitopes.

In some aspects, the bispecific anti-HER2 antibody comprises a first immunoglobulin antigen binding-domain and a second immunoglobulin antigen-binding domain, wherein:
(i) the first immunoglobulin antigen-binding domain comprises a VH and a VL, wherein the VL comprises the amino acids of SEQ ID NO:16 or SEQ ID NO:44, and the VH comprises the amino acids of SEQ ID NO:15 or SEQ ID NO:45;
(ii) the second immunoglobulin antigen-binding domain comprises an scFv antibody fragment; and,
(iii) the first and second immunoglobulin antigen-binding domains specifically bind to distinct HER2 epitopes.

In some aspects, the bispecific anti-HER2 antibody comprises a first immunoglobulin antigen binding-domain and a second immunoglobulin antigen-binding domain, wherein:
(i) the first immunoglobulin antigen-binding domain comprises a VH and a VL, wherein the VL consists of the amino acids of SEQ ID NO:16 or SEQ ID NO:44, and the VH consists of the amino acids of SEQ ID NO:15 or SEQ ID NO: 43;
(ii) the second immunoglobulin antigen-binding domain comprises an scFv antibody fragment; and,
(iii) the first and second immunoglobulin antigen-binding domains specifically bind to distinct HER2 epitopes.

In some aspects, the first immunoglobulin antigen binding domain of the bispecific anti-HER2 antibody comprises or consists of:
(a) a VH further comprising a heavy chain constant region or a fragment thereof, and a VL comprising a light chain constant region (LC) or a fragment thereof;
(b) a single chain Fv ("scFv");
(c) a diabody;
(d) a minibody;
(e) an F(ab')2; or
(f) an F(ab).

In some aspects, the heavy chain constant region or fragment thereof of the bispecific anti-HER2 antibody is an IgG constant region. In some aspects, the IgG constant region or fragment thereof is an IgG1, IgG2, IgG3, or IgG4 constant region. In specific aspects, the IgG constant region is an IgG1 constant region. In some aspects, the first immunoglobulin antigen binding domain of the bispecific anti-HER2 antibody comprises a VL comprising a light chain constant region (LC), wherein the LC constant region is a kappa constant region. In some aspects, the first immunoglobulin antigen binding domain of the bispecific anti-HER2 antibody comprises a VL comprising a light chain constant region (LC), wherein the LC constant region is a lambda constant region.

In some aspects, the first immunoglobulin antigen-binding domain of the bispecific anti-HER2 antibody is, for example, a monoclonal antibody, a humanized antibody, a chimeric antibody, or an affinity optimized antibody. In some aspects, the first immunoglobulin antigen-binding domain of the bispecific anti-HER2 antibody is, for example, a human antibody. In some aspects, the human antibody is expressed in a transgenic mouse (see, for example, Bruggemann, "Human antibody expression in transgenic mice," *Arch. Immunol. Therap. Exper.* 49: 203-208, 2001, which is herein incorporated by reference in its entirety).

In some aspects, the first immunoglobulin antigen-binding domain of the bispecific anti-HER2 antibody does not compete with trastuzumab or pertuzumab for epitope binding. In some aspects, the first and second immunoglobulin antigen binding domains of the bispecific anti-HER2 antibody specifically bind to distinct HER2 epitopes. In some aspects, the distinct HER2 epitopes are non-overlapping.

In some aspects, the second immunoglobulin antigen-binding domain of the bispecific anti-HER2 antibody (i) specifically binds to the same HER2 epitope as the trastuzumab antibody; and/or (ii) competitively inhibits HER2 binding by the trastuzumab antibody; and/or (iii) comprises at least one, at least two, at least three, at least four, at least five, or at least six complementarity determining regions (CDRs) of comprising the amino acids of any one of SEQ ID NOs: 54 to 59.

In some aspects, the second immunoglobulin antigen-binding domain of the bispecific anti-HER2 antibody comprises an scFv. In some specific aspects, the second immunoglobulin antigen-binding domain of the bispecific anti-HER2 antibody comprises a disulfide stabilized scFv (ds-scFv). In some aspects, the disulfide stabilized scFv specifically binds to the same HER2 epitope as the trastuzumab antibody.

A stabilizing disulfide can be engineered between the VH and VL regions of an scFv by introducing cysteine substitutions at positions selected such that the cysteine residues can form a disulfide bond. In particular, such a disulfide can be introduced in the framework regions such that the VL and VH regions are linked by a disulfide bond. The position of representing but not limiting residues in the VH and VL regions meeting these criteria are provided in TABLE 2.

TABLE 2

| VH-VL pairs‡ | | |
|---|---|---|
| VH44 + VL100 | VH55 + VL101 | VH101 + VL46 |
| VH44 + VL105 | VH100 + VL50 | VH105 + VL43 |
| VH45 + VL87 | VH98 + VL 46 | VH106 + VL57 |

‡Numbering in TABLE 2 is according to the Kabat index as set forth in Kabat.. It will be understood that the wild type amino acid residue at these positions will vary. Regardless of the wild type amino acid residue each position of a given pair will be substituted with a Cysteine.

The scFv disclosed herein are obtainable from or produced by any suitable source, whether natural or not, or it may be a recombinant scFv, a synthetic scFv, a semi-synthetic scFv, a derivatized scFv, a fermentation optimized scFv, a fusion protein or equivalents, mutants and derivatives thereof as long as it retains the required binding specificity of the scFv's of the present disclosure. These include a scFv with binding specificity which has amino acid substitutions or has sugars or other molecules attached to amino acid functional groups. The term "derivative" or "derivatized" as used herein with respect to an scFv includes chemical modification of an scFv. Illustrative of such modifications would be replacement of hydrogen by an alkyl, acyl, or amino group.

In some aspects, the second immunoglobulin antigen-binding domain is an scFv comprising:
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and,
(vi) a VL-CDR3 comprising the amino acids of SEQ ID NO:59.

In some aspects, the second immunoglobulin antigen-binding domain of the bispecific anti-HER2 antibody consists of a scFv that specifically binds to the same HER2 epitope as the trastuzumab antibody and comprises VH and VL derived from the VH and VL of the trastuzumab antibody (e.g., the native VH and/or VL present in the trastuzumab antibody, or VH and/or VL mutants with stabilizing mutations, e.g., the pairs of mutations shown in TABLE 2). See Goldenger, Clin. Ther. 21:309-18 (1999). Accordingly, in some aspects, the scFv that binds the same epitope as trastuzumab comprises a VH comprising the amino acids of SEQ ID NO:17, and a VL comprising the amino acids of SEQ ID NO:18. In some aspects, the scFv that binds the same epitope as trastuzumab comprises a VH consisting of the amino acids SEQ ID NO:17, and a VL consisting of the amino acids of SEQ ID NO:18. In some specific aspects, the VH and VL of the scFv that binds the same epitope as trastuzumab are covalently linked via a peptide linker. In some aspects, the peptide linker comprises the amino acids of SEQ ID NO:19. In some aspects, the peptide linker consists of the amino acids of SEQ ID NO:19.

As discussed above, a person skilled in the art will appreciate that scFv's that bind the same epitope as trastuzumab include sequences derived from trastuzumab, comprising for example mutant sequences wherein at least one amino acid has been deleted or substituted with respect to a parent sequence in the trastuzumab antibody, as long as the resulting molecule is capable of specifically binding to the same HER2 epitope as the trastuzumab antibody, e.g., mutations designed to introduce at least one stabilizing disulfide between the VH and VL of the scFv.

In some aspects, the second immunoglobulin antigen-binding domain of the bispecific anti-HER2 antibody is covalently linked to the carboxy-terminus of the HC of the first immunoglobulin antigen-binding domain. In some aspects, the bispecific anti-HER2 antibody comprises at least one linker interposed between the second immunoglobulin antigen binding domain and the carboxy-terminus of the HC of the first immunoglobulin antigen-binding domain. In some specific aspects, one linker is interposed between the second immunoglobulin antigen binding domain and the carboxy-terminus of the HC of the first immunoglobulin antigen-binding domain.

In some aspects, the second immunoglobulin antigen-binding domain is covalently linked to the amino-terminus of the HC of the first immunoglobulin antigen-binding domain. In some aspects, the bispecific anti-HER2 antibody comprises at least one linker interposed between the second immunoglobulin antigen-binding domain and the amino-terminus of the HC of the first immunoglobulin antigen-binding domain. In specific aspects, one linker is interposed between the second immunoglobulin antigen-binding domain and the amino-terminus of the HC of the first immunoglobulin antigen-binding domain.

In some aspects, the second immunoglobulin antigen binding domain of the bispecific anti-HER2 antibody is covalently intercalated in the sequence of the HC of the first immunoglobulin antigen-binding domain. In some aspects, the second immunoglobulin antigen binding domain of the bispecific anti-HER2 antibody is covalently intercalated between the CH1 region and CH2 region of the HC of the first immunoglobulin antigen-binding domain. In some aspects, one or more linkers connect the second immunoglobulin antigen binding domain of the bispecific anti-HER2 antibody to the CH1 region and/or the CH2 region of the HC of the first immunoglobulin antigen-binding domain.

In some specific aspects, the bispecific anti-HER2 antibody comprises (i) a linker interposed between the CH1 region of the HC of the first immunoglobulin antigen binding domain and the second immunoglobulin antigen binding domain; and (ii) a second linker interposed between the second immunoglobulin antigen binding domain and the CH2 region of the HC of the of the first immunoglobulin antigen-binding domain. In some aspects, the first linker and the second linker are identical. In some aspects, the first linker and the second linker are different. In some aspects, one or more of the linkers comprise a peptide linker. In some aspects, the peptide linker comprises at least one, at least two, at least three, at least four, at least five, at least 10, at least 15, at least 20, at least 25, or at least 30 amino acids. In some aspects, the peptide linker comprises more than 20 amino acids. In some aspects, the peptide linker comprises a peptide having the formula Ser$_x$[(Gly)$_y$-Ser$_4$]$_z$ where x is from 0 to 1, y is from 1 to 4, and z is from 1 to 10 (SEQ ID NO: 60). In some aspects, the peptide linker comprises a sequence selected from SEQ ID NOS:19, 20, 21 or 22.

In some aspects, the bispecific anti-HER2 antibody comprises a heavy chain comprising a constant region comprising an Fc domain. In some aspects, the Fc domain comprises a CH2 region, and/or a CH3 region, and/or fragments thereof. In some specific aspects, the Fc domain comprises a CH2 region and a CH3 region. In some aspects, the Fc domain consists of a CH2 region and a CH region. In some aspects, the Fc domain is an IgG Fc domain, from example, an Fc domain from an IgG1, IgG2, IgG3, or IgG4. In some aspects, the IgG Fc domain is a human or humanized IgG Fc domain. In some aspects, the Fc domain is an IgG1 Fc domain.

In some aspects, the IgG Fc domain, for example an IgG1 Fc domain, is a native (wild type) domain. In some aspects, the native IgG1 Fc domain comprises the amino acids of SEQ ID NO: 23. In other aspects, the native IgG1 Fc domain consists of the amino acids of SEQ ID NO: 23. In other aspects, the Fc domain is a mutant IgG domain, for example, a mutant IgG1, IgG2, IgG3, or IgG4 domain. In some specific aspects, the mutant Fc domain is a mutant IgG1 Fc domain.

In some aspects, the mutant IgG domain, for example, a human or humanized IgG1 Fc domain, comprises at least one mutation capable of reducing the ADCC activity of the bispecific anti-HER2 antibody. In certain aspects, at least one mutation capable of reducing the ADCC activity of the anti-HER2 bispecific antibody is an amino acid substitution. In some aspects, the bispecific anti-HER2 antibody with reduced ADCC activity comprises at least one amino acid substitution selected from L234F, S239C, S239A, a cysteine amino acid insertion between positions 239 and 240, or any combination thereof, wherein the amino acid position numbering is according to the EU index as set forth in Kabat. Numerous mutations capable of reducing the ADCC activity of an antibody are known in the art. For example, see the mutations described in WO2012175751, WO2011149999, WO2011066501, WO2000042072, WO2011120134, which are herein incorporated by reference in their entireties. Antibodies with reduced ADCC effector function also include those with substitution of one or more of Fc region residues 238, 265, 269, 270, 297, 327 and 329 (U.S. Pat. No. 6,737,056), wherein the amino acid position numbering is according to the EU index as set forth in Kabat. Such Fc mutants also include Fc mutants with substitutions at two or more of amino acid positions 265, 269, 270, 297 and 327, including Fc mutant with substitution of residues 265 and 297 to alanine (U.S. Pat. No. 7,332,581, wherein the amino acid position numbering is according to the EU index as set forth in Kabat).

In some aspects, the mutant IgG domain, for example, a human or humanized IgG1 Fc domain, comprises at least one mutation capable of enhancing the ADCC activity of the bispecific anti-HER2 antibody. In certain aspects, at least one mutation capable of enhancing the ADCC activity of the anti-HER2 bispecific antibody is an amino acid substitution. In some aspects, the bispecific anti-HER2 antibody with enhanced ADCC activity comprises at least one amino acid substitution selected from S239A, S239D, A330L, I332E, E333A, K334A or any combination thereof, wherein the amino acid position numbering is according to the EU index as set forth in Kabat. Additional mutations which enhance ADCC activity are known to one skilled in the art including but not limited to those exemplified in Tables 2, and 6-10 of U.S. Pat. No. 6,737,056; the tables presented in FIG. 41 of US 2006/024298; the tables presented in FIGS. 5, 12, and 15 of US 2006/235208; the tables presented in FIGS. 8, 9 and 10 of US 2006/0173170 and the tables presented in FIGS. 8, 9 and 10 of WO 09/058492.

In some aspects, the mutant IgG1 Fc domain can comprise at least one amino acid substitution introducing a derivatizable functional group. In some aspects, the mutant IgG1 Fc domain comprises one to three amino acid substitutions introducing a derivatizable functional group. In some aspects, the derivatizable group is the sulfhydryl side chain of a cysteine amino acid. In particular aspects, the substituted amino acid or amino acids occur at accessible sites of the anti-HER2 binding molecule. By substituting those amino acid residues with cysteine, reactive thiol groups are thereby positioned at accessible sites of the anti-HER2 binding molecule and can be used to conjugate the anti-HER2 binding molecule to other moieties, such as drug moieties or linker-drug moieties, to create an immunoconjugate, as described further herein. Cysteine engineered antibodies can be generated as described, e.g., in U.S. Pat. No. 7,521,541.

In some aspects, the derivatizable group is introduced at Kabat position 239, 248, 254, 258, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 435, 440, 441, 442, 443 or 446, at an amino acid inserted between positions 239 and 240, or any combination thereof, wherein the amino acid position numbering is according to the EU index as set forth in Kabat. In some aspects, the amino acid or amino acid substitution introducing a derivatizable sulfhydryl group is selected from the group consisting of S239C, 248C, 254C, 258C, 273C, 279C, 282C, 284C, 286C, 287C, 289C, 297C, 298C, 312C, 324C, 326C, 330C, 335C, 337C, 339C, 350C, 355C, 356C, 359C, 360C, 361C, 375C, 383C, 384C, 389C, 398C, 400C, 413C, 415C, 418C, 422C, 435C, 440C, 441C, S442C, 443C and 446C, a cysteine amino acid insertion between positions 239 and 240, or any combination thereof, wherein the amino acid position numbering is according to the EU index as set forth in Kabat. In some aspects, the amino acid or amino acid substitution introducing a derivatizable sulfhydryl group is S239C and/or S442C.

Selectively derivatizable groups are well known in the art, such as an amino group, sulfhydryl group, pendant oxyamino, or other nucleophilic groups. Derivatizable groups can be joined to a polypeptide chain via one or more linkers. Ligands (e.g., therapeutic moieties, detectable labels, half-life extending polymers, etc.) can be attached to the derivatizable groups using the appropriate attachment chemistry. This coupling chemistry can include, for example, amide, urea, thiourea, oxime, aminoacetylamide, etc.

In some aspects, the Fc domain has an altered type of glycosylation that enhances ADCC activity. The glycosylation of the Fc region can be modified to increase or decrease effector function (see for examples, Umana et al, 1999, Nat. Biotechnol 17:176-180; Davies et al., 2001, Biotechnol Bioeng 74:288-294; Shields et al, 2002, J Biol Chem 277:26733-26740; Shinkawa et al., 2003, J Biol Chem 278:3466-3473; U.S. Pat. Nos. 6,602,684; 6,946,292; 7,064,191; 7,214,775; 7,393,683; 7,425,446; 7,504,256; U.S. Publication. Nos. 2003/0157108; 2003/0003097; 2009/0010921; POTELLEGENT™ technology (Biowa, Inc.

Princeton, N.J.); GLYCOMAB™ glycosylation engineering technology (GLYCART biotechnology AG, Zurich, Switzerland)). In some aspects, the Fc domain is a hypofucosylated antibody Fc domain having reduced amounts of fucosyl residues (see for examples, U.S. Patent Application Publication No. 2005/0226867). In one aspect, these antibodies with increased effector function, specifically ADCC, as generated in host cells (e.g., CHO cells, Lemna minor) engineered to produce highly defucosylated antibody with over 100-fold higher ADCC compared to antibody produced by the parental cells (e.g., Mori et al., 2004, Biotechnol Bioeng 88:901-908; Cox et al., 2006, Nat Biotechnol., 24:1591-7). In some aspects, the Fc domain has increased bisecting GlcNAc structures (e.g., Umana et al, 1999, Nat. Biotechnol 17:176-180; US2009/0010921).

In some aspects, the mutant Fc domain comprises the amino acids of SEQ ID NO: 24, 63, 25 or 65.

In some aspects, the mutant Fc domain comprises the amino acids of SEQ ID NO: 62 or SEQ ID NO: 64.

Also provided in the instant disclosure are bispecific anti-HER2 antibodies comprising a first and a second polypeptide chain associated with each other, wherein the first polypeptide chain is selected from:

 (1)

 (2)

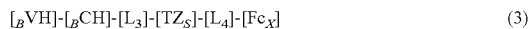 (3)

wherein
TZs is an scFv that binds the same epitope recognized by the trastuzumab antibody;
L₁, L₂, L₃, and L₄ are peptide linkers;
Fcx is an Fc domain;
$_B$VH and $_B$CH are the VH and CH1 regions, respectively, of an antibody capable of binding to an HER2 epitope distinct from the epitope recognized by the trastuzumab antibody.

In some aspects, the distinct epitope comprises one or more amino acids within SEQ ID NO: 52.

In some aspects, the epitope recognized by the trastuzumab antibody comprises one or more amino acid residues in SEQ ID NO: 53.

In some aspects, the second polypeptide chain comprises [$_B$VL]-[CL] wherein $_B$VL is the VL region of an antibody capable of binding to an HER2 epitope distinct from the epitope recognized by the trastuzumab antibody, and CL is an IgG light chain constant region. In some aspects, CL is selected from the group consisting of a human kappa constant region and a human lambda constant region.

In some aspects, $_B$VL comprises the amino acids of SEQ ID NO:16. In some aspects, $_B$VL comprises the amino acids of SEQ ID NO:44. In some aspects, $_B$VL comprises:
(i) a variable light chain CDR-1 (VL-CDR1) identical to SEQ ID NO: 4 or identical to SEQ ID NO: 4 except for up to 1, 2, 3, or 4 amino acid substitutions;
(ii) a variable light chain CDR-2 (VL-CDR2) identical to SEQ ID NO: 5 or identical to SEQ ID NO: 5 except for up to 1, 2, 3, or 4 amino acid substitutions; and,
(iii) a variable light chain CDR-3 (VL-CDR3) identical to SEQ ID NO: 6 or identical to SEQ ID NO: 6 except for up to 1, 2, 3, or 4 amino acid substitutions.

In some specific aspects, CL comprises the amino acids of SEQ ID NO:27.

In some specific aspects, CL comprises the amino acids of SEQ ID NO:66.

In some aspects, [TZ$_S$] comprises:
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and
(vi) a VL-CDR3 comprising the amino acids of SEQ ID NO:59.

In some aspects, [TZ$_S$] is a disulfide stabilized scFv. In some aspects, [TZ$_S$] comprises (i) a VH comprising or consisting of the amino acids of SEQ ID NO:17, or a variant thereof, and (ii) a VL comprising or consisting of the amino acids of SEQ ID NO:18, or a variant thereof, covalently linked by a peptide linker. Numerous linkers (for example, peptide linkers) suitable for linking the VH and VL moieties of an scFv are known in the art. In some aspects, the linker is a peptide linker comprising or consisting of the amino acids of SEQ ID NO:19. In other aspects, [TZ$_S$] comprises or consists of the amino acids of SEQ ID NO:28.

In some aspects, a hinge polypeptide links the [$_B$CH] and [Fcx]. In some aspects, the hinge polypeptide comprises or consists of the amino acids of SEQ ID NO: 26. In some aspects, the [Fcx] comprises at least one amino acid substitution introducing a derivatizable group. In other aspects, the [Fcx] comprises one to three amino acid substitution introducing a derivatizable group. In yet other aspects, the [Fcx] comprises more than three amino acid substitutions introducing a derivatizable. In some aspects, all the derivatizable groups are identical. In other aspects, at least one derivatizable group is different from the rest. In some aspects, all the derivatizable groups are different. In some aspects, the derivatizable group is a sulfhydryl group (e.g., the sulfhydryl group of a cysteine). In some aspects, the derivatizable group is protected.

In some aspects, the derivatizable group is introduced at position 239, 248, 254, 258, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 435, 440, 441, 442, 443, or 446, or between positions 239 and 240, or any combination thereof, wherein the amino acid position numbering is according to the EU index as set forth in Kabat. In some aspects, the derivatizable group is a sulfhydryl group in at least one cysteine amino acid substitution comprising S239C, 248C, 254C, 258C, 273C, 279C, 282C, 284C, 286C, 287C, 289C, 297C, 298C, 312C, 324C, 326C, 330C, 335C, 337C, 339C, 350C, 355C, 356C, 359C, 360C, 361C, 375C, 383C, 384C, 389C, 398C, 400C, 413C, 415C, 418C, 422C, 435C, 440C, 441C, S442C, 443C and 446C, a cysteine amino acid insertion between positions 239 and 240, or any combination thereof, wherein the amino acid position numbering is according to the EU index as set forth in Kabat. In some aspects, the amino acid or amino acid substitution introducing a derivatizable sulfhydryl group is S239C and/or S442C. In some aspects, the amino acid or amino acid substitution introducing a derivatizable sulfhydryl group is a cysteine amino acid insertion between positions 239 and 240 and/or S442C.

In other aspects, [Fcx] comprises the amino acids of any one of SEQ ID NOs: 23, 24, 63, 25 or 65.

In other aspects, [Fcx] comprises the amino acids of any one of SEQ ID NOs: 23, 62, or 64.

In certain aspects, [L₁], [L₂], [L₃], and [L₄] comprise the amino acids of linker sequences independently selected from the group consisting of SEQ ID NOs: 19, 20, 21, and 22. In some aspects, all the linkers are different. In some aspects, at least two of the linkers are identical. One skilled in the art would understand that the linkers can be peptide, non-peptide, or combination of peptide and non-peptide linkers. In some specific aspects, (i) [L₁] comprises or consists of the amino acids of SEQ ID NO:20; (ii) [L₂] comprises or consists of the amino acids of SEQ ID NO:20; (iii) [L₃] comprises or consists of the amino acids of SEQ ID NO:21; and, (iv) [L₄] comprises or consists of the amino acids of SEQ ID NO:22.

In some aspects, [$_B$VH] comprises:
(i) a variable heavy chain CDR-1 (VH-CDR1) identical to SEQ ID NO: 1 or identical to SEQ ID NO: 1 except for up to 1, 2, 3, or 4 amino acid substitutions;
(ii) a variable heavy chain CDR-2 (VH-CDR2) identical to SEQ ID NO: 2 or identical to SEQ ID NO: 2 except for up to 1, 2, 3, or 4 amino acid substitutions; and
(iii) a variable heavy chain CDR-3 (VH-CDR3) identical to SEQ ID NO: 3 or identical to SEQ ID NO: 3 except for up to 1, 2, 3, or 4 amino acid substitutions.

In some aspects, [$_B$VH] comprises or consists of the amino acids of SEQ ID NO:15 or SEQ ID NO: 43.

In some aspects, [$_B$VL] comprises:
(i) a variable light chain CDR-1 (VL-CDR1) identical to SEQ ID NO: 4 or identical to SEQ ID NO: 4 except for up to 1, 2, 3, or 4 amino acid substitutions;
(ii) a variable light chain CDR-2 (VL-CDR2) identical to SEQ ID NO: 5 or identical to SEQ ID NO: 5 except for up to 1, 2, 3, or 4 amino acid substitutions; and,
(iii) a variable light chain CDR-3 (VL-CDR3) identical to SEQ ID NO: 6 or identical to SEQ ID NO: 6 except for up to 1, 2, 3, or 4 amino acid substitutions.

In some specific aspects, [$_B$VL] comprises or consists of the amino acids of SEQ ID NO:16 or SEQ ID NO: 44. In some aspects, [$_B$CH] comprises or consists of the amino acids of SEQ ID NO: 29.

In some specific aspects, the instant disclosure provides bispecific anti-HER2 antibodies comprising a first polypeptide chain and a second polypeptide chain, wherein (i) the first polypeptide chain comprises or consists of an amino acid sequence selected from the group consisting of SEQ ID NOs: 30, 31, 32, 69, 33, 71, 34, 35, 36, 74, 37, 76, 38, 39, 40, 79, 41 and 81, and (ii) the second polypeptide chain comprises or consists of the sequence of SEQ ID NO:42 or 82, wherein the bispecific anti-HER2 antibodies are conjugated to a therapeutic moiety.

In some specific aspects, the instant disclosure provides bispecific anti-HER2 antibodies comprising a first polypeptide chain and a second polypeptide chain, wherein (i) the first polypeptide chain comprises or consists of an amino acid sequence selected from the group consisting of SEQ ID NO: 30, 67, 68, 70, 72, 73, 75, 77, 78, and 80, and (ii) the second polypeptide chain comprises or consists of the sequence of SEQ ID NO:42 or 82, wherein bispecific anti-HER2 antibodies have enhanced ADCC activity.

IV. Antibody-Drug Conjugates (ADCs)

The instant disclosure also provides antibody-drug conjugates (ADCs) comprising at least one of the anti-HER2 binding molecules disclosed herein (e.g., antibodies which bind the same epitope as or are derived from the 39S antibody or HER2-binding fragments thereof, or the bispecific anti-HER2 antibodies disclosed herein) conjugated to least one therapeutic moiety. Accordingly, in some aspects, the ADC comprises a bispecific anti-HER2 antibody disclosed herein conjugated to at least one therapeutic moiety (e.g., a cytotoxin), wherein said bispecific anti-HER2 antibody comprises (i) a first immunoglobulin antigen-binding domain and (ii) a second immunoglobulin antigen-binding domain, wherein the first immunoglobulin antigen-binding domain comprises a heavy chain (HC) variable region (VH) and a light chain (LC) variable region (VL) comprising:
(i) a variable heavy chain CDR-1 (VH-CDR1) sequence identical to SEQ ID NO: 1 or identical to SEQ ID NO: 1 except for up to 1, 2, 3, or 4 amino acid substitutions;
(ii) a variable heavy chain CDR-2 (VH-CDR2) sequence identical to SEQ ID NO: 2 or identical to SEQ ID NO: 2 except for up to 1, 2, 3, or 4 amino acid substitutions;
(iii) a variable heavy chain CDR-3 (VH-CDR3) sequence identical to SEQ ID NO: 3 or identical to SEQ ID NO: 3 except for up to 1, 2, 3, or 4 amino acid substitutions;
(iv) a variable light chain CDR-1 (VL-CDR1) sequence identical to SEQ ID NO: 4 or identical to SEQ ID NO: 4 except for up to 1, 2, 3, or 4 amino acid substitutions;
(v) a variable light chain CDR-2 (VL-CDR2) sequence identical to SEQ ID NO: 5 or identical to SEQ ID NO: 5 except for up to 1, 2, 3, or 4 amino acid substitutions; and,
(vi) a variable light chain CDR-3 (VL-CDR3) sequence identical to SEQ ID NO: 6 or identical to SEQ ID NO: 6 except for up to 1, 2, 3, or 4 amino acid substitutions;
wherein:
(a) the second immunoglobulin antigen-binding domain comprises an scFv antibody fragment; and,
(b) the first and second immunoglobulin antigen-binding domains specifically bind to distinct HER2 epitopes.

In some aspects, the first immunoglobulin antigen-binding domain of the ADC comprises at least one heterologous variable domain framework region (FW) different relative to the FW regions of an immunoglobulin antigen-binding domain comprising a VH comprising the amino acids of SEQ ID NO:43, and a VL comprising the amino acids of SEQ ID NO:44;

In some aspects, the ADC further comprises at least one optional spacer which can be intercalated between the side chain of an amino acid in a polypeptide chain of the anti-HER2 binding molecule (for example, an amino in the heavy chain of an anti-HER2 bispecific antibody disclosed herein) and the therapeutic moiety. In some aspects, the at least one spacer is a peptidic spacer. In other aspects, the at least one spacer is a non-peptidic spacer. In some aspects, the spacer is unstable, such an acid labile spacer (e.g., a hydrazine). In other aspects, the spacer is an enzyme cleavable peptide, e.g., a cleavable dipeptide. In some aspects, the spacer is uncleavable (hydrolytically stable), for example, a thioether spacer or a hindered disulfide spacer. In some aspects, the intercalated between the side chain of an amino acid in a polypeptide chain of the anti-HER2 binding molecule (for example, an amino in the heavy chain of an anti-HER2 bispecific antibody disclosed herein) and the additional therapeutic moiety is MCC (N-succinimidyl-4 (maleimidomethyl) cyclohexane)).

Hydrolytically stable spacers are substantially stable in water and do not react with water at useful pH values, including but not limited to, under physiological conditions for an extended period of time. Hydrolytically unstable or degradable spacers are degradable in water or in aqueous solutions, including for example, blood.

Enzymatically unstable or degradable spacers can be degraded by one or more enzymes. By way of example only, PEG and related polymers can include degradable spacers in the polymer backbone or in the linker group between the polymer backbone and one or more of the terminal functional groups of the polymer molecule. Such degradable spacers include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable spacers include but are not limited to carbonate linkages; imine linkages resulting from reaction of an amine and an aldehyde; phosphate ester linkages formed by reacting an alcohol with a phosphate group; hydrazone linkages which are a reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

In some aspects, the ADC comprises two, three, four, five, six, seven, eight, nine or ten therapeutic moieties. In some specific aspects, the ADC comprises two, three, or four therapeutic moieties. In some aspects, all therapeutic moieties are the same. In some aspects, at least one therapeutic moiety is different from the rest. In some aspects, all therapeutic moieties are different. In some aspects, all the spacers (e.g., peptidic and/or non-peptidic spacers) are the same. In some aspects, at least one spacer is different from the rest. In still other aspects, all the spacers are different.

In some aspects, each therapeutic moiety is chemically conjugated to the side chain of an amino acid at a specific position in the Fc region of the anti-HER2 binding molecule (e.g., a bispecific anti-HER2 antibody disclosed herein).

In some aspects, the specific positions in the Fc region are selected from the group consisting of 239, 248, 254, 258, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 435, 440, 441, 442, 443, 446, an insertion between positions 239 and 240, and combinations thereof, wherein the amino acid position numbering is according to the EU index as set forth in Kabat.

In some aspects, the specific positions in the Fc region are 239, 442, or both, wherein the amino acid position numbering is according to the EU index as set forth in Kabat. In some aspects, the specific positions in the Fc region consist of 442 and an amino acid insertion between positions 239 and 240, wherein the amino acid position numbering is according to the EU index as set forth in Kabat.

In some aspects, the amino acid side chain where the therapeutic moiety is conjugated is a sulfhydryl side chain, for example, the sulfhydryl group of a cysteine amino acid. In some aspects, at least one therapeutic moiety is chemically conjugated to the side chain of an amino acid located at a position outside of the Fc region of the anti-HER2 binding molecule (e.g., a bispecific anti-HER2 antibody disclosed herein). In some aspects, all the therapeutic moieties are chemically conjugated to the side chain of an amino acid located at a position outside of the Fc region of the anti-HER2 binding molecule (e.g., a bispecific anti-HER2 antibody disclosed herein). In some aspects, at least one therapeutic moiety is genetically incorporated into the polypeptide chain of the anti-HER2 binding molecule (e.g., a bispecific anti-HER2 antibody disclosed herein) using recombinant techniques known in the art.

In some aspects, the therapeutic moiety comprises a cytotoxin, a radioisotope, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate. a chelating agentor combinations thereof.

In some specific aspects, the cytotoxin is an auristatin, a tubulysin, a maytansinoid or a pyrrolobenzodiazepine (PBD). In another specific aspect, the cytotoxin is tubulysin 1508.

In specific aspects, the ADC comprises a bispecific anti-HER2 antibody disclosed herein, wherein said antibody comprises:

(i) a first polypeptide chain comprising or consisting of the amino acids of SEQ ID NO: 32 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat;

(ii) a first polypeptide chain comprising or consisting of the amino acids of SEQ ID NO:33 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442 wherein the amino acid position numbering is according to the EU index as set forth in Kabat;

(iii) a first polypeptide chain comprising or consisting of the amino acids of SEQ ID NO:36 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat;

(iv) a first polypeptide chain comprising or consisting of the amino acids of SEQ ID NO:37 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442, wherein the amino acid position numbering is according to the EU index as set forth in Kabat;

(v) a first polypeptide chain comprising or consisting of the amino acids of SEQ ID NO:40 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat; or, (vi) a first polypeptide chain comprising or consisting of the amino acids of SEQ ID NO:41 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442, wherein the amino acid position numbering is according to the EU index as set forth in Kabat.

In specific aspects, the ADC comprises a bispecific anti-HER2 antibody disclosed herein, wherein said antibody comprises:
(i) a first polypeptide chain comprising or consisting of the amino acids of SEQ ID NO:62 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat;
(ii) a first polypeptide chain comprising or consisting of the amino acids of SEQ ID NO: 71 and a second polypeptide chain comprising or consisting of the amino acids of SEQ ID NO:42, wherein the first polypeptide chain comprises two therapeutic moieties (e.g., two tubulysin 1508 molecules) covalently linked to a cysteine amino inserted between positions 239 and 240 and a cysteine amino acid located at position 442, wherein the amino acid position numbering is according to the EU index as set forth in Kabat;
(iii) a first polypeptide chain comprising or consisting of the amino acids of SEQ ID NO:74 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat;
(iv) a first polypeptide chain comprising or consisting of the amino acids of SEQ ID NO:76 and a second polypeptide chain comprising or consisting of the amino acids of SEQ ID NO:42, wherein the first polypeptide chain comprises two therapeutic moieties (e.g., two tubulysin MEDI 1508 molecules) covalently linked to a cysteine amino inserted between positions 239 and 240 and a cysteine amino acid located at position 442, wherein the amino acid position numbering is according to the EU index as set forth in Kabat;
(v) a first polypeptide chain comprising or consisting of the amino acids of SEQ ID NO:79 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat; or,
(vi) a first polypeptide chain comprising or consisting of the amino acids of SEQ ID NO:81 and a second polypeptide chain comprising or consisting of the amino acids of SEQ ID NO:42, wherein the first polypeptide chain comprises two therapeutic moieties (e.g., two tubulysin 1508 molecules) covalently linked to a cysteine amino inserted between positions 239 and 240 and a cysteine amino acid located at position 442, wherein the amino acid position numbering is according to the EU index as set forth in Kabat.

ADC molecules disclosed herein comprise at least one of the anti-HER2 binding molecules disclosed herein (e.g., antibodies which bind the same epitope as or are derived from the 39S antibody or HER2-binding fragments thereof, or the bispecific anti-HER2 antibodies disclosed herein) which has been derivatized or linked (e.g., chemically or recombinantly) to another molecule (e.g., a peptide, small drug molecule, detectable molecule, etc.). In general, anti-HER2 antibodies or portions thereof are derivatized such that their HER2 binding is not affected adversely by the derivatization or labeling. Accordingly, the anti-HER2 antibodies and antibody portions of the instant disclosure are intended to include both intact and modified forms of the anti-HER2 binding molecules described herein. For example, an anti-HER2 binding molecule disclosed herein or HER2-binding portion thereof can be functionally linked (by chemical coupling, genetic fusion, noncovalent association, or otherwise) to one or more other molecular entities, such as a cytotoxic agent, a pharmaceutical agent, a detection agent, and/or a protein or peptide that can mediate association of the anti-HER2 binding molecule with another molecule (such as a streptavidin core region or a polyhistidine tag).

One type of derivatized molecule can be produced by crosslinking two or more molecular entities, e.g., an anti-HER2 binding molecule disclosed herein and a therapeutic moiety (e.g., a cytotoxin such as tubulysin 1508). Suitable crosslinkers include those that are heterobifunctional, i.e., having two distinctly reactive groups separated by an appropriate spacer (e.g., m-maleimidobenzoyl-N-hydroxysuccinimide ester); or homobifunctional (e.g., disuccinimidyl suberate). Such crosslinkers are available, for example, from Pierce Chemical Company, Rockford, II. Additional bifunctional coupling agents include N-succinimidyl-3-(2-pyridyl-dithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene).

Another type of derivatized molecule can be produced by incorporating a detectable label. Useful detection agents include fluorescent compounds (e.g., fluorescein, fluorescein isothiocyanate, rhodamine, 5-dimethylamine-1-napthalenesulfonyl chloride, phycoerythrin, lanthanide phosphors and the like), enzymes that are useful for detection (e.g., horseradish peroxidase, β-galactosidase, luciferase, alkaline phosphatase, glucose oxidase and the like), epitopes recognized by a secondary reporter (e.g., leucine zipper pair sequences, binding sites for secondary antibodies, metal binding domains, epitope tags, etc.). In some aspects, detectable labels can be attached by at least one spacer arm. Spacer arms can be of various lengths to reduce potential steric hindrance.

An anti-HER2 binding molecule can also be labeled with a radiolabeled amino acid. The radiolabel can be used for both diagnostic and therapeutic purposes. For instance, the radiolabel can be used to detect HER2-expressing cells by X-ray or other diagnostic techniques such as positron emission tomography (PET).

Further, the radiolabel can be used therapeutically as a toxin for HER2-expressing cells, such as those which cause unwanted immune response. Examples of labels for polypeptides include, but are not limited to, the following radioisotopes or radionuclides: $^{3}H$, $^{14}C$, $^{15}N$, $^{35}s$, $^{90}Y$, $^{99}Tc$, $^{111}In$, $^{125}I$ and $^{131}I$. In some aspects, the anti-HER2 binding molecule can be labeled with a paramagnetic, radioactive, or fluorogenic ion that is detectable upon imaging. In some aspects, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other aspects, the radioactive ion is iodine-123, technetium-99, indium-111, rhenium-188, rhenium-186, copper-67, iodine-131, yttrium-90, iodine-125, astatine-211, and gallium-67. In other aspects, the anti-HER2 binding molecule is labeled with an X-ray imaging agent such as lanthanum (III), gold (III), lead (II), and bismuth (III). An anti-HER2 binding molecule can also be derivatized with a chemical group, for example a polymer such as polyethylene glycol (PEG), a methyl group, an ethyl group, or a carbohydrate group. These groups are useful to improve the biological characteristics of the antibody, e.g., to increase serum half-life or to increase tissue binding.

The term "cytotoxic agent" as used herein is defined broadly and refers to a substance that inhibits or prevents the function of cells and/or causes destruction of cells (cell death), and/or exerts anti-neoplastic/anti-proliferative effects. For example, cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, as well as other HER2 antagonists, anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, Vinca alkaloids and derivatives of podophyllotoxin; cytotoxic antibiotics and camptothecin derivatives. Other chemotherapeutic agents are amifostine (ETHYOL®), cisplatin, dacarbazine (DTIC), dactinomycin, mechlorethamine (nitrogen mustard), streptozocin, cyclophosphamide, carmustine (BCNU), lomustine (CCNU), doxorubicin (ADRIAMYCIN®), doxorubicin lipo (DOXIL®), gemcitabine (GEMZAR®), daunorubicin, daunorubicin lipo (DAUNOXOME®), procarbazine, mitomycin, cytarabine, etoposide, methotrexate, 5-fluorouracil (5-FU), vinblastine, vincristine, bleomycin, paclitaxel (TAXOL®), docetaxel (TAXOTERE®), aldesleukin, asparaginase, busulfan, carboplatin, cladribine, camptothecin, CPT-11, 10-hydroxy-7-ethyl-camptothecin (SN38), gefitinib (IRESSA ®), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

IV.A Tubulysins

In some aspects, the ADC comprises an anti-HER2 binding molecule disclosed herein (e.g., the 39S antibody or a derivative thereof, or one of the bispecific anti-HER2 antibodies disclosed herein) conjugated to one or more tubulysin molecules (see structure of tubulysin A and tubulysin 1508 below).

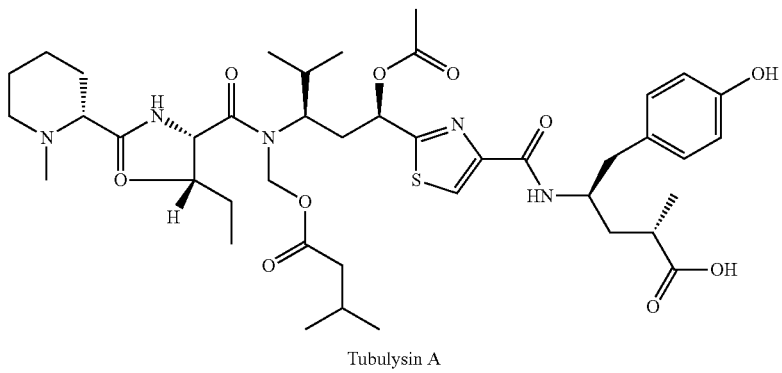

Tubulysin A

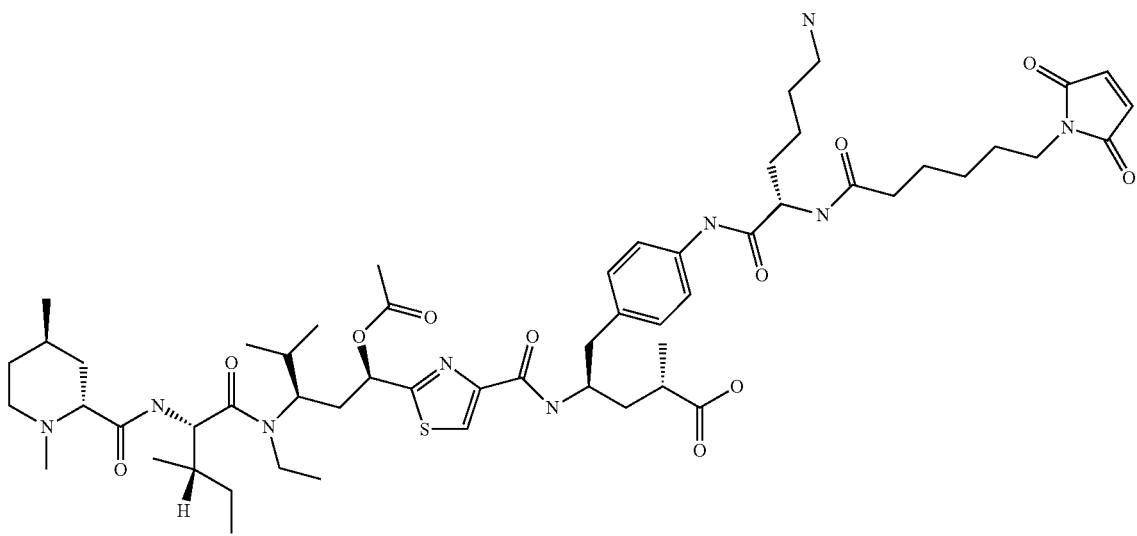

Tubulysin 1508 (compound T32)

Tubulysins are members of a class of natural products isolated from myxobacterial species (Sasse et al., J. Antibiot. 53:879-885 (2000)). As cytoskeleton interacting agents, tubulysins are mitotic poisons that inhibit tubulin polymerization and lead to cell cycle arrest and apoptosis (Steinmetz et al., Chem. Int. Ed. 43:4888-4892 (2004); Khalil et al., ChemBioChem. 7:678-683 (2006); Kaur et al., Biochem. J. 396: 235-242 (2006)). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling et al., Mol. Diversity 9:141-147 (2005)). These compounds show high cytotoxicity tested against a panel of cancer cell lines with $IC_{50}$ values in the low picomolar range; thus, they are of interest as anticancer therapeutics. See, e.g., WO2012019123, which is herein incorporated by reference in its entirety. Tubulysin conjugates are disclosed, e.g., in U.S. Pat. No. 7,776,814.

In some aspects, the tubulysin molecule or derivative thereof is a prodrug.

IV.B Maytansine and Maytansinoids

In some aspects, the ADC comprises an anti-HER2 binding molecule disclosed herein (e.g., the 39S antibody or a derivative thereof, or one of the bispecific anti-HER2 antibodies disclosed herein) conjugated to one or more maytansinoid molecules.

Maytansinoids are mitotic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533.

Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Immunoconjugates containing maytansinoids, methods of making same, and their therapeutic use are disclosed, for example, in U.S. Pat. Nos. 5,208,020, 5,416,064 and European Patent EP0425235B1; Liu et al., Proc. Natl. Acad. Sci. USA 93:8618-8623 (1996) (described immunoconjugates comprising a maytansinoid designated DM1); and Chari et al., Cancer Research 52:127-131 (1992).

Trastuzumab emtansine (ado-trastuzumab emtansine, T-DM1, trade name KADCYLA®) is an antibody-drug conjugate consisting of the monoclonal antibody trastuzumab (HERCEPTIN®) conjugated to the maytansinoid mertansine (DM1). See, e.g., LoRusso et al., Clin. Cancer Res. 20:6437-47 (2011), which is herein incorporated by reference in its entirety. An engineered thio-Trastuzumab-DM1 ADC has also been described in Junutual et al., Clin, Cancer Res. 16:4769-78 (2010), which is herein incorporated by reference in its entirety.

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020.

In some aspects, the maytansinoid molecule, variant, or derivative thereof is a prodrug.

IV.C Auristatins and Dolastatins

In some aspects, the ADC comprises an anti-HER2 binding molecule disclosed herein (e.g., the 39S antibody or a derivative thereof, or one of the bispecific anti-HER2 antibodies disclosed herein) conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. No. 5,663, 149). The dolastatin or auristatin drug moiety can be attached to the antibody through the N (amino) terminus or the C (carboxyl) terminus of the peptidic drug moiety (See, e.g., WO2002088172).

In some aspects, the auristatine or dolastatine molecule, variant, or derivative thereof is a prodrug.

IV.D Calicheamicin

In some aspects, the ADC comprises an anti-HER2 binding molecule disclosed herein (e.g., the 39S antibody or a derivative thereof, or one of the bispecific anti-HER2 antibodies disclosed herein) conjugated to one or more calicheamicin molecules. Members of the calicheamicin family of antibiotics are capable of producing double-stranded DNA breaks at sub-picomolar concentrations. The calicheamicins are a class of enediyne antibiotics derived from the bacterium *Micromonospora echinospora*, with calicheamicin γ1 being the most notable. Other calicheamicins are β1Br, γ1Br, α2I, α3I, β1I, γ1I, and Δ1I. See Lee et al., Journal of Antibiotics 42(7):1070-87 (1989). For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Structural analogues of calicheamicin which can be used include, but are not limited to, γ1I, α2I, α3I, N-acetyl-γ1I, PSAG and θ1I (Hinman et al., Cancer Research 53:3336-3342 (1993), Lode et al., Cancer Research 58:2925-2928 (1998) and the aforementioned U.S. patents to American Cyanamid).

In some aspects, the calicheamicin molecule, variant, or derivative thereof is a prodrug.

IV.E Duocarmycins

In some aspects, the ADC comprises an anti-HER2 binding molecule disclosed herein (e.g., the 39S antibody or a derivative thereof, or one of the bispecific anti-HER2 antibodies disclosed herein) conjugated to one or more duocarmycin molecules. Duocarmycins are members of a series of related natural products first isolated from *Streptomyces* bacteria and they are potent antitumor antibiotics. See Boger. (1991). Chemtracts: Organic Chemistry 4 (5): 329-349 (1991); Tercel et al., Chem. Int. Ed. Engl. 52(21):5442-6 (2013); Boger & Douglas, Proc. Natl. Acad. Sci. USA 92(9): 3642-3649 (1995); Cacciari et al., Expert Opinion on Therapeutic Patents 10(12):1853-71 (2000).

Natural duocarmycins include duocarmycin A, duocarmycin B 1, duocarmycin B2, duocarmycin C1, duocarmycin C2, duocarmycin D, duocarmycin SA, and CC-1065. Synthetic analogs include adozelesin, bizelesin, and carzelesin (U-80244).

In some aspects, the duocarmycin molecule, variant, or derivative thereof is a prodrug.

IV.F Pyrrolobenzodiazepine

In some aspects, the drug is a pyrrolobenzodiazepine (PBD). PBDs are relatively small molecules and some have the ability to recognize and covalently bind to specific sequences in the minor groove of DNA and thus exhibit antibiotic/antitumor activity. A number of PBDs and derivatives thereof are known in the art, for example, PBD dimers (e.g., SJG-136 or SG2000), C2-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274). PBDs are further described WO 2000/012507, WO 2007/039752, WO 2005/110423, WO 2005/085251, and WO 2005/040170, and U.S. Pat. No. 7,612,062, each of which is incorporated by reference herein in its entirety.

IV.G Other Cytotoxic Agents

In some aspects, the ADC comprises an anti-HER2 binding molecule disclosed herein (e.g., the 39S antibody or a derivative thereof, or one of the bispecific anti-HER2 antibodies disclosed herein) conjugated to other antitumor agents, for example, BCNU, anthracyclines (e.g., daunomycin or adriamycin), taxenes (e.g., paclitaxel), streptozoicin, Vinca alkaloids (e.g., vincristine), 5-fluorouracil, the family of agents known collectively as LL-E33288 complex (see U.S. Pat. Nos. 5,053,394, and 5,770,710), esperamicins (see U.S. Pat. No. 5,877,296). The ADC can also comprise an anti-HER2 binding molecule disclosed herein (e.g., the 39S antibody or a derivative thereof, or one of the bispecific anti-HER2 antibodies disclosed herein) conjugated to enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin and the tricothecenes. See, for example, WO199321232. In some aspects, the cytotoxic agent is a light activated drug.

V. Anti-HER2 Binding Molecules that Bind to the Same Epitope as the 39S Antibody In another aspect, the present disclosure provides anti-HER2 binding molecules that bind to the same epitope(s) as do the 39S antibody (e.g., antibodies derived from the 39S antibody or antigen-binding fragments thereof, bispecific anti-HER2 antibodies, or ADCs).

Such anti-HER2 binding molecules that bind to the same epitope as the 39S antibody can be identified based on their ability to cross-compete (e.g., to competitively inhibit the binding of, in a statistically significant manner) with the 39S antibody in standard HER2 binding assays. Accordingly, in one aspect, the instant disclosure provides anti-HER2 binding molecules (e.g., antibodies derived from the 39S antibody or antigen-binding fragments thereof, bispecific anti-HER2 antibodies, or ADCs) that compete for binding to HER2 with the 39S antibody antigen-binding fragments thereof. The ability of a test antibody to inhibit the binding of, e.g., the 39S antibody or binding molecules derived from the 39S antibody (e.g., bispecific antibodies or ADCs) demonstrates that the test antibody can compete with the 39S antibody for binding to HER2; such anti-HER2 binding molecule can, according to non-limiting theory, bind to the same or a related (e.g., a structurally similar or spatially proximal) epitope on HER2 as the 39S antibody or antigen-binding fragment thereof with which it competes.

In one aspect, the anti-HER2 molecule that binds to the same epitope on HER2 as the 39S antibody or binding molecules derived from the 39S antibody is a human monoclonal antibody or an antigen-binding fragment thereof, a bispecific anti-HER2 antibody (e.g., a bispecific antibody comprising two HER2 binding regions, at least one of which recognizes the same epitope as the 39S antibody), or an ADC (e.g., an ADC comprising at least one antigen-binding moiety recognizing the same epitope as the 39S; or an ADC comprising a bispecific antibody which comprises two HER2 binding regions, at least one of which recognizes the same epitope as the 39S antibody).

VI. Mechanisms of Action of Anti-HER2 Binding Molecules

The present disclosure provides anti-HER2binding molecules (e.g., bispecific anti-HER2 antibodies, or ADCs) comprising a HER2-binding domain binding the same epitope as or derived from the 1.39.1 or 39S antibodies, wherein such anti-HER2-binding molecules induce internalization upon binding to the HER2 target. Also provided are anti-HER2 binding molecules (e.g., bispecific anti-HER2 antibodies, or ADCs) comprising a HER2-binding domain binding the same epitope as or derived from the 1.39.1 or 39S antibodies, wherein such anti-HER2-binding molecules promote effective lysosomal trafficking following internalization. The present disclosure also provides anti-HER2 binding molecules (e.g., bispecific anti-HER2 antibodies, or ADCs) comprising a HER2-binding domain binding the same epitope as or derived from the 1.39.1 or 39S antibodies, wherein such and-HER2-binding molecules induce HER2 target internalization and/or degradation.

In some aspects, an anti-HER2 binding molecule disclosed herein can reduce, block, or suppress HER2 phosphorylation. In other aspects, an anti-HER2 binding molecule disclosed herein can reduce, block, or suppress ligand-induced AKT phosphorylation. In some aspects, the anti-HER2 binding molecule can reduce, block, or suppress ligand-induced AKT phosphorylation in low HER2-expressing cancer cells.

In still other aspects, an anti-HER2 binding molecule, e.g., an anti-HER2 antibody or antigen-binding fragment thereof disclosed in the instant application can reduce, disrupt, or suppress ligand-induced HER2-HER3 dimerization.

In some aspects, an ADC comprising an anti-HER2 binding molecule disclosed herein can inhibit cancer stem cell (CSC) sphere formation and/or proliferation. In some aspects, an anti-HER2 binding molecule disclosed herein exhibits a cytotoxic effect on CSCs. In some aspects, an ADC comprising an anti-HER2 binding molecule disclosed herein can inhibit tumor growth and/or induce tumor regression in tumors expressing low levels of HER2 (e.g. +1 to +2 via HercepTest). In certain aspects, an ADC comprising an anti-HER2 binding molecule disclosed herein can inhibit tumor growth and/or induce tumor regression in tumors resistant to T-DM1.

In some aspects, an HER2 binding molecule, e.g., an anti-HER2 antibody or antigen-binding fragment thereof lacks ADCC activity. In specific aspects, an anti-HER2 binding molecule, e.g., an anti-HER2 antibody or antigen-binding fragment thereof can reduce or suppress HER2 phosphorylation, AKT phosphorylation, and/or tumor colony formation via a ligand-independent mechanism of action.

VII. Preparation of Anti-HER2 Binding Molecules

Anti-HER2 binding molecules of the present disclosure (for example, antibodies or antigen-binding fragments thereof which bind the same epitope as or are derived from the 1.39.1 or 39S antibodies, bispecific antibodies and ADCs comprising the same) can be prepared according to methods known in the art. For example, anti-HER2 binding molecules binding to the same epitope as the 39S antibody disclosed herein can be generated using hybridoma methods, such as those described by Kohler & Milstein (1975) Nature 256:495.

Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Anti-HER2 binding molecules of the present disclosure (for example, antibodies or antigen-binding fragments thereof which bind the same epitope as or are derived from the 1.39.1 or 39S antibodies, bispecific antibodies and ADCs comprising the same) can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, monoclonal antibodies are generated by the host cells. Also, recombinant anti-HER2 monoclonal antibodies or molecules comprising antigen-binding fragments thereof of the desired species can be isolated from phage display libraries expressing CDRs of the desired species as described (McCafferty et al., Nature 348:552-554 (1990); Clarkson et al., Nature 352:624-628 (1991); and Marks et al., J. Mol. Biol. 222:581-597 (1991)).

The polynucleotide(s) encoding an anti-HER2 binding molecule of the present disclosure (for example, antibodies or antigen-binding fragments thereof which bind the same epitope as or are derived from the 39S antibody, bispecific antibodies and ADCs comprising the same) can further be modified in a number of different manners using recombinant DNA technology to generate alternative anti-HER2 binding molecules. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-HER2 binding molecule of the present disclosure is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., J. Immunol. 147:86-95 (1991); and U.S. Pat. No. 5,750,373). One or more cDNAs encoding the antibody in the immortalized B lymphocyte can then be prepared and inserted into an expression vector and/or a heterologous host cell for expression of a non-naturally-occurring recombinant version of the antibody.

Also, the anti-HER2 human antibody or antigen-binding fragment thereof can be selected from a phage library, where that phage library expresses human antibodies or fragments thereof as fusion proteins with heterologous phage proteins, as described, for example, in Vaughan et al., Nat. Biotech. 14:309-314 (1996); Sheets et al., Proc. Natl. Acad. Sci. 95:6157-6162 (1998); Hoogenboom and Winter, J. Mol. Biol. 227:381 (1991), and Marks et al., J. Mol. Biol. 222:581 (1991)). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963, each of which is incorporated by reference in its entirety.

Affinity maturation strategies and chain shuffling strategies (Marks et al., BioTechnology 10:779-783 (1992), incorporated by reference in its entirety) are known in the art and can be employed to generate high affinity human antibodies or antigen-binding fragments thereof.

In some aspects, an anti-HER2 binding molecule of the present disclosure can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing HER2 binding. Accordingly, part or all of the non-human or human CDR sequences are maintained while the non-human sequences of the variable and constant regions can be replaced with human or other amino acids. In certain aspects, human CDRs are inserted into non-human antibody scaffolds to make an antibody with reduced immunogenicity in an animal model system, e.g., a "murinized" antibody.

Anti-HER2 binding molecules, e.g., antibodies, can optionally be humanized, resurfaced, or engineered with retention of high affinity for the antigen HER2 and other favorable biological properties. To achieve this goal, humanized (or human) or engineered anti-HER2 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as HER2. In this way, framework residues can be selected and combined from the consensus and import sequences so that the desired antibody characteristic, such as increased affinity for the target antigen(s), is achieved.

Humanization, resurfacing or engineering of the anti-HER2 binding molecules disclosed herein can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; WO90/14443; WO90/14424; WO90/14430; and EP229246, each of which is entirely incorporated herein by reference, including the references cited therein.

In certain aspects an anti-HER2 antibody fragment is provided. Various techniques are known for the production of antibody fragments. Traditionally, these fragments are derived via proteolytic digestion of intact antibodies (for example Morimoto et al., J. Biochem. Biophy. Methods 24:107-117 (1993); Brennan et al., Science, 229:81 (1985)). In certain aspects, anti-HER2 antibody fragments are produced recombinantly. Fab, Fv, and scFv antibody fragments can all be expressed in and secreted from E. coli or other host cells, thus allowing the production of large amounts of these fragments. Such anti-HER2 antibody fragments can also be isolated from the antibody phage libraries discussed above. The anti-HER2 antibody fragments can also be linear antibodies as described in U.S. Pat. No. 5,641,870. Other techniques for the production of antibody fragments will be apparent to the skilled practitioner.

Techniques can be adapted for the production of single-chain antibodies specific to the same HER2 epitope as the 39S antibody (see, e.g., U.S. Pat. No. 4,946,778). In addition, methods can be adapted for the construction of Fab expression libraries (see, e.g., Huse et al., Science 246:1275-1281 (1989)) to allow rapid and effective identification of monoclonal Fab fragments with the desired specificity for HER2, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

In some aspects, especially in the case of antibody fragments, an anti-HER2 antibody or antigen-binding fragment thereof can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are well known in the art.

Heteroconjugate anti-HER2 binding molecules, e.g., bispecific antibodies which bind the same epitope as or are derived from the 39S antibody disclosed herein or ADCs, can be prepared using recombinant biology technology as well as in vitro using known methods in synthetic protein chemistry, including those involving crosslinking agents. For example, bispecific antibodies or ADCs can be chemically constructed using a disulfide exchange reaction or by forming a thioether bond. Suitable reagents for this purpose are known in the art, and include iminothiolate and methyl-4-mercaptobutyrimidate.

It will be noted that in certain aspects, the anti-HER2 binding molecules can be engineered to fuse the CH3 domain directly to the hinge region of the respective modified antibodies or fragments thereof. In other constructs, a peptide spacer can be inserted between the hinge region and the modified CH2 and/or CH3 domains. For example, compatible constructs can be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-HER2 binding molecule can be provided by the partial deletion or substitution of a few or even a single amino acid. For example, the mutation of a single amino acid in selected areas of the CH2 domain can be enough to substantially reduce Fc binding and thereby increase tumor localization. Moreover, as alluded to above, the constant regions of the disclosed anti-HER2 binding molecule can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain aspects can comprise the addition of one or more amino acids to the constant region to enhance desirable characteristics such as decreasing or increasing effector function or provide for more cytotoxin or carbohydrate attachment. In such aspects, specific sequences derived from selected constant region domains can be inserted or replicated.

VIII. Polynucleotides Encoding HER2-Binding Molecules

In certain aspects, the present disclosure provides polynucleotides comprising nucleic acid sequences that encode an anti-HER2 binding molecule disclosed herein that specifically binds HER2. For example, the instant disclosure provides a polynucleotide comprising a nucleic acid sequence that encodes an anti-HER2 binding molecule such as an antibody or a fragment thereof (e.g., a molecule which binds the same epitope as or is derived from the 39S antibody). The polynucleotides of the instant disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain aspects the DNA is a cDNA that is used to produce a non-naturally-occurring recombinant antibody.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide (either natural or heterologous) which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for an anti-HER2 binding molecule proprotein which is the mature protein plus additional 5' amino acid residues. In certain aspects, the polynucleotides are altered to optimize codon usage for a certain host cell.

In certain aspects the polynucleotides comprise the coding sequence for the mature anti-HER2 binding molecule, e.g., an anti-HER2 antibody or an antigen-binding fragment thereof fused in the same reading frame to a heterologous marker sequence that allows, for example, for purification of the encoded polypeptide. For example, the marker sequence can be a hexa-histidine (His6) tag (SEQ ID NO: 61) supplied, for example, by a pQE-9 vector to provide for purification of the mature polypeptide fused to the marker in the case of a bacterial host. In other aspects, the marker sequence can be a hemagglutinin (HA) tag derived, for example, from the influenza hemagglutinin protein, when a mammalian host (e.g., COS-7 cells) is used.

The present disclosure further relates to variants of the described polynucleotides encoding, for example, HER2-binding fragments, analogs, and derivatives of the anti-HER2 binding molecules of the present disclosure.

The polynucleotide variants can contain alterations in the coding regions, non-coding regions, or both. In some aspects the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as E. coli). Vectors and cells comprising the polynucleotides described herein are also provided.

In some aspects a DNA sequence encoding an anti-HER2 binding molecule, e.g., an anti-HER2 antibody or an antigen-binding fragment thereof can be constructed by chemical synthesis, for example, using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed, for example, by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-HER2 binding molecules. Recombinant expression vectors are replicable DNA constructs which have synthetic or cDNA-derived DNA fragments encoding, for example, a polypeptide chain of an anti-HER2 antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription.

The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of anti-HER2 binding molecules, e.g., anti-HER2 antibodies or antigen-binding fragments thereof, include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Additional information regarding methods of protein production, including antibody production, can be found, e.g., in U.S. Publ. No. 2008/0187954, U.S. Pat. Nos. 6,413,746 and 6,660,501, and Int'l Pat. Publ. No. WO 04009823, each of which is hereby incorporated by reference in its entirety.

Various mammalian or insect cell culture systems can also be advantageously employed to express recombinant anti-HER2 binding molecules, e.g., anti-HER2 antibodies or antigen-binding fragments thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa, and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow & Summers, BioTechnology 6:47 (1988).

Anti-HER2 binding molecules, e.g., anti-HER2 antibodies or antigen-binding fragments thereof, produced by a transformed host can be purified according to any suitable method. Such standard methods include, for example, chromatography (e.g., ion exchange, affinity and sizing column chromatography), centrifugation, differential solubility, or by any other standard technique for protein purification. Affinity tags such as hexahistidine (SEQ ID NO: 61), maltose binding domain, influenza coat sequence, glutathione-S-transferase, etc., can be attached to the protein to allow easy purification by passage over an appropriate affinity column. Isolated proteins can also be physically characterized using, for example, proteolysis, nuclear magnetic resonance or x-ray crystallography.

For example, supernatants from systems which secrete recombinant protein into culture media can be first concentrated using a commercially available protein concentration filter, for example, an AMICON® or Millipore PELLICON® ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed.

Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an HER2-binding molecule. Some or all of the foregoing purification steps, in various combinations, can also be employed to provide a homogeneous recombinant protein.

A recombinant anti-HER2 binding molecule, e.g., an anti-HER2 antibody or antigen-binding fragment thereof, produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Pat. Publ. Nos. US20080312425, US20080177048, and US20090187005, each of which is hereby incorporated by reference in its entirety.

IX. Treatment Methods Using Therapeutic Anti-HER2 Binding Molecules

The present disclosure also provides methods directed to the use of anti-HER2 binding molecules, e.g., antibodies, including antigen-binding fragments, variants, and derivatives thereof, to treat patients having a disease associated with HER2 expression or HER2-expressing cells.

By "HER2-expressing cell" is meant a cell expressing the HER2 protein. Methods for detecting and/or quantitating HER2 expression in cells are well known in the art and include, but are not limited to, PCR techniques, immunohistochemistry (e.g., HERCEPTEST™), flow cytometry, Western blot, ELISA, and the like. In some aspects, the methods disclosed herein are applied to treatment and diagnostic method where the cancer cells are expressing HER2 at low levels.

The methods for diagnosis and treatment of various diseases and disorders with an anti-HER2 binding molecule disclosed herein, refer to anti-HER2 antibodies (e.g., the 39S antibody, variants, derivatives, and HER2-binding fragments; bispecific anti-HER2 molecules of the instant disclosure; and ADC molecules of the instant disclosure) that retain the desired properties of the anti-HER2 binding molecules of the instant disclosure, e.g., capable of specifically binding HER2 and neutralizing HER2 activity.

In some aspects, the anti-HER2 binding molecules are human or humanized anti-HER2 binding molecules that mediate human ADCC; or comprise known anti-HER2 antibodies that mediate ADCC; or comprise anti-HER2 binding molecules that are engineered such that they mediate ADCC.

In some aspects, the anti-HER2 binding molecules are human or humanized anti-HER2 binding molecules that do not mediate human ADCC; or comprise known anti-HER2 antibodies that do not mediate ADCC; or comprise anti-HER2 binding molecules that are engineered such that they do not mediate ADCC.

In one aspect, treatment includes the application or administration of an anti-HER2 binding molecule, e.g., an antibody or antigen binding fragment, variant, or derivative thereof of the current disclosure to a subject or patient, or application or administration of the anti-HER2 binding molecule to an isolated tissue or cell line from a subject or patient, where the subject or patient has a disease, a symptom of a disease, or a predisposition toward a disease. In another aspect, treatment is also intended to include the application or administration of a pharmaceutical composition comprising the anti-HER2 binding molecule, e.g., an antibody or antigen binding fragment, variant, or derivative thereof of the current disclosure to a subject or patient, or application or administration of a pharmaceutical composition comprising the anti-HER2 binding molecule to an isolated tissue or cell line from a subject or patient, who has a disease, a symptom of a disease, or a predisposition toward a disease.

The anti-HER2 binding molecules, e.g., antibodies or antigen-binding fragments, variants, or derivatives thereof of the present disclosure are useful for the treatment of various cancers. In one aspect, the instant disclosure relates to anti-HER2 binding molecules, e.g., antibodies or antigen-binding fragments, variants, or derivatives thereof for use as a medicament, in particular for use in the treatment or prophylaxis of cancer. Examples of cancer include, but are not limited to breast cancer, colon cancer, lung cancer, gastric cancer, head and neck squamous cells cancer, melanoma, pancreatic cancer, or prostate cancer. In some specific cases, the cancer expresses low levels of HER2 as determined, for example, via HERCEPTEST™.

In accordance with the methods of the present disclosure, at least one anti-HER2 binding molecule, e.g., an antibody or antigen binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-HER2 binding molecules, e.g., antibodies or antigen-binding fragments, variants, or derivatives thereof, and/or an improvement in the symptoms associated with the disease.

For example, an improvement in the disease can be characterized as a complete response. The term "complete response" refers to an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-HER2 binding molecule of the instant disclosure.

In specific aspects, such terms refer to one, two or three or more results following the administration of anti-HER2 binding molecules of the instant disclosure:

(1) a stabilization, reduction or elimination of the cancer cell population;
(2) a stabilization or reduction in cancer growth;
(3) an impairment in the formation of cancer;
(4) eradication, removal, or control of primary, regional and/or metastatic cancer;
(5) a reduction in mortality;
(6) an increase in disease-free, relapse-free, progression-free, and/or overall survival, duration, or rate;
(7) an increase in the response rate, the durability of response, or number of patients who respond or are in remission;
(8) a decrease in hospitalization rate,
(9) a decrease in hospitalization lengths,
(10) the size of the cancer (e.g., in volume) is maintained and does not increase or increases by less than 10%, preferably less than 5%, preferably less than 4%, preferably less than 2%, and
(11) an increase in the number of patients in remission.
(12) a decrease in the number of adjuvant therapies (e.g., chemotherapy or hormonal therapy) that would otherwise be required to treat the cancer.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-HER2 binding molecule, e.g., an antibody or antigen-binding fragment, variant, or derivative thereof, can experience the beneficial effect of an improvement in the symptoms associated with the disease.

The anti-HER2 binding molecules, e.g., antibodies or antigen-binding fragments, variants, or derivatives thereof of the instant disclosure can be used in combination with any known therapies for cancer, including any agent or combination of agents that are known to be useful, or which have been used or are currently in use, for treatment of cancer, e.g., colon cancer, lung cancer, gastric cancer, head and neck squamous cells cancer, and breast cancer. The second agent or combination of agents of the pharmaceutical combination formulation or dosing regimen preferably has complementary activities to anti-HER2 binding molecule(s) of the instant disclosure such that they do not adversely affect each other.

Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone.

Anti-cancer agents for use in certain methods of the present disclosure include, among others, antibodies (e.g., antibodies which bind IGF-1R, antibodies which bind EGFR, antibodies which bind HER2 or HER3), small molecules targeting IGF1R, small molecules targeting EGFR, small molecules targeting HER2, antimetabolites, alkylating agents, topoisomerase inhibitors, microtubule targeting agents, kinase inhibitors, protein synthesis inhibitors, immunotherapeutic agents, hormonal therapies, glucocorticoids, aromatase inhibitors, mTOR inhibitors, chemotherapeutic agents, protein kinase B inhibitors, phosphatidylinositol 3-kinase (PI3K) inhibitors, cyclin dependent kinase (CDK) inhibitors, RLr9, CD289, enzyme inhibitors, anti-TRAIL, MEK inhibitors, etc.

In specific aspects, the anti-HER2 binding molecules disclosed herein, e.g., antibodies or antigen-binding fragments thereof, can be administered in combination with other antibodies or antibody fragments targeting epidermal growth factor receptor (EGFR), e.g. Erbitux® (cetuximab) or panitumumab (VECTIBIX®).

In other aspects, the anti-HER2 binding molecules disclosed herein can be administered in combination with kinase inhibitors, e.g., tyrosine kinase inhibitors. In some other specific aspects, the anti-HER2 binding molecules disclosed herein can be administered in combination with inhibitors of the tyrosine kinase activity associated with EGFR and/or HER2/neu, e.g., lapatinib. In some aspects, the anti-HER2 binding molecules of the instant disclosure can be administered in combination with antimitotic agents. In some specific aspects, the anti-HER2 binding molecules of the instant disclosure can be administered in combination with agents that stabilize the mitotic spindle microtubule assembly, e.g., paclitaxel or docetaxel.

Where the combined therapies comprise administration of an anti-HER2 binding molecule in combination with administration of another therapeutic agent, the methods of the instant disclosure encompass co-administration, using separate formulations or a single pharmaceutical formulation, and consecutive administration in either order. In some aspects, the anti-HER2 binding molecules described herein are administered in combination with other drugs, wherein the antibody or antigen-binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In some aspects, the anti-HER2 binding molecule, e.g., an anti-HER2 antibody or antigen binding fragment thereof of the instant disclosure, can be administered in a synergistic combination with a growth factor receptor (EGFR) inhibitor. In some aspects, the EGFR inhibitor is an antibody. In specific aspects, the EGFR inhibitor antibody is ERBITUX® (cetuximab) or VECTIBIX® (panitumumab). In specific aspects, the anti-HER2 binding molecules of the instant disclosure, e.g., antibodies or antigen-binding fragments thereof, can be administered in a synergistic combination with inhibitors of the tyrosine kinase activity associated with EGFR and/or HER2/neu, e.g., lapatinib. In some aspects, the anti-HER2 binding molecules of the instant disclosure can be administered in a synergistic combination with an antimitotic agent. In some specific aspects the antimitotic agent stabilizes the mitotic spindle microtubule assembly. In some specific aspects, the antimitotic agent is paclitaxel or docetaxel.

A further aspect is the use of anti-HER2 binding molecules of the instant disclosure, e.g., antibodies or antigen-binding fragments, variants, or derivatives thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{35}S$, or $^{3}H$.

A further aspect is the use of anti-HER2 binding molecules of the instant disclosure, e.g., antibodies or antigen-binding fragments, variants, or derivatives thereof, to treat a cancer patient resistant to a HER2-targeting therapeutic agent, for example an antibody targeting an epitope within domain IV of HER2 such as trastuzumab. In some aspects, the therapeutic agent comprises a moiety targeting the same epitope as trastuzumab, and a cytotoxic moiety. In some aspects, such cytotoxic moiety is a maytansinoid. In some specific aspects, the maytansinoid is DM-1.

In some aspects, the methods of treatment disclosed herein comprise the administration of an anti-HER2 binding molecule which is an anti-HER2 antibody comprising a heavy chain (HC) variable region (VH) and a light chain (LC) variable region (VL) comprising:
(i) a variable heavy chain CDR-1 (VH-CDR1) identical to SEQ ID NO: 1 or identical to SEQ ID NO: 1 except for up to 1, 2, 3, or 4 amino acid substitutions;
(ii) a variable heavy chain CDR-2 (VH-CDR2) identical to SEQ ID NO: 2 or identical to SEQ ID NO: 2 except for up to 1, 2, 3, or 4 amino acid substitutions;
(iii) a variable heavy chain CDR-3 (VH-CDR3) identical to SEQ ID NO: 3 or identical to SEQ ID NO: 3 except for up to 1, 2, 3, or 4 amino acid substitutions;
(iv) a variable light chain CDR-1 (VL-CDR1) identical to SEQ ID NO: 4 or identical to SEQ ID NO: 4 except for up to 1, 2, 3, or 4 amino acid substitutions;
(v) a variable light chain CDR-2 (VL-CDR2) identical to SEQ ID NO: 5 or identical to SEQ ID NO: 5 except for up to 1, 2, 3, or 4 amino acid substitutions; and,
(vi) a variable light chain CDR-3 (VL-CDR3) identical to SEQ ID NO: 6 or identical to SEQ ID NO: 6 except for up to 1, 2, 3, or 4 amino acid substitutions.

In some aspects, the methods of treatment disclosed herein comprise the administration of an anti-HER2 binding molecule which is a bispecific anti-HER2 antibody comprising a first immunoglobulin antigen-binding domain and a second immunoglobulin antigen-binding domain, wherein (i) the first and second immunoglobulin antigen-binding domains specifically bind to distinct HER2 antibody binding sites, (ii) the first immunoglobulin antigen-binding domain binds to a first HER2 antibody binding site which comprises an epitope within domain II of HER2, and (iii) the first HER2 antibody binding site is distinct from the antibody binding site of pertuzumab.

In some aspects, the methods of treatment disclosed herein comprise the administration of an anti-HER2 binding molecule which is a bispecific anti-HER2 antibody comprising a first immunoglobulin antigen-binding domain and a second immunoglobulin antigen-binding domain, wherein the first immunoglobulin antigen-binding domain comprises a heavy chain (HC) variable region (VH) and a light chain (LC) variable region (VL) comprising:

(i) a variable heavy chain CDR-1 (VH-CDR1) identical to SEQ ID NO: 1 or identical to SEQ ID NO: 1 except for up to 1, 2, 3, or 4 amino acid substitutions;
(ii) a variable heavy chain CDR-2 (VH-CDR2) identical to SEQ ID NO: 2 or identical to SEQ ID NO: 2 except for up to 1, 2, 3, or 4 amino acid substitutions;
(iii) a variable heavy chain CDR-3 (VH-CDR3) identical to SEQ ID NO: 3 or identical to SEQ ID NO: 3 except for up to 1, 2, 3, or 4 amino acid substitutions;
(iv) a variable light chain CDR-1 (VL-CDR1) identical to SEQ ID NO: 4 or identical to SEQ ID NO: 4 except for up to 1, 2, 3, or 4 amino acid substitutions;
(v) a variable light chain CDR-2 (VL-CDR2) identical to SEQ ID NO: 5 or identical to SEQ ID NO: 5 except for up to 1, 2, 3, or 4 amino acid substitutions; and,
(vi) a variable light chain CDR-3 (VL-CDR3) identical to SEQ ID NO: 6 or identical to SEQ ID NO: 6 except for up to 1, 2, 3, or 4 amino acid substitutions.

In some aspects, the first immunoglobulin antigen-binding domain of such anti-HER2 binding molecule comprises at least one heterologous variable domain framework region (FW) different relative to the FW regions of an immunoglobulin antigen-binding domain comprising a VH comprising the amino acids SEQ ID NO:43 and a VL comprising the amino acids of SEQ ID NO:44. In some aspects, the first immunoglobulin antigen-binding domain comprises:

(i) a variable light chain framework 1 (VL-FW1) comprising the amino acids of SEQ ID NO:11;
(ii) a VL-FW2 comprising the amino acids of SEQ ID NO:12;
(iii) a VL-FW3 comprising the amino acids of SEQ ID NO:13;
(iv) a VL-FW4 comprising the amino acids of SEQ ID NO:14; or
(vi) any combination thereof.

In some aspects, the first immunoglobulin antigen-binding domain of such anti-HER2 binding molecule comprises a VH and a VL, wherein the VH comprises the amino acids of SEQ ID NO:15 or 43; and wherein the first and second immunoglobulin antigen-binding domains specifically bind to distinct HER2 epitopes. In some aspects, the first immunoglobulin antigen-binding domain of such anti-HER2 binding molecule a VH and a VL, wherein the VL comprises the amino acids of SEQ ID NO:16 or 44; and wherein the first and second immunoglobulin antigen-binding domains specifically bind to distinct HER2 epitopes. In some aspects, the first immunoglobulin antigen-binding domain of such anti-HER2 binding molecule comprises a VH and a VL, wherein the VH comprises the amino acids of SEQ ID NO:15; and wherein the VL comprises the amino acids of SEQ ID NO: 16.

In some aspects, the second immunoglobulin antigen-binding domain of such anti-HER2 binding molecule (a) specifically binds to the same HER2 epitope as the trastuzumab antibody; and/or (b) competitively inhibits HER2 binding by the trastuzumab antibody; and/or (c) comprises at least one, at least two, at least three, at least four, at least five, or at least six complementarity determining regions (CDRs) comprising the amino acids of any one of SEQ ID NOs: 54 to 59. In some aspects, the second immunoglobulin antigen-binding domain of such anti-HER2 binding molecule is an scFv comprising (i) a VH-CDR1 comprising the amino acids of SEQ ID NO:54; (ii) a VH-CDR2 comprising the amino acids of SEQ ID NO:55; (iii) a VH-CDR3 comprising the amino acids of SEQ ID NO:56; (iv) a VL-CDR1 comprising the amino acids of SEQ ID NO:57; (v) a VL-CDR2 comprising the amino acids of SEQ ID NO:58; and (vi) a VL-CDR3 comprising the amino acids of SEQ ID NO:59.

In other aspects, the methods of treatment disclosed herein comprise the administration of an anti-HER2 binding molecule which is an ADC comprising a bispecific anti-HER2 antibody, wherein said antibody comprises:

(i) a first polypeptide chain comprising or consisting of the amino acids of SEQ ID NO: 32 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat;
(ii) a first polypeptide chain comprising or consisting of the amino acids of SEQ ID NO:33 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442 wherein the amino acid position numbering is according to the EU index as set forth in Kabat;
(iii) a first polypeptide chain comprising or consisting of the amino acids of SEQ ID NO:36 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat;
(iv) a first polypeptide chain comprising or consisting of the amino acids of SEQ ID NO:37 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442, wherein the amino acid position numbering is according to the EU index as set forth in Kabat;
(v) a first polypeptide chain comprising or consisting of the amino acids of SEQ ID NO:40 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid at position 239, wherein the amino acid position numbering is according to the EU index as set forth in Kabat; or,
(vi) a first polypeptide chain comprising or consisting of the amino acids of SEQ ID NO:41 and a second polypeptide chain comprising or consisting of the amino acids of SEQ ID NO:42, wherein the first polypeptide chain comprises two therapeutic moieties (e.g., two tubulysin 1508 molecules) covalently linked to cysteine amino acids respectively located at positions 239 and 442, wherein the amino acid position numbering is according to the EU index as set forth in Kabat.

In other aspects, the methods of treatment disclosed herein comprise the administration of an anti-HER2 binding molecule which is an ADC comprising a bispecific anti-HER2 antibody, wherein said antibody comprises:

(i) a first polypeptide chain comprising or consisting of the amino acids of SEQ ID NO:69 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat;

(ii) a first polypeptide chain comprising or consisting of the amino acids of SEQ ID NO: 71 and a second polypeptide chain comprising or consisting of the amino acids of SEQ ID NO:42, wherein the first polypeptide chain comprises two therapeutic moieties (e.g., two tubulysin 1508 molecules) covalently linked to a cysteine amino inserted between positions 239 and 240 and a cysteine amino acid located at position 442 wherein the amino acid position numbering is according to the EU index as set forth in Kabat;

(iii) a first polypeptide chain comprising or consisting of the amino acids of SEQ ID NO:74 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat;

(iv) a first polypeptide chain comprising or consisting of the amino acids of SEQ ID NO:76 and a second polypeptide chain comprising or consisting of the amino acids of SEQ ID NO:42, wherein the first polypeptide chain comprises two therapeutic moieties (e.g., two tubulysin 1508 molecules) covalently linked to a cysteine amino inserted between positions 239 and 240 and a cysteine amino acid located at position 442, wherein the amino acid position numbering is according to the EU index as set forth in Kabat;

(v) a first polypeptide chain comprising or consisting of the amino acids of SEQ ID NO:79 and a second polypeptide chain comprising or consisting of the amino acids of SEQ ID NO:42, wherein the first polypeptide chain comprises a therapeutic moiety (e.g., a tubulysin 1508 molecule) covalently linked to a cysteine amino acid inserted between positions 239 and 240, wherein the amino acid position numbering is according to the EU index as set forth in Kabat; or, (vi) a first polypeptide chain comprising or consisting of the amino acids of SEQ ID NO:67 and a second polypeptide chain comprising or consisting of the amino acids of SEQ ID NO:42, wherein the first polypeptide chain comprises two therapeutic moieties (e.g., two tubulysin 1508 molecules) covalently linked to a cysteine amino inserted between positions 239 and 240 and a cysteine amino acid located at position 442, wherein the amino acid position numbering is according to the EU index as set forth in Kabat.

X. Pharmaceutical Compositions and Administration Methods

Methods of preparing and administering anti-HER2 binding molecules, e.g., antibodies, or antigen-binding fragments, variants, or derivatives thereof (e.g., an ADC such as Bs2-4T), to a subject in need thereof are well known to or are readily determined by those skilled in the art. The route of administration of the anti-HER2 binding molecule, e.g., antibody, or antigen-binding fragment, variant, or derivative thereof (e.g., an ADC such as Bs2-4T), can be, e.g., oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-HER2 binding molecules, e.g., antibodies, or antigen-binding fragments, variants, or derivatives thereof (e.g., an ADC such as Bs2-4T), of the instant disclosure can be delivered directly to the site of the adverse cellular population thereby increasing the exposure of the diseased tissue to the therapeutic agent.

As discussed herein, anti-HER2 binding molecules of the instant disclosure, e.g., antibodies, or antigen-binding fragments, variants, or derivatives thereof (e.g., an ADC such as Bs2-4T), can be administered in a pharmaceutically effective amount for the in vivo treatment of HER2-expressing cell-mediated diseases such as certain types of cancers. The pharmaceutical compositions can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in the therapeutic methods disclosed herein are described in Remington's Pharmaceutical Sciences (Mack Publishing Co.) 16th ed. (1980).

In any case, sterile injectable solutions can be prepared by incorporating an active compound (e.g., an anti-HER2 antibody, or antigen-binding fragment, variant, or derivative thereof, e.g., an ADC such as Bs2-4T, by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present disclosure, for treatment of HER2-expressing cell-mediated diseases such as certain types of cancers including e.g., colon cancer, lung cancer, gastric cancer, head and neck squamous cells cancer, melanoma, pancreatic cancer, prostate cancer, and breast cancer, vary depending upon many different factors, including means of administration, target site, physiological state of the patient, whether the patient is human or an animal, other medications administered, and whether treatment is prophylactic or therapeutic. In some specific aspects, the cancer expresses low levels of HER2 as determined, for example, using HERCEPTEST™. Usually, the patient is a human, but non-human mammals including transgenic mammals can also be treated. Treatment dosages can be titrated using routine methods known to those of skill in the art to optimize safety and efficacy.

The amount of at least one anti-HER2 binding molecule, e.g., antibody or binding fragment, variant, or derivative thereof (e.g., an ADC such as Bs2-4T) to be administered can be readily determined by one of ordinary skill in the art without undue experimentation. Factors influencing the mode of administration and the respective amount of at least one anti-HER2 binding molecule, e.g., antibody, antigen-binding fragment, variant or derivative thereof (e.g., an ADC such as Bs2-4T), include, but are not limited to, the severity of the disease, the history of the disease, and the age, height, weight, health, and physical condition of the individual undergoing therapy. Similarly, the amount of anti-HER2 binding molecule, e.g., antibody, or fragment, variant, or derivative thereof (e.g., an ADC such as Bs2-4T), to be administered will be dependent upon the mode of administration and whether the subject will undergo a single dose or multiple doses of this agent.

The present disclosure also provides for the use of an anti-HER2 binding molecule, e.g., an antibody or antigen-binding fragment, variant, or derivative thereof (e.g., an ADC such as Bs2-4T), in the manufacture of a medicament for treating a type of cancer, including, e.g., breast cancer, colon cancer, lung cancer, gastric cancer, head and neck squamous cells cancer, melanoma, pancreatic cancer, and prostate cancer. In some specific aspects, the cancer expresses low levels of HER2 as determined, for example, using HERCEPTEST™.

The disclosure also provides for the use of an anti-HER2 binding molecule, e.g., antibody of the instant disclosure, or antigen-binding fragment, variant, or derivative thereof, in the manufacture of a medicament for treating a subject for treating a type of cancer. In some specific aspects, the cancer expresses low levels of HER2 as determined, for example, using HERCEPTEST™. In certain aspects, the medicament is used in a subject that has been pretreated with at least one other therapy.

By "pretreated" or "pretreatment" is intended the subject has received one or more other therapies (e.g., been treated with at least one other anti-cancer therapy) prior to receiving the medicament comprising the anti-HER2 binding molecule, e.g., antibody or antigen-binding fragment, variant, or derivative thereof (e.g., an ADC such as Bs2-4T). It is not necessary that the subject was a responder to pretreatment with the prior therapy or therapies. Thus, the subject that receives the medicament comprising the anti-HER2 binding molecule, e.g., an antibody or antigen-binding fragment, variant, or derivative thereof (e.g., an ADC such as Bs2-4T) could have responded, responded poorly, or could have failed to respond to pretreatment with the prior therapy, or to one or more of the prior therapies where pretreatment comprised multiple therapies. Accordingly, the present disclosure provides methods to treat patients that are poor responders or non-responders to other therapies (e.g., treatment with an antibody or an ADC such as T-DM1) comprising administering an anti-HER2 binding molecule disclosed herein, e.g., an antibody or binding fragment, a variant, or a derivative thereof (e.g., an ADC such as Bs2-4T). Also provided are methods to prevent resistance to cancer therapies (e.g., resistance to treatment with an antibody or an ADC such as T-DM1) comprising administering an anti-HER2 binding molecule disclosed herein, e.g., an antibody or binding fragment, a variant, or a derivative thereof (e.g., an ADC such as Bs2-4T).

Even if a patient has been previously treated with a HER2 inhibitor, a person skilled in the art can determine whether a person showed no response after the treatment with the HER2 inhibitor. For example, a non-response to an inhibitor may be reflected in an increased suffering from cancer, such as an increased growth of a cancer/tumor and/or increase in the size of a tumor, the (increase in) the formation of metastases or a increase in the number or size of metastases. A non-response may also be the development of a tumor or metastases, for example after resection of a tumor, in the shortening of time to disease progression, or in the increase in the size of (a) tumor(s) and/or (a) metastases, for example in neoadjuvant therapy. Based on these parameters or other parameters known in the art, a patient group can be identified that does not respond to treatment with HER2 inhibitors, like pertuzumab, trastuzumab, or T-DM1. Such group of patients then could be treated with the anti-HER2 binding molecules disclosed herein, e.g., antibody of the disclosure, or antigen-binding fragment, variant, or derivative thereof (e.g., an ADC such as Bs2-4T).

The present disclosure provides also methods to treat patients that are, for example, poor-responders or non-responders to another therapy. The term "non-responder" as used herein can refer to an individual/patient/subject that is less likely to respond to a treatment using a HER2 inhibitor (e.g., pertuzumab, trastuzumab, or T-DM1). "Less likely to respond" as used herein refers to a decreased likeliness that a pathological complete response will occur in a patient treated with a HER2 inhibitor. In some aspects, a patient can be initially a good responder, and resistance to HER2 inhibitors can develop during treatment with such HER2 inhibitors (e.g., pertuzumab, trastuzumab, or T-DM1), leading to poor or no-response to the treatment.

The term "good responder" as used herein refers to an individual whose tumor does not demonstrate growth, metastases, increase in number or size of metastases, etc. during or after treatment using a HER2 inhibitor (like pertuzumab, trastuzumab, or T-DM1), for example based on serial imaging studies, an individual that does not experience tumor growth, metastases, increase in number or size of metastases, etc. over a period of time (e.g., about 1 year following initial diagnosis), and/or an individual that experiences a certain life span (e.g., about 2 years or more following initial diagnosis).

The term "poor responder" as used herein refers to an individual whose tumor grows or metastasizes during or shortly therafter standard therapy, for example using a HER2 inhibitor (like pertuzumab, trastuzumab, or T-DM1), or who experiences adverse clinical effects attributable to the tumor.

In cases where it is assessed that the subject is a "non-responder," a "poor-responder" or is "less likely to respond" (based, for example, on the presence of certain biomarkers in the cancer cells), the subject could be treated with the anti-HER2 binding molecules disclosed herein, e.g., antibody of the disclosure, or antigen-binding fragment, variant, or derivative thereof (e.g., an ADC such as Bs2-4T).

The instant disclosure also provides for the co-administration of an anti-HER2 binding molecule, e.g., antibody of the disclosure, or antigen-binding fragment, variant, or derivative thereof (e.g., an ADC such as Bs2-4T), and at least one other therapy. The anti-HER2 binding molecule and the at least one other therapy can be co-administered together in a single composition or can be co-administered together at the same time or overlapping times in separate compositions. In some aspects, an anti-HER2 binding molecule, e.g., antibody of the disclosure, or antigen-binding fragment, variant, or derivative thereof (e.g., an ADC such as Bs2-4T), can be used as an adjuvant therapy.

The instant disclosure also provides for the use of an anti-HER2 binding molecule, e.g., antibody of the disclosure, or antigen-binding fragment, variant, or derivative thereof (e.g., an ADC such as Bs2-4T), in the manufacture of a medicament for treating a subject for treating cancer, wherein the anti-HER2 binding molecule is administered before a subject has been treated with at least one other therapy.

XI. Diagnostics

The present disclosure further provides diagnostic methods useful for during diagnosis of HER2-expressing cell-mediated diseases such as certain types of cancer including, e.g., colon cancer, lung cancer, gastric cancer, head and neck squamous cells cancer, melanoma, pancreatic cancer, prostate cancer, and breast cancer, which involves measuring the expression level of HER2 protein or transcript in tissue or other cells or body fluid from an individual and comparing the measured expression level with a standard HER2 expression level in normal tissue or body fluid, whereby an increase in the expression level compared to the standard is indicative of a disorder.

The anti-HER2 binding molecules of the instant disclosure and antigen-binding fragments, variants, and derivatives thereof, can be used to assay HER2 protein levels in a biological sample using classical immunohistological methods known to those of skill in the art (e.g., see Jalkanen, et al., *J. Cell. Biol.* 101:976-985 (1985); Jalkanen et al., *J. Cell Biol.* 105:3087-3096 (1987)). Other antibody-based methods useful for detecting HER2 protein expression include immunoassays, such as the enzyme linked immunosorbent assay (ELISA), immunoprecipitation, or Western blotting. Suitable assays are described in more detail elsewhere herein.

By "assaying the expression level of HER2 polypeptide" is intended qualitatively or quantitatively measuring or estimating the level of HER2 polypeptide in a first biological sample either directly (e.g., by determining or estimating absolute protein level) or relatively (e.g., by comparing to the disease associated polypeptide level in a second biological sample). HER2 polypeptide expression level in the first biological sample can be measured or estimated and compared to a standard HER2 polypeptide level, the standard being taken from a second biological sample obtained from an individual not having the disorder or being determined by averaging levels from a population of individuals not having the disorder. As will be appreciated in the art, once the "standard" HER2 polypeptide level is known, it can be used repeatedly as a standard for comparison.

By "biological sample" is intended any biological sample obtained from an individual, cell line, tissue culture, or other source of cells potentially expressing HER2. Methods for obtaining tissue biopsies and body fluids from mammals are well known in the art.

XII. Kits Comprising Anti-HER2 Binding Molecules

The present disclosure also provides kits that comprise an anti-HER2 binding molecule disclosed herein, e.g., an anti-HER2 antibody or antigen binding fragment thereof, that can be used to perform the methods described herein. In certain aspects, a kit comprises at least one purified anti-HER2 binding molecule or an antigen-binding fragment thereof in one or more containers. In some aspects, the kits contain all of the components necessary and/or sufficient to perform a detection assay, including all controls, directions for performing assays, and any necessary software for analysis and presentation of results. One skilled in the art will readily recognize that the disclosed anti-HER2 binding molecules disclosed herein, e.g., an anti-HER2 antibody or antigen binding fragment thereof, can be readily incorporated into one of the established kit formats which are well known in the art.

XIII. Immunoassays

Anti-HER2 binding molecules, e.g., antibodies or antigen-binding fragments thereof, variants, or derivatives thereof of the molecules of the instant disclosure can be assayed for immunospecific binding by any method known in the art. The immunoassays that can be used include but are not limited to competitive and non-competitive assay systems using techniques such as Western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al., eds, (1994) Current Protocols in Molecular Biology (John Wiley & Sons, Inc., NY) Vol. 1, which is incorporated by reference herein in its entirety).

Anti-HER2 binding molecules disclosed herein, e.g., bispecific anti-HER2 antibodies or antigen-binding fragments thereof, variants, or derivatives thereof of the molecules of the instant disclosure, can be employed histologically, as in immunofluorescence, immunoelectron microscopy or non-immunological assays, for in situ detection of HER2 receptors or conserved variants or peptide fragments thereof. In situ detection can be accomplished by removing a histological specimen from a patient, and applying thereto a labeled HER2-binding molecule, e.g., a bispecific anti-HER2 antibody or antigen-binding fragment thereof, variant, or derivative thereof, preferably applied by overlaying the labeled HER2-binding molecule (e.g., an antibody or fragment) onto a biological sample. Through the use of such a procedure, it is possible to determine not only the presence of HER2, or conserved variants or peptide fragments, but also its distribution in the examined tissue. Using the present disclosure, those of ordinary skill will readily perceive that any of a wide variety of histological methods (such as staining procedures) can be modified in order to achieve such in situ detection.

The binding activity of a given lot of anti-HER2 binding molecule, e.g., a bispecific anti-HER2 antibody or antigen-binding fragment thereof, variant, or derivative thereof, can be determined according to well-known methods. Those skilled in the art will be able to determine operative and optimal assay conditions for each determination by employing routine experimentation.

Methods and reagents suitable for determination of binding characteristics of an anti-HER2 binding molecule of the instant disclosure, e.g., a bispecific anti-HER2 antibody or antigen-binding fragment thereof, variant, or an altered/mutant derivative thereof, are known in the art and/or are commercially available. Equipment and software designed for such kinetic analyses are commercially available (e.g., BIAcore, BIAevaluation software, GE Healthcare; KinExa Software, Sapidyne Instruments).

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Sambrook et al., ed. (1989) Molecular Cloning A Laboratory Manual (2nd ed.; Cold Spring Harbor Laboratory Press); Sambrook et al., ed. (1992) Molecular Cloning: A Laboratory Manual, (Cold Springs Harbor Laboratory, NY); D. N. Glover ed., (1985) DNA Cloning, Volumes I and II; Gait, ed. (1984) Oligonucleotide Synthesis; Mullis et al. U.S. Pat. No. 4,683,195; Hames and Higgins, eds. (1984) Nucleic Acid Hybridization; Hames and Higgins, eds. (1984) Transcription And Translation; Freshney (1987) Culture Of Animal Cells (Alan R. Liss, Inc.); Immobilized Cells And Enzymes (IRL Press) (1986); Perbal (1984) A Practical Guide To Molecular Cloning; the treatise, Methods In Enzymology (Academic Press, Inc., N.Y.); Miller and Calos eds. (1987) Gene Transfer Vectors For Mammalian Cells, (Cold Spring Harbor Laboratory); Wu et al., eds., Methods In Enzymology, Vols. 154 and 155; Mayer and Walker, eds. (1987) Immunochemical Methods In Cell And Molecular Biology (Academic Press, London); Weir and Blackwell, eds., (1986) Handbook Of Experimental Immunology, Volumes I-IV; Manipulating the Mouse Embryo, Cold Spring Harbor Laboratory Press, Cold Spring Harbor, N.Y., (1986); and in Ausubel et al. (1989) Current Protocols in Molecular Biology (John Wiley and Sons, Baltimore, Md.).

General principles of antibody engineering are set forth in Borrebaeck, ed. (1995) Antibody Engineering (2nd ed.; Oxford Univ. Press). General principles of protein engineering are set forth in Rickwood et al., eds. (1995) Protein Engineering, A Practical Approach (IRL Press at Oxford Univ. Press, Oxford, Eng.). General principles of antibodies and antibody-hapten binding are set forth in: Nisonoff (1984) Molecular Immunology (2nd ed.; Sinauer Associates, Sunderland, Mass.); and Steward (1984) Antibodies, Their Structure and Function (Chapman and Hall, New York, N.Y.). Additionally, standard methods in immunology known in the art and not specifically described are generally followed as in Current Protocols in Immunology, John Wiley & Sons, New York; Stites et al., eds. (1994) Basic and Clinical Immunology (8th ed; Appleton & Lange, Norwalk, Conn.) and Mishell and Shiigi (eds) (1980) Selected Methods in Cellular Immunology (W.H. Freeman and Co., NY).

Standard reference works setting forth general principles of immunology include Current Protocols in Immunology, John Wiley & Sons, New York; Klein (1982) J., Immunology: The Science of Self-Nonself Discrimination (John Wiley & Sons, NY); Kennett et al., eds. (1980) Monoclonal Antibodies, Hybridoma: A New Dimension in Biological Analyses (Plenum Press, NY); Campbell (1984) "Monoclonal Antibody Technology" in Laboratory Techniques in Biochemistry and Molecular Biology, ed. Burden et al., (Elsevere, Amsterdam); Goldsby et al., eds. (2000) Kuby Immunnology (4th ed.; H. Freemand & Co.); Roitt et al. (2001) Immunology (6th ed.; London: Mosby); Abbas et al. (2005) Cellular and Molecular Immunology (5th ed.; Elsevier Health Sciences Division); Kontermann and Dubel (2001) Antibody Engineering (Springer Verlan); Sambrook and Russell (2001) Molecular Cloning: A Laboratory Manual (Cold Spring Harbor Press); Lewin (2003) Genes VIII (Prentice Hall2003); Harlow and Lane (1988) Antibodies: A Laboratory Manual (Cold Spring Harbor Press); Dieffenbach and Dveksler (2003) PCR Primer (Cold Spring Harbor Press).

XIV. Embodiments

Embodiments are designated according to an "EnXm" schema, where E means "embodiment"; n is the embodiment ordinal number; X is optional and can be A or B, where A denotes embodiments specifically related to ADC constructs, and B denotes embodiments specifically related to construct with enhanced ADCC; and in is an optional sub-ordinal number indicating additional embodiments within a class (e.g., A1, B 1, etc.).

E1. A bispecific anti-HER2 antibody comprising a first immunoglobulin antigen-binding domain and a second immunoglobulin antigen-binding domain, wherein (i) the first and second immunoglobulin antigen-binding domains specifically bind to distinct HER2 antibody binding sites, (ii) the first immunoglobulin antigen-binding domain binds to a first HER2 antibody binding site which comprises an epitope within domain II of HER2, and (iii) the first HER2 antibody binding site is distinct from the antibody binding site of pertuzumab.

E2. The bispecific anti-HER2 antibody of E1 wherein the second immunoglobulin antigen-binding domain binds to a second HER2 antibody binding site which comprises an epitope within domain IV of HER2.

E3. The bispecific anti-HER2 antibody of E2 wherein the second HER2 antibody binding site is identical to the HER2 antibody binding site of trastuzumab.

E4. The bispecific anti-HER2 antibody of E2 wherein the second HER2 antibody binding site partially overlaps with the HER2 antibody binding site of trastuzumab.

E5. The bispecific anti-HER2 antibody of E2 wherein the second HER2 antibody binding site is distinct from the HER antibody binding site of trastuzumab.

E6. A bispecific HER2 antibody comprising a first immunoglobulin antigen-binding domain and a second immunoglobulin antigen-binding domain, wherein the first and second immunoglobulin antigen-binding domains specifically bind to distinct HER2 epitopes; and wherein the first immunoglobulin antigen-binding domain binds HER2 to one or more amino acid residues in SEQ ID NO: 52.

E7. The bispecific antibody according to E6, wherein the second immunoglobulin antigen-binding domain binds HER2 at an epitope within domain IV.

E8. The bispecific antibody according to E6, wherein the second immunoglobulin antigen binding domain binds HER2 to one or more amino acid residues in SEQ ID NO: 53.

E9. The bispecific antibody according to E1-E8, wherein the first immunoglobulin antigen-binding domain comprises a heavy chain (HC) variable region (VH) and a light chain (LC) variable region (VL) comprising:
(i) a variable heavy chain CDR-1 (VH-CDR1) identical to SEQ ID NO: 1 or identical to SEQ ID NO: 1 except for up to 1, 2, 3, or 4 amino acid substitutions;
(ii) a variable heavy chain CDR-2 (VH-CDR2) identical to SEQ ID NO: 2 or identical to SEQ ID NO: 2 except for up to 1, 2, 3, or 4 amino acid substitutions;
(iii) a variable heavy chain CDR-3 (VH-CDR3) identical to SEQ ID NO: 3 or identical to SEQ ID NO: 3 except for up to 1, 2, 3, or 4 amino acid substitutions;
(iv) a variable light chain CDR-1 (VL-CDR1) identical to SEQ ID NO: 4 or identical to SEQ ID NO: 4 except for up to 1, 2, 3, or 4 amino acid substitutions;
(v) a variable light chain CDR-2 (VL-CDR2) identical to SEQ ID NO: 5 or identical to SEQ ID NO: 5 except for up to 1, 2, 3, or 4 amino acid substitutions; and,
(vi) a variable light chain CDR-3 (VL-CDR3) identical to SEQ ID NO: 6 or identical to SEQ ID NO: 6 except for up to 1, 2, 3, or 4 amino acid substitutions.

E10. The bispecific antibody according to E9, wherein the first immunoglobulin antigen-binding domain comprises at least one heterologous variable domain framework region (FW) different relative to the FW regions of an immunoglobulin antigen-binding domain comprising a VH comprising the amino acids SEQ ID NO:43 and a VL comprising the amino acids of SEQ ID NO:44.

E11. The bispecific anti-HER2 antibody according to E10, wherein the first immunoglobulin antigen-binding domain comprises:
(i) a variable light chain framework 1 (VL-FW1) comprising the amino acids of SEQ ID NO:11;
(ii) a VL-FW2 comprising the amino acids of SEQ ID NO:12;
(iii) a VL-FW3 comprising the amino acids of SEQ ID NO:13;
(iv) a VL-FW4 comprising the amino acids of SEQ ID NO:14; or
(v) any combination thereof.

E12. A bispecific anti-HER2 antibody comprising a first immunoglobulin antigen binding-domain and a second immunoglobulin antigen-binding domain, wherein the first immunoglobulin antigen-binding domain comprises a VH and a VL,
wherein the VH comprises the amino acids of SEQ ID NO:15 or 43; and
wherein the first and second immunoglobulin antigen-binding domains specifically bind to distinct HER2 epitopes.

E13. A bispecific anti-HER2 antibody comprising a first immunoglobulin antigen binding-domain and a second immunoglobulin antigen-binding domain, wherein the first immunoglobulin antigen-binding domain comprises a VH and a VL,
wherein the VL comprises the amino acids of SEQ ID NO:16 or 44; and
wherein the first and second immunoglobulin antigen-binding domains specifically bind to distinct HER2 epitopes.

E14. The bispecific anti-HER2 antibody of E12 or E13, wherein the VH comprises the amino acids of SEQ ID NO:15; and
wherein the VL comprises the amino acids of SEQ ID NO: 16.

E15. The bispecific anti-HER2 antibody according to any one of E1 to E14, wherein the first immunoglobulin antigen-binding domain comprises an scFv antibody fragment.

E16. The bispecific anti-HER2 antibody according to any one of E1 to E15, wherein the second immunoglobulin antigen-binding domain comprises an scFv antibody fragment.

E17. The bispecific anti-HER2 antibody according to thereof of any one of E1 to E16, wherein the first immunoglobulin antigen binding domain comprises or consists of:
(a) a VH further comprising a heavy chain constant region or a fragment thereof and a VL comprising a light chain constant region (LC) or a fragment thereof;
(b) a single chain Fv ("scFv");
(c) a diabody;
(d) a minibody;
(e) an F(ab')2; or
(f) an F(ab).

E18. The bispecific anti-HER2 antibody according to E17, wherein the heavy chain constant region or fragment thereof is an IgG constant region.

E19. The bispecific HER2 antibody according to E18, wherein the IgG constant region or fragment thereof is an IgG1 constant region.

E20. The bispecific HER2 antibody according to any one of E17 to E19, wherein the LC constant region is a kappa constant region.

E21. The bispecific HER2 antibody according to any one of E17 to E19, wherein the LC constant region is a lambda constant region.

E22. The bispecific anti-HER2 antibody according to any one of E1 to E21, wherein the first immunoglobulin antigen-binding domain is a monoclonal antibody.

E23. The bispecific anti-HER2 antibody according to any one of E1 to E22, wherein the first immunoglobulin antigen-binding domain is a humanized antibody.

E24. The bispecific anti-HER2 antibody according to any one of E1 to E22, wherein the first immunoglobulin antigen-binding domain is a human antibody.

E25. The bispecific anti-HER2 antibody according to any one of E1 to E22, wherein the first immunoglobulin antigen-binding domain is a chimeric antibody.

E26. The bispecific anti-HER2 antibody according to any one of E1 to E25, wherein the first immunoglobulin antigen-binding domain is an affinity optimized antibody.

E27. The bispecific anti-HER2 antibody according to any one of E1 to E26, wherein the first immunoglobulin antigen-binding domain does not compete with trastuzumab or pertuzumab for epitope binding.

E28. The bispecific anti-HER2 antibody according to any one of E1 to E27, wherein the first and second immunoglobulin antigen binding domains specifically bind to distinct non-overlapping HER2 epitopes.

E29. The bispecific anti-HER2 antibody according to any one of E1 to E28, wherein:
(a) the second immunoglobulin antigen-binding domain specifically binds to the same HER2 epitope as the trastuzumab antibody;
(b) the second immunoglobulin antigen-binding domain competitively inhibits HER2 binding by the trastuzumab antibody; or
(c) the second immunoglobulin antigen-binding domain comprises at least one, at least two, at least three, at least four, at least five, or at least six complementarity determining regions (CDRs) comprising the amino acids of any one of SEQ ID NOs: 54 to 59.

E30. The bispecific anti-HER2 antibody according to E29, wherein the second immunoglobulin antigen-binding domain is anscFv comprising:
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and
(vi) a VL-CDR3 comprising the amino acids of SEQ ID NO:59.

E31. The bispecific anti-HER2 antibody according to E30, wherein the scFv is a disulfide stabilized scFv.

E32. The bispecific anti-HER2 antibody according to E30 or E31, wherein said scFv comprises a VH comprising the amino acids of SEQ ID NO:17, and a VL comprising the amino acid of SEQ ID NO:18.

E33. The bispecific anti-HER2 antibody according to E32, wherein the VH and VL of the scFv are covalently linked via a peptide linker.

E34. The bispecific anti-HER2 antibody according to E33, wherein the peptide linker comprises the amino acids of SEQ ID NO:19.

E35. The bispecific anti-HER2 antibody according to any one of E29 to E34, wherein the second immunoglobulin antigen-binding domain is covalently linked to the carboxy-terminus of the HC of the first immunoglobulin antigen-binding domain.

E36. The bispecific anti-HER2 antibody according to E35, comprising a linker interposed between the second immunoglobulin antigen binding domain and the carboxy-terminus of the HC of the first immunoglobulin antigen-binding domain.

E37. The bispecific anti-HER2 antibody according to any one of E29 to E34, wherein the second immunoglobulin antigen-binding domain is covalently linked to the amino-terminus of the HC of the first immunoglobulin antigen-binding domain.

E38. The bispecific anti-HER2 antibody according to E37, comprising a linker interposed between the second immunoglobulin antigen-binding domain and the amino-terminus of the HC of the first immunoglobulin antigen-binding domain.

E39. The bispecific anti-HER2 antibody according to E29 to E34, wherein the second immunoglobulin antigen binding domain is covalently intercalated in the polypeptide chain of the HC of the first immunoglobulin antigen-binding domain.

E40. The bispecific anti-HER2 antibody according to E39, wherein the second immunoglobulin antigen binding domain is covalently intercalated between the CH1 region and CH2 region of the HC of the first immunoglobulin antigen-binding domain.

E41. The bispecific anti-HER2 antibody according to E40, comprising:
(i) a linker interposed between the CH1 region of the HC of the first immunoglobulin antigen binding domain and the second immunoglobulin antigen binding domain; and
(ii) a second linker interposed between the second immunoglobulin antigen binding domain and the CH2 region of the HC of the of the first immunoglobulin antigen-binding domain.

E42. The bispecific anti-HER2 antibody according to E41, wherein the first linker and the second linker are identical.

E43. The bispecific anti-HER2 antibody according to E41, wherein the first linker and the second linker are different.

E44. The bispecific anti-HER2 antibody according to any one of E36, E38, and E41 to E43, wherein one or more of the linkers comprise a peptide linker.

E45. The bispecific anti-HER2 antibody according to E44, wherein the peptide linker comprises at least two, at least three, at least four, at least five, at least 10, at least 20, or at least 30 amino acids.

E46. The bispecific anti-HER2 antibody according to any one of E44 or E45, wherein the peptide linker comprises a peptide having the formula $Ser_x[(Gly)_y\text{-}Ser_4]_z$ where x is from 0 to 1, y is from 1 to 4, and z is from 1 to 10.

E47. The bispecific anti-HER2 antibody according to E46, wherein the peptide linker comprises SEQ ID NO:19-22.

E48. The bispecific anti-HER2 antibody according to any one of E1 to E47, wherein the heavy chain comprises a constant region comprising an Fc domain.

E49. The bispecific anti-HER2 antibody according to E48, wherein the Fc domain comprises a CH2 region and a CH3 region.

E50. The bispecific anti-HER2 antibody according to E48, wherein the Fc domain is an IgG1 Fc domain.

E51. The bispecific anti-HER2 antibody according to E50, wherein the IgG1 Fc domain is a native IgG1 Fc domain.

E52. The bispecific anti-HER2 antibody according to E51, wherein the native IgG1 Fc domain comprises the amino acids of SEQ ID NO: 23.

E53. The bispecific anti-HER2 antibody according to E48, wherein the Fc domain is a mutant IgG1 Fc domain.

E54A. The bispecific anti-HER2 antibody according to E53, wherein the mutant IgG1 Fc domain comprises at least one mutation capable of reducing the ADCC activity of the bispecific antibody.

E54B. The bispecific anti-HER2 antibody according to E53, wherein the mutant IgG1 Fc domain comprises at least one mutation capable of enhancing the ADCC activity of the bispecific antibody.

E55A. The bispecific anti-HER2 antibody according to E54A, wherein at least one mutation capable of reducing the ADCC activity of the bispecific antibody is an amino acid substitution.

E55B. The bispecific anti-HER2 antibody according to E54B, wherein at least one mutation capable of enhancing the ADCC activity of the bispecific antibody is an amino acid substitution.

E56A. The bispecific anti-HER2 antibody according to E55A, comprising at least one amino acid substitution comprising L234F, S239A, S239C, a cysteine amino acid insertion between positions 239 and 240 or any combination thereof, wherein the amino acid position numbering is according to the EU index as set forth in Kabat.

E56B. The bispecific anti-HER2 antibody according to E55B, comprising at least one amino acid substitution comprising, S239A, S239D, A330L, I332E, E333A, K334A, or any combination thereof, wherein the amino acid position numbering is according to the EU index as set forth in Kabat.

E57A. The bispecific anti-HER2 antibody according to E55A or E56A, wherein said mutant IgG1 Fc domain comprises at least one amino acid substitution introducing a derivatizable group.

E57B. The bispecific anti-HER2 antibody according to any one of E48 to E53, E54B, E55B or E56B wherein the Fc domain has an altered type of glycosylation that enhances ADCC activity.

E58A. The bispecific anti-HER2 antibody according to E57A, wherein said mutant IgG1 Fc domain comprises one to three amino acid substitution introducing a derivatizable group.

E58B. The bispecific anti-HER2 antibody according to E57B, wherein the Fc domain is a hypofucosylated antibody having reduced amounts of fucosyl residues.

E59A. The bispecific anti-HER2 antibody according to E57A or E58A, wherein the derivatizable group in a sulfhydryl group.

E59B. The bispecific anti-HER2 antibody according to E57B or E58B, wherein the Fc domain has increased bisecting GlcNAc structures.

E60. The bispecific anti-HER2 antibody according to E59A, wherein the at least one amino acid substitution comprises S239C, 248C, 254C, 258C, 273C, 279C, 282C, 284C, 286C, 287C, 289C, 297C, 298C, 312C, 324C, 326C, 330C, 335C, 337C, 339C, 350C, 355C, 356C, 359C, 360C, 361C, 375C, 383C, 384C, 389C, 398C, 400C, 413C, 415C, 418C, 422C, 435C, 440C, 441C, S442C, 443C, a cysteine amino acid insertion between positions 239 and 240, and 446C, or any combination thereof, wherein the amino acid position numbering is according to the EU index as set forth in Kabat.

E61A. The bispecific anti-HER2 antibody according to any one E54A, E55A, E56A, E57A, E58A, E59A, or E60, wherein the mutant Fc domain comprises the amino acids of SEQ ID NO: 24, SEQ ID NO: 63, SEQ ID NO: 25 or SEQ ID NO:65.

E61B. The bispecific anti-HER2 antibody according to any one E54B, E55B, E56B, E57B, E58B, E59B, or E60, wherein the mutant Fc domain comprises the amino acids of SEQ ID NO: 62 or SEQ ID NO:64.

E62. A bispecific anti-HER2 antibody comprising a first and a second polypeptide chain associated with each other, wherein the first polypeptide chain is selected from:

$$[TZ_S]\text{-}[L_1][_BVH]\text{-}[_BCH]\text{-}[Fc_x] \quad (1)$$

$$[_BVH]\text{-}[_BCH]\text{-}[Fc_x]\text{-}[L_2]\text{-}[TZ_S] \quad (2)$$

$$[_BVH]\text{-}[_BCH]\text{-}[L_3]\text{-}[TZ_S]\text{-}[L_4]\text{-}[Fc_x] \quad (3)$$

wherein
TZs is an scFv that binds the same epitope as trastuzumab;
$L_1$, $L_2$, $L_3$, and $L_4$ are peptide linkers;
$Fc_x$ is an Fc domain;
$_BVH$ and $_BCH$ are the VH and CH1 regions, respectively, of an antibody capable of binding to an HER2 epitope distinct from the epitope recognized by the trastuzumab antibody.

E63. The bispecific anti-HER2 antibody according to E62, wherein the distinct epitope comprises one or more amino acids within SEQ ID NO: 52.

E64. The bispecific anti-HER2 antibody according to E62 or E63, wherein the second chain comprises $[_BVL]\text{-}[CL]$ wherein BVL is the VL region of an antibody capable of binding to an HER2 epitope distinct from the epitope recognized by the trastuzumab antibody, and CL is a IgG light chain constant region.

E65. The bispecific anti-HER2 antibody according to E64, wherein CL is selected from the group consisting of a human kappa constant region and a human lambda constant region.

E66. The bispecific anti-HER2 antibody according to E64 or E65, wherein $_BVL$ comprises:
(i) a variable light chain CDR-1 (VL-CDR1) identical to SEQ ID NO: 4 or identical to SEQ ID NO: 4 except for up to 1, 2, 3, or 4 amino acid substitutions;
(ii) a variable light chain CDR-2 (VL-CDR2) identical to SEQ ID NO: 5 or identical to SEQ ID NO: 5 except for up to 1, 2, 3, or 4 amino acid substitutions; and,
(iii) a variable light chain CDR-3 (VL-CDR3) identical to SEQ ID NO: 6 or identical to SEQ ID NO: 6 except for up to 1, 2, 3, or 4 amino acid substitutions.

E67. The bispecific anti-HER2 antibody according to E64, E65 or E66, wherein $_BVL$ comprises the amino acids of SEQ ID NO:16 or 44.

E68. The bispecific anti-HER2 antibody according to E65, wherein CL comprises the amino acids of SEQ ID NO:27 or SEQ ID NO: 66.

E69. The bispecific anti-HER2 antibody according to any one of E62 to E68, wherein $[TZ_S]$ comprises:
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and
(vi) a VL-CDR3 comprising the amino acids of SEQ ID NO:59.

E70. The bispecific anti-HER2 antibody according to any one of E62 to E69, wherein $[TZ_S]$ is a disulfide stabilized scFv.

E71. The bispecific anti-HER2 antibody according to any one of E62 to E70, wherein $[TZ_S]$ comprises a VH comprising the amino acids of SEQ ID NO:17 and a VL comprising the amino acids of SEQ ID NO:18, covalently linked by a peptide linker.

E72. The bispecific anti-HER2 antibody according to E71, wherein the peptide linker comprises the amino acids of SEQ ID NO:19.

E73. The bispecific anti-HER2 antibody according to any one of E69 to E72, wherein $[TZ_S]$ comprises of the amino acids of SEQ ID NO:28.

E74. The bispecific anti-HER2 antibody according to any one of E62 to E73, wherein a hinge polypeptide links the $[_BCH]$ and $[FcX]$.

E75. The bispecific anti-HER2 antibody according to E74, wherein the hinge polypeptide comprises or consists of the amino acids of SEQ ID NO: 26.

E76A. The bispecific anti-HER2 antibody according to any one of E62 to E75, wherein the [Fcx] comprises at least one amino acid substitution introducing a derivatizable group.

E76B. The bispecific anti-HER2 antibody according to any one of E62 to E75, wherein [Fcx] comprises at least one mutation capable of enhancing the ADCC activity of the bispecific antibody.

E77A. The bispecific anti-HER2 antibody according to E76A, wherein the [Fcx] comprises one to three amino acid substitution introducing a derivatizable group.

E77B. The bispecific anti-HER2 antibody according to E76B, wherein at least one mutation capable of enhancing the ADCC activity of the bispecific antibody is an amino acid substitution.

E78A. The bispecific anti-HER2 antibody according to E76A or E77A, wherein the derivatizable group in a sulfhydryl group.

E78B. The bispecific anti-HER2 antibody according to E77B, comprising at least one amino acid substitution comprising, S239A, S239D, A330L, 1332E, E333A, K334A, or any combination thereof, wherein the amino acid position numbering is according to the EU index as set forth in Kabat.

E78B1. The bispecific anti-HER2 antibody according to any one of E62 to E75, E76B, E77B or E78B wherein the Fc domain has an altered type of glycosylation that enhances ADCC activity.

E78B2. The bispecific anti-HER2 antibody according to E78B1, wherein the Fc domain is a hypofucosylated antibody having reduced amounts of fucosyl residues.

E78B3. The bispecific anti-HER2 antibody according to E78B1 or E78B2, wherein the Fc domain has increased bisecting GlcNAc structures.

E79. The bispecific anti-HER2 antibody according to E78A, wherein the at least one amino acid substitution comprises S239C, 248C, 254C, 258C, 273C, 279C, 282C, 284C, 286C, 287C, 289C, 297C, 298C, 312C, 324C, 326C, 330C, 335C, 337C, 339C, 350C, 355C, 356C, 359C, 360C, 361C, 375C, 383C, 384C, 389C, 398C, 400C, 413C, 415C, 418C, 422C, 435C, 440C, 441C, S442C, 443C, 446C, a cysteine amino acid insertion between positions 239 and 240, or any combination thereof, wherein the amino acid position numbering is according to the EU index as set forth in Kabat.

E80A. The bispecific anti-HER2 antibody according to any one of E62 to E75, E76A, E77A, E78A, or E79, wherein [Fcx] comprises the amino acids of any one of SEQ ID NOS: 23, 24, 63, 25 and 65.

E80B. The bispecific anti-HER2 antibody according to any one of E62 to E75, E76B, E77B, E78B, E78B1, E78B2, E78B3, or E79, wherein [Fcx] comprises the amino acids of any one of SEQ ID NOS: 23, 62, and 64.

E81. The bispecific anti-HER2 antibody according to any one of E62 to E79, wherein $[L_1]$, $[L_2]$, $[L_3]$, and $[L_4]$ comprise amino acids independently selected from the group consisting of SEQ ID NOs: 19, 20, 21, and 22.

E82. The bispecific anti-HER2 antibody according to any one of E62 to E79, wherein:
(i) $[L_1]$ comprises the amino acids of SEQ ID NO:19;
(ii) $[L_2]$ comprises the amino acids of SEQ ID NO:20;
(iii) $[L_3]$ comprises the amino acids of SEQ ID NO:21; and,
(iv) $[L_4]$ comprises the amino acids of SEQ ID NO:22.

E83. The bispecific anti-HER2 antibody according to any one of E62 to E82, wherein [BVH] comprises:
(i) a variable heavy chain CDR-1 (VH-CDR1) identical to SEQ ID NO: 1 or identical to SEQ ID NO: 1 except for up to 1, 2, 3, or 4 amino acid substitutions;
(ii) a variable heavy chain CDR-2 (VH-CDR2) identical to SEQ ID NO: 2 or identical to SEQ ID NO: 2 except for up to 1, 2, 3, or 4 amino acid substitutions; and
(iii) a variable heavy chain CDR-3 (VH-CDR3) identical to SEQ ID NO: 3 or identical to SEQ ID NO: 3 except for up to 1, 2, 3, or 4 amino acid substitutions E84. The bispecific anti-HER2 antibody according to any one of E62 to E82, wherein [BVH] comprises SEQ ID NO:15 or 43.

E85. The bispecific anti-HER2 antibody according to any one of E62 to E84, wherein [BCH] comprises the amino acids of SEQ ID NO: 29.

E86. The bispecific anti-HER2 antibody according to any one of E64 to E85, wherein [BVL] comprises:
(i) a variable light chain CDR-1 (VL-CDR1) identical to SEQ ID NO: 4 or identical to SEQ ID NO: 4 except for up to 1, 2, 3, or 4 amino acid substitutions;
(ii) a variable light chain CDR-2 (VL-CDR2) identical to SEQ ID NO: 5 or identical to SEQ ID NO: 5 except for up to 1, 2, 3, or 4 amino acid substitutions; and
(iii) a variable light chain CDR-3 (VL-CDR3) identical to SEQ ID NO: 6 or identical to SEQ ID NO: 6 except for up to 1, 2, 3, or 4 amino acid substitutions.

E87. The bispecific anti-HER2 antibody according to any one of E64 to E85, wherein [BVL] comprises the amino acids of SEQ ID NO:16 or 44.

E88A. The bispecific HER2 antibody according to claim any one of E62 to E87, wherein first polypeptide chain comprises the amino acids of any one of SEQ ID NOs: 30, 31, 32, 69, 33, 71, 34, 35, 36, 74, 37, 76, 38, 39, 40, 79, 41 or 81, and a second polypeptide chain comprising the amino acids of SEQ ID NO:42 or 82, wherein the bispecific HER2 antibody is conjugated to a therapeutic moiety.

E88B. The bispecific HER2 antibody according to claim any one of E62 to E87, wherein first polypeptide chain comprises the amino acids of any one of SEQ ID NOs: 30, 67, 68, 70, 34, 72, 73, 75, 38, 77, 78, or 80, and a second polypeptide chain comprising the amino acids of SEQ ID NO:42 or 82, wherein the bispecific HER2 antibody has enhanced ADCC activity.

E89. The bispecific HER2 antibody according to any one of E1 to E88B, wherein the bispecific HER2 antibody induces internalization upon binding to the HER2 target.

E90. The bispecific HER2 antibody according to E89, wherein the bispecific HER2 antibody promotes effective lysosomal trafficking following internalization.

E91. The bispecific HER2 antibody according to any one of E1 to E88B, wherein the bispecific HER2 antibody induces HER2 target degradation.

E92. The bispecific HER2 antibody according to any one of E1 to E88B, wherein the bispecific HER2 antibody blocks ligand-induced AKT phosphorylation in low HER2-expressing cancer cells.

E93. The bispecific HER2 antibody according to any one of E1 to E88B, wherein the bispecific HER2 antibody disrupts ligand-induced HER2:HER3 dimerization.

E94. An anti-HER2 binding molecule comprising an immunoglobulin heavy chain (VH) and an immunoglobulin light chain (VL), wherein the binding molecule comprises:
(i) VH-CDR1 comprising the amino acids of SEQ ID NO: 1;
(ii) VH-CDR2 comprising the amino acids of SEQ ID NO: 2;
(iii) VH-CDR3 comprising the amino acids of SEQ ID NO: 3;
(iv) VL-CDR1 comprising the amino acids of SEQ ID NO: 4;
(v) VL-CDR2 comprising the amino acids of SEQ ID NO: 5; and,
(vi) VL-CDR3 comprising the amino acids of SEQ ID NO: 6.

E95. An anti-HER2 binding molecule comprising an immunoglobulin heavy chain (VH) and an immunoglobulin light chain (VL), wherein the VH comprises the amino acids of SEQ ID NO:15.

E96. An anti-HER2 binding molecule comprising a VH and a VL, wherein the VL comprises the amino acids of SEQ ID NO:16.

E97. The binding molecule of E94 or E95 or E96, wherein the VH comprises the amino acids of SEQ ID NO:15 and the VL comprises the amino acids of SEQ ID NO:16.

E98. The binding molecule of any one of E94 to E97 comprising an antibody, or antigen-binding fragment thereof.

E99A. An antibody-drug conjugate (ADC) comprising the bispecific HER2 antibody according to any one E1 to E93 or the anti-HER2 binding molecule according to any of E94 to E98 and at least one therapeutic moiety.

E100A. The ADC according to E99A, further comprising at least one optional spacer.

E101A. The ADC according to E100A, where at least one spacer is a peptidic spacer.

E102A. The ADC according to E100A, wherein at least one spacer is a nonpeptidic spacer.

E103A. The ADC according to any one of E99A to E102A, comprising two, three, or four therapeutic moieties.

E104A. The ADC according to any one of E99A to E103A, where all therapeutic moieties are the same.

E105A. The ADC according to any one of E99A to E104A, wherein each therapeutic moiety is chemically conjugated to the side chain of an amino acid at a specific position in the Fc region of the bispecific antibody.

E106A. The ADC according to E105A, where the specific positions are selected from the group consisting of 239, 248, 254, 258, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 435, 440, 441, 442, 443, 446, an insertion between positions 239 and 240, and combinations thereof, wherein the amino acid position numbering is according to the EU index as set forth in Kabat.

E107A. The ADC according to E105A or 106A, wherein the specific positions are 239, 442, or both, wherein the amino acid position numbering is according to the EU index as set forth in Kabat.

E108A. The ADC according to E105A or 106A, wherein the specific positions are 442 and an amino acid insertion between positions 239 and 240, wherein the amino acid position numbering is according to the EU index as set forth in Kabat.

E109A. The ADC according to E105A to E108A, wherein the amino acid side chain is a sulfhydryl side chain.

E110A. An ADC comprising the bispecific HER2 antibody according to any one of E1 to E98, wherein said antibody comprises:
(i) a first polypeptide chain comprising the amino acids of SEQ ID NO: 32 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat;
(ii) a first polypeptide chain comprising the amino acids of SEQ ID NO:33 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat;
(iii) a first polypeptide chain comprising the amino acids of SEQ ID NO:36 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat;
(iv) a first polypeptide chain comprising the amino acids of SEQ ID NO:37 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat;
(v) a first polypeptide chain comprising the amino acids of SEQ ID NO:40 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat; or
(vi) a first polypeptide chain comprising the amino acids of SEQ ID NO:41 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat.

E111A1. An ADC comprising the bispecific HER2 antibody according to any one of claims 1 to 113, wherein said antibody comprises:
(i) a first polypeptide chain comprising or consisting of the amino acids of SEQ ID NO:69 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat;
(ii) a first polypeptide chain comprising or consisting of the amino acids of SEQ ID NO:71 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat;
(iii) a first polypeptide chain comprising or consisting of the amino acids of SEQ ID NO:74 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat;
(iv) a first polypeptide chain comprising or consisting of the amino acids of SEQ ID NO:76 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat;
(v) a first polypeptide chain comprising or consisting of the amino acids of SEQ ID NO:79 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat; or,
(vi) a first polypeptide chain comprising or consisting of the amino acids of SEQ ID NO:81 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat.

E112A. The ADC according to any one of E99A to E111A, wherein the therapeutic moiety comprises a cytotoxin, a radioisotope, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or combinations thereof.

E113A. The ADC according to E112A, wherein the cytotoxin is a tubulysin, an auristatin, a maytansinoid or a pyrrolobenzodiazepine (PBD).

E114. An isolated nucleic acid molecule or a set of nucleic acid molecules encoding a bispecific HER2 antibody according to any one of E1 to E93 or an anti-HER2 binding molecule according to any one of E94 to E98, or a complement thereof.

E115. A vector or a set of vectors comprising the nucleic acid molecule or set of the nucleic acid molecules of E114, or a complement thereof.

E116. A host cell comprising an isolated nucleic acid molecule or a set of nucleic acid molecules according to E114, or the vector or set of vectors according to E115.

E117. A host cell expressing a bispecific HER2 antibody according to any one of E1 to E93 or an anti-HER2 binding molecule according to any one of E94 to E98.

E118. A method for producing a bispecific HER2 antibody according to any one of E1 to E93 or an anti-HER2 binding molecule according to any one of E94 to E98 comprising culturing the host cell according to any one of E116 or E117 and recovering the antibody from the culture medium.

E119. A pharmaceutical composition comprising a bispecific HER2 antibody according to any one of E1 to E93, an anti-HER2 binding molecule according to any one of E94 to E98, or an ADC according to any one of E99A to E113A1, and a pharmaceutically acceptable carrier.

E120. A method of treating a HER2-expressing cancer comprising administering a bispecific HER2 antibody according to any one of E1 to E93, an anti-HER2 binding molecule according to any one of E94 to E98, an ADC according to any one of E99A to E113A1 or the composition according to E119 to a subject in need thereof.

E121. The method according to E120, wherein the cancer is a low HER2-expressing cancer.

E122. The method according to any one of E120 or E121, further comprising administering at least one additional therapeutic agent.

E123. The method according to E122, wherein the at least one additional therapeutic agent is a radionuclide or a chemotherapeutic agent.

E124. A method to target a therapeutic moiety to cells expressing HER2 comprising administering the therapeutic moiety fused or conjugated to a bispecific HER2 antibody according to any one of E1 to E93, an anti-HER2 binding molecule according to any one of E94 to E98, or an ADC according to any one of E99A to E113A1.

E125. A method to increase the activity of a therapeutic moiety comprising conjugating the moiety to a bispecific HER2 antibody according to any one of E1 to E93, an anti-HER2 binding molecule according to any one of E94 to E98, or an ADC according to any one of E99A to E113A1.

E126. A method to improve the pharmacokinetic properties of a therapeutic moiety comprising conjugating the moiety to a bispecific HER2 antibody according to any one of E1 to E93, an anti-HER2 binding molecule according to any one of E94 to E98, or an ADC according to any one of E99A to E113A1.

E127. The method according to any of E122 to E126, wherein the therapeutic moiety is a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, or a chelating agent.

E128. The method according to E127, wherein the cytotoxin is a tubulysin, an auristatin, a maytansinoid or a pyrrolobenzodiazepine (PBD).

E129. The ADC according to E113A or the method according to E128, wherein the cytoxin is tubulysin 1508 having the following structure:

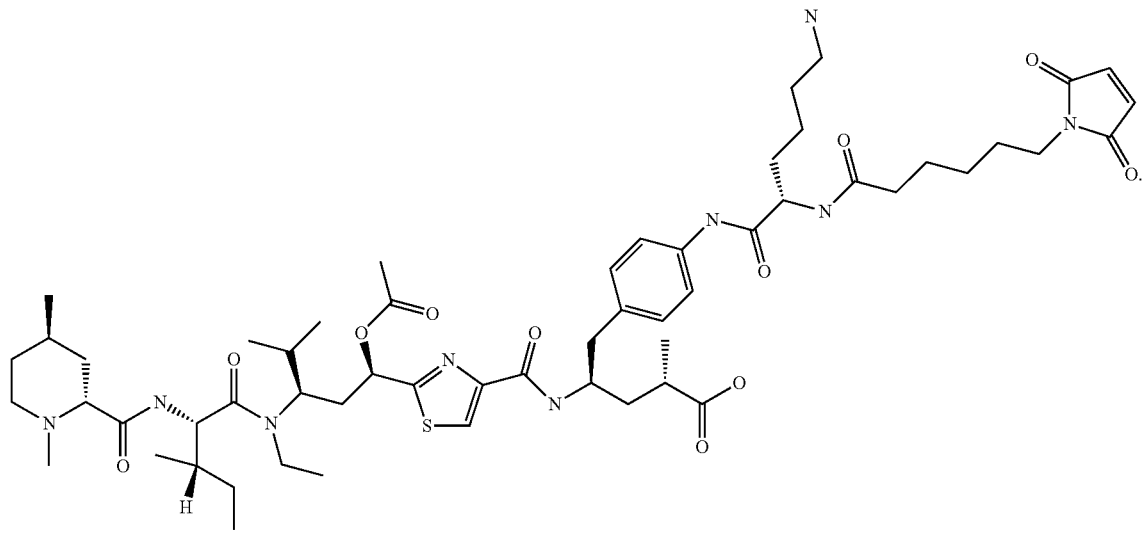 [SMILES: CC[C@H](C)[C@H](NC(=O)[C@H]1C[C@H](C)CCN1C)C(=O)N(CC)[C@H](C[C@@H](OC(C)=O)c1nc(C(=O)N[C@@H](Cc2ccc(NC(=O)[C@H](CCCCN)NC(=O)CCCCCN3C(=O)C=CC3=O)cc2)C[C@H](C)C(=O)O)cs1)C(C)C]

E130. A method to treat resistance to a HER2-targeting therapeutic agent comprising administering a bispecific HER2 antibody according to any one of E1 to E93, an anti-HER2 binding molecule according to any one of E94 to E98, or an ADC according to any one of E99A to E113A to a patient in need thereof.

XV. Sequences

Table 3 below provides the sequence reference number (SEQ ID NO:), amino acid sequence and comments regarding the sequences.

TABLE 3

| SEQ ID NO | SEQUENCE | Comments |
|---|---|---|
| 1 | SYSMS | VH-CDR1 from affinity optimized S39 antibody |
| 2 | SISSSSSYIYYADSVKG | VH-CDR2 from affinity optimized S39 antibody |
| 3 | GGDAYNYYYFDY | VH-CDR3 from affinity optimized S39 antibody |
| 4 | KSSQSVFFRSNNKNILA | VL-CDR1 from affinity optimized S39 antibody |
| 5 | WASSRES | VL-CDR2 from affinity optimized S39 antibody |
| 6 | QQYFGSPFT | VL-CDR3 from affinity optimized S39 antibody |
| 7 | EVQLVESGGGLVKPGGSLRLSCAASGFTFS | VH-FR1 from affinity optimized S39 antibody |
| 8 | WVRQAPGKGLEWVS | VH-FR2 from affinity optimized S39 antibody |
| 9 | RFTISRDNAKNSLYLQMNSLRAEDTAVYYCAR | VH-FR3 from affinity optimized S39 antibody |
| 10 | WGQGTLVTVSS | VH-FR4 from affinity optimized S39 antibody |
| 11 | DIVMTQTPLSLSVTPGQPASISC | VL-FR1 from affinity optimized S39 antibody |
| 12 | WYLQKPGQPPQLLIY | VL-FR2 from affinity optimized S39 antibody |
| 13 | GVPDRFSGSGSGTDFTLKISRVEAEDVGVYYC | VL-FR3 from affinity optimized S39 antibody |
| 14 | FGPGTKVDIK | VL-FR4 from affinity optimized S39 antibody |
| 15 | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSS | VH2 - VH from clone 39S antibody |
| 16 | DIVMTQTPLSLSVTPGQPASISCKSSQSVFFRSNNKNILAWYLQKPGQPP QLLIYWASSRESGVPDRFSGSGSGTDFTLKISRVEAEDVGVYYCQQYFGS PFTFGPGTKVDIK | VL2 - VL from clone 39S antibody |
| 17 | EVQLVESGGGLVQPGGSLRLSCAASGFNIKDTYIHWVRQAPGKXLEWVAR IYPTNGYTRYADSVKGRFTISADTSKNTAYLQMNSLRAEDTAVYYCSRWG GDGFYAMDYWGQGTLVTVSS | VH1 - VH of the Domain IV scFv<br>X in SEQ ID NO: 17 is K or C |
| 18 | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGX GTKVEIK | VL1 - VL from of the Domain IV scFv<br>X in SEQ ID NO: 18 is Q or C |
| 19 | GGGGSGGGGSGGGGSGGGGS | L$_x$ linker, x = 1-4 - scFv Linker - Located between VL and VH in scFv |
| 20 | GGGGSGGGGSGGGGS | L$_x$ linker, x = 1-4 - Used in Bs2Ab-FCC and Bs2Ab-FC constructs |
| 21 | EPKSCGKTGGGGSGGGGS | L$_x$ linker, x = 1-4 - Used in Bs4Ab-FCC and Bs4Ab-FC constructs |
| 22 | SGGGGSGGGGS | L$_x$ linker, x = 1-4 - Hinge |
| 23 | CPPCPAPELLGGPSVFLFPPKPKDTLMISRTPEVTCVVVDVSHEDPEVKF NWYVDGVEVHNAKTKPREEQYNSTYRVVSVLTVLHQDWLNGKEYKCKVSN KALPAPIEKTISKAKGQPREPQVYTLPPSREEMTKNQVSLTCLVKGFYPS DIAVEWESNGQPENNYKTTPPVLDSDGSFFLYSKLTVDKSRWQQGNVFSC SVMHEALHNHYTQKSLSLSPGK | Native IgG1 Fc<br>Fc portion can include EU residues 226 to its carboxyl-terminus. The highlighted positions correspond to sites of known allelic variation. |

TABLE 3-continued

| SEQ ID NO | SEQUENCE | Comments |
|---|---|---|
| 24A | CPPCPAPE[F]LGGP[C]VFLFPPKPKDTLMISRTPEVTCVVVDVSHEDPEVKF NWYVDGVEVHNAKTKPREEQYNSTYRVVSVLTVLHQDWLNGKEYKCKVSN KALPAPIEKTISKAKGQPREPQVYTLPPSR<u>EEM</u>TKNQVSLTCLVKGFYPS DIAVEWESNGQPENNYKTTPPVLDSDGSFFLYSKLTVDKSRWQQGNVFSC SVMHEALHNHYTQKSLSLSPGK | Fc IgG1 L234F S239C ("FC"), for ADC constructs. Mutations within boxes. The highlighted positions correspond to sites of known allelic variation. |
| 24B | CPPCPAPELLGGP[D]VFLFPPKPKDTLMISRTPEVTCVVVDVSHEDPEVKF NWYVDGVEVHNAKTKPREEQYNSTYRVVSVLTVLHQDWLNGKEYKCKVSN KALPAP[E]EKTISKAKGQPREPQVYTLPPSR<u>EEM</u>TKNQVSLTCLVKGFYPS DIAVEWESNGQPENNYKTTPPVLDSDGSFFLYSKLTVDKSRWQQGNVFSC SVMHEALHNHYTQKSLSLSPGK | Fc IgG1 S239D I332E, for ADCC constructs. Mutations within boxes. The highlighted positions correspond to sites of known allelic variation. |
| 24C | CPPCPAPELLGGPS[C]VFLFPPKPKDTLMISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPSR<u>EEM</u>TKNQVSLTCLVKGFYPS SDIAVEWESNGQPENNYKTTPPVLDSDGSFFLYSKLTVDKSRWQQGNVFS CSVMHEALHNHYTQKSLSLSPGK | Fc IgG1 C239-ins, for ADC constructs. Mutations within boxes. The highlighted positions correspond to sites of known allelic variation. |
| 25A | CPPCPAPE[F]LGGP[C]VFLFPPKPKDTLMISRTPEVTCVVVDVSHEDPEVKF NWYVDGVEVHNAKTKPREEQYNSTYRVVSVLTVLHQDWLNGKEYKCKVSN KALPAPIEKTISKAKGQPREPQVYTLPPSR<u>EEM</u>TKNQVSLTCLVKGFYPS DIAVEWESNGQPENNYKTTPPVLDSDGSFFLYSKLTVDKSRWQQGNVFSC SVMHEALHNHYTQKSL[C]LSPGK | Fc IgG1 L234F S239C S442C ("FCC"), for ADC constructs. Mutations within boxes. The highlighted positions correspond to sites of known allelic variation. |
| 25B | CPPCPAPELLGGP[D]VFLFPPKPKDTLMISRTPEVTCVVVDVSHEDPEVKF NWYVDGVEVHNAKTKPREEQYNSTYRVVSVLTVLHQDWLNGKEYKCKVSN KALP[L]P[E]EKTISKAKGQPREPQVYTLPPSR<u>EEM</u>TKNQVSLTCLVKGFYPS DIAVEWESNGQPENNYKTTPPVLDSDGSFFLYSKLTVDKSRWQQGNVFSC SVMHEALHNHYTQKSLSLSPGK | Fc IgG1 S239D A330L I332E, for ADCC constructs. Mutations within boxes. The highlighted positions correspond to sites of known allelic variation. |
| 25C | CPPCPAPELLGGPS[C]VFLFPPKPKDTLMISRTPEVTCVVVDVSHEDPEVK FNWYVDGVEVHNAKTKPREEQYNSTYRVVSVLTVLHQDWLNGKEYKCKVS NKALPAPIEKTISKAKGQPREPQVYTLPPSR<u>EEM</u>TKNQVSLTCLVKGFYP SDIAVEWESNGQPENNYKTTPPVLDSDGSFFLYSKLTVDKSRWQQGNVFS CSVMHEALHNHYTQKSL[C]LSPGK | Fc IgG1 C239-ins S442C, for ADC constructs. Mutations within boxes. The highlighted positions correspond to sites of known allelic variation. |
| 26 | EPKSCDKTHT | IgG1 hinge present in Bs2 and Bs3 |
| 27A | RTVAAPSVFIFPPSDEQLKSGTASVVCLLNNFYPREAKVQWKVDNALQSG NSQESVTEQDSKDSTYSLSSTLTLSKADYEKHKVYACEVTHQGLSSPVTK SFNRGEC | CL kappa. The highlighted positions correspond to sites of known allelic variation. |
| 27B | QPKAAPSVTLFPPSSEELQANKATLVCLiSDFYPGAVTVAWKADSSPVKA GVETTTPSKQSNNKYAASSYLSLTPEQWKSHRSYSCQVTHEGSTVEKTVA PTEC | CL lambda. The highlighted positions correspond to sites of known allelic variation. |
| 28 | EVQLVESGGGLVQPGGSLRLSCAASGFNIKDTYIHWVRQAPGK$X_1$LEWVA RIYPTNGYTRYADSVKGRFTISADTSKNTAYLQMNSLRAEDTA<u>VYY</u>CSRW GGDGFYAMDYWGQGTLVTSSGGGGSGGGGSGGGGSGGGGSDIQMTQSPSS SLSASVGDRVTITCRASQDVNTAVAWYQQKPGKAPKLLIYSASFLYSGVP SRFSGSRSGTDFTLTISSLQPEDFATYYCQQHYTTPPTFG$X_2$GTKVEIK | Trastuzumab scFv sequence. $X_1$ = K or C; $X_2$ = Q or C. In disulfide-stabilized scFv $X_1$ = $X_2$ = C. |
| 29 | ASTKGPSVFPLAPSSKSTSGGTAALGCLVKDYFPEPVTVSWNSGALTSGV HTFPAVLQSSGLYSLSSVVTVPSSSLGTQTYICNVNHKPSNTKVDK<u>R</u>V | CH1 from 39S antibody - EU residues 118 to 215. The highlighted positions correspond to sites of known allelic variation. |
| 30 | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGC GTKVEIKGGGGSGGGGSGGGGSGGGGSEVQLVESGGGLVQPGGSLRLSCA ASGFNIKDTYIHWVRQAPGKGLEWVARIYPTNGYTRYADSVKGRFTISAD TSKNTAYLQMNSLRAEDTAVYYCSRWGGDGFYAMDYWGQGTLVTVSSGGG GSGGGGSGGGGSEVQLVESGGGLVKPGGSLRLSCAASGFTFSSYSMSWVR QAPGKGLEWVSSISSSSSYIYYADSVKGRFTISRDNAKNSLYLQMNSLRA EDTAVYYCARGGDAYNYYYFDYWGQGTLVTVSSASTKGPSVFPLAPSSKS TSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPE<u>L</u> | Heavy chain of Bs2Ab-native Fc construct. The underlined positions indicate where certain substitutions may be made. The highlighted positions correspond to sites of known allelic variation. |

| SEQ ID NO | SEQUENCE | Comments |
|---|---|---|
| | LGGPSVFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIEK<br>TISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHN<br>HYTQKSLSLSPGK | |
| 31A | DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGC<br>GTKVEIKGGGGSGGGGSGGGGSGGGGSEVQLVESGGGLVQPGGSLRLSCA<br>ASGFNIKDTYIHWVRQAPGKCLEWVARIYPTNGYTRYADSVKGRFTISAD<br>TSKNTAYLQMNSLRAEDTAVYYCSRWGGDGFYAMDYWGQGTLVTVSSGGG<br>GSGGGGSGGGGSEVQLVESGGGLVKPGGSLRLSCAASGFTFSSYSMSWVR<br>QAPGKGLEWVSSISSSSSYIYYADSVKGRFTISRDNAKNSLYLQMNSLRA<br>EDTAVYYCARGGDAYNYYYFDYWGQGTLVTVSSASTKGPSVFPLAPSSKS<br>TSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPE<br>LGGP VFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIEK<br>TISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHN<br>HYTQKSLSLSPGK | Heavy chain of Bs2Ab2 with L234F ("F"). Construct for ADC. The highlighted positions correspond to sites of known allelic variation. |
| 31B | DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGC<br>GTKVEIKGGGGSGGGGSGGGGSGGGGSEVQLVESGGGLVQPGGSLRLSCA<br>ASGFNIKDTYIHWVRQAPGKCLEWVARIYPTNGYTRYADSVKGRFTISAD<br>TSKNTAYLQMNSLRAEDTAVYYCSRWGGDGFYAMDYWGQGTLVTVSSGGG<br>GSGGGGSGGGGSEVQLVESGGGLVKPGGSLRLSCAASGFTFSSYSMSWVR<br>QAPGKGLEWVSSISSSSSYIYYADSVKGRFTISRDNAKNSLYLQMNSLRA<br>EDTAVYYCARGGDAYNYYYFDYWGQGTLVTVSSASTKGPSVFPLAPSSKS<br>TSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPE<br>LGGP VFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPEEK<br>TISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHN<br>HYTQKSLSLSPGK | Heavy chain of Bs2Ab2 with I332E. Construct with enhanced ADCC. The highlighted positions correspond to sites of known allelic variation. |
| 32A | DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGC<br>GTKVEIKGGGGSGGGGSGGGGSGGGGSEVQLVESGGGLVQPGGSLRLSCA<br>ASGFNIKDTYIHWVRQAPGKCLEWVARIYPTNGYTRYADSVKGRFTISAD<br>TSKNTAYLQMNSLRAEDTAVYYCSRWGGDGFYAMDYWGQGTLVTVSSGGG<br>GSGGGGSGGGGSEVQLVESGGGLVKPGGSLRLSCAASGFTFSSYSMSWVR<br>QAPGKGLEWVSSISSSSSYIYYADSVKGRFTISRDNAKNSLYLQMNSLRA<br>EDTAVYYCARGGDAYNYYYFDYWGQGTLVTVSSASTKGPSVFPLAPSSKS<br>TSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPE<br>LGGP VFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPIEK<br>TISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHN<br>HYTQKSLSLSPGK | Heavy chain of Bs2Ab with L234F, S239C ("FC"). Construct for ADC. The highlighted positions correspond to sites of known allelic variation. |
| 32B | DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGC<br>GTKVEIKGGGGSGGGGSGGGGSGGGGSEVQLVESGGGLVQPGGSLRLSCA<br>ASGFNIKDTYIHWVRQAPGKCLEWVARIYPTNGYTRYADSVKGRFTISAD<br>TSKNTAYLQMNSLRAEDTAVYYCSRWGGDGFYAMDYWGQGTLVTVSSGGG<br>GSGGGGSGGGGSEVQLVESGGGLVKPGGSLRLSCAASGFTFSSYSMSWVR<br>QAPGKGLEWVSSISSSSSYIYYADSVKGRFTISRDNAKNSLYLQMNSLRA<br>EDTAVYYCARGGDAYNYYYFDYWGQGTLVTVSSASTKGPSVFPLAPSSKS<br>TSGGTAALGCLVKDYFPEPVTVSWNSGALTSGVHTFPAVLQSSGLYSLSS<br>VVTVPSSSLGTQTYICNVNHKPSNTKVDKRVEPKSCDKTHTCPPCPAPE<br>LGGP VFLFPPKPKDTLMISRTPEVTCVVVDVSHEDPEVKFNWYVDGVEV<br>HNAKTKPREEQYNSTYRVVSVLTVLHQDWLNGKEYKCKVSNKALPAPEEK<br>TISKAKGQPREPQVYTLPPSREEMTKNQVSLTCLVKGFYPSDIAVEWESN<br>GQPENNYKTTPPVLDSDGSFFLYSKLTVDKSRWQQGNVFSCSVMHEALHN<br>HYTQKSLSLSPGK | Heavy chain of Bs2Ab with S239D and I332E. Construct with enhanced ADCC. The highlighted positions correspond to sites of known allelic variation. |
| 32C | DIQMTQSPSSLSASVGDRVTITCRASQDVNTAVAWYQQKPGKAPKLLIYS<br>ASFLYSGVPSRFSGSRSGTDFTLTISSLQPEDFATYYCQQHYTTPPTFGC<br>GTKVEIKGGGGSGGGGSGGGGSGGGGSEVQLVESGGGLVQPGGSLRLSCA<br>ASGFNIKDTYIHWVRQAPGKCLEWVARIYPTNGYTRYADSVKGRFTISAD<br>TSKNTAYLQMNSLRAEDTAVYYCSRWGGDGFYAMDYWGQGTLVTVSSGGG<br>GSGGGGSGGGGSEVQLVESGGGLVKPGGSLRLSCAASGFTFSSYSMSWVR | Heavy chain of Bs2Ab with C239-ins ("C"). Construct for ADC. The highlighted positions correspond to sites of known allelic variation. |

TABLE 3-continued

| SEQ ID NO | SEQUENCE | Comments |
|---|---|---|
| | QAPGKGLEWVSSISSSSSYIYYADSVKGRFTISRDNAKNSLYLQMNSLRA EDTAVYYCARGGDAYNYYYFDYWGQGTLVTVSSASTKGPSVFPLAPSSKS TSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPE LGGPS VFLFPPKPKDTLMISRTPEVTCVVVDVSHEDPEVKFNWYVDGVE VHNAKTKPREEQYNSTYRVVSVLTVLHQDWLNGKEYKCKVSNKALPAPIE KTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALH NHYTQKSLSLSPGK | |
| 33A | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGC GTKVEIKGGGGSGGGGSGGGGSGGGGSEVQLVESGGGLVQPGGSLRLSCA ASGFNIKDTYIHWVRQAPGKCLEWVARIYPTNGYTRYADSVKGRFTISAD TSKNTAYLQMNSLRAEDTAVYYCSRWGGDGFYAMDYWGQGTLVTVSSGGG GSGGGGSGGGGSEVQLVESGGGLVKPGGSLRLSCAASGFTFSSYSMSWVR QAPGKGLEWVSSISSSSSYIYYADSVKGRFTISRDNAKNSLYLQMNSLRA EDTAVYYCARGGDAYNYYYFDYWGQGTLVTVSSASTKGPSVFPLAPSSKS TSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPE LGGP VFLFPPKPKDTLMISRTPEVTCVVVDVSHEDPEVKFNWYVDGVEV HNAKTKPREEQYNSTYRVVSVLTVLHQDWLNGKEYKCKVSNKALPAPIEK TISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHN HYTQKSLCLSPGK | Heavy chain of Bs2Ab with L234F, S239C and S442C ("FCC"). Construct for ADC. The highlighted positions correspond to sites of known allelic variation. |
| 33B | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGC GTKVEIKGGGGSGGGGSGGGGSGGGGSEVQLVESGGGLVQPGGSLRLSCA ASGFNIKDTYIHWVRQAPGKCLEWVARIYPTNGYTRYADSVKGRFTISAD TSKNTAYLQMNSLRAEDTAVYYCSRWGGDGFYAMDYWGQGTLVTVSSGGG GSGGGGSGGGGSEVQLVESGGGLVKPGGSLRLSCAASGFTFSSYSMSWVR QAPGKGLEWVSSISSSSSYIYYADSVKGRFTISRDNAKNSLYLQMNSLRA EDTAVYYCARGGDAYNYYYFDYWGQGTLVTVSSASTKGPSVFPLAPSSKS TSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPE LGGP VFLFPPKPKDTLMISRTPEVTCVVVDVSHEDPEVKFNWYVDGVEV HNAKTKPREEQYNSTYRVVSVLTVLHQDWLNGKEYKCKVSNKALPLPEEK TISKAKGQPREPQVYTLPPSREEMTKNQVSLTCLVKGFYPSDIAVEWESN GQPENNYKTTPPVLDSDGSFFLYSKLTVDKSRWQQGNVFSCSVMHEALHN HYTQKSLSLSPGK | Heavy chain of Bs2Ab with S239D, A330L, and I332E. Construct with enhanced ADCC. The highlighted positions correspond to sites of known allelic variation. |
| 33C | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGC GTKVEIKGGGGSGGGGSGGGGSGGGGSEVQLVESGGGLVQPGGSLRLSCA ASGFNIKDTYIHWVRQAPGKCLEWVARIYPTNGYTRYADSVKGRFTISAD TSKNTAYLQMNSLRAEDTAVYYCSRWGGDGFYAMDYWGQGTLVTVSSGGG GSGGGGSGGGGSEVQLVESGGGLVKPGGSLRLSCAASGFTFSSYSMSWVR QAPGKGLEWVSSISSSSSYIYYADSVKGRFTISRDNAKNSLYLQMNSLRA EDTAVYYCARGGDAYNYYYFDYWGQGTLVTVSSASTKGPSVFPLAPSSKS TSGGTAALGCLVKDYFPEPVTVSWNSGALTSGVHTFPAVLQSSGLYSLSS VVTVPSSSLGTQTYICNVNHKPSNTKVDKRVEPKSCDKTHTCPPCPAPE LGGPS VFLFPPKPKDTLMISRTPEVTCVVVDVSHEDPEVKFNWYVDGVE VHNAKTKPREEQYNSTYRVVSVLTVLHQDWLNGKEYKCKVSNKALPAPIE KTISKAKGQPREPQVYTLPPSREEMTKNQVSLTCLVKGFYPSDIAVEWES NGQPENNYKTTPPVLDSDGSFFLYSKLTVDKSRWQQGNVFSCSVMHEALH NHYTQKSLCLSPGK | Heavy chain of Bs2Ab with C239-ins and S442C ("CC"). Construct for ADC. The highlighted positions correspond to sites of known allelic variation. |
| 34 | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab native Fc. The highlighted positions correspond to sites of known allelic variation. |
| 35A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG | Heavy chain of Bs3Ab with L234F ("F"). Construct for ADC. The |

| SEQ ID NO | SEQUENCE | Comments |
|---|---|---|
| | DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | highlighted positions correspond to sites of known allelic variation. |
| 35B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPK PKDTLMISRTPEVTCVVVDVSHEDPEVKFNWYVDGVEVHNAKTKPREEQY NSTYRVVSVLTVLHQDWLNGKEYKCKVSNKALPAPEEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab with I332E. Construct with enhanced ADCC. The highlighted positions correspond to sites of known allelic variation. |
| 36A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab with L234F and S239C ("FC"). Construct for ADC. The highlighted positions correspond to sites of known allelic variation. |
| 36B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPEL GGP VFLFPPK PKDTLMISRTPEVTCVVVDVSHEDPEVKFNWYVDGVEVHNAKTKPREEQY NSTYRVVSVLTVLHQDWLNGKEYKCKVSNKALPAPEEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab with S239D and I332E. Construct with enhanced ADCC. The highlighted positions correspond to sites of known allelic variation. |
| 36C | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGPS VFLFPP KPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLSLSP GKGGGGSGGGGSGGGGSDIQMTQSPSSLSASVGDRVTITCRASQDVNTAV AWYQQKPGKAPKLLIYSASFLYSGVPSRFSGSRSGTDFTLTISSLQPEDF ATYYCQQHYTTPPTFGCGTKVEIKGGGGSGGGGSGGGGSGGGGSEVQLVE | Heavy chain of Bs3Ab with L234F and C239-ins ("C"). Construct for ADC. The highlighted positions correspond to sites of known allelic variation. |

| SEQ ID NO | SEQUENCE | Comments |
|---|---|---|
| | SGGGLVQPGGSLRLSCAASGFNIKDTYIHWVRQAPGKCLEWVARIYPTNG YTRYADSVKGRFTISADTSKNTAYLQMNSLRAEDTAVYYCSRWGGDGFYA MDYWGQGTLVTVSS | |
| 37A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPPK PKDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLCLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab with L234F S239C and S442C ("FC"). Construct for ADC. The highlighted positions correspond to sites of known allelic variation. |
| 37B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGP VFLFPPPK PKDTLMISRTPEVTCVVVDVSHEDPEVKFNWYVDGVEVHNAKTKPREEQY NSTYRVVSVLTVLHQDWLNGKEYKCKVSNKALPLPEEKTISKAKGQPREP QVYTLPPSREEMTKNQVSLTCLVKGFYPSDIAVEWESNGQPENNYKTTPP VLDSDGSFFLYSKLTVDKSRWQQGNVFSCSVMHEALHNHYTQKSLSLSPG KGGGGSGGGGSGGGGSDIQMTQSPSSLSASVGDRVTITCRASQDVNTAVA WYQQKPGKAPKLLIYSASFLYSGVPSRFSGSRSGTDFTLTISSLQPEDFA TYYCQQHYTTPPTFGCGTKVEIKGGGGSGGGGSGGGGSGGGGSEVQLVES GGGLVQPGGSLRLSCAASGFNIKDTYIHWVRQAPGKCLEWVARIYPTNGY TRYADSVKGRFTISADTSKNTAYLQMNSLRAEDTAVYYCSRWGGDGFYAM DYWGQGTLVTVSS | Heavy chain of Bs3Ab with S239D, A330L, and I332E. Construct with enhanced ADCC. The highlighted positions correspond to sites of known allelic variation. |
| 37C | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCDKTHTCPPCPAPE LGGPS VFLFPP KPKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYTLPPSREEMTKNQVSLTCLVKGFYPSDIAVEWESNGQPENNYKTTP PVLDSDGSFFLYSKLTVDKSRWQQGNVFSCSVMHEALHNHYTQKSLCLSP GKGGGGSGGGGSGGGGSDIQMTQSPSSLSASVGDRVTITCRASQDVNTAV AWYQQKPGKAPKLLIYSASFLYSGVPSRFSGSRSGTDFTLTISSLQPEDF ATYYCQQHYTTPPTFGCGTKVEIKGGGGSGGGGSGGGGSGGGGSEVQLVE SGGGLVQPGGSLRLSCAASGFNIKDTYIHWVRQAPGKCLEWVARIYPTNG YTRYADSVKGRFTISADTSKNTAYLQMNSLRAEDTAVYYCSRWGGDGFYA MDYWGQGTLVTVSS | Heavy chain of Bs3Ab with C239-ins and S442C ("CC"). Construct for ADC. The highlighted positions correspond to sites of known allelic variation. |
| 38 | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLS**LSPGK | Heavy chain of Bs4Ab-native Fc. The highlighted positions correspond to sites of known allelic variation. |
| 39A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW | Heavy chain of Bs4Ab with L234F ("F"). Construct for ADC. The highlighted positions correspond to sites of known allelic variation. |

| SEQ ID NO | SEQUENCE | Comments |
|---|---|---|
| | VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP FLFPPKPKDTLMISRTPEVTCVVVDVSHEDPEVKFNWYVD GVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK | |
| 39B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPA PEEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK | Heavy chain Bs4Ab with I332E. Construct with enhanced ADCC. The highlighted positions correspond to sites of known allelic variation. |
| 40A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK | Heavy chain of Bs4Ab with L234F and S239C ("FC"). Construct for ADC. The highlighted positions correspond to sites of known allelic variation. |
| 40B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPA PEEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK | Heavy chain of Bs4Ab with S239D and I332E for ADCC. Construct with enhanced ADCC. The highlighted positions correspond to sites of known allelic variation. |
| 40C | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGPS VFLFPPKPKDTLMISRTPEVTCVVVDVSHEDPEVKFNWYV DGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMH EALHNHYTQKSLSLSPGK | Heavy chain of Bs4Ab with and C239-ins ("C"). Construct for ADC. The highlighted positions correspond to sites of known allelic variation. |
| 41A | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV | Heavy chain of Bs4Ab with L234F, S239C and S442C ("FCC"). Construct for ADC. The highlighted |

TABLE 3-continued

| SEQ ID NO | SEQUENCE | Comments |
|---|---|---|
| | KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPA PIEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLCLSPGK | positions correspond to sites of known allelic variation. |
| 41B | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGP VFLFPPKPKDTLMISRTPEVTCVVVDVSHEDPEVKFNWYVD GVEVHNAKTKPREEQYNSTYRVVSVLTVLHQDWLNGKEYKCKVSNKALPL PEEKTISKAKGQPREPQVYTLPPSREEMTKNQVSLTCLVKGFYPSDIAVE WESNGQPENNYKTTPPVLDSDGSFFLYSKLTVDKSRWQQGNVFSCSVMHE ALHNHYTQKSLSLSPGK | Heavy chain of Bs4Ab with S239D, A330L, and I332E. Construct with enhanced ADCC. The highlighted positions correspond to sites of known allelic variation. |
| 41C | EVQLVESGGGLVKPGGSLRLSCAASGFTFSSYSMSWVRQAPGKGLEWVSS ISSSSSYIYYADSVKGRFTISRDNAKNSLYLQMNSLRAEDTAVYYCARGG DAYNYYYFDYWGQGTLVTVSSASTKGPSVFPLAPSSKSTSGGTAALGCLV KDYFPEPVTVSWNSGALTSGVHTFPAVLQSSGLYSLSSVVTVPSSSLGTQ TYICNVNHKPSNTKVDKRVEPKSCGKTGGGGSGGGGSDIQMTQSPSSLSA SVGDRVTITCRASQDVNTAVAWYQQKPGKAPKLLIYSASFLYSGVPSRFS GSRSGTDFTLTISSLQPEDFATYYCQQHYTTPPTFGCGTKVEIKGGGGSG GGGSGGGGSGGGGSEVQLVESGGGLVQPGGSLRLSCAASGFNIKDTYIHW VRQAPGKCLEWVARIYPTNGYTRYADSVKGRFTISADTSKNTAYLQMNSL RAEDTAVYYCSRWGGDGFYAMDYWGQGTLVTVSSSGGGGSGGGGSCPPCP APE LGGPS VFLFPPKPKDTLMISRTPEVTCVVVDVSHEDPEVKFNWYV DGVEVHNAKTKPREEQYNSTYRVVSVLTVLHQDWLNGKEYKCKVSNKALP APIEKTISKAKGQPREPQVYTLPPSREEMTKNQVSLTCLVKGFYPSDIAV EWESNGQPENNYKTTPPVLDSDGSFFLYSKLTVDKSRWQQGNVFSCSVMH EALHNHYTQKSLCLSPGK | Heavy chain of Bs4Ab with C239-ins and S442C ("CC"). Construct for ADC. The highlighted positions correspond to sites of known allelic variation. |
| 42A | DIVMTQTPLSLSVTPGQPASISCKSSQSVFFRSNNKNILAWYLQKPGQPP QLLIYWASSRESGVPDRFSGSGSGTDFTLKISRVEAEDVGVYYCQQYFGS PFTFGPGTKVDIKRTVAAPSVFIFPPSDEQLKSGTASVVCLLNNFYPREA KVQWKVDNALQSGNSQESVTEQDSKDSTYSLSSTLTLSKADYEKHKVYAC EVTHQGLSSPVTKSFNRGEC | LC construct with kappa chain common to all the antibody constructs. The highlighted positions correspond to sites of known allelic variation. |
| 42B | DIVMTQTPLSLSVTPGQPASISCKSSQSVFFRSNNKNILAWYLQKPGQPP QLLIYWASSRESGVPDRFSGSGSGTDFTLKISRVEAEDVGVYYCQQYFGS PFTFGPGTKVDIKQPKAAPSVTLFPPSSEELQANKATLVCLiSDFYPGAV TVAWKADSSPVKAGVETTTPSKQSNNKYAASSYLSLTPEQWKSHRSYSCQ VTHEGSTVEKTVAPTEC | LC construct with lambda chain option for all the antibody constructs. The highlighted positions correspond to sites of known allelic variation. |
| 43 | EVQLVESGGGLVKPGGSLRLSCAASGFTFSSYSMNWVRQAPGKGLEWVSS ISSSSSYIYYADSVKGRFTISRDNAKNSLYLQMNSLRAEDTAVYYCARGG DGYNYYYFDYWGQGTLVTVSS | VH from clone 1.39.1 antibody |
| 44 | DIVMTQSPDSLAVSLGERATITCKSSQSVFFRSNNKNCLAWYQQRPGQPP NLLIYWASSRESGVPDRFSGSGSGTDFALTISSLQTEDVAVYYCQQYFGS PFTFGPGTKVDIK | VL from clone 1.39.1 antibody |
| 45 | SYSM | VH clone 1.39.1 CDR1 (sequence from non lead optimized antibody) |
| 46 | GGDGYNYYYFDY | VH clone 1.39.1 CDR3 (sequence from non lead optimized antibody) |
| 47 | KSSQSVFFRSNNKNCLA | VL clone 1.39.1 CDR1 (sequence from non lead optimized antibody) |
| 48 | DIVMTQSPDSLAVSLGERATITC | VL clone 1.39.1 FW1 (sequence from non lead optimized antibody) |

TABLE 3-continued

| SEQ ID NO | SEQUENCE | Comments |
|---|---|---|
| 49 | WYQQRPGQPPNLLIY | VL clone 1.39.1 FW2 (sequence from non lead optimized antibody) |
| 50 | GVPDRFSGSGSGTDFALTISSLQTEDVAVYYC | VL clone 1.39.1 FW3 (sequence from non lead optimized antibody) |
| 51 | TQVCTGTDMKLRLPASPETHLDMLRHLYQGCQVVQGNLELTYLPTNASLS FLQDIQEVQGYVLIAHNQVRQVPLQRLRIVRGTQLFEDNYALAVLDNGDP LNNTTPVTGASPGGLRELQLRSLTEILKGGVLIQRNPQLCYQDTILWKDI FHKNNQLALTLIDTNRSRACHPCSPMCKGSRCWGESSEDCQSLTRTVCAG GCARCKGPLPTDCCHEQCAAGCTGPKHSDCLACLHFNHSGICELHCPALV TYNTDTFESMPNPEGRYTFGASCVTACPYNYLSTDVGSCTLVCPLHNQEV TAEDGTQRCEKCSKPCARVCYGLGMEHLREVRAVTSANIQEFAGCKKIFG SLAFLPESFDGDPASNTAPLQPEQLQVFETLEEITGYLYISANPDSLPDL SVPQNLQVIRGRILHNGAYSLTLQGLGISWLGLRSLRELGSGLALIHHNT HLCFVHTVPWDQLFRNPHQALLHTANRPEDECVGEGLACHQLCARGHCWG PGPTQCVNCSQFLRGQECVEECRVLQGLPREYVNARHCLPCHPECQPQNG SVTCFGPEADQCVACAHYKDPPFCVARCPSGVKPDLSYMPIWKFPDEEGA CQPCPINCTHSCVDLDDKGCPAEQRASPLT | Extracellular portion of mature HER2 (positions 23-652 of canonical Isoform 1; without signal sequence). Natural variant: W452C. See Uniprot P04626. See also "Structure of the extracellular region of HER2 alone and in complex with the Herceptin Fab." Cho et al., Nature 421:756-760 (2003), incorporated herein by reference in its entirety. |
| 52 | SLTRTVCAGGCARCKGP | HER2 epitope of clone 1.39.1 derived antibodies. |
| 53 | LPCHPECQPQNGSVTCFGPEADQCVACAHYKDPPFCVARCPSGVKPDLSY MPIWKFPDEEGACQP | HER2 epitope binding region of trastuzumab (HERCEPTIN ®). Reported to span residues 538-603 (or residues 561-625 in HER2 with signal sequence); reported to be a conformational epitope with contacts at three loop regions. |
| 54 | DTYIH | Domain IV scFv VH-CDR1 |
| 55 | RTYPTNGYTRYADSVKG | Domain IV scFv VH-CDR2 |
| 56 | WGGDGFYAMDY | Domain IV scFv VH-CDR3 |
| 57 | RASQDVNTAVA | Domain IV scFv VL-CDR1 |
| 58 | SASFLYS | Domain IV scFv VL-CDR2 |
| 59 | QQHYTTPPT | Domain IV scFv VL-CDR3 |

The following examples are offered by way of illustration and not by way of limitation.

EXAMPLES

Aspects of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

A number of HER2 antibodies have been approved for use in the treatment of breast cancer patients whose tumor(s) overexpress HER2 including trastuzumab (HERCEPTIN®; see U.S. Pat. No. 5,821,337), pertuzumab (PERJETA™; Patent Publication WO2001/00245) and T-DM1 (ado-trastuzumab emtansine, KADCYLA™, an antibody-drug conjugate consisting of the monoclonal antibody trastuzumab linked to the cytotoxic agent mertansine (DM1), Niculescu-Duvaz et. al., 2010, Curr. Opin. Mol. Ther. 12:350-60). However, these therapies are not indicated for the majority of patients, who express lower levels of HER2. Additionally, there are patients who do not respond to these therapies or who become resistant. Thus, there is an unmet medical need for superior therapeutics to address these patients.

As detailed in the specific examples provided below, highly potent bispecific antibodies were generated by combining an optimized fully human anti-HER2 antibody binding a newly described epitope within domain II of HER2 with an scFv binding a known epitope within domain IV of HER2. A number of different bispecific antibody configurations were generated and tested. The unique bispecific antibodies provided exhibit biological activities not seen with any of the mono-specific anti-HER2 antibodies tested. In many assays the bispecific antibodies also demonstrate a synergistic activity over mono-specific anti-HER2 antibodies. A number of the in vitro and in vivo activities of the bispecific antibodies provided herein are further enhanced by the addition of cytotoxic agents (e.g., tubulysin 1508) in the absence of or severely reduced binding activities to Fc gamma receptors. Additionally, it was found that the in vitro activity of the unique bispecific antibodies provided herein may also be enhanced by enhancing ADCC activity, for example by altering glycosylation (e.g., using POTELLEGENT™ technology (Biowa, Inc. Princeton, N.J.) to generated hypofucoslyated antibodies having enhanced ADCC activity). These data suggest that the bispecific antibodies may have therapeutic use, particularly as ADCs or as ADCC enhanced antibodies, for the treatment of cancers expressing a wide range of HER2 levels, including patients currently ineligible for treatment with trastuzumab, pertuzumab or T-DM1. In addition, the bispecific antibodies may have therapeutic use for the treatment of cancer patients that have failed existing anti-HER2 therapies.

Example 1

1.1. Lead Optimization

Figure 1:
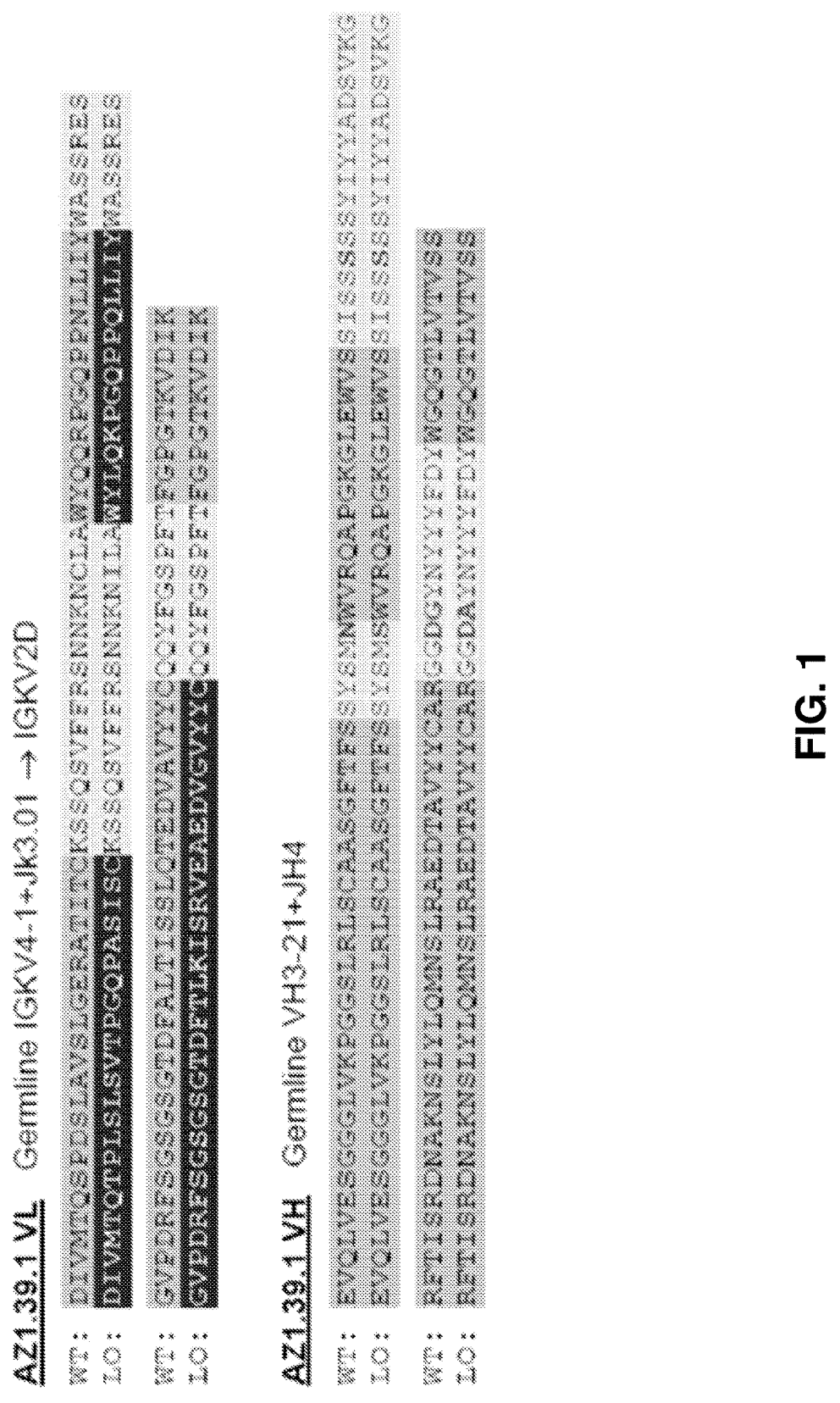

AZ1.39.1 is a fully human monoclonal antibody against human HER2 that does not compete for binding with either trastuzumab or pertuzumab (Patent Publication WO 2008/019290). 39S is a lead-optimized antibody generated from AZ1.39.1 (FIG. 1) as detailed below. Site directed mutagenesis was used to replace an unpaired Cys residue in the CDR1 of light chain with Ile and a potential isomerization site (DG) in the CDR3 of heavy chain was removed by changing the DG to DA. The resulting variant demonstrated the same binding specificity and in vitro anti-proliferative activity as AZ1.39.1 (data not shown). To generate higher affinity binders, mutagenesis was applied to the CDR residues of heavy chain and the mutants were expressed as IgG in mammalian cells and screened for their binding activity to the recombinant human HER2 extracellular domain protein by capture ELISA. Clones with significantly higher binding signal than the wild-type control were sequenced to reveal the mutation information. A combinatory library was constructed from the identified mutations and screened for binding activity to the recombinant human HER2 extracellular domain protein by capture ELISA. 39S was found to have the highest binding activity, and further sequence analysis revealed that 39S carried a single N5S mutation in the CDR1 of heavy chain. The affinity of 39S to human HER2 ($K_D$) is ~1.0 nM, determined by BIAcore, in contrast the reported affinity of the parent 1.39.1 antibody is ~2.0 nM. Thus, this single mutation resulted in a 2 fold increase in binding affinity over the parental antibody. To improve the antibody expression level the framework sequence, in particular FR1, FR2 and FR3 of the light chain, was swapped from IGKV4-1+Jk3.01 to the IGVK2D germline sequence, resulting in an approximately 2-fold increase in IgG expression level measured after 7 days in culture (FIG. 2).

1.2. Binding Specificity and Species Cross-Reactivity of Lead-Optimized Antibody 39S To determine whether 39S retains the binding specificity and species cross-reactivity of its parental antibody AZ1.39.1, binding of 39S to the receptors of human ErbB family (EGFR, HER2, HER3, and HER4), the mouse Her2, and the cynomolgus monkey Her2 was examined by capture ELISA. Briefly, 96-well plates were coated with one of the following recombinant extracellular domain proteins: human EGFR, human HER2, human HER3, human HER4, mouse Her2, or cynomolgus monkey Her2. Antibody to be tested was prepared by diluting in a stepwise 1:3 serial dilution ranging from 50 nM down to 0.28 pM and then added to the wells in duplicate. After one hour of incubation, plates were washed, and goat anti-human IgG Fab HRP-conjugated secondary antibody was added to each well and the plates were incubated for 1 hour. The plates were washed and TMB substrate was added and incubated for 5-20 min to allow color development. The stop solution was added to the wells at the end of reaction and the plates were read at 450 nm. Binding signal (absorbance at 450 nm) was plotted against antibody concentration using Prism software. Results show that 39S, similar to AZ1.39.1, can bind to human HER2 and cynomolgus monkey Her2, but not to Human EGFR, HER3, HER4, or mouse Her2 (data not shown).

1.3. 39S Epitope Mapping and Characterization

The domain II of human HER2 was identified as the epitope of 39S by swapping domains between human and mouse Her2 molecules. Mouse Her2 was chosen as the chimeric partner because it is not recognized by 39S, but shares 85% sequence identity with human HER2. Chimeric variants targeting each domain of HER2 were constructed (see method below) as listed in Table 4, including four knock-out (KO, loss-of-function) variants replacing domain I, II, III, or IV of human HER2 with the mouse counterpart, and one knock-in (KI, gain-of-function) variant grafting the domain II of human HER2 into mouse Her2 molecule. The chimeric variant nomenclature denotes types of variants (KO/KI) and the number of domains swapped. The binding profiles of 39S to these variants were characterized using a SPR based instrument ProteOn™ by capturing variants on sensor surfaces using anti-human and mouse Her2 polyclonal antibodies (see method below). The expression of the variants was monitored by anti-His polyclonal antibody using ProteOn™. The binding results of 39S to the loss-of-function variants have demonstrated that domain II is the epitope-containing domain. 39S did not bind to the variant of KO_II encoding for mouse domain II (Table 4), while retained binding to the variant of KO_I encoding for mouse domain I. Although the variants knocking out human domain III and IV (KO_III and KO_IV) did not express, these two domains were excluded as the epitope of 39S basing on the binding results on the gain-of-function variant KI_II. This gain-of-function variant (KI_II), encoding for mouse domain I, III and IV and human domain II, was recognized by 39S with similar binding affinity (168 pM) as to human HER2 (84 pM). Therefore, the domain II (amino acid 146-310) of human HER2 was identified as the epitope-containing domain of 39S by both loss-of-function and gain-of-function variants.

We further refined the epitope of 39S and identified the region of amino acid 192-208 in domain II as the critical epitope region. A series of chimeric human/mouse variants were constructed targeting short regions of domain II possessing different amino acid sequences between human and mouse Her2 proteins, as listed in Table 4. Seven knock-out variants were generated by replacing each of the following human HER2 regions with the mouse counterparts, including amino acids 146-208, 159-162, 171-187, 192-208, 250-261, 276-285, and 295-296. In addition, one knock-in variant was constructed by grafting the region of amino acid 192-208 of human HER2 to the mouse molecule. The variant nomenclature denotes types of variants (KO/KI) and the swapped regions with amino acid numbering. All variants had detectable expression levels by anti-His polyclonal antibody (Table 4). 39S did not bind to any of the chimeric variants, in which the region of amino acid 192-208 of human HER2 was replaced by mouse residues (KO_146-208, KO_192-208). The binding of 39S was not impacted when substituting any other regions of human HER2 with mouse amino acids (KO_159-162, KO_171-187, KO_250-261, KO_276-285, and KO_295-296). Furthermore, 39S bind to the KI variant encoding human 192-208 (KI_192-208) with a KD of 72 pM, comparable to the KD (84 pM) of human HER2. Taken together, the region of amino acid 192-208 in domain II of human HER2 was identified as the functional epitope of 39S.

The variant nomenclature denotes types of variants (KO/KI) and the swapped regions with amino acid numbering.

Amino acid positions were denoted basing on the numbering scheme of mature human HER2 sequences without its signal peptide. The expression levels of all variants were monitored by an anti-His polyclonal antibody. The binding profiles of 39S to these variants were characterized using a SPR based instrument ProteOn™ by capturing variants on sensor surfaces using anti-human and mouse Her2 polyclonal antibodies. By capturing Her2 proteins on sensor surfaces, the measured apparent binding affinities of 39S are expected to be higher than the monovalent binding affinity in the format of immobilizing 39S on chip surfaces.

TABLE 4

Binding profiles of 39S to chimeric human/mouse Her2 variants

| | Variants | The swapped human HER2 amino acids | Expression | The binding affinity of 39S ($K_D$) |
|---|---|---|---|---|
| Chimeric variants targeting domains | KO_I | 1-145 | Yes | 95 pM |
| | KO_II | 146-310 | Yes | No binding |
| | KO_III | 311-433 | No expression | — |
| | KO_IV | 434-646 | No expression | — |
| | KI_II | 146-310 | Yes | 163 pM |
| Chimeric variants targeting short regions of domain II of human HER2, which possess different protein sequences between human and mouse | KO_146-208 | 146-208 | Yes | No binding |
| | KO_159-162 | 159-162 | Yes | 101 pM |
| | KO_171-187 | 171-187 | Yes | 38 pM |
| | KO_192-208 | 192-208 | Yes | No binding |
| | KO_250-261 | 250-261 | Yes | 187 pM |
| | KO_276-285 | 276-285 | Yes | 106 pM |
| | KO_295-296 | 295-296 | Yes | 84.7 pM |
| Controls | KI_192-208 | 192-208 | Yes | 72 pM |
| | Mouse Her2 | N/A | Yes | No binding |
| | Human Her2 | N/A | Yes | 84 pM |

Construction and expression of chimeric human/mouse Her2 variants were constructed as follows. Briefly, DNAs encoding chimeric human/mouse Her2 variants with a His tag were assembled and amplified by overlapping PCR using human and mouse Her2 plasmids as templates (MedImmune). The assembled DNAs were cloned into the mammalian expression vector pEBNA (MedImmune). HEK293F cells were then transiently transfected with the various constructs using 293fectin and standard protocols according to the manufacturer's instructions (Invitrogen).

The binding characteristics of 39S to chimeric human/mouse variants were studied using a ProteOn™ XPR36 instrument (BioRad). Standard amine coupling was used to immobilize an anti-human or mouse Her2 polyclonal antibody (R&D System) in 10 mM sodium acetate (pH 5.0) to the surface of a GLC biosensor chip at ~5000 resonance units (RU) for each channel. The chimeric proteins in cell culture supernatant were injected and captured by anti-human or mouse polyclonal antibodies onto the GLC surface with a ~200RU response. Anti-HER2 mAb 39S was diluted in phosphate-buffered saline (PBS) (pH 7.4) with 0.005% Tween-20 from 10 nM to 0.625 nM (1:2 dilution), and injected at 100 µL/min for 180 sec with a 600-second dissociation time. Expression levels of chimeric variants were monitored by flowing anti-His polyclonal antibody (MedImmune) under the same conditions as injecting 39S. The surface was regenerated twice by injecting glycine buffer (10 mM, pH 1.5) at 100 µL/min for 30 sec. All sensorgram data were processed with the ProteOn™ Manager 3.0.1 software.

A FACS-based binding competition assay was used to determine whether antibodies competed for binding to the same epitope as trastuzumab, and/or pertuzumab. BT-474 cells were harvested, resuspended in FACS buffer, and $2.5 \times 10^5$ cells/well were added to a 96-well U-bottom plate. Antibody to be tested (R347 IgG1 isotype control, trastuzumab, pertuzumab, AZ1.39.1, and 39S) was prepared by diluting in FACS buffer containing 2 µg/mL of Alexa-Fluor 647-labeled 39S antibody in a stepwise 1:4 serial dilution ranging from 500 µg/mL down to 1.9 ng/mL and then added to cells in triplicate. After 1 hour of staining on ice, cells were washed 3 times with ice-cold FACS buffer and then fixed with 2% PFA. Cells were analyzed by a BD LSR II machine with BD FACSDiva™ software. Data were analyzed with FlowJo software and presented as mean MFI±SEM (n=3).

Figure 3:
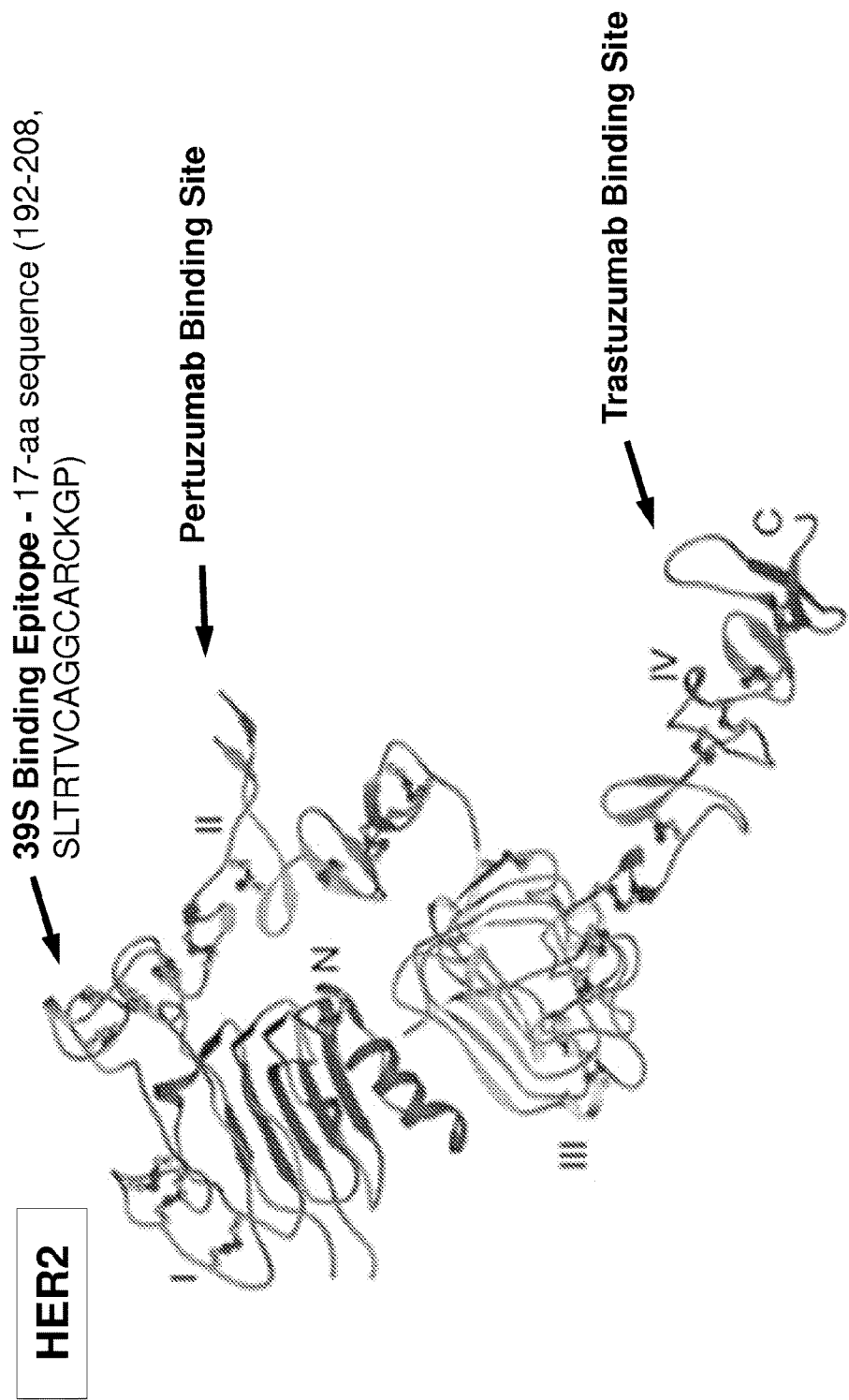
Figure 4:
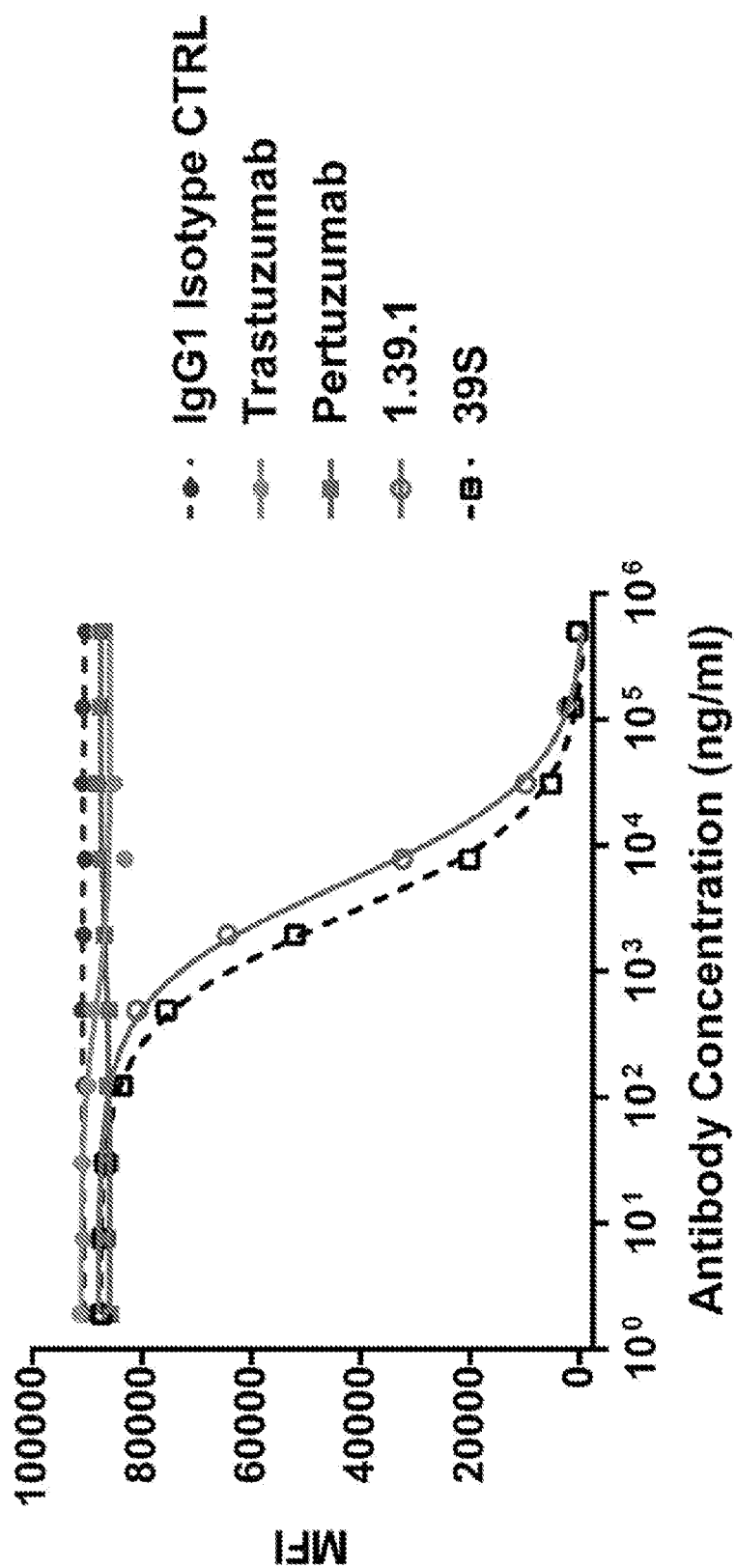

FIG. 4 shows that 39S binds to the same epitope as its parental antibody AZ1.39.1; and 39S does not compete with trastuzumab or pertuzumab for binding. The binding sites of 39S, pertuzumab and trastuzumab are indicated by arrows on the ribbon structure of HER2 provided in FIG. 3.

1.4. In Vitro Activity of 39S

A panel of human cancer cell lines expressing various levels of HER2 was selected for evaluating the anti-proliferative activity of antibodies or antibody combinations. HER2 expression level in cells was determined by HercepTest® and quantitative FACS (Table 5).

TABLE 5

HER2 Expression Levels on Human Cancer Cell Lines

| Cell Line | Cancer Type | HercepTest ® Score | Relative HER2 Density on Cell |
|---|---|---|---|
| BT-474 | Breast | 3+ | 1,841,884 |
| SKBR-3 | Breast | 3+ | 1,517,135 |
| NCI-N87 | Gastric | 3+ | 1,292,978 |
| SKOV-3 | Ovarian | 3+ | 349,178 |
| MDA-MB-361 | Breast | 2+/3+ | 252,249 |
| JIMT-1 | Breast | 2+ | 65,573 |
| MDA-MB-453 | Breast | 2+ | 77,314 |
| MDA-MB-175-VII | Breast | 2+ | 29,437 |
| RT-112 | Bladder | 2+ | 7,664 |
| MCF7-GTU | Breast | 2+ | 6,058 |
| ZR-75-1 | Breast | 1+ | 5,892 |
| T47D | Breast | 1+ | 6,124 |
| MCF-7 | Breast | 0 | 3,646 |
| MDA-MB-468 | Breast | 0 | Undetectable |

Proliferation Inhibition Assay:

Cells were plated in serum-containing culture media at a density of 5,000 to 20,000 per well (depending on the growth kinetics of each cell line) of 96-well plates in a volume of 100 µL. A 2× concentration of each dose of antibody or antibody combination to be tested was prepared by diluting the test articles in culture medium. One hundred microliters of each test article was added to cells in triplicate such that the final dose curve ranged from 10 µg/mL down to 0.15 ng/mL in a stepwise 1:4 serial dilution series. For ligand-dependent proliferation inhibition assay, cells were plated in serum-free media and a 4× concentration of each dose of antibody or antibody combination to be tested was prepared by diluting the test articles in serum-free medium. Fifty microliters of each test article was added to cells in triplicate and then 50 µL, of Heregulin-β1 at a concentration of 32 ng/mL diluted in serum-free medium was added to cells to achieve the final Heregulin-β1 concentration of 8 ng/mL and the final antibody dose curve ranged from 100 μg/mL down to 6.1 ng/mL in a stepwise 1:4 serial dilution series. The treated cells were cultured at 37° C./5% $CO_2$ for 4 to 7 days (depending on the growth kinetics of each particular cell line). Cell viability was determined using Cell Titer Glo from Promega according to manufacturer's instructions. Data are analyzed using the GraphPad Prism software and presented as percent growth inhibition relative to the untreated control.

Figure 5:
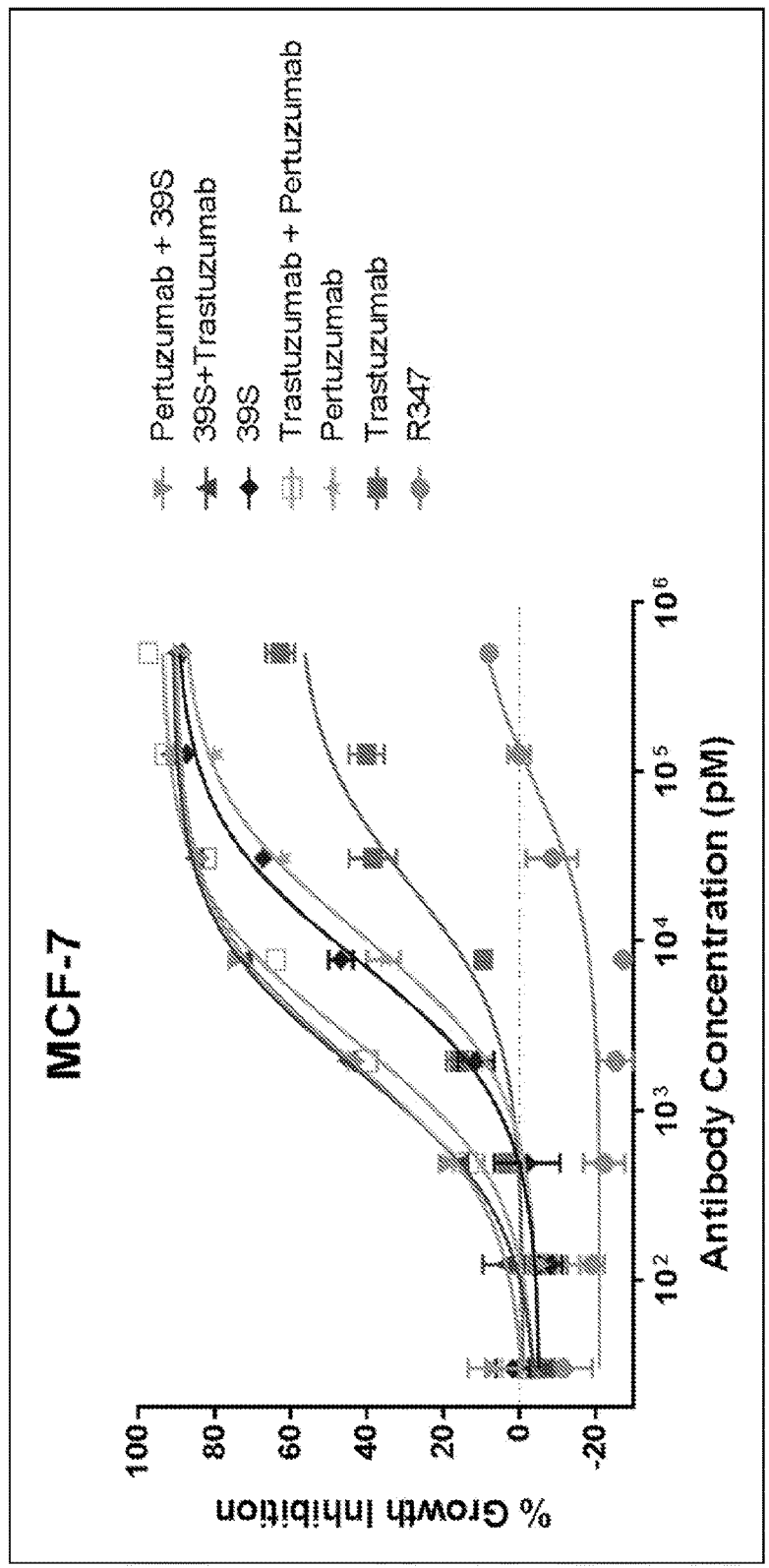

FIG. 5 shows that 39S has a similar activity as pertuzumab in inhibiting ligand-driven proliferation in MCF-7 cells. In combination with trastuzumab or pertuzumab, 39S shows additive or synergistic inhibition of ligand-dependent proliferation with potency comparable to trastuzumab and pertuzumab combination. Similar results were observed in other cells lines such as MDA-MB-361 and RT-112 (data not shown).

FIG. 6 shows that 39S, like pertuzumab, has a limited activity in inhibiting NCI-N87 cell proliferation in serum-containing media. However when combined with trastuzumab or pertuzumab 39S demonstrates a strong synergistic effect in inhibiting cell growth. Synergy between 39S and trastuzumab or pertuzumab is much greater than that seen with the combination of trastuzumab and pertuzumab. Similar results were observed in BT-474 cells (data not shown).

Example 2

2.1. Bispecific Antibody Construction

Cloning of Bs2Ab-39SH, Bs3Ab-39SH and Bs4Ab-39SH.

Bispecific expression constructs were generated by cloning the variable domains for the anti-HER2 domain IV antibody (SEQ ID NOs: 17 and 18 where X is C) anti-HER2 antibody 39S (SEQ ID NOs: 15 and 16) into expression vectors comprising the appropriate constant regions. The anti-HER2 domain IV variable binding domain was constructed as single-chain Fv (scFv). Using the amino acid sequences of SEQ ID NOs: 17 and 18 (where X-C) above a codon optimized DNA sequence for maximum mammalian protein expression was designed and synthesized. The Bs2Ab and Bs3Ab constructs were generated using methods similar to those described in Dimasi et al., (2009) J. Mol. Biol. 393, 672-692. The Bs4Ab construct was generated using method similar to those described in Patent Publication WO2013070565A1. The final synthetic gene contains two cysteine mutations, one in the light-chain at position 100 and one on the heavy chain at position 44, respectively. These cysteines will form an interchain disulfide bond between the VL and VH domains in order to stabilize the scFv. The two VL and VH domains of the scFv were linked using 20 amino acids residues $(G_4S)_4$ (SEQ ID NO: 19). The scFv in Bs2Ab was linked to the N-terminus of the heavy chain by using a 10 amino acid residue linker $(G_4S)_2$ (SEQ ID NO: 83). The scFv in the Bs3Ab format was linked to the C-terminus of the antibody CH3 domain by using a 10 amino acid residue linker $(G_4S)_2$ (SEQ ID NO: 83). Two linkers of sequence $(G_4S)_2$ (SEQ ID NO: 83) were used for linking the scFv in the Bs4Ab backbone. Construct identity and fidelity was determined using DNA sequence.

Figure 7:
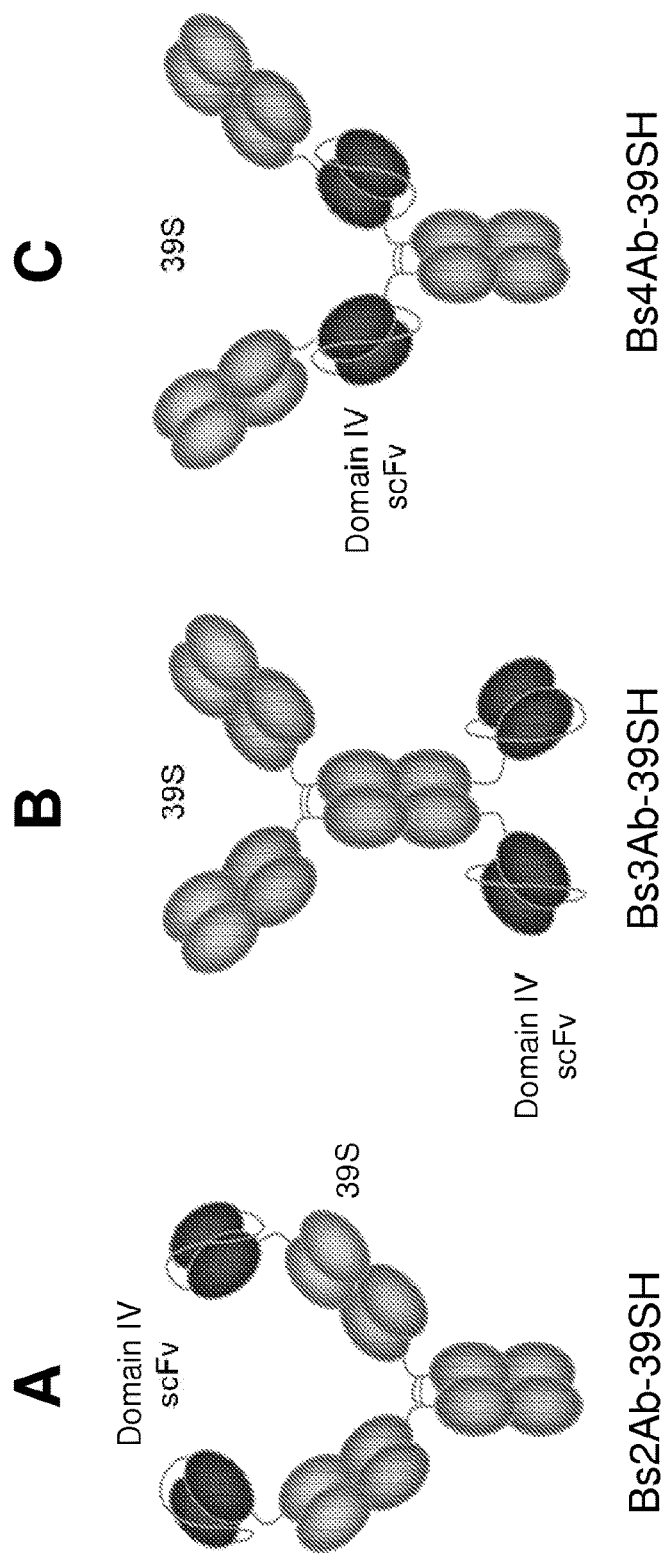

FIG. 7 provides a schematic diagram of each of the Bs2Ab-39SH, Bs3Ab-39SH, Bs4Ab-39SH bispecific antibody formats (Panels A, B and C, respectively) generated for binding to HER2 antigen. The bispecific antibodies have two binding units, each of which binds a different epitope on the same antigen. The binding units are labeled on the figure. The molecule is bilaterally symmetric with respect to the binding units. As depicted, Bs2Ab-39SH, Bs3Ab-39SH, Bs4Ab-39SH formats refers to bispecific antibodies in which a scFv is fused to the amino terminus of the variable region (Bs2Ab-39SH), inserted into a modified hinge region (Bs4Ab-39SH) or the carboxy-terminus of CH3 (Bs3Ab-39SH) of a heavy chain through a linker (e.g., $(G_4S)_2$ (SEQ ID NO: 83)). The three bispecific constructs shown are comprised of an anti-HER2 domain IV binding scFv fused to an anti-HER2 domain II human IgG1 via a glycine serine linker (e.g., $(G_4S)_2$ (SEQ ID NO: 83)).

The amino acid sequences of the Bs2Ab-39SH, Bs3Ab-39SH and Bs4Ab-39SH constructs are provided in FIG. 8 (also see SEQ ID NOs: 30, 34, and 38 native Fc region). FIG. 8A shows the bispecific antibody heavy chain amino acid sequences for Bs2Ab-39SH and possible substitution sites for enhanced ADCC and or site specific Antibody Drug Conjugation for two and four drug loading. The anti-HER2 domain IV scFv is in the VL-$(G_4S)_4$ linker-VH format ('$(G_4S)_4$' disclosed as SEQ ID NO: 19) and is genetically linked to the amino terminus of the anti-HER2 domain II antibody heavy chain via a $(G_4S)_2$ linker (SEQ ID NO: 83). The amino acid substitutions and or insertions depicted within can be made in the CH2 and CH3 of the antibody for enhanced ADCC and site specific conjugation. FIG. 8B shows the bispecific antibody heavy chain amino acid sequences for Bs3Ab-39SH and possible substitution sites for enhanced ADCC and or site specific Antibody Drug Conjugation for two and four drug loading. The anti-HER2 domain IV scFv is in the VL-$(G_4S)_4$ linker-VH format ('$(G_4S)_4$' disclosed as SEQ ID NO: 19) and is genetically linked to the carboxy-terminus of the anti-HER2 domain II antibody heavy chain via a $(G_4S)_2$ linker (SEQ ID NO: 83). The amino acid substitutions and or insertions depicted within can be made in the CH2 and CH3 of the antibody for enhanced ADCC and site specific conjugation. FIG. 8C shows the bispecific antibody heavy chain amino acid sequences for Bs4Ab-39SH and possible substitution sites for enhanced ADCC and or site specific Antibody Drug Conjugation for two and four drug loading. The anti-HER2 domain IV scFv is in the VL-$(G_4S)_4$ linker-VH format ('$(G_4S)_4$' disclosed as SEQ ID NO: 19) and is inserted into a modified hinge region of the anti-HER2 domain II antibody heavy chain via two $(G_4S)_2$ linkers (SEQ ID NO: 83). The amino acid substitutions and or insertions depicted within can be made in the CH2 and CH3 of the antibody for enhanced ADCC and site specific conjugation.

2.2. Binding Specificity and Species Cross-Reactivity of Bispecific Antibody

Binding specificity and species cross-reactivity of bispecific antibodies to the recombinant extracellular domain protein of human EGFR, human HER2, human HER3, human HER4, mouse Her2, or cynomolgus monkey Her2 were determined by capture ELISA as described in Example 1. Results show that all bispecific antibodies tested, including Bs2Ab-39SH, Bs3Ab-39SH and Bs4Ab-39SH, are able to bind to human HER2 and cynomolgus monkey Her2 at similar potency and none of them shows binding to the Human EGFR, HER3, HER4, or the mouse Her2 (data not shown), suggesting the bispecific antibodies retain the binding specificity of species cross-reactivity of their parental monoclonal antibodies.

Binding kinetics of the bispecific antibodies to human HER2 and cynomolgus monkey Her2 are determined by BIAcore (data not shown). The affinity to human HER2 ($K_D$) is 113 pM for Bs2Ab-39SH, and 236 pM for Bs4Ab-39SH.

2.3. In Vitro Activity of Bispecific Antibody

Activity of bispecific antibody in inhibiting ligand-driven cell proliferation was determined using method described in Example 1. Results show that Bs2Ab-39SH, Bs3Ab-39SH and Bs4Ab-39SH have similar potency in MDA-MB-361 cells (FIG. 9A) and MCF-7 cells (FIG. 9B), which is also comparable to the activity of parental antibody combination (39S plus trastuzumab). Similar results were observed in other cell lines including NCI-N87 and RT-112 (data not shown).

2.4. Disruption of HER2:HER3 Heterodimerization by Bispecific Antibody

T47D cells were harvested, washed and resuspended in serum-free media. Cells were seeded at a density of $1 \times 10^6$ cells/well in a 6-well plate and then incubated overnight at 37° C./5% $CO_2$. The next day cells were pre-treated for 1 hour with antibody to be tested (R347 IgG1 isotype control, trastuzumab, pertuzumab, 39S, and Bs2Ab-39SH) at a concentration of 500 nM. After pre-treatment, heregulin-β1 was added at a final concentration of 8 ng/mL and cells were incubated for 5 min at 37° C./5% $CO_2$. Cells were then washed twice with ice-cold 1×PBS, lysed and immune-precipitated using mouse anti-human HER2 (clone 44E7) antibody and the Pierce Classic IP Kit from Thermo Scientific according to manufacturer's instructions. Immune-precipitated protein samples were eluted in Laemmli buffer containing 2-mecaptoethanol and analyzed by Western blot using standard protocol. Rabbit anti-human HER2 (clone 29D8) antibody was used to detect HER2 and rabbit anti-human HER3 (C-17) polyclonal antibody was used to detect HER3 in the Western blot analysis.

FIG. 10 shows that Bs2Ab-39SH and 39S, similar to pertuzumab, can disrupt HER2:HER3 heterodimerization induced by ligand stimulation.

2.5. Clustering of HER2 by Bispecific Antibody

To examine whether the bispecific antibody can cross-link HER2 to form a large complex, the recombinant human HER2 extracellular domain protein was mixed with Bs2Ab-39SH or trastuzumab at various molar ratios and incubated at room temperature for 30 min. The formed immune complexes were separated by HPLC size-exclusion chromatography; the sizes of which were then analyzed by Multi-Angle Light Scattering (MALS) assay.

FIG. 11 shows the representative data derived from antibody:HER2 molar ratio of 1:1 (data at other molar ratios not shown). Results indicate that Bs2Ab-39SH can cross-link many HER2 molecules to form a protein complex as large as 1716 kDa in size, while trastuzumab can only bind to two HER2 molecules in maximal to form a 320 kDa complex. Similar results were observed with Bs4Ab-39SH (data not shown).

2.6. Enhanced Internalization and Lysosomal Trafficking by Bispecific Antibody Antibody internalization was measured by FACS. BT-474 cells were harvested from a T150 flask, resuspended in ice-cold culture media and then added to a 96-well U-bottom plate at $1 \times 10^6$ cells/well. Cells were pelleted by centrifugation at 4° C. Media were flicked off, and cell pellets were resuspended in triplicate in 150 μL of ice-cold culture media containing 10 μg/mL antibody or antibody combination to be tested (R347 IgG1 isotype control, trastuzumab, pertuzumab, AZ1.39.1, 39S, trastuzumab+39S, trastuzumab+pertuzumab, pertuzumab+39S, trastuzumab+pertuzumab+39S, Bs2Ab-39SH, Bs3Ab-39SH, and Bs4Ab-39SH). Cells were incubated on ice for 1 hour and then washed to remove unbound antibodies. An aliquot of cells was kept on ice; the rest was incubated at 37° C./5% $CO_2$ for a different period of time (30 min, 1 hour, 2 hours, or 4 hours) and then cooled on ice immediately. Cells were washed twice with ice-cold FACS buffer and then fixed with 4% PFA for 20 min. Following fixation, cells were stained with anti-human IgG Alexa-Fluor 488 and analyzed by a BD LSR II machine and BD FACSDiva™ software. Data were analyzed with FlowJo software. Receptor-antibody complex internalization was calculated as percent mean fluorescent intensity (MFI) loss at 37° C. relative to that on ice after subtracted by the background value of MFI derived from the untreated control.

FIG. 12 shows that the bispecific antibody (Bs2Ab-39SH, Bs3Ab-39SH, Bs4Ab-39SH) can induce a much faster and stronger internalization than any single mono-specific antibody or antibody combination. Pertuzumab, AZ1.39.1, trastuzumab+pertuzumab, pertuzumab+39S, and trastuzumab+pertuzumab+39S have similar or lower internalization profiles to that of 39S and are not shown in the graph. Similar results were observed in cell lines NCI-N87, MDA-MB-361 and RT-112 (data not shown).

Confocal microscopy method was used to visualize antibody internalization and lysosomal trafficking. BT-474 cells were harvested from a T-150 flask and resuspended in ice-cold culture media and then added to a 96-well U-bottom plate at $2.5 \times 10^5$ cells/well. Cells were pelleted by centrifugation at 4° C. Media were flicked off, and cell pellets were resuspended in 150 μL of ice-cold culture media in the presence of 10 μg/mL antibody to be tested, such as R347 IgG1 isotype control, trastuzumab, Bs2Ab-39SH, and Bs4Ab-39SH. Cells were incubated at 37° C./5% $CO_2$ for a different period of time (30 min, 2 hours, 4 hours, or 6 hours) and then cooled on ice immediately. Cells were washed twice with ice-cold FACS buffer and then fixed and permeabilized using BD Biosciences Cytofix/Cytoperm™ Fixation/Permeabilization Solution according to manufacturer's instructions. Cells were stained in the dark with anti-human IgG Alexa-Fluor 488, and mouse anti-human LAMP-1 (clone H4A3) followed by anti-mouse IgG Alexa-Fluor 647. After staining, cells were cytospun onto positive charge slides and coversliped with ProLong® Gold Antifade Reagent containing DAPI. Cells were then visualized by Leica SP5 Confocal Microscope and the Leica Application Suite Advanced Fluorescence software suite.

FIG. 13 shows the antibody internalization and trafficking to the lysosomes. Both Bs2Ab-39SH and Bs4Ab-39SH promote much faster internalization and stronger lysosomal trafficking than trastuzumab, which show little to no internalization (data for Bs4Ab-39SH not shown).

Western blot analysis was used to monitor lysosomal degradation of HER2. BT-474 cells were harvested, washed and resuspended in culture media. Cells were seeded at a density of $5 \times 10^4$ cells/well in a 96-well plate and treated at 37° C./5% $CO_2$ with antibody to be tested (R347 IgG1 isotype control, trastuzumab, pertuzumab, 39S, trastuzumab+pertuzumab, trastuzumab+39S, pertuzumab+39S, trastuzumab+pertuzumab+39S, Bs2Ab-39SH, Bs3Ab-39SH, and Bs4Ab-39SH) at a concentration of 500 nM for 2 hours, 6 hours, or 24 hours. At the end of treatment, cells were washed twice with ice-cold 1×PBS and then lysed in M-PER Mammalian Protein Extract buffer from Thermo Scientific according to manufacturer's instructions. Protein concentration of each lysate was measured by BCA assay. Equal amount of protein in each lysate was loaded onto gel in Western blot. Rabbit anti-human HER2 (clone 29D8) antibody and rabbit anti-human GAPDH (clone D16H11) antibody were used to detect HER2 and GAPDH, respectively.

FIG. 14 shows that treatment with the bispecific antibody (Bs2Ab-39SH, Bs3Ab-39SH, or Bs4Ab-39SH) leads to the significant HER2 degradation in BT-474 cells, and monospecific antibody or antibody combination induces no or limited HER2 degradation.

Example 3

3.1. Cloning of Site-Specific Mutants for Site-Specific Conjugation and for Ablating Fc Gamma Receptor Binding Activities Standard overlapping PCR methods were used to introduce the mutation L234F, S239C and S442C, independently or in combination (L234F-S239C (FC) and L234F-S239C-S442C (FCC)) into the Fc portion of the Bs2Ab-39SH and Bs4Ab-39SH constructs. The Primers were designed to contain desired mutations and flanking primers, containing restriction sites to facilitate directional cloning, were used to amplify the Fc fragments containing the specific mutations. Modified Fc PCR products were cloned into mammalian expression vectors using defined restrictions sites. Identities of Fc mutations were confirmed by DNA sequence analysis.

FIG. 15 shows illustrations of three anti-HER2 bispecific antibodies, (Bs2Ab-39SH, Bs3Ab-39SH, Bs4Ab-39SH) with amino acids substitutions for site specific conjugation. In addition, the L234F substitution on the CH2 of the antibody heavy chain (not depicted in the figure) is used to minimize Fc gamma receptor binding. Where 2 DAR is desired a cysteine substitution is engineered at site 1 (e.g., S239C) or site 2 (e.g., S442C), and for 4 DAR a cysteine substitution is engineered at both sites. The bispecific-drug constructs are also referred to herein as Bs2-2T/Bs2-4T, Bs3-2T/Bs34T, and Bs4-2T/Bs4-4T.

The resulting bispecific antibodies were conjugated to the tubulysin 1508 payload essentially as described below (see Example 5).

3.2. Binding Specificity and Species Cross-Reactivity of Bispecific ADC

To determine whether the conjugation of tubulysin 1508 alters antigen binding specificity and species cross-reactivity, binding activity of bispecific ADC to the recombinant extracellular domain protein of human EGFR, human HER2, human HER3, human HER4, mouse Her2, and cynomolgus monkey Her2 were confirmed by capture ELISA as described in Example 1. Results show that conjugation did not change the antigen binding specificity and species cross-reactivity of the bispecific ADC. Both Bs2-4T and Bs4-4T can bind to human HER2 and cynomolgus monkey Her2 at the same potency as their unconjugated version; and none of them shows binding to the human EGFR, HER3, HER4, or the mouse Her2 (data not shown). Binding kinetics of the bispecific ADC to human HER2 are determined by BIAcore and results show that the affinity to human HER2 ($K_D$) is 120 pM for Bs2-4T, and 271 pM for Bs4-4T.

3.3. Disruption of Intracellular Microtubule Network by Bispecific ADC

To examine the disruption of intracellular microtubule network by anti-HER2 ADC, three cell lines were selected: SKOV-3, JIMT-1, and RT112, which represent the T-DM1 eligible, the T-DM1 non-responder, and the T-DM1 ineligible, respectively. On day 1, cells were harvested by trypsinization, resuspended in culture media, and then seeded in 8-well chamber slides at a density of $6 \times 10^4$ cells/well. Slides were incubated at 37° C./5% $CO_2$ overnight. On day 2, media were aspirated to remove any unattached cells and then fresh media containing 5 nM ADC to be tested were added to the cells. Slides were incubated at 37° C./5% $CO_2$ overnight. On day 3, each chamber was washed twice with 1×PBS. Cells were then fixed with 4% PFA for 20 min. At the end of fixation, the chambers were removed and slides were stained following standard immunofluorescence procedures. Briefly, cells were permeabilized using Triton X-100 and washed with 1×PBS containing Tween-20. Rabbit anti-human α-Tubulin Alexa-Fluor 488 (clone 11H10) was diluted by 1:100 in DAKO antibody diluent and added to the slides. After incubation at room temperature for 1 hour, slides were coversliped with ProLong® Gold Antifade Reagent containing DAPI. Stained cells were visualized by the Leica SP5 Confocal Microscope and the Leica Application Suite Advanced Fluorescence software suite.

FIG. 16A shows in SKOV-3, a cell line representing T-DM1 eligible patients, that both T-DM1 and Bs2-4T are capable of disrupting microtubule networks. Similar results were observed in SKBR-3 cells (data not shown).

FIG. 16B shows in JIMT-1, a cell line representing T-DM1 non-responder patients, that only Bs2-4T is able to disrupt intracellular microtubule networks.

FIG. 16C shows in RT-112, a cell line representing T-DM1 ineligible patients, that Bs2-4T is able to disrupt intracellular microtubule networks, while T-DM1 is inactive.

3.4. In Vitro Activity of Bispecific ADC

A panel of human cancer cell lines expressing various levels of HER2 was used to evaluate the cytotoxic activity of bispecific ADC (Table 5 in Example 1). Briefly, cells were harvested, resuspended, and plated in serum-containing culture media at a density of 5,000 to 20,000 per well (depending on the growth kinetics of each cell line) of 96-well plates in a volume of 100 μL. A 2× concentration of each dose of antibody or ADC to be tested was prepared by diluting the test articles in culture medium. One hundred microliters of each test article was added to cells in triplicate such that the final dose curve ranged from 5 nM down to 0.08 pM in a stepwise 1:4 serial dilution series. The treated cells were incubated at 37° C./5% $CO_2$ for 3 to 4 days, depending on the growth kinetics of each particular cell line. Cell viability was determined using Cell Titer Glo according to manufacturer's instructions. Data are analyzed by the GraphPad Prism software and presented as percent growth inhibition relative to the untreated control. $EC_{50}$ values were determined using Sigmoidal non-linear regression analysis with GraphPad Prism software and were summarized in Table 6.

TABLE 6

In vitro potency of anti-HER2 ADC in a panel of cancer cell lines (EC50 in pM)

| Cell Line | T-DM1 | Bs2-2T | Bs4-2T | Bs2-4T | Bs4-4T |
|---|---|---|---|---|---|
| SKBR-3 | 82.6 | 12.9 | 10.4 | 4.0 | 2.6 |
| NCI-N87 | 275.1 | 36.8 | 25.6 | 23.7 | 20.0 |
| SKOV-3 | 116.1 | 13.6 | 8.9 | 8.7 | 5.6 |
| MDA-MB-361 | 266.0 | 15.1 | 10.0 | 4.0 | 2.7 |
| JIMT-1 | Inactive | 13.3 | 7.1 | 5.1 | 3.1 |
| MDA-MB-453 | 344.3 | 19.0 | 13.0 | 10.5 | 8.6 |
| RT-112 | Inactive | 4635 | 2938 | 36.5 | 23.5 |
| MCF7-GTU | Inactive | Inactive | Inactive | 84.5 | 61.4 |
| ZR-75-1 | Inactive | 1543 | 753.5 | 18.1 | 20.9 |
| T47D | Inactive | Inactive | Inactive | Inactive | Inactive |
| MCF-7 | Inactive | Inactive | Inactive | Inactive | Inactive |
| MDA-MB-468 | Inactive | Inactive | Inactive | Inactive | Inactive |

FIG. 17A shows the cytotoxic activity of Bs2-2T and Bs2-4T relative to T-DM1 and various controls in SKBR-3, a human breast cancer cell line representing the T-DM1 eligible patients. Data indicate that both Bs2-2T and Bs2-4T are more potent than T-DM1 in SKBR-3 cells.

FIG. 17B shows the cytotoxic activity of Bs4-2T and Bs4-4T relative to T-DM1 and various controls in SKBR-3, a human breast cancer cell line representing the T-DM1 eligible patients. Data indicate that both Bs4-2T and Bs4-4T are more potent than T-DM1 in SKBR-3 cells.

FIG. 18A shows the cytotoxic activity of Bs2-2T and Bs2-4T relative to T-DM1 and various controls in JIMT-1, a human breast cancer cell line representing the T-DM1 eligible but non-responder patients. Data indicate that both Bs2-2T and Bs2-4T are very potent in killing JIMT-1 cells, while T-DM1 shows no activity.

FIG. 18B shows the cytotoxic activity of Bs4-2T and Bs4-4T relative to T-DM1 and various controls in JIMT-1, a human breast cancer cell line representing the T-DM1 eligible but non-responder patients. Data indicate that both Bs4-2T and Bs4-4T are very potent in killing JIMT-1 cells, while T-DM1 shows no activity.

FIG. 19A shows the cytotoxic activity of Bs2-2T and Bs2-4T relative to T-DM1 and various controls in ZR-75-1, a human breast cancer cell line representing the T-DM1 ineligible patients. Data indicate that Bs2-4T is the most active in killing ZR-75-1 cells, while Bs2-2T has a lower level of activity and T-DM1 shows no or limited cytotoxic activity.

FIG. 19B shows the cytotoxic activity of Bs4-2T and Bs4-4T relative to T-DM1 and various controls in ZR-75-1, a human breast cancer cell line representing the T-DM1 ineligible patients. Data indicate that Bs4-4T is the most active in killing ZR-75-1 cells, while Bs4-2T has a lower level of activity and T-DM1 shows no or limited cytotoxic activity.

FIG. 20 shows the cytotoxic activity of Bs2-2T and Bs2-4T relative to T-DM1 and various controls in MDA-MB-468, a human breast cancer cell line with no HER2 expression. Data indicate that neither Bs2-2T nor Bs2-4T is active in MDA-MB-468 cells, indicating that the cytotoxic activity of Bs2-2T and Bs2-4T is target (i.e. HER2)-dependent. Similar results were observed with Bs4-2T and Bs4-4T (data not shown).

3.5. In Vivo Activity of Bispecific ADC Constructs

Cell Line-Based Xenograft (CBX) Tumor Models and Patient-Derived Xenograft (PDX) Tumor Models:

All mouse experiments were carried out in compliance with the guidelines published by the Association for Assessment and Accreditation of Laboratory Animal Care (AAALAC) and protocols approved by the MedImmune Institutional Animal Care and Use Committee. Athymic nude mice between 4-8 weeks of age were used in the studies. In subcutaneous CBX models, animals were injected unilaterally on the right flank with tumor cells harvested from culture at a specific passage lot. In orthotopic CBX models, xenografts were established by injecting $5\times10^6$ cells per mouse (suspended in 50% matrigel) into the mammary fat pad on the right flank of animals. In PDX models, animals are implanted unilaterally on the flank with tumor fragments harvested from host animals each implanted from a specific passage lot. Pre-study tumor volumes were recorded for each experiment beginning approximately one week prior to its estimated start date. When tumors reach the appropriate tumor volume initiation (TVI) range (typically 150-250 mm$^3$), animals are randomized into treatment and control groups and dosing initiated. Animals were dosed once weekly unless otherwise specified with test articles via intravenous or intraperitoneal injection. Animals were observed daily and tumor dimensions and body weights were measured and recorded twice weekly. Tumor volumes are calculated using the following formula: tumor volume=$\pi\div6$ (length×width$^2$). Tumor growth curve was presented as the mean tumor volume (mm$^3$)±SEM.

FIG. 21A shows that even at lower concentrations (1 mg/kg) Bs2-4T has higher in vivo activity relative to T-DM1 (3 mg/kg) and various controls (all at 3 mg/kg) in MDA-MB-361 model, a human breast cancer CBX tumor model representing the T-DM1 ineligible patients. Data demonstrate that Bs2-4T induced a dose-dependent tumor growth inhibition, and at 3 mg/kg dose Bs2-4T induced complete tumor regression while T-DM1 showed limited activity. At 3 mg/kg Bs4-4T also exhibited higher in vivo activity relative to T-DM1 (FIG. 21B).

FIG. 22 shows the in vivo activity of Bs2-2T relative to Bs2-4T and T-DM1 in ST996 model. ST996 is a primary PDX model derived from a triple-negative breast cancer patient (HER2 IHC: 1+; ER−; PR−). Data demonstrate that Bs2-2T at 3 mg/kg dose induced a robust tumor growth inhibition, although its anti-tumor potency was slightly reduced as compared to Bs2-4T. In contrast, T-DM1 showed no activity in ST996 model. Similar results were observed in additional low HER2-expressing PDX models ST738, ST455B, and ST821 (data not shown).

FIG. 23 shows the in vivo activity of Bs2-4T relative to T-DM1 and various controls in ST225 model, a human breast cancer PDX tumor model representing T-DM1 eligible patients. Data demonstrate that Bs2-4T at 3 mg/kg dose induced complete and durable tumor regression. In contrast, T-DM1 only induced tumor stasis during the treatment phase and the tumor re-grew quickly after the treatment was stopped.

FIG. 24 shows the in vivo activity of Bs2-4T relative to T-DM1 and various controls in JIMT-1 model, a human breast cancer CBX orthotopic tumor model representing T-DM1 eligible but non-responder patients. Data demonstrate that Bs2-4T at 3 mg/kg dose induced complete and durable tumor regression. In contrast, T-DM1 or T-DM1 plus pertuzumab combination showed no activity.

FIG. 25 shows the in vivo activity of Bs2-4T relative to T-DM1 and various controls in ST455B model. ST455B is a primary PDX model derived from a triple-negative breast cancer patient (HER2 IHC: 1+, ER−, PR−). Data demonstrate that Bs2-4T at 3 mg/kg dose induced complete tumor regression while T-DM1 showed no activity. To further expand the finding shown in FIG. 25, we have examined Bs2-4T in another 16 PDX models derived from breast cancer patients with relatively low levels of HER2 expression (+1 to +2 via HercepTest). Other criteria were also considered in the selection of these models, including the degree of heterogeneity in HER2 expression, ER/PR status and histopathologic subclass, to maximize the diversity of tumor subtypes in the study. Table 7 summarizes the in vivo activity of Bs2-4T in these 17 different PDX breast cancer models. Bs2-4T demonstrated potent anti-tumor activity regardless of the histopathologic subclass and ER/PR status of the tumor. At the dose of 1 mg/kg, 41% of the tumor models showed tumor regression and 6% showed tumor stasis. At the dose of 3 mg/kg, 71% of the models showed tumor regression and 12% showed tumor stasis.

These studies demonstrate the superior activity of the Bispecific ADCs of the instant invention as compared to mono-specific ADC therapies (e.g. T-DM1) across a wide range of breast cancer models. In particular, the Bispecific ADCs of the instant invention have in vivo activity in cancer models with low levels of HER2 expression and in models of T-DM1 non-responder patients.

TABLE 7

Summary of in vivo efficacy of Bs2-4T in a panel of PDX breast cancer models representing HER2-low/T-DM1 ineligible patients. At the time-point showing maximal response to the Bs2-4T treatment, if the tumor volume is decreased as compared to the tumor volume at dosing initiated (TVI), the in vivo efficacy is expressed as percent tumor volume change over the TVI. Otherwise the in vivo efficacy is expressed as percent tumor volume change relative to the vehicle control. Responsiveness to the treatment ranked as "regression" if the tumor volume decreased by >20%, "stasis" if the tumor volume changed <20%, and "progression" if the tumor volume increased by >20%.

| Efficacy | 1 mg/kg | 3 mg/kg |
| --- | --- | --- |
| Regression | 41% (7/17) | 70% (12/17) |
| Stasis | 6% (1/17) | 12% (2/17) |
| Progression | 53% (9/17) | 18% (3/17) |

3.6. Activity of Bispecific ADC in Tumor Models with Acquired T-DM1 Resistance

NCI-N87 cells with acquired resistance to T-DM1 were generated through continuous treatment with gradually increased concentration of T-DM1 up to 5 µg/mL. In vitro cytotoxic activity of Bs2-4T relative to T-DM1 was examined in both parental and resistant cell lines as described in Example 3. Results shown in FIG. 26A indicate that both Bs2-4T and T-DM1 are active in the parental NCI-N87 cells although Bs2-4T is more potent than T-DM1 (left panel). In the resistant cell line, T-DM1 has lost the activity, whereas Bs2-4T is still active in killing the resistant cells (right panel). Other resistant cell lines were also generated through continuous treatment with T-DM1, including BT-474, SKOV-3, and MDA-MB-361, and similar cytotoxic activity was observed with Bs2-4T in these resistant cell lines (data not shown).

To establish an in vivo tumor model with acquired T-DM1 resistance, the T-DM1-resistant NCI-N87 cells were injected subcutaneously into the immune-deficient mice. The tumor-bearing mice were treated with 3 mg/kg of T-DM1. It appeared that the in vitro T-DM1 resistance was not fully translated into the in vivo resistance, reflected by considerable variations in tumor growth among animals. Thus, mice with large refractory tumors (~1000 mm³ in volume) were selected and the tumor tissue fragments were passaged to new mice until the tumors grew consistently in the presence of weekly treatment of 3 mg/kg T-DM1. After three passages, stable resistant tumors evolved and these tumors were fragmented and implanted into mice to evaluate the in vivo activity of Bs2-4T. As demonstrated in FIG. 26B, tumors relapsed from the repeated T-DM1 treatment were not only resistant to T-DM1, but also unresponsive to T-DM1 and pertuzumab combination treatment. In contrast, Bs2-4T induced a robust and sustained tumor regression after treatment, suggesting its potential as an effective therapy for the T-DM1 relapsed/refractory patients.

FIG. 26B shows that Bs2-4T induces tumor regression in the T-DM1 resistant NCI-N87 tumor model. Tumor growth curves, in response to weekly intravenous dosing of Bs2-4T (3 mg/kg), T-DM1 (3 mg/kg) or other control antibody/ADC (3 mg/kg, except for pertuzumab which is 10 mg/kg) for a total of 4 doses, are shown as the mean tumor volume (mm³)±SEM (n=7). *P<0.001 by Student's t test as compared to the untreated control group.

3.7. In Vivo Anti-Tumor Activity of Bispecific ADC is not Attenuated by Pretreatment of Trastuzumab ST225 PDX tumor fragments were implanted unilaterally on the flank of athymic nude mice. Mice were randomized into treatment and control groups and dosing initiated when tumor volumes reached 200-250 mm³. In the treatment groups, mice were either dosed with vehicle buffer or trastuzumab (3 mg/kg). Three days later, mice received weekly intravenous injection of Bs2-4T for a total 4 doses. FIG. 27 shows that pretreatment of trastuzumab does not attenuate the anti-tumor activity of Bs2-4T in the ST225 PDX model, suggesting that a washout period may not be needed if Bs2-4T is used to treat patients that are relapsed/refractory to trastuzumab or T-DM1. ST225 is a primary breast cancer PDX model with HER2 overexpression. Tumor growth curves in response to various treatment are presented in FIG. 27 as the mean tumor volume (mm3) ±SEM (n=10).

3.8. Bystander Effect of Bispecific ADC

NCI-N87 cells were stably transfected with green fluorescent protein (GFP) and MDA-MB-468 cells were stably transfected with red fluorescent protein (RFP). Both cell lines were harvested, washed, resuspended in culture media and then seeded in the same well of a 6-well plate as co-culture. As a control, each cell line was seeded in a different 6-well plate as single culture (FIG. 28A). To adjust to different growth kinetics, NCI-N87 cells were seeded at $5 \times 10^5$ cells/well and MDA-MB-468 cells were seeded at $2 \times 10^5$ cells/well. Cells were incubated for 2 days at 37° C./5% $CO_2$. Media were aspirated and fresh media containing 5 nM of antibody or ADC to be tested was added to cells and the plates were incubated for 4 days at 37° C./5% $CO_2$. At the end of treatment, cells in each well were collected, washed, resuspended in 100 µL of ice-cold FACS buffer and then fixed with 2% PFA. Cells were analyzed by a BD LSR II machine and BD FACSDiva™ software. Data were analyzed with FlowJo software.

FIG. 28B demonstrates that Bs2-4T can kill both HER2-overexpressing and HER2-null cells in a co-culture, suggesting that Bs2-4T has bystander effect. In contrast, T-DM1 cannot kill HER2-null cells in a co-culture, suggesting that it does not have bystander effect. As controls, both Bs2-4T and T-DM1 showed potent killing of NCI-N87 cells in single cultures and neither Bs2-4T nor T-DM1 showed killing of MDA-MB-468 cells in single cultures (data not shown).

3.9. Activity of Bispecific ADC Against Cancer Stem Cells

Cancer Stein Cell Sphere Assay:

MDA-MB-361 cells were cultured under standard tissue culture conditions in Leibovitz's L-15 medium supplemented with 20% FBS. Cells were harvested by trypsinization, washed twice with PBS, and resuspended to 30,000 cells per mL in stem cell medium (SCM: DMEM/F12 supplemented with 20 ng/mL EGF, 10 ng/mL bFGF, 5 mg/mL insulin, 0.4% BSA and 1% knock-out serum replacement). To form primary spheres, 1 mL of cells were plated into 24-well ultra-low attachment plates and treated with 10 pM of either R347-4T, T-DM1 or BS2-4T and incubated for 4 days at 37° C./5% $CO_2$. At the end of treatment, the primary spheres were harvested, dissociated using 0.05% trypsin and resuspended at a density of 30,000 cells/mL in SCM containing the same antibody treatment as the primary sphere culture. Cells were then plated in triplicate into 96-well ultra-low attachment plates and incubated for 4 days. Sphere cell viability was determined using Cell Titer Glo according to manufacturer's instructions. Data are presented as fold of CSC sphere formation relative to the untreated control. FIG. 29 (left panel) shows that Bs2-4T inhibited CSC sphere formation by 84% and T-DM1 had no activity in inhibiting CSC sphere formation. Similar results were observed in other cancer cell lines including BT-474, JIMT-1 and T47D (data not shown).

Assessment of Cancer Stem Cells in Xenograft Tumors Treated with Bs2-4T:

Tumors from MDA-BM-361 xenograft studies evaluating the in vivo activity of Bs2-4T were excised, cut into 4 mm pieces and cryopreserved using Cryostor. Frozen tumor pieces were thawed at 37° C., washed twice in Hank's Balanced Salt Solution (HBSS) and further minced using sterile scalpel blades. To obtain single-cell suspensions, the tumor pieces were then mixed with 200 units of ultrapure collagenase III per mL of DMEM/F12 medium. The tumor suspension was incubated at 37° C. for approximately 1 hour, with mechanical disruption every 30 minutes. At the end of the incubation, cells were filtered through a 70-μm nylon mesh and washed twice with HBSS. Following the last wash, cells were put through a 40-μm cell strainer and counted using a Vi-Cell XR Cell Viability Analyzer. Cells were assayed for aldehyde dehydrogenase activity as a measure of CSCs using the Stemcell Technologies Aldefluor kit and following manufacturer's instructions. The cells were run on an LSRII flow cytometer and analyzed with FlowJo.

FIG. 29 (right panel) shows that the treatment with Bs2-4T resulted in reduction of CSC by 54% in MDA-MB-361 breast cancer xenograft model.

Example 4

4.1. Afucosylated Bispecific Antibody Production and Characterization

The bispecific antibodies were expressed using POTEL-LEGENT™ technology (Biowa, Inc. Princeton, N.J.) to generated afucoslyated antibodies having enhanced ADCC activity. Table 8 shows the $K_D$ (nM) as measured by BIAcore of Bs2Ab-39SH and Bs4Ab-39SH bispecific antibodies and trastuzumab with fucosylation (_Fuc) and without fucosylation (_aFuc) binding to Fc gamma receptors (FcγRs) and C1q demonstrating that the afucosylated antibodies have enhanced binding to FcγRI, and both alleles of FcγRIIIa.

TABLE 8

| | $K_D$ (nM) Measured by BIAcore | | | | | |
|---|---|---|---|---|---|---|
| Antibody | FcgRI | FcgRIIa | FcgRIIb | FcgRIIIa (158F) | FcgRIIIa (158V) | C1q |
| Bs2Ab-39SH_Fuc | 7.0 | 1300 | 2750 | 1990 | 267 | 75.6 |
| Bs2Ab-39SH_aFuc | 0.98 | 1250 | 2400 | 216 | 40 | 130 |
| Bs4Ab-39SH_Fuc | 13.0 | 1190 | 2790 | 1780 | 228 | 88.6 |
| Bs4Ab-39SH_aFuc | 0.98 | 1260 | 2560 | 223 | 45 | 446 |
| Trastuzumab_Fuc | 5.1 | 1270 | 2650 | 2119 | 240 | 72.7 |
| Trastuzumab_aFuc | 0.65 | 1210 | 2190 | 305 | 60 | 134 |

Measurement of Equilibrium Binding Constants: Human Fc Gamma Receptors:

The binding constants ($K_D$) for the binding of anti-HER2 bispecific antibodies to human FcγRs were measured on a ProteOn XPR36 instrument. Briefly, the bispecific antibodies were immobilized at high density on a GLC sensor chip using a standard amino coupling chemistry as outlined by the instrument manufacturer. The final surface density of IgG measured approximately 3000 RU. A reference flow cell was also prepared on this sensor chip using the identical immobilization protocol minus protein. Stock solutions of each FcγR were prepared at either 4000 nM, 16,000 nM, or 32,000 nM in instrument buffer (phosphate buffered saline [PBS]/Tween/Ethylenediaminetetraaceticacid [EDTA] buffer containing 50 mM phosphate, pH 7.4, 0.15 M NaCl, 3 mM EDTA, and 0.005% Tween-20), and then serially diluted (1:3) in the same buffer to obtain the desired concentration series for each receptor: 1.82 nM-4,000 nM (FcγRI), 197.5 nM-16,000 nM (FcγRIIA), 395.1 nM-16,000 nM (FcγRIIb), 21.9 nM-16,000 nM (hFcgRIIIA-158V), and 395-32,000 mM (FcγRIIIA-158F). Each concentration of FcγR was injected over both the bispecific antibody and reference cell surfaces at a flow rate of 25 μL/min for 8 min, during which binding data were collected. Between injections, the surfaces were regenerated (i.e., bound FcγR was removed) with a 60-sec pulse of 5 mM HCl. Several buffer injections were also interspersed throughout the injection series. Later, one of these buffer injections along with the reference cell data was used to correct the binding data for any injection artifacts (e.g., nonspecific binding) through a technique commonly referred to as "double-referencing" (Myszka, 1999). After all binding data were collected, individual data sets were averaged for binding (Response at equilibrium [Req]) at each concentration (C), and then fit to a 1:1 binding isotherm (Req vs. C) plot. From this, the equilibrium binding constants, $K_D$, were derived using the vendor's evaluation software, version 3.1.0.6.

Measurement of Equilibrium Binding Constants: Human FcRn Protein:

The affinity ($K_D$) for the binding of the bispecific antibodies to human FcRn protein (huFcRn) was measured on a ProteOn XPR36 instrument. Briefly, bispecific antibodies were immobilized at high density on a GLC sensor chip using a standard amino coupling chemistry, as described above. A stock solutions of huFcRn protein was prepared at 3000 nM in instrument buffer (50 mM sodium phosphate buffer, pH 6, containing 150 mM NaCl, and 0.05% Tween-20), and then serially diluted (3:1) to 1.37 nM in the same buffer. Each concentration of huFcRn was sequentially injected over the bispecific antibody and reference cell surfaces, connected in series, at a flow rate of 25 μL/min for 16 min. Binding data were collected, followed by a 60-sec injection of 50 mM sodium phosphate buffer, pH 7.4, containing 150 mM NaCl, and 0.05% Tween 20 between injections of each receptor or buffer blank to regenerate the IgG surface (i.e., remove bound huFcRn protein). Several buffer injections were also interspersed throughout the injection series. Later, one of these buffer injections was used along with the reference cell data to correct the raw data sets for injection artifacts (e.g., nonspecific binding) through "double-referencing" (Myszka, 1999). After all binding data was collected, individual data sets were averaged for binding (Req) at each concentration (C), and then fit to a 1:1 binding isotherm (Req vs. C) plot. From this, the equilibrium binding constants, $K_D$, were derived using the vendor's BIAevaluation software, v. 4.1. Results show that the bispecific antibodies have similar $K_D$ values which are comparable to conventional IgG 1.

4.2. In Vitro Activity of Afucosylated Bispecific Antibody

Activity of afucosylated bispecific antibody in inhibiting ligand-driven cell proliferation was determined using method described in Example 1. Results show that afucosylated Bs2Ab-39SH, afucosylated Bs3Ab-39SH and afucosylated Bs4Ab-39SH have similar anti-proliferative potency in MDA-MB-361 cells (FIG. 30A) and MCF-7 cells (FIG. 30B), which is also comparable to the activity of parental antibody combination (39S plus trastuzumab). Similar results were observed in other cell lines including NCI-N87 and RT-112 (data not shown).

4.3. Enhanced ADCC Activity of Afucosylated Bispecific Antibody

KC1333, a human natural killer (NK) cell line expressing FcγRIIIa, was used as an effector cell and MDA-MB-361 cell line was used as a target cell in the ADCC assay to evaluate the ADCC activity of anti-HER2 antibodies. Both cell lines were harvested, washed and resuspended in assay medium. KC1333 were resuspended at a density of $1\times10^6$ cells/mL and MDA-MB-361 at $4\times10^5$ cells/mL. Fifty microliter of each cell line was added to the wells in a 96-well U-bottom plate to achieve target:effector ratio of 1:2.5. A 3× concentration of each dose of antibody was prepared by diluting the test articles in assay medium. Fifty microliter of each test article was added to cells in triplicate such that the final dose curve ranged from 10 μg/mL down to 0.15 ng/mL in a stepwise 1:4 serial dilution series. Plates were centrifuged to pellet cells in each well and then incubated overnight at 37° C./5% $CO_2$. The next day LDH in the supernatant of each well was quantified using Promega's CytoTox 96® Non-Radioactive Cytotoxicity Assay according to manufacturer's instructions. Data are analyzed using the GraphPad Prism software and presented as percent cytotoxicity relative to the untreated control.

FIGS. 31A through 31C show the ADCC activity of afucosylated bispecific antibodies relative to trastuzumab and afucosylated trastuzumab in MDA-MB-361 cells. Data suggest that the ADCC activity of afucosylated antibody is higher than its fucosylated version and the rank of ADCC potency among afucosylated bispecific antibodies is Bs2Ab-39SH_aFuc >Bs4Ab-39SH_aFuc >Bs3Ab-39SH_aFuc. Similar results were observed in other cell lines including BT-474, NCI-N87, MDA-MB-453, T47D, and JIMT-1 (data not shown).

Example 5

5.1. Tubulysin 1508 Payload Synthesis

Synthesis of tubulysin 1508 cytotoxin payload as shown in FIG. 32 for conjugation is detailed in the following illustrative example in which, unless stated otherwise:
(i) temperatures are given in degrees Celsius (° C.); when operations were carried out at room temperature or ambient temperature, that is, in a range of 18–25° C., unless otherwise stated;
(ii) solutions were dried over anhydrous sodium sulphate or magnesium sulphate; evaporation of organic solvent was carried out using a rotary evaporator under reduced pressure (4.5-30 mmHg) with a bath temperature of up to 30° C.;
(iii) chromatography means flash chromatography on silica gel; thin layer chromatography (TLC) was carried out on silica gel plates;

(iv) in general, the course of reactions was followed by TLC or liquid chromatography/mass spectroscopy (LC/MS) and reaction times are given for illustration only;
(v) final products have satisfactory proton nuclear magnetic resonance (NMR) spectra and/or mass spectra data;
(vi) yields are given for illustration only and are not necessarily those which can be obtained by diligent process development; preparations were repeated if more material was required;
(vii) when given, nuclear magnetic resonance (NMR) data is in the form of delta (δ) values for major diagnostic protons, given in part per million (ppm) relative to tetramethylsilane (TMS) as an internal standard, determined at 300 or 400 MHz in $d_6$-DMSO unless otherwise stated;
(viii) chemical symbols have their usual meanings;
(ix) solvent ratio is given in volume:volume (v/v) terms; and
(x) purification of the compounds was carried out using one or more of the following methods:
a) flash chromatography on regular silica gel;
b) flash chromatography on silica gel using Isco Combiflash® separation system: RediSep normal phase flash column, flow rate, 30-40 ml/min (ISCO MPLC); please add the ISCO reverse phase column
c) Gilson semiprep HPLC separation system: YMC pack ODS-AQ column, 100×20 mm, S 5 μm 12 nm, water (0.1% trifluoroacetic acid) and acetonitrile (0.1% trifluoroacetic acid) as solvents, 20 min run;

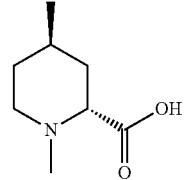

Compound T1

To a solution of (2R,4R)-4-methylpiperidine-2-carboxylic acid (2 g, 13.97 mmol) in MeOH (40 mL) and water (40.0 mL) was added paraformaldehyde (2.52 g, 27.94 mmol) and Pd/C (10%) (0.8 g, 7.52 mmol). The reaction mixture was stirred under a hydrogen atmosphere at room temperature overnight. From TLC, the reaction was not completed. Another one equivalent of paraformaldehyde (2.52 g, 27.94 mmol) was added and the reaction mixture was stirred another 24 hours. TLC indicated the reaction was completed and reaction mixture was filtered, washed the catalyst with MeOH (2×30 mL). The filtrate was concentrated in vacuo to give crude product as a white solid, which was washed with ether (3×30 mL), dried in high vacuum overnight to yield (2R,4R)-1,4-dimethylpiperidine-2-carboxylic acid (T1) (1.870 g, 85%) as a white solid. LC-MS: 158 (M+1); 1H NMR (400 MHz, DEUTERIUM OXIDE) δ ppm 0.97 (d, J=5.52 Hz, 3 H), 1.54 (br. s, 1H), 1.71-1.87 (m, 3H), 1.91-2.07 (m, 1H), 2.84 (s, 3H), 3.13 (td, J=8.41, 3.76 Hz, 1H), 3.35 (m, 1H), 3.65 (m, 1H).

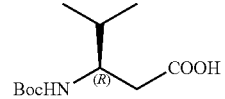

Compound T2

Di-tert-Butyl dicarbonate (243.0 g, 1.1 mol) was added dropwise to a suspension of (R)-3-amino-4-methyl pentanoic acid (commercially available) (133.0 g, 1.0 mol) and Na$_2$CO$_3$ (212 g, 2.0 mol) in acetone (1 L) and water (1 L) with stirring at room temperature. The reaction mixture was stirred overnight and the organic solvent was removed under reduced pressure. The residue was diluted with water (1 L) and washed with EtOAc (500 mL×3). The aqueous phase was acidified with 2N HCl solution to pH=3 and the resulting mixture was extracted with EtOAc (800 mL×3). The combined extracts were washed with brine (800 mL×1), dried (anhydrous Na2SO4) and concentrated to give compound (T2) (224.0 g, 97% yield) as an oil, which was used in the next step without further purification.

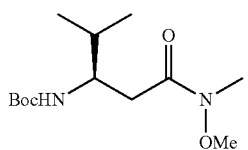

Compound T3

Triethylamine (67 g, 0.61 mol) was added to a suspension of compound (T2) (140.0 g, 0.61 mol) and N,O-dimethylhydroxylamine hydrochloride (74.1 g, 0.76 mol) in CH$_2$Cl$_2$ (1.4 L) with stirring at 0° C. The suspension was stirred for 0.5 hour and EDCI (74 g, 0.61 mol) was added in portions at 0° C. The reaction mixture was stirred for 2 hours at 0° C. and water (800 mL) was added. The organic phase was separated, washed with 5% KHSO4 solution (800 mL×3), saturated NaHCO$_3$ solution (800 mL×3) and brine (800 mL×1), was dried (anhydrous Na$_2$SO$_4$) and concentrated to dryness. The residue was purified by flash column chromatography on silica gel (EtOAc/Hexane=1:5) to afford compound (T3) (141.0 g, 84% yield) as an oil. 1H NMR (300 MHz, CDCl3): δ 5.26 (m, 1H), 3.75 (m, 1H), 3.70 (s, 3H), 3.15 (s, 3H), 2.60-2.80 (m, 2H), 1.85 (m, 1H), 1.41 (s, 9H), 0.90 (d, J=6.6 Hz, 3H), 0.88 (d, J=6.6 Hz, 3H).

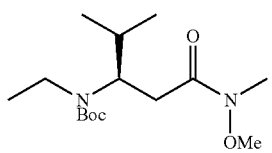

Compound T4

Iodoethane (250.0 g, 1.6 mol) was added to a solution of compound (T3) (55.0 g, 0.2 mol) in DMF (1.1 L) with stirring at 0° C. Then NaH (60% suspension, 24.0 g, 0.60 mol) was added in portions at 0° C. and the reaction mixture was allowed to warm to room temperature and stirred for 12 hours. The reaction was quenched with water (2 L) carefully and EtOAc (2 L) was added. The organic phase was separated, washed with 5% KHSO4 solution (800 mL×3), saturated NaHCO$_3$ solution (800 mL×3) and brine (800 mL×1), dried (anhydrous Na$_2$SO$_4$) and concentrated to dryness. The residue was purified by flash column chromatography on silica gel (EtOAc/Hexane=1:10) to afford compound (T4) (35.1 g, 58% yield) as an oil. 1H NMR (300 MHz, CDCl$_3$): δ 3.70 (s, 3H), 3.65 (m, 1H), 3.10-3.30 (m, 5H), 2.50-2.95 (m, 2H), 1.90-2.20 (m, 1H), 1.40-0.55 (m, 9H), 1.10 (t, J=7.2 Hz, 3H), 0.90 (d, J=6.6 Hz, 3H), 0.88 (d, J=6.6 Hz, 3H).

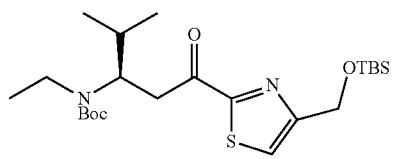

Compound T5

A solution of n-BuLi (106 ml, 2.5N in hexane, 0.17 mol) was added dropwise to a solution of 2-bromo-4-((tert-butyldimethylsilyloxy)methyl)thiazole (74 g, 0.24 mol) (prepared as described in Wipf, P et al Org. Lett. 2007, 9(8), p. 1605) in dry THF (500 mL) at −78° C. under N2 with stirring over 1 hour. The suspension was stirred for further 30 min and then a solution of compound (T4) (51.0 g, 0.17 mol) in dry THF (300 mL) was added dropwise over 30 min at −78° C. The reaction mixture was stirred for 1 hour at −78° C. and then allowed to warm to room temperature and stirred for 12 hours. The reaction was quenched with 20% aqueous ammonium chloride solution (1 L) and the organic solvent was removed under reduced pressure. The resulting mixture was extracted with EtOAc (800 mL×3). The combined organic phases were washed with 5% KHSO4 solution (800 mL×3), saturated NaHCO$_3$ solution (800 mL×3) and brine (800 mL×1), dried (Na$_2$SO$_4$) and concentrated to dryness. The crude material was purified by flash column chromatography on silica gel (EtOAc/Hexane=1:10) to afford compound (T5) (58.1 g, 73% yield) as an oil. 1H NMR (300 MHz, CDCl$_3$): δ 7.53 (m, 1H), 4.90 (s, 2H), 4.04 (m, 1H), 3.35 (m, 2H), 3.15 (m, 2H), 2.00 (m, 1H), 1.40 (s, 9H), 0.80-1.20 (m, 18H), 0.14 (s, 6H).

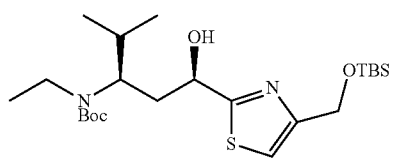

Compound T6

LiBH$_4$ (4.8 g, 0.22 mol) was added in portions to a solution of compound (T5) (47.1 g, 0.1 mol) in methanol (500 mL) at room temperature over a period of 0.5 hour with stirring. The suspension was stirred for 2 hours and the solvent was removed under reduced pressure. The residue was dissolved in EtOAc (800 mL) and the resulting solution was washed with saturated NaHCO$_3$ solution (500 mL×3) and brine (500 mL×1), dried (Na$_2$SO$_4$) and concentrated to dryness. The crude material was purified by flash column chromatography (EtOAc/Hexane=1:6) to afford compound (T6) (13.5 g, 28% yield) and its isomer (T6') (21.0 g, 45% yield). $^1$H NMR (300 MHz, CHLOROFORM-d) δ ppm −0.06-0.05 (m, 6H) 0.76-0.89 (m, 15H) 1.12 (t, J=6.97 Hz, 3H) 1.39 (s, 9H) 1.55-2.05 (m, 3H) 2.86-3.21 (m, 2H) 3.76-3.96 (m, 1H) 4.73 (d, J=1.13 Hz, 4H) 7.01 (s, 1H).

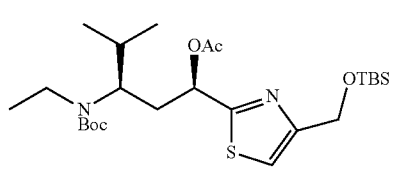

Compound T7

Acetyl chloride (45.2 g, 0.58 mol) was added dropwise to a solution of compound (T6) (34.0 g, 72 mmol) in pyridine (500 mL) at 0° C. with stirring over 10 min. The reaction mixture was allowed to warm to room temperature and stirred for 12 hours. The reaction was quenched with water (200 mL) and the solvent was removed under reduced pressure. The residue was treated with $CH_2Cl_2$ (800 mL) and the resulting mixture was washed with 5% $KHSO_4$ solution (800 mL×3), saturated $NaHCO_3$ solution (800 mL×3) and brine (800 mL×1), dried ($Na_2SO_4$) and concentrated to dryness. The crude material was purified by flash column chromatography on silica gel (EtOAc/Hexane=1:10) to afford compound (T7) (25.7 g, 69% yield) as an oil. $^1$H NMR (300 MHz, $CDCl_3$): δ 7.15 (m, 1H), 5.95 (m, 1H), 4.84 (s, 2H), 4.04 (m, 1H), 3.10 (m, 2H), 2.35 (m, 1H), 2.15 (s, 3H), 2.00 (m, 1H), 1.70 (m, 1H), 1.45 (s, 9H), 1.25 (t, J=7.2 Hz, 3H), 0.80-1.10 (m, 15H), 0.08 (s, 6H).

Compound T8

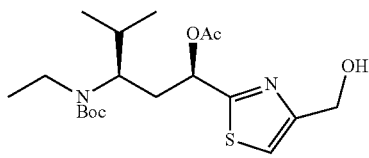

A solution of tetrabutylammonium fluoride (65.3 g, 0.25 mol) in THF (200 mL) was added dropwise to a solution of compound (7) (25.7 g, 50 mmol) in THF (300 mL) at 0° C. with stirring. The reaction mixture was allowed to warm to room temperature and stirred for 4 hours. Water (800 mL) was added and the organic solvent was removed under reduced pressure. The residue was treated with $CH_2Cl_2$ (800 mL) and the resulting mixture was washed with 5% $KHSO_4$ solution (800 mL×3), saturated $NaHCO_3$ solution (800 mL×3) and brine (800 mL×1), dried (Na2SO4) and concentrated to dryness. The crude material was purified by flash column chromatography on silica gel (EtOAc/Hexane=1:4) to afford compound (T8) (19.5 g, 98% yield) as an oil. 1H NMR (300 MHz, CDCl3): δ 8.26 (m, 1H), 5.95 (m, 1H), 4.83 (m, 2H), 4.10 (m, 1H), 3.17 (m, 2H), 2.40 (m, 1H), 2.20 (s, 3H), 2.18 (m, 1H), 1.75 (m, 1H), 1.56 (s, 9H), 1.10-1.30 (m, 3H), 0.80-1.05 (m, 6H).

Compound T9

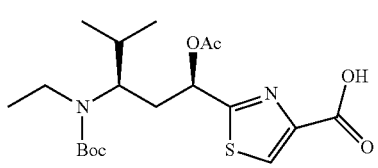

Dess-Martin reagent (32.7 g, 75 mmol) was added to a solution of compound (T8) (20.0 g, 50 mmol) in dichloromethane (300 mL) and the reaction mixture was stirred at room temperature for 12 hours. The mixture was washed with sodium hydroxide solution (1N, 300 mL×3), sodium thiosulfate solution (1N, 300 mL×3), saturated $NaHCO_3$ (300 mL×3) solution and brine (300 mL×1), respectively. The organic layer was dried ($Na_2SO_4$) and concentrated to dryness to give the corresponding aldehyde.

This crude aldehyde was dissolved in tert-butyl alcohol (500 mL) and a solution of sodium chlorite (80%, 36.4 g, 320 mmol) and sodium dihydrogenphosphate monohydrate (105 g, 0.77 mol) in water (300 mL) was added dropwise over 1 hour at room temperature. The reaction mixture was stirred for 3 hours and diluted with hydrochloric acid solution (0.1N, 500 mL). The resulting mixture was extracted with EtOAc (500 mL×1) and the combined organic layers were washed with 5% $KHSO_4$ solution (500 mL×3) and brine (500 mL×1), dried over $Na_2SO_4$ and concentrated to dryness. The residue was purified by flash column chromatography on silica gel ($CH_2Cl_2$/MeOH=100:5) to afford compound (T9) (15.4 g, 58% yield). $^1$H NMR (300 MHz, $CDCl_3$): δ 9.90 (br s, 1H), 8.27 (s, 1H), 5.96 (m, 1H), 4.07 (m, 1H), 3.15 (m, 1H), 2.35 (m, 1H), 2.20 (s, 3H), 2.18 (m, 1H), 1.75 (m, 1H), 1.45 (s, 9H), 1.20 (t, J=7.2 Hz, 3H), 0.98 (d, J=6.6 Hz, 3H), 0.88 (d, J=6.6 Hz, 3H).

Compound T10

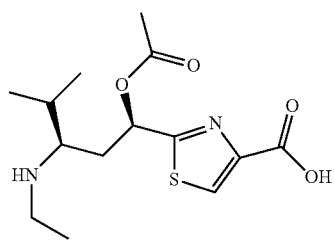

To a solution of 2-((1R,3R)-1-acetoxy-3-((tert-butoxycarbonyl)(ethyl)amino)-4-methylpentyl)thiazole-4-carboxylic acid (T9) (6.5 g, 15.68 mmol) in DCM (60 mL) was added TFA (30 mL) in dropwise at 0° C. The mixture was stirred at 0° C. for 1 hour. The solvent was evaporated in vacuo to give crude product (T10). The crude product was used to next step reaction without further purification (7.2 grams). LC-MS: 315 (M+1).

Compound T11

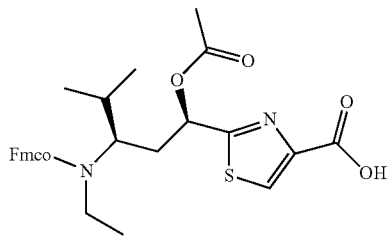

To the solution of 2-((1R,3R)-1-acetoxy-3-(ethylamino)-4-methylpentyl)thiazole-4-carboxylic acid 4, Trifluoroacetic acid salt (T10) (5 g, 11.67 mmol) and sodium bicarbonate (9.80 g, 116.71 mmol) in a mixture of acetone (300 mL) and water (150 mL) was added (9H-fluoren-9-yl)methyl (2,5-dioxopyrrolidin-1-yl) carbonate (3.94 g, 11.67 mmol). The mixture was stirred at room temperature overnight. LCMS indicated the reaction was completed. The mixture was acidified to (pH 2) with hydrochloric acid and acetone was evaporated in vacuo. The product was extracted with DCM (3×300 mL). The combined organic extracts were washed with 0.1% HCl solution (200 mL), brine (200 mL), dried over $Na_2SO_4$, and evaporated in vacuo. The residue was purified by flash chromatography (silica gel, MeOH/DCM, MeOH from 0% to 5%) to give 2-((1R,3R)-3-((((9H-fluoren-9-yl)methoxy)carbonyl)(ethyl)amino)-1-acetoxy-4-methylpentyl)thiazole-4-carboxylic acid (T11) (3.53 g, 54.6%) as a white solid. LC-MS: 537.2 (M+1); $^1$H NMR (400 MHz, CHLOROFORM-d) δ ppm 0.84 (d, J=6.78 Hz, 3H), 0.92-1.05 (m, 5H), 1.14 (d, J=3.01 Hz, 1H), 1.73 (dt, J=10.23, 6.43 Hz, 1H), 1.92-2.05 (m, 1H), 2.12-2.27 (m, 4H), 2.28-2.44 (m, 1H), 2.90-3.33 (m, 2H), 3.98 (t, J=9.29 Hz, 1H), 4.12-4.32 (m, 1H), 4.47-4.82 (m, 2H), 5.95 (dd, J=10.92, 2.89 Hz, 1H), 7.29-7.45 (m, 4H), 7.55-7.69 (m, 2H), 7.72-7.81 (m, 2H), 8.22-8.29 (m, 1H).

Compound T12

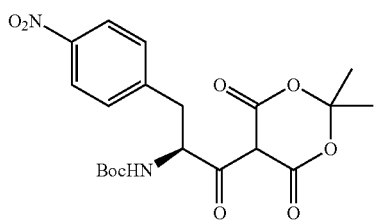

DMAP (106 g, 0.86 mol) was added to a solution of Boc-L-4-nitro-Phenylalanine (1800 g, 0.58 mol) and Meldrum's acid (92 g, 0.64 mol) in dichloromethane (1.5 L). The resulting solution was cooled at −5° C. under N2 atmosphere, followed by addition of DCC (240 g, 1.16 mol) in dichloromethane (1 L) over 1 h. The mixture was stirred overnight at 0-5° C. Then the precipitated N,N'-dicyclohexylurea was removed by filtration and the filtrate was washed with 5% aqueous HCl (1 L×3), and brine (1 L×1), and was dried over MgSO4. After removal of MgSO4 by filtration, the organic phase was concentrated to dryness. The residue was triturated with EtOAc/hexane (1:1, 500 mL), and was dried to afford compound (T12) (130.0 g, 51% yield) as a yellow solid.

Compound T13

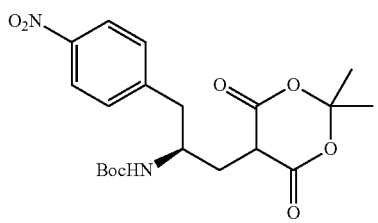

AcOH (400 mL) was added to a solution of compound (T12) (130.0 g, 0.298 mol) in dichloromethane (1.5 L) at −5° C. under N2. Solid NaBH4 (22.7 g, 0.597 mol) was added in small portions over 2 hours (gas evolution and exothermic). After stirring for additional 3 h at −5° C., TLC indicated the reaction was complete. The mixture was quenched with brine (1 L). The organic layer was separated, and washed sequentially with water (1 L×2), aqueous saturated NaHCO3 (1 L×3) and brine (1 L×3), and was dried over MgSO4. The filtrate was concentrated to dryness and afford compound (T13) (70.3 g, 55% yield) as a yellow solid. 1H NMR (300 MHz, CDCl3): δ 8.18 (d, J=8.7 Hz, 2H), 7.41 (d, J=8.7 Hz, 2H), 4.58 (m, 1H), 4.29 (m, 1H), 3.85 (m, 1H), 2.97 (d, J=6.6 Hz, 2H), 2.27 (m, 2H), 1.80 (s, 3H), 1.76 (s, 3H), 1.35 (s, 9H).

Compound T14

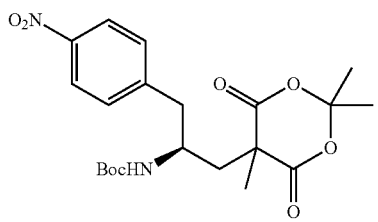

K2CO3 (35 g, 0.25 mol) and MeI (36 g, 0.25 mol) were added to a solution of compound (T13) (70.3 g, 0.167 mol) in acetone (400 mL) and DMF (400 mL). The mixture was stirred overnight at room temperature. TLC showed the starting material was consumed. Water (2 L) was added and the mixture was stirred for an additional hour. The precipitated solid was collected by filtration, was washed with water, was dried to afford compound (T14) (34.5 g, 47% yield) as a pale yellow solid. 1H NMR (300 MHz, CDCl3): δ 8.17 (d, J=8.7 Hz, 2H), 7.34 (d, J=8.7 Hz, 2H), 4.22 (m, 1H), 3.85 (m, 1H), 2.85 (m, 2H), 2.22 (m, 2H), 1.73 (s, 3H), 1.73 (s, 3H), 1.52 (s, 3H), 1.31 (s, 9H).

Compound T15

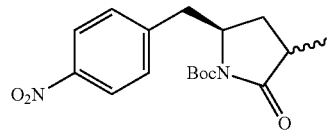

Compound (T14) (34.5 g, 79.1 mmol) was dissolved in toluene (500 mL). The solution was heated under reflux for 40 hours. TLC indicated the reaction complete. The solvent was removed to afford compound (T15) (30 g), which was used for next step without further purification.

Compound T16

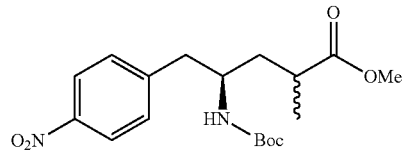

K2CO3 (22 g, 0.16 mol) was added to a solution of compound (T15) (30 g, 79 mmol) in MeOH (300 mL). The mixture was stirred for 3 hours at room temperature. TLC showed complete conversion. The solvent was removed, the residue was dissolved in dichloromethane (500 mL), washed with brine (500 mL×3), dried over MgSO4. After removal of MgSO4 by filtration, the organic phase was concentrated to dryness. The residue was further purified by silica gel chromatography (EtOAc/Hexane=1:10) and afforded compound (T16) (23.5 g, 81% yield for two steps) as 1:1 diastereomeric mixture. 1H NMR (300 MHz, CDCl3): δ 8.13 (d, J=8.7 Hz, 2H), 7.34 (d, J=8.7 Hz, 2H), 4.43 (m, 1H), 3.85 (m, 1H), 3.65 (s, 3H), 2.85 (m, 2H), 2.65 (m, 1H), 1.85 (m, 1H), 1.50 (m, 1H), 1.30 (s, 9H), 1.15 (t, J=6.6 Hz, 3H).

Compound T17

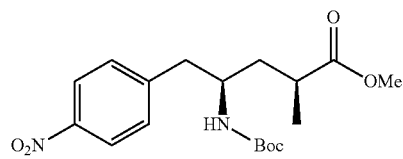

50 g of compound (T16) was subjected to chiral chromatography using SFC (supercritical fluid chromatography) on a Chiralpak ID 21×250 mm, 5µ column using mobile phase A 90% carbon dioxide and phase B isopropanol 10% at a 60 ml/min flow rate. The separation was performed at 40° C.

and detection at 270 nM. Baseline separation was achieved and two fractions were isolated. Peak B was desired compound (T17) and was obtained as a solid 27.4 g (55%).

>99:1 diastereomeric excess on a Chiralpak IA column 4.6×250 mm, 5μ, 10% 1:1 Methanol:Isopropanol in hexane with 0.1% diethylamine modifier.

LC/MS (2 minute, Acid_CV10.olp method 367 (M+1), 1.16 minutes.

$^1$H NMR (400 MHz, METHANOL-$d_4$) δ ppm 8.16 (d, J=8.53 Hz, 2H) 7.46 (d, J=8.53 Hz, 2H) 3.79-3.93 (m, 1H) 3.68 (s, 3H) 2.90-2.99 (m, 1H) 2.71-2.81 (m, 1H) 2.47-2.59 (m, 1H) 1.81-1.95 (m, 1H) 1.55-1.66 (m, 1H) 1.32 (s, 9H) 1.21-1.25 (m, 2H) 1.16 (d, J=7.03 Hz, 3H).

Compound T18

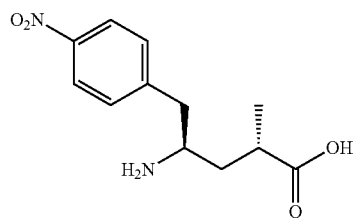

A solution of (2S,4R)-methyl 4-((tert-butoxycarbonyl)amino)-2-methyl-5-(4-nitrophenyl)pentanoate (T17) (3.5 g, 9.55 mmol) in 6N HCl aqueous solution (8.0 mL, 263.30 mmol) was heated at 130° C. in microwave for 30 min. The reaction mixture was lyophilized to afford (2S,4R)-4-amino-2-methyl-5-(4-nitrophenyl)pentanoic acid (T18) as a solid. The product was used in the next step reaction without further purification. (3.2 g). LC-MS: 253 (M+1); $^1$H NMR (400 MHz, DEUTERIUM OXIDE) δ ppm 1.12 (d, J=7.28 Hz, 3H), 1.62-1.76 (m, 1H), 1.90-2.02 (m, 1H), 2.56-2.68 (m, 1H), 3.02-3.11 (m, 2H), 3.58-3.69 (m, 1H), 7.47 (d, J=8.53 Hz, 2H), 8.18 (d, J=8.78 Hz, 2H).

Compound T19

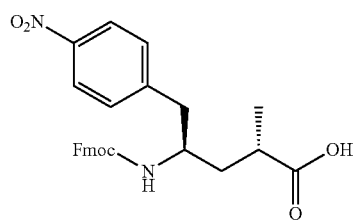

To the solution of compound (T18) (0.43 g, 1.49 mmol) and sodium bicarbonate (1.251 g, 14.89 mmol) in a mixture of acetone (30 mL) and water (15 mL) was added (9H-fluoren-9-yl)methyl 2,5-dioxopyrrolidin-1-yl carbonate (0.502 g, 1.49 mmol). The mixture was stirred at room temperature for overnight. LCMS indicated the reaction was completed. The mixture was acidified to pH 2 with hydrochloric acid and acetone was evaporated in vacuo. The product was extracted with DCM (3×60 mL). The combined organic extracts were washed with 1N HCl solution (40 mL), brine (40 mL), dried over $Na_2SO_4$, and evaporated in vacuo. The residue was purified by silica gel flash chromatography, EtOAc from 0% to 100% in DCM, to give (2S,4R)-4-(((9H-fluoren-9-yl)methoxy)carbonylamino)-2-methyl-5-(4-nitrophenyl)pentanoic acid (0.630 g, 89%) (T19) as a white solid. LC-MS: 475.5 (M+H); $^1$H NMR (400 MHz, CHLOROFORM-d) δ ppm 0.81-1.06 (m, 1H), 1.08-1.28 (m, 2H), 1.33-1.75 (m, 1H), 1.77-2.11 (m, 1H), 2.36-2.69 (m, 2H), 2.76-3.18 (m, 1H), 3.43-4.08 (m, 1H), 4.09-4.19 (m, 1H), 4.21-4.53 (m, 2H), 4.54-4.80 (m, 1H), 7.18-7.58 (m, 8H), 7.66-7.82 (m, 2H), 7.95-8.17 (m, 2H), 8.67 (br. s., 1H).

Compound T20

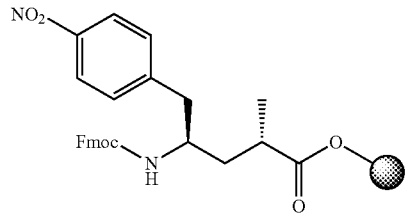

DIEA (0.419 mL, 2.40 mmol) was added to a solution of (2S,4R)-4-(((9H-fluoren-9-yl)methoxy)carbonylamino)-2-methyl-5-(4-nitrophenyl)pentanoic acid (0.380 g, 0.80 mmol) (T19) in DCM (4.5 mL), and the mixture was stirred at room temperature for 5 min, then 2-Chlorotrityl chloride resin (0.5 g, 0.80 mmol) was added to the mixture. The mixture was shaken at room temperature overnight, the resulting resin was washed with DMF (3×6 mL), MeOH (3×6 mL), and DCM (3×6 mL), then treated with DIEA (0.419 mL, 2.40 mmol) and MeOH/DCM (1:1, 5 mL) at room temperature for 30 min. Resulting resin was filtered, washed with DMF (3×6 mL), MeOH (3×6 mL), and DCM (3×6 mL), dried in high vacuum overnight. Small amount of compound was cleaved from resin, and analyzed by LCMS. The resulting resin (T20) was used for next step reaction. LC-MS: 475 (M+1)

Compound T21

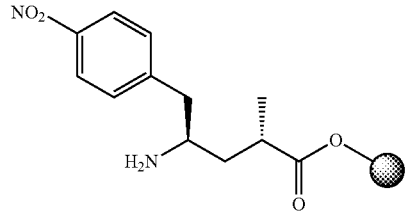

To the resin (T20) (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LCMS, which indicated the reaction was completed. The resulting resin (T21) was used for the next step reaction. LC-MS: 253 (M+H).

Compound T22

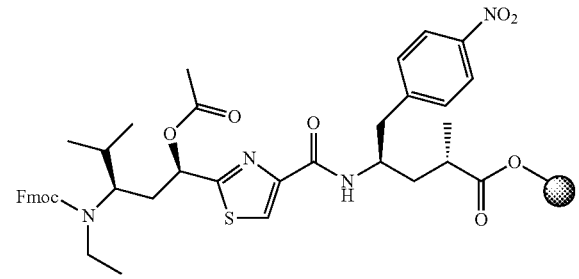

To the resin (T21) (0.5 g, 1.88 mmol) was added a solution of 2-((1R,3R)-3-((((9H-fluoren-9-yl)methoxy)carbonyl)(ethyl)amino)-1-acetoxy-4-methylpentyl)thiazole-4-carboxylic acid (3) (1.108 g, 2.07 mmol), HATU (1.428 g, 3.76 mmol), 2,4,6-trimethylpyridine (0.500 mL, 3.76 mmol), and DIEA (0.656 mL, 3.76 mmol) in DMF (5 mL) at room temperature. The mixture was shaken at room temperature for two hours, and the resulting resin was filtered, washed with DMF (3×6 mL), MeOH (3×6 mL), and DCM (3×6 mL), dried in vacuo. Small amount of the compound was cleaved from resin, analyzed by LCMS, which indicated the reaction was completed. The resulting resin (T22) was used for the next step. LC-MS: 771 (M+H).

Compound T23

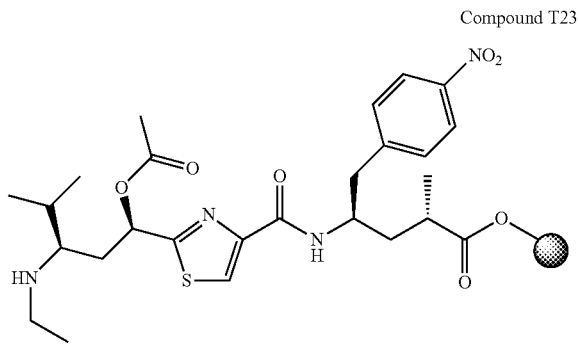 [SMILES: CCN[C@H](C[C@@H](OC(C)=O)c1nc(C(=O)N[C@@H](Cc2ccc([N+](=O)[O-])cc2)C[C@H](C)C(=O)OC)cs1)C(C)C]

To the resin (T22) (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LCMS, which indicated the reaction was completed. The resulting resin (T23) was used in the next reaction step. LC-MS: 549 (M+1).

Compound T24

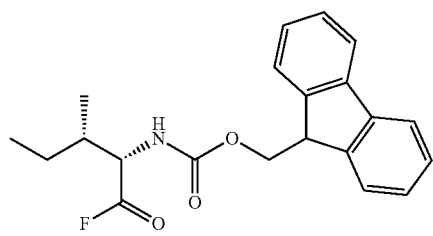

To a solution of (2S,3S)-2-(((9H-fluoren-9-yl)methoxy)carbonylamino)-3-methylpentanoic acid (Fmoc-Isoleucine) (7 g, 19.81 mmol) and pyridine (1.602 mL, 19.81 mmol) in DCM (120 mL) was added via cannula a solution of DAST (3.11 mL, 23.77 mmol) in DCM (20 mL) over 10 min. The reaction mixture was stirred at room temperature for 1 hour, diluted with DCM (80 mL), washed with ice-cold water (2×200 mL), the organic layer was dried over MgSO4, filtered, and evaporated in vacuo to give (9H-fluoren-9-yl)methyl (2S,3S)-1-fluoro-3-methyl-1-oxopentan-2-ylcarbamate (6.65 g, 94%) as a white solid. An esterification test was performed to assure quantitative acid fluoride formation by dissolving Fmoc-Ile-F (5 mg) in anhydrous MeOH (0.3 mL) and DIEA (0.030 mL) and allowing to react at room temperature for 15 min. The mixture was then evaporated in vacuo and analyzed by LCMS, showed less than 1% of Fmoc-Ile-OH present.

$^1$H NMR (400 MHz, CHLOROFORM-d) δ ppm 0.83-1.12 (m, 6H) 1.18-1.37 (m, 1H) 1.42-1.59 (m, 1H) 2.01 (br. s., 1H) 4.26 (t, J=6.78 Hz, 1H) 4.44-4.63 (m, 3H) 5.20 (d, J=8.53 Hz, 1H) 7.31-7.39 (m, 2H) 7.40-7.47 (m, 2H) 7.61 (d, J=7.28 Hz, 2H) 7.80 (d, J=7.53 Hz, 2H).

Compound T25

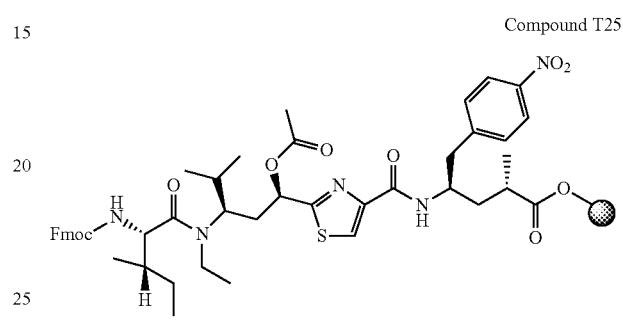

To the resin (T23) (0.5 g, 0.80 mmol) was added a solution of (9H-fluoren-9-yl)methyl (2S,3S)-1-fluoro-3-methyl-1-oxopentan-2-ylcarbamate (T24) (0.569 g, 1.60 mmol), DMAP (4.89 mg, 0.04 mmol), and DIEA (0.419 mL, 2.40 mmol) in DCM (5 mL) at room temperature. The mixture was shaken at room temperature for overnight, the resulting resin was filtered, washed with DMF (3×6 mL), MeOH (3×6 mL), DCM (3×6 mL), dried in high vacuum. Small amount of compound was cleaved from resin, and analyzed by LC/MS, LCMS indicated the reaction was completed. The resulting resin (T25) was used in the next reaction step. LC-MS: 884 (M+H).

Compound T26

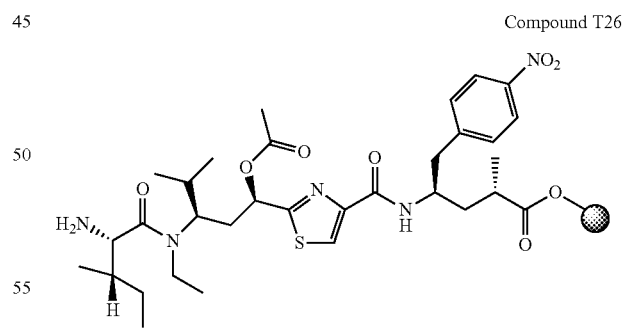

To the resin (T25) (0.5 g, 0.80 mmol) was added 20% piperidine in DMF (5 mL). The mixture was shaken at room temperature for 6 min, the resulting resin was filtered, washed with DMF (3×6 mL), MeOH (3×6 mL), DCM (3×6 mL), dried in vacuo. Small amount of the compound was cleaved from resin, analyzed by LCMS, which indicated the reaction was completed. The resulting resin (T26) was used in the next reaction step. LC-MS: 662 (M+1).

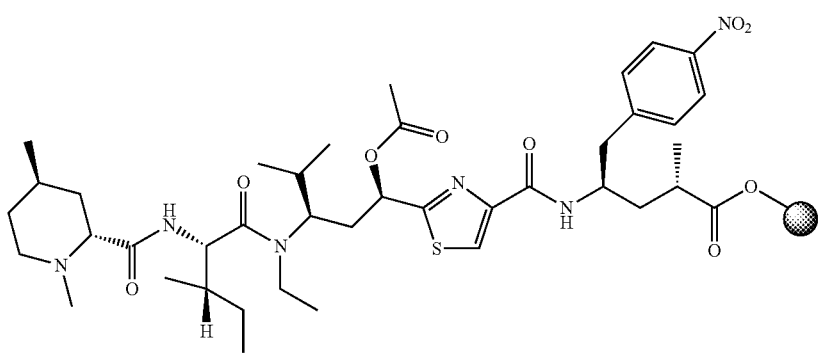

Compound T27

To the resin (T26) (0.5 g, 0.80 mmol) was added a solution of (2R,4R)-1,4-dimethylpiperidine-2-carboxylic acid (1) (0.252 g, 1.60 mmol), HATU (0.608 g, 1.60 mmol), 2,4,6-trimethylpyridine (0.320 mL, 2.40 mmol), and DIEA (0.419 mL, 2.40 mmol) in DMF (5 mL). The mixture was shaken at room temperature for 2 hours, the resulting resin was filtered, washed with DMF (3×6 mL), MeOH (3×6 mL), and DCM (3×6 mL), dried in vacuo. Small amount of the compound was cleaved from resin, analyzed by LCMS, which indicated the reaction was completed. The resulting resin (T27) was used in the next reaction step. LC-MS: 801 (M+1).

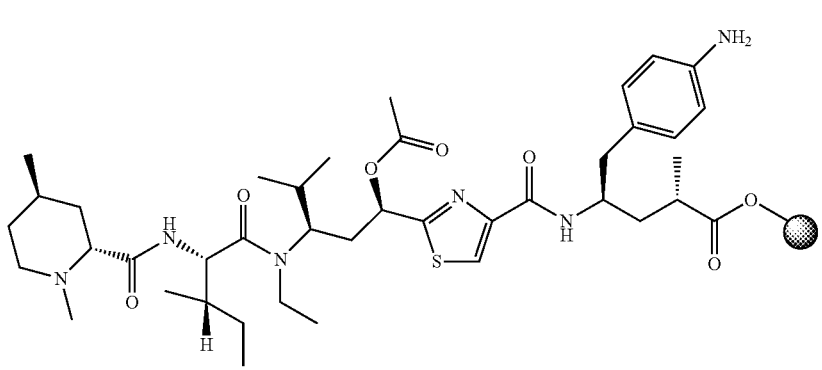

Compound T28

To the resin (T27) was added a solution of tin(II) chloride dehydrate (1.805 g, 8.00 mmol), and sodium acetate (0.197 g, 2.40 mmol) in DMF (5 mL). The mixture was shaken at room temperature for 4 hours, the resulting resin was filtered, washed with DMF (3×6 mL), MeOH (3×6 mL), and DCM (3×6 mL), and dried in vacuo. Small amount of the compound was cleaved from resin, analyzed by LCMS, which indicated the reaction was completed. The resulting resin (T28) was used for the next step. LC-MS: 771 (M+H).

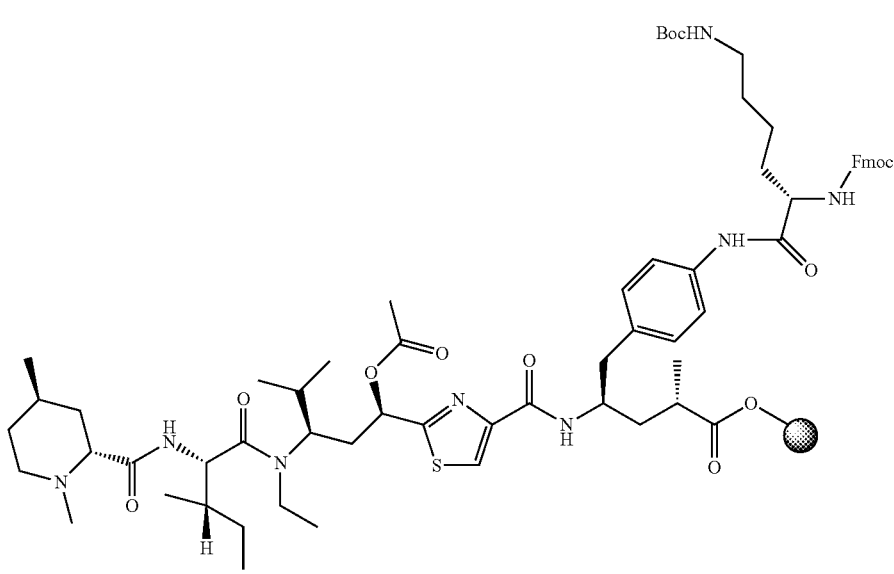

Compound T29

To the resin (T28) (0.2 g, 0.32 mmol) was added a solution of (S)-2-(((9H-fluoren-9-yl)methoxy)carbonylamino)-6-(tert-butoxycarbonylamino)hexanoic acid (commercially available) (0.300 g, 0.64 mmol), HATU (0.243 g, 0.64 mmol), 2,4,6-trimethylpyridine (0.128 mL, 0.96 mmol), and DIEA (0.168 mL, 0.96 mmol) in DMF (4 mL). The mixture was shaken at room temperature for 2 hours, the resulting resin was filtered, washed with DMF (3×2 mL), MeOH (3×2 mL), and DCM (3×2 mL), and dried in vacuo. Small amount of the compound was cleaved from resin, analyzed by LCMS, which indicated the reaction was completed. The resulting resin (T29) was used to next step reaction. LC-MS: 1221 (M+1).

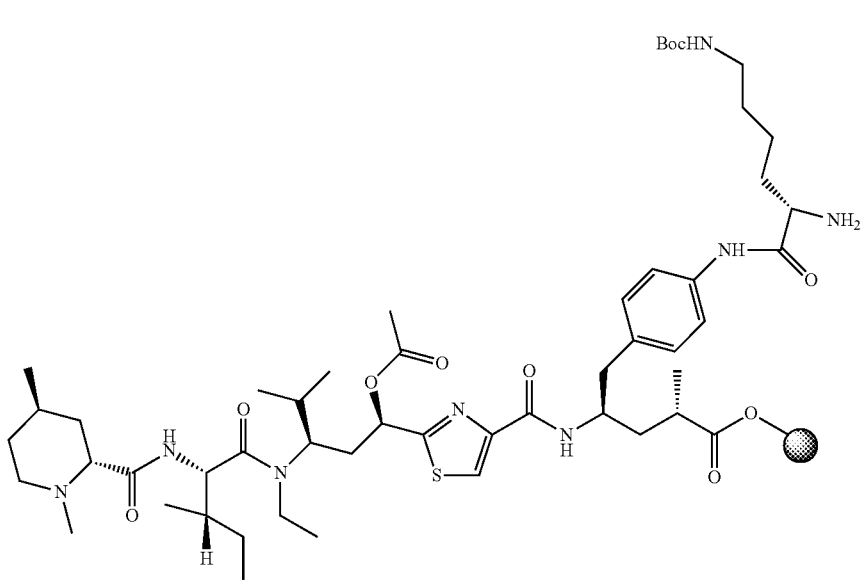

Compound T30

To the resin (T29) (0.2 g, 0.32 mmol) was added 20% piperidine in DMF (2 mL). The mixture was shaken at room temperature for 6 min, the resulting resin was filtered, washed with DMF (3×3 mL), MeOH (3×3 mL), DCM (3×3 mL), dried in vacuo. Small amount of the compound was cleaved from resin, analyzed by LCMS, which indicated the reaction was completed. The resulting resin (T30) was used to next step reaction. LC/MS: 999 (M+H).

Compound T31

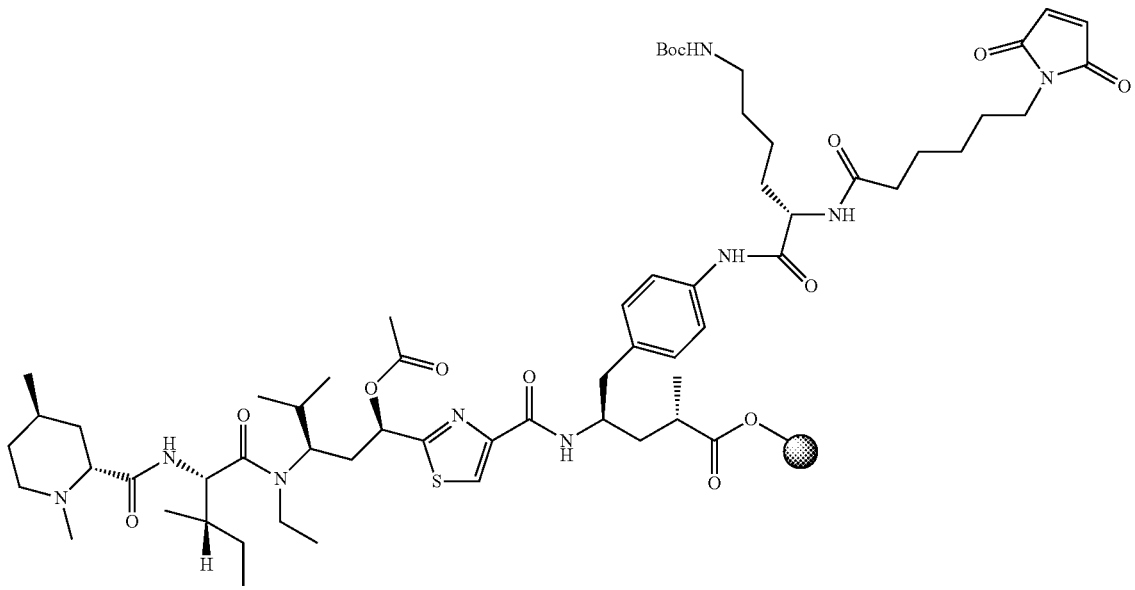

To the resin (T30) (0.2 g, 0.32 mmol) was added a solution of 2,5-dioxopyrrolidin-1-yl 6-(2,5-dioxo-2,5-dihydro-1H-pyrrol-1-yl)hexanoate (0.148 g, 0.48 mmol) in DMF (2 mL), followed by N-METHYLMORPHOLINE (0.106 mL, 0.96 mmol) at room temperature. The mixture was shaken at room temperature for 2 hours, the resulting resin was filtered, washed with DMF (3×3 mL), DCM (3×3 mL), dried in vacuo. Small amount of the compound was cleaved from resin, analyzed by LCMS, which indicated the reaction was completed. The resulting resin (T31) was used for the next step. LC-MS: 1192 (M+1).

Compound T32 (tubulysin 1508)

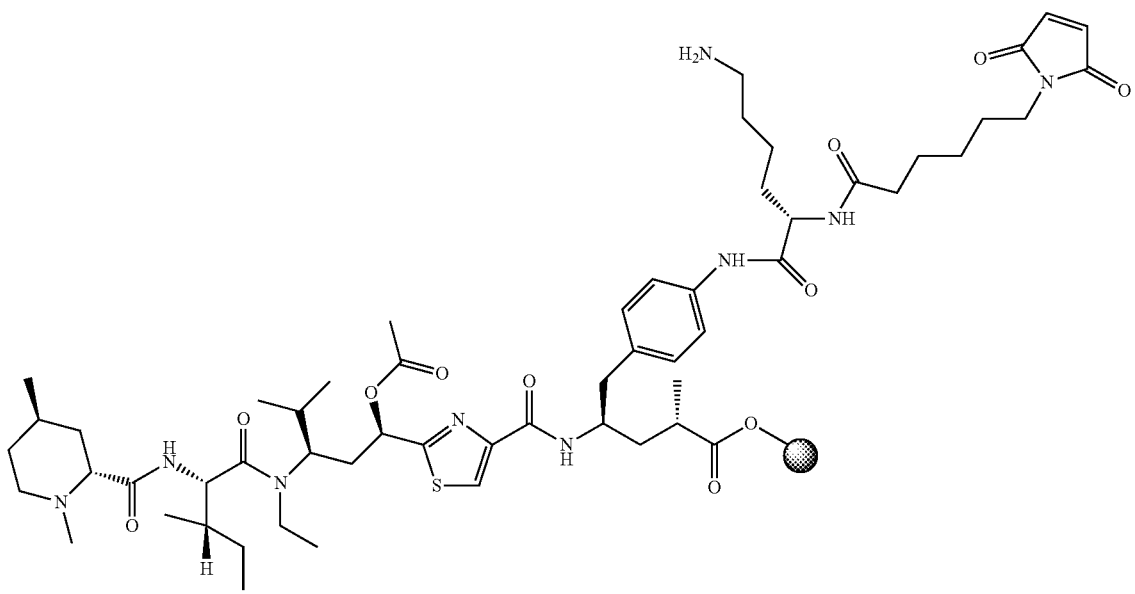

To the resin (T31) (0.2 g, 0.32 mmol) was added DCM (1 mL), and TFA (1 mL) at room temperature. The mixture was shaken at room temperature for 20 min, then filtered. The resin was washed with DCM/TFA (1:1, 3×2 mL), the filtrates were evaporated in vacuo. The residue was purified by reverse phase HPLC (ACN/H$_2$O (contained 0.1% TFA), ACN from 5% to 75% in 14 min.) The pure fractions were lyophilized to give (2S,4R)-4-(2-((1R,3R)-1-acetoxy-3-((2S,3S)-2-((2R,4R)-1,4-dimethylpiperidine-2-carboxamido)-N-ethyl-3-methylpentanamido)-4-methylpentyl)thiazole-4-carboxamido)-5-(4-((S)-6-amino-2-(6-(2,5-dioxo-2,5-dihydro-1H-pyrrol-1-yl)hexanamido)hexanamido)phenyl)-2-methylpentanoic acid (T32) (0.095 g, 22.48%) as a white solid. LC-MS: 1092 [M+1]; $^1$H NMR (400 MHz, METHANOL-d4) δ ppm 7.99 (s, 1H), 7.34 (d, J=8.53 Hz, 2H), 7.10 (d, J=8.53 Hz, 2H), 6.66 (s, 2H), 5.64 (d, J=10.79 Hz, 1H), 4.50-4.61 (m, 1H), 4.21-4.35 (m, 2H), 3.92 (d, J=9.29 Hz, 1H), 3.69 (br. s., 1H), 3.37 (t, J=7.15 Hz, 2H), 3.15-3.35 (m, 4H), 3.04 (dt, J=3.58, 1.85 Hz, 1H), 2.84 (t, J=7.65 Hz, 2H), 2.76 (d, J=7.03 Hz, 2H), 2.62 (br. s., 2H), 2.38-2.52 (m, 2H), 2.25 (t, J=11.54 Hz, 1H), 2.16 (t, J=7.40 Hz, 2H), 2.04-2.11 (m, 4H), 1.70-2.00 (m, 7H) 1.42-1.69 (m, 11H), 1.34-1.40 (m, 1H), 1.27 (t, J=6.78 Hz, 3H), 1.16-1.24 (m, 2H), 1.01-1.14 (m, 7H), 0.90 (d, J=6.78 Hz, 3H), 0.94 (d, J=6.53 Hz, 3H), 0.84 (t, J=7.40 Hz, 3H), 0.79 (d, J=6.53 Hz, 3H).

5.2. Conjugation of Tubulysin 1508

Compound T32 (tubulysin 1508) comprises a linker and a maleimide group that is readily conjugated to a thiol residue of an antibody forming a thiol-maleimide linkage. Cytotoxins comprising a maleimide group (e.g., tubulysin 1508) may be conjugated to specific cysteine residues engineered into the anti-HER2 antibodies provided herein (e.g. Bs2Ab-39SH, Bs3Ab-39SH, or Bs4Ab-39SH) of the invention. Alternatively, or optionally one may use classical conjugation methods to attach a cytotoxic agent the antibodies described. Method for conjugation to native lysine and cysteine residues are well known in the art. Representative methods for site specific (at engineered cysteine residues) and classic conjugation (at native cysteine residues) are provided below.

A representative site-specific antibody drug conjugation process is outlined in FIG. 33 and includes the steps of (a) uncapping the size chains of the derivatizable amino acids (e.g., cysteines), (b) oxidizing, (c) conjugating a payload (e.g., a cytotoxic agent such as tubulysin 1508), and (d) polishing by removing conjugation reagents and non-reacted payload. For example conjugation to an engineered cysteine may be carried out by formulating the antibody in 1×PBS with 1 mM thylenediaminetetraacetic acid. Mild reduction is used generate free thiols by adding forty equivalences of Tris(2-carboxyethyl)phosphine hydrochloride per antibody is incubated at 37° C. for three hours. Three successive dialysis in 1×PBS with 1 mM Ethylenediaminetetraacetic acid are used to remove the Tris(2-carboxyethyl)phosphine hydrochloride (alternatively desalting columns may be used). The antibody interchain disulphide bonds are allowed to re-form by addition ~20 equivalences of dehydroabietic acid (dhAA) and incubation ~four hours at room temperature. In preparation for conjugation, dimethyl sulfoxide was add to the antibody to ten percent v/v and 8 or 12 equivalences of the tubulysis 1508 payload in Dimethyl sulfoxide is added and incubated at room temperature for ~1 hour (alternatively incubate at 4° C. for ~16 hours) for 2T and 4T drug loading, respectively. The reaction is quenched by adding ~4 molar equivalence of N-actey cysteine (NAC) per payload. The free payload was removed from the conjugated antibody by Ceramic Hydroxyapatite following the manufacture recommendations. The final product may be subjected to buffer-exchange if desired. The conjugated antibodies may be analysed by non-reducing and reducing SDS-PAGE to confirm purity and conjugation to the heavy chain.

Antibody-drug conjugates with drugs randomly conjugated to native cysteine residues are prepared by partial reduction of the antibody followed by reaction with desired linker-drug. The antibody at a concentration of 5 mg/mL is partially reduced by addition of ~3 molar equivalents of DTT at pH 8.0, followed by incubation at ~37° C. for ~2 h. The reduction reaction is then chilled in ice and the excess DTT removed, for example via diafiltration. The linker-drug is then added to linker-drug/thiol molar ratio of ~1:10. The conjugation reaction is carried out in the presence of ~10% v/v of DMSO. After conjugation, excess free cysteine (~2 fold molar ration over linker-drug) is added to quench unreacted linker-drug to produce the cysteine-linker-drug adduct. The reaction mixture is purified (e.g, by hydrophobic interaction chromatography) and may be subjected to buffer-exchange into PBS. Drug load distribution is determined using standard methods such as hydrophobic interaction chromatography and reduced reverse phase chromatography.

5.3. Chemical Abbreviations

Ac acetyl
ACN acetonitrile
Boc di-tert-butyl dicarbonate
t-Bu tert-butyl
Bzl benzyl, where Bzl-OMe is methoxybenzyl and Bzl-Me is methylbenzene
Cbz or Z benzyloxy-carbonyl, where Z—Cl and Z—Br are chloro- and bromobenzyloxy carbonyl, respectively
DAST diethylaminosulfur trifluoride
DCM dichloromethane
DIAD diisopropyl azodicarboxylate
DIC N,N'-diisopropylcarbodiimide
DIEA diethylisopropylamine
DMF N,N-dimethylformamide
DTT dithiothreitol
EtOAc ethyl acetate
Et2O diethylether
Fmoc 9H-fluoren-9-ylmethoxycarbonyl
HATU 1-[Bis(dimethylamino)methylene]-1H-1,2,3-triazolo[4,5-b]pyridinium 3-oxid hexafluorophosphate
HCl hydrochloric acid
LC-MS liquid chromatography-mass spectrometry
MeOH methanol
Na2CO3 sodium bicarbonate
NaHCO3 sodium hydrogen carbonate
PAB para-aminobenzyloxycarbonyl
RT room temperature
TEA triethylamine
TFA trifluoroacetic acid
THF tetrahydrofuran
TLC thin layer chromatography

INCORPORATION BY REFERENCE

All references cited herein, including patents, patent applications, papers, text books, and the like, and the references cited therein, to the extent that they are not already, are hereby incorporated herein by reference in their entireties for all purposes.

EQUIVALENTS

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiments may be practiced in many ways and the claims include any equivalents thereof.

What is claimed is:

1. A bispecific anti-HER2 antibody comprising a first immunoglobulin antigen-binding domain and a second immunoglobulin antigen-binding domain, wherein (i) the first and second immunoglobulin antigen-binding domains specifically bind to distinct HER2 antibody binding sites, (ii) the first immunoglobulin antigen-binding domain binds to a first HER2 antibody binding site which comprises an epitope within domain II of HER2, and (iii) the first HER2 antibody binding site is distinct from the antibody binding site of pertuzumab;

and wherein the first immunoglobulin antigen-binding domain comprises a heavy chain (HC) variable region (VH) and a light chain (LC) variable region (VL) comprising:

(a) a variable heavy chain CDR-1 (VH-CDR1) identical to SEQ ID NO: 1;
(b) a variable heavy chain CDR-2 (VH-CDR2) identical to SEQ ID NO: 2;
(c) a variable heavy chain CDR-3 (VH-CDR3) identical to SEQ ID NO: 3;
(d) a variable light chain CDR-1 (VL-CDR1) identical to SEQ ID NO: 4;
(e) a variable light chain CDR-2 (VL-CDR2) identical to SEQ ID NO: 5; and
(f) a variable light chain CDR-3 (VL-CDR3) identical to SEQ ID NO: 6.

2. A bispecific anti-HER2 antibody comprising a first immunoglobulin antigen binding-domain and a second immunoglobulin antigen-binding domain, wherein the first immunoglobulin antigen-binding domain comprises a VH and a VL, wherein
(a) the VH comprises the amino acids of SEQ ID NO:15;
(b) the VL comprises the amino acids of SEQ ID NO:16;
and wherein the first and second immunoglobulin antigen-binding domains specifically bind to distinct HER2 epitopes.

3. The bispecific anti-HER2 antibody according to claim 1, wherein the first immunoglobulin antigen binding domain and/or the second immunoglobulin antigen-binding domain comprises or consists of (a) a VH further comprising a HC constant region or a fragment thereof and a VL further comprising a LC constant region or a fragment thereof; (b) a single chain Fv ("scFv"); (c) a diabody; (d) a minibody; (e) an F(ab')2; or (f) an F(ab).

4. The bispecific anti-HER2 antibody according to claim 3, wherein (a) the HC constant region or fragment thereof is an IgG constant region; and/or (b) the LC constant region is a kappa constant region or a lambda constant region.

5. The bispecific anti-HER2 antibody according to claim 1, wherein:
(a) the second immunoglobulin antigen-binding domain specifically binds to the same HER2 epitope as the trastuzumab antibody;
(b) the second immunoglobulin antigen-binding domain competitively inhibits HER2 binding by the trastuzumab antibody; or
(c) the second immunoglobulin antigen-binding domain comprises at least one, at least two, at least three, at least four, at least five, or at least six complementarity determining regions (CDRs) comprising the amino acids of any one of SEQ ID NOs: 54 to 59.

6. The bispecific anti-HER2 antibody according to claim 5, wherein the second immunoglobulin antigen-binding domain is an scFv comprising:
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and
(vi) a VL-CDR3 comprising the amino acids of SEQ ID NO:59.

7. The bispecific anti-HER2 antibody according to claim 6, wherein
(a) the second immunoglobulin antigen-binding domain is covalently linked to the carboxy-terminus of the HC of the first immunoglobulin antigen-binding domain;
(b) the second immunoglobulin antigen-binding domain is covalently linked to the amino-terminus of the HC of the first immunoglobulin antigen-binding domain; or,
(c) the second immunoglobulin antigen binding domain is covalently intercalated in the polypeptide chain of the HC of the first immunoglobulin antigen-binding domain.

8. The bispecific anti-HER2 antibody according to claim 1, wherein the heavy chain comprises a constant region comprising an Fc domain and wherein the Fc domain comprises at least one mutation capable of reducing or enhancing the ADCC activity of the bispecific antibody.

9. A bispecific anti-HER2 antibody comprising a first and a second polypeptide chain associated with each other, wherein the first polypeptide chain is selected from:

$$[TZ_S]\text{-}[L_1]\text{-}[_BVH]\text{-}[_BCH]\text{-}[Fc_x] \quad (1)$$

$$[_BVH]\text{-}[_BCH]\text{-}[Fc_x]\text{-}[L_2]\text{-}[TZ_S] \quad (2)$$

$$[_BVH]\text{-}[_BCH]\text{-}[L_3]\text{-}[TZ_S]\text{-}[L_4]\text{-}[Fc_x] \quad (3)$$

wherein
$TZ_S$ is an scFv that binds the same epitope as trastuzumab;
$L_1$, $L_2$, $L_3$, and $L_4$ are peptide linkers;
$Fc_x$ is an Fc domain;
$_BVH$ and $_BCH$ are the VH and CH1 regions, respectively, of an antibody capable of binding to a HER2 epitope distinct from the epitope recognized by the trastuzumab antibody;
and wherein the second chain comprises $[_BVL]\text{-}[CL]$ wherein $_BVL$ is the VL region of an antibody capable of binding to a HER2 epitope distinct from the epitope recognized by the trastuzumab antibody, and CL is a IgG light chain constant region selected from the group consisting of a human kappa constant region and a human lambda constant region;
and wherein the $_BVL$ comprises
(i) a variable light chain CDR-1 (VL-CDR1) identical to SEQ ID NO: 4;
(ii) a variable light chain CDR-2 (VL-CDR2) identical to SEQ ID NO: 5; and,
(iii) a variable light chain CDR-3 (VL-CDR3) identical to SEQ ID NO: 6;
and wherein $[TZ_S]$ comprises
(i) a VH-CDR1 comprising the amino acids of SEQ ID NO:54;
(ii) a VH-CDR2 comprising the amino acids of SEQ ID NO:55;
(iii) a VH-CDR3 comprising the amino acids of SEQ ID NO:56;
(iv) a VL-CDR1 comprising the amino acids of SEQ ID NO:57;
(v) a VL-CDR2 comprising the amino acids of SEQ ID NO:58; and
(vi) a VL-CDR3 comprising the amino acids of SEQ ID NO:59;
and wherein the [Fcx] comprises
(i) at least one amino acid substitution introducing a derivatizable group; and/or,
(ii) at least one mutation capable of enhancing the ADCC activity of the bispecific antibody;
and wherein $[_BVH]$ comprises
(i) a variable heavy chain CDR-1 (VH-CDR1) identical to SEQ ID NO: 1;
(ii) a variable heavy chain CDR-2 (VH-CDR2) identical to SEQ ID NO: 2; and
(iii) a variable heavy chain CDR-3 (VH-CDR3) identical to SEQ ID NO: 3.

10. An antibody-drug conjugate (ADC) comprising the bispecific HER2 antibody according to claim 1 and least one, two, three, or four therapeutic moieties, and optionally comprising at least one spacer, wherein a therapeutic moiety is chemically conjugated to the side chain of an amino acid at a specific position in the Fc region of the bispecific antibody and wherein the specific position is selected from the group consisting of 239, 248, 254, 258, 273, 279, 282, 284, 286, 287, 289, 297, 298, 312, 324, 326, 330, 335, 337, 339, 350, 355, 356, 359, 360, 361, 375, 383, 384, 389, 398, 400, 413, 415, 418, 422, 435, 440, 441, 442, 443, 446, an insertion between positions 239 and 240, and combinations thereof, wherein the amino acid position numbering is according to the EU index as set forth in Kabat.

11. The ADC according to claim 10, wherein the specific positions are 239, 442, or both, wherein the amino acid position numbering is according to the EU index as set forth in Kabat.

12. An ADC comprising the bispecific HER2 antibody according to claim 1, wherein said antibody comprises:
   (i) a first polypeptide chain comprising the amino acids of SEQ ID NO: 32 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat;
   (ii) a first polypeptide chain comprising the amino acids of SEQ ID NO:33 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat;
   (iii) a first polypeptide chain comprising the amino acids of SEQ ID NO:36 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat;
   (iv) a first polypeptide chain comprising the amino acids of SEQ ID NO:37 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat;
   (v) a first polypeptide chain comprising the amino acids of SEQ ID NO:40 and a second polypeptide chain comprising the amino acids of SEQ ID NO:42, wherein the first polypeptide chain comprises a therapeutic moiety covalently linked to a cysteine amino acid at position 239, wherein the amino acid position numbering is according to the EU index as set forth in Kabat; or,
   (vi) a first polypeptide chain comprising the amino acids of SEQ ID NO:41 and a second polypeptide chain comprising the amino acids of SEQ ID NO:42, wherein the first polypeptide chain comprises two therapeutic moieties covalently linked to cysteine amino acids respectively located at positions 239 and 442, wherein the amino acid position numbering is according to the EU index as set forth in Kabat;
   (vii) a first polypeptide chain comprising or consisting of the amino acids of SEQ ID NO:32 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat;
   (viii) a first polypeptide chain comprising or consisting of the amino acids of SEQ ID NO:71 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat;
   (ix) a first polypeptide chain comprising or consisting of the amino acids of SEQ ID NO:74 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat;
   (x) a first polypeptide chain comprising or consisting of the amino acids of SEQ ID NO:76 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat;
   (xi) a first polypeptide chain comprising or consisting of the amino acids of SEQ ID NO:79 and a second polypeptide chain comprising or consisting of the amino acids of SEQ ID NO:42, wherein the first polypeptide chain comprises a therapeutic moiety covalently linked to a cysteine amino acid inserted between positions 239 and 240, wherein the amino acid position numbering is according to the EU index as set forth in Kabat; or,
   (xii) a first polypeptide chain comprising or consisting of the amino acids of SEQ ID NO:81 and a second polypeptide chain comprising or consisting of the amino acids of SEQ ID NO:42, wherein the first polypeptide chain comprises two therapeutic moieties covalently linked to a cysteine amino inserted between positions 239 and 240 and a cysteine amino acid located at position 442, wherein the amino acid position numbering is according to the EU index as set forth in Kabat.

13. The ADC according to claim 10, wherein the therapeutic moiety comprises a cytotoxin, a radioisotope, an immunomodulator, a cytokine, a lymphokine, a chemokine, a growth factor, a tumor necrosis factor, a hormone, a hormone antagonist, an enzyme, an oligonucleotide, a DNA, an RNA, an siRNA, an RNAi, a microRNA, a photoactive therapeutic agent, an anti-angiogenic agent, a pro-apoptotic agent, a peptide, a lipid, a carbohydrate, a chelating agent, or combinations thereof.

14. The ADC according to claim 13, wherein the cytotoxin is a tubulysin, an auristatin, a maytansinoid or a pyrrolobenzodiazepine (PBD).

15. A pharmaceutical composition comprising an ADC according to claim 10, and a pharmaceutically acceptable carrier.

16. A method of treating a HER2-expressing cancer comprising administering an ADC according to claim 10 to a subject in need thereof.

17. The method according to claim 16, wherein the cancer is a low HER2-expressing cancer.

18. A method to treat resistance to a HER2-targeting therapeutic agent comprising administering an ADC according to claim 10 to a subject in need thereof.

* * * * *

```
                          SEQUENCE LISTING

<160> NUMBER OF SEQ ID NOS: 86

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Tyr Ser Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ile Ser Ser Ser Ser Ser Tyr Ile Tyr Tyr Ala Asp Ser Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Asp Ala Tyr Asn Tyr Tyr Tyr Phe Asp Tyr
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Lys Ser Ser Gln Ser Val Phe Phe Arg Ser Asn Asn Lys Asn Ile Leu
1               5                   10                  15

Ala

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ala Ser Ser Arg Glu Ser
1               5
```

```
<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gln Gln Tyr Phe Gly Ser Pro Phe Thr
1               5

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Val Arg Gln Ala Pro Gly Lys Gly Leu Glu Trp Val Ser
1               5                   10

<210> SEQ ID NO 9
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Arg Phe Thr Ile Ser Arg Asp Asn Ala Lys Asn Ser Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Gly Gln Gly Thr Leu Val Thr Val Ser Ser
1               5                   10

<210> SEQ ID NO 11
<211> LENGTH: 23
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 11

Asp Ile Val Met Thr Gln Thr Pro Leu Ser Leu Ser Val Thr Pro Gly
1               5                   10                  15

Gln Pro Ala Ser Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Trp Tyr Leu Gln Lys Pro Gly Gln Pro Pro Gln Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Phe Gly Pro Gly Thr Lys Val Asp Ile Lys
1               5                   10

<210> SEQ ID NO 15
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val

```
                50                  55                  60
Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Gly Gly Asp Ala Tyr Asn Tyr Tyr Phe Asp Tyr Trp Gly
                100                 105                 110

Gln Gly Thr Leu Val Thr Val Ser Ser
            115                 120
```

<210> SEQ ID NO 16
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

```
Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Val Phe Phe Arg
            20                  25                  30

Ser Asn Asn Lys Asn Ile Leu Ala Trp Tyr Leu Gln Lys Pro Gly Gln
        35                  40                  45

Pro Pro Gln Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Val Gly Val Tyr Tyr Cys Gln Gln
                 85                  90                  95

Tyr Phe Gly Ser Pro Phe Thr Phe Gly Pro Gly Thr Lys Val Asp Ile
                100                 105                 110

Lys
```

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (44)..(44)
<223> OTHER INFORMATION: Lys or Cys

<400> SEQUENCE: 17

```
Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Xaa Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
```

```
                    85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 18
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (100)..(100)
<223> OTHER INFORMATION: Gln or Cys

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Xaa Gly Thr Lys Val Glu Ile Lys
            100                 105

<210> SEQ ID NO 19
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Gly Gly Gly Ser Gly Gly Gly Ser Gly Gly Gly Gly Ser Gly
1               5                   10                  15

Gly Gly Gly Ser
            20

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Gly Gly Gly Ser Gly Gly Gly Gly Ser Gly Gly Gly Gly Ser
1               5                   10                  15

<210> SEQ ID NO 21
<211> LENGTH: 18
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 21

Glu Pro Lys Ser Cys Gly Lys Thr Gly Gly Gly Ser Gly Gly Gly
1               5                   10                  15

Gly Ser

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gly Gly Gly Gly Ser Gly Gly Gly Gly Ser
1               5                   10

<210> SEQ ID NO 23
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Cys Pro Pro Cys Pro Ala Pro Glu Leu Leu Gly Gly Pro Ser Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220
```

<210> SEQ ID NO 24
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Cys Pro Pro Cys Pro Ala Pro Glu Phe Leu Gly Gly Pro Cys Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 25
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Cys Pro Pro Cys Pro Ala Pro Glu Phe Leu Gly Gly Pro Cys Val Phe
1               5                   10                  15

Leu Phe Pro Pro Lys Pro Lys Asp Thr Leu Met Ile Ser Arg Thr Pro
            20                  25                  30

Glu Val Thr Cys Val Val Val Asp Val Ser His Glu Asp Pro Glu Val
        35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

```
Leu Thr Val Leu His Gln Asp Trp Leu Asn Gly Lys Glu Tyr Lys Cys
                 85                  90                  95

Lys Val Ser Asn Lys Ala Leu Pro Ala Pro Ile Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Glu Pro Lys Ser Cys Asp Lys Thr His Thr
1               5                   10

<210> SEQ ID NO 27
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 28
<211> LENGTH: 247
<212> TYPE: PRT
<213> ORGANISM: Artificial Sequence
<220> FEATURE:
```

<223> OTHER INFORMATION: Description of Artificial Sequence: Synthetic
     polypeptide
<220> FEATURE:
<221> NAME/KEY: MOD_RES
<222> LOCATION: (44)..(44)
<223> OTHER INFORMATION: Lys or Cys
<220> FEATURE:
<221> NAME/KEY: MOD_RES
<222> LOCATION: (240)..(240)
<223> OTHER INFORMATION: Gln or Cys

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Xaa Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Gly Gly Gly Ser Gly Gly Gly
        115                 120                 125

Gly Ser Gly Gly Gly Gly Ser Gly Gly Gly Ser Asp Ile Gln Met
130                 135                 140

Thr Gln Ser Pro Ser Ser Leu Ser Ala Ser Val Gly Asp Arg Val Thr
145                 150                 155                 160

Ile Thr Cys Arg Ala Ser Gln Asp Val Asn Thr Ala Val Ala Trp Tyr
                165                 170                 175

Gln Gln Lys Pro Gly Lys Ala Pro Lys Leu Leu Ile Tyr Ser Ala Ser
            180                 185                 190

Phe Leu Tyr Ser Gly Val Pro Ser Arg Phe Ser Gly Ser Arg Ser Gly
        195                 200                 205

Thr Asp Phe Thr Leu Thr Ile Ser Ser Leu Gln Pro Glu Asp Phe Ala
    210                 215                 220

Thr Tyr Tyr Cys Gln Gln His Tyr Thr Thr Pro Pro Thr Phe Gly Xaa
225                 230                 235                 240

Gly Thr Lys Val Glu Ile Lys
                245

<210> SEQ ID NO 29
<211> LENGTH: 98
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 29

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser

```
                    35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                     85                  90                  95

Arg Val

<210> SEQ ID NO 30
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Asp Val Asn Thr Ala
                 20                  25                  30

Val Ala Trp Tyr Gln Gln Lys Pro Gly Lys Ala Pro Lys Leu Leu Ile
             35                  40                  45

Tyr Ser Ala Ser Phe Leu Tyr Ser Gly Val Pro Ser Arg Phe Ser Gly
 50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
        275                 280                 285

Phe Thr Phe Ser Ser Tyr Ser Met Ser Trp Val Arg Gln Ala Pro Gly
```

```
              290                 295                 300
Lys Gly Leu Glu Trp Val Ser Ser Ile Ser Ser Ser Ser Tyr Ile
305                 310                 315                 320

Tyr Tyr Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
                340                 345                 350

Thr Ala Val Tyr Tyr Cys Ala Arg Gly Gly Asp Ala Tyr Asn Tyr Tyr
                355                 360                 365

Tyr Phe Asp Tyr Trp Gly Gln Gly Thr Leu Val Thr Val Ser Ser Ala
            370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
                420                 425                 430

Val His Thr Phe Pro Ala Val Leu Gln Ser Ser Gly Leu Tyr Ser Leu
            435                 440                 445

Ser Ser Val Val Thr Val Pro Ser Ser Ser Leu Gly Thr Gln Thr Tyr
            450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Leu Leu Gly Gly Pro Ser Val Phe Leu Phe Pro Pro Lys
                500                 505                 510

Pro Lys Asp Thr Leu Met Ile Ser Arg Thr Pro Glu Val Thr Cys Val
            515                 520                 525

Val Val Asp Val Ser His Glu Asp Pro Glu Val Lys Phe Asn Trp Tyr
            530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Ala Leu Pro Ala Pro Ile Glu Lys Thr Ile Ser Lys Ala Lys Gly Gln
            595                 600                 605

Pro Arg Glu Pro Gln Val Tyr Thr Leu Pro Pro Ser Arg Glu Glu Met
        610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
            675                 680                 685

Phe Ser Cys Ser Val Met His Glu Ala Leu His Asn His Tyr Thr Gln
            690                 695                 700

Lys Ser Leu Ser Leu Ser Pro Gly Lys
705                 710
```

<210> SEQ ID NO 31
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
        275                 280                 285

Phe Thr Phe Ser Ser Tyr Ser Met Ser Trp Val Arg Gln Ala Pro Gly
    290                 295                 300

Lys Gly Leu Glu Trp Val Ser Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr

```
                355                 360                 365
Tyr Phe Asp Tyr Trp Gly Gln Gly Thr Leu Val Thr Val Ser Ser Ala
370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
                420                 425                 430

Val His Thr Phe Pro Ala Val Leu Gln Ser Ser Gly Leu Tyr Ser Leu
                435                 440                 445

Ser Ser Val Val Thr Val Pro Ser Ser Ser Leu Gly Thr Gln Thr Tyr
450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Phe Leu Gly Gly Pro Ser Val Phe Leu Phe Pro Pro Lys
                500                 505                 510

Pro Lys Asp Thr Leu Met Ile Ser Arg Thr Pro Glu Val Thr Cys Val
                515                 520                 525

Val Val Asp Val Ser His Glu Asp Pro Glu Val Lys Phe Asn Trp Tyr
530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
                580                 585                 590

Ala Leu Pro Ala Pro Ile Glu Lys Thr Ile Ser Lys Ala Lys Gly Gln
                595                 600                 605

Pro Arg Glu Pro Gln Val Tyr Thr Leu Pro Pro Ser Arg Glu Glu Met
610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
                660                 665                 670

Tyr Ser Lys Leu Thr Val Asp Lys Ser Arg Trp Gln Gln Gly Asn Val
                675                 680                 685

Phe Ser Cys Ser Val Met His Glu Ala Leu His Asn His Tyr Thr Gln
                690                 695                 700

Lys Ser Leu Ser Leu Ser Pro Gly Lys
705                 710

<210> SEQ ID NO 32
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32
```

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
    275                 280                 285

Phe Thr Phe Ser Ser Tyr Ser Met Ser Trp Val Arg Gln Ala Pro Gly
    290                 295                 300

Lys Gly Leu Glu Trp Val Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr
        355                 360                 365

Tyr Phe Asp Tyr Trp Gly Gln Gly Thr Leu Val Thr Val Ser Ser Ala
    370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
            405                 410                 415

Pro Glu Pro Val Thr Val Ser Trp Asn Ser Gly Ala Leu Thr Ser Gly
```

```
                420                 425                 430
Val His Thr Phe Pro Ala Val Leu Gln Ser Ser Gly Leu Tyr Ser Leu
            435                 440                 445

Ser Ser Val Val Thr Val Pro Ser Ser Ser Leu Gly Thr Gln Thr Tyr
        450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Phe Leu Gly Gly Pro Cys Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
        530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Ala Leu Pro Ala Pro Ile Glu Lys Thr Ile Ser Lys Ala Lys Gly Gln
        595                 600                 605

Pro Arg Glu Pro Gln Val Tyr Thr Leu Pro Pro Ser Arg Glu Glu Met
        610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
        690                 695                 700

Lys Ser Leu Ser Leu Ser Pro Gly Lys
705                 710

<210> SEQ ID NO 33
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

```
Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                 85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
        275                 280                 285

Phe Thr Phe Ser Ser Tyr Ser Met Ser Trp Val Arg Gln Ala Pro Gly
        290                 295                 300

Lys Gly Leu Glu Trp Val Ser Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
            325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr
            355                 360                 365

Tyr Phe Asp Tyr Trp Gly Gln Gly Thr Leu Val Thr Val Ser Ser Ala
        370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
            405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
        435                 440                 445

Ser Ser Val Val Thr Val Pro Ser Ser Ser Leu Gly Thr Gln Thr Tyr
        450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
```

```
            485                 490                 495
Ala Pro Glu Phe Leu Gly Gly Pro Cys Val Phe Leu Phe Pro Pro Lys
            500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
    530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
                565                 570                 575

Gln Asp Trp Leu Asn Gly Lys Glu Tyr Lys Cys Lys Val Ser Asn Lys
            580                 585                 590

Ala Leu Pro Ala Pro Ile Glu Lys Thr Ile Ser Lys Ala Lys Gly Gln
        595                 600                 605

Pro Arg Glu Pro Gln Val Tyr Thr Leu Pro Pro Ser Arg Glu Glu Met
    610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
                645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Cys Leu Ser Pro Gly Lys
705                 710

<210> SEQ ID NO 34
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
                275                 280                 285

His Asn Ala Lys Thr Lys Pro Arg Glu Glu Gln Tyr Asn Ser Thr Tyr
                290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys Gly Gly Gly Gly Ser Gly Gly Gly Gly Ser Gly Gly Gly
                450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
                500                 505                 510

Leu Ile Tyr Ser Ala Ser Phe Leu Tyr Ser Gly Val Pro Ser Arg Phe
                515                 520                 525

Ser Gly Ser Arg Ser Gly Thr Asp Phe Thr Leu Thr Ile Ser Ser Leu
530                 535                 540

Gln Pro Glu Asp Phe Ala Thr Tyr Tyr Cys Gln Gln His Tyr Thr Thr
```

```
                545                 550                 555                 560
Pro Pro Thr Phe Gly Cys Gly Thr Lys Val Glu Ile Lys Gly Gly
                    565                 570                 575

Gly Ser Gly Gly Gly Ser Gly Gly Gly Ser Gly Gly Gly Gly
                580                 585                 590

Ser Glu Val Gln Leu Val Glu Ser Gly Gly Leu Val Gln Pro Gly
                595                 600                 605

Gly Ser Leu Arg Leu Ser Cys Ala Ala Ser Gly Phe Asn Ile Lys Asp
            610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                    645                 650                 655

Val Lys Gly Arg Phe Thr Ile Ser Ala Asp Thr Ser Lys Asn Thr Ala
                660                 665                 670

Tyr Leu Gln Met Asn Ser Leu Arg Ala Glu Asp Thr Ala Val Tyr Tyr
            675                 680                 685

Cys Ser Arg Trp Gly Gly Asp Gly Phe Tyr Ala Met Asp Tyr Trp Gly
    690                 695                 700

Gln Gly Thr Leu Val Thr Val Ser Ser
705                 710

<210> SEQ ID NO 35
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                    405                 410                 415

Asp Lys Ser Arg Trp Gln Gln Gly Asn Val Phe Ser Cys Ser Val Met
                    420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gly Gly Gly
            450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                    485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
            515                 520                 525

Ser Gly Ser Arg Ser Gly Thr Asp Phe Thr Leu Thr Ile Ser Ser Leu
            530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
                    565                 570                 575

Gly Ser Gly Gly Gly Gly Ser Gly Gly Gly Gly Ser Gly Gly Gly Gly
            580                 585                 590

Ser Glu Val Gln Leu Val Glu Ser Gly Gly Gly Leu Val Gln Pro Gly
            595                 600                 605

Gly Ser Leu Arg Leu Ser Cys Ala Ala Ser Gly Phe Asn Ile Lys Asp
```

```
                    610                 615                 620
Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                    645                 650                 655

Val Lys Gly Arg Phe Thr Ile Ser Ala Asp Thr Ser Lys Asn Thr Ala
                660                 665                 670

Tyr Leu Gln Met Asn Ser Leu Arg Ala Glu Asp Thr Ala Val Tyr Tyr
                675                 680                 685

Cys Ser Arg Trp Gly Gly Asp Gly Phe Tyr Ala Met Asp Tyr Trp Gly
                690                 695                 700

Gln Gly Thr Leu Val Thr Val Ser Ser
705                 710

<210> SEQ ID NO 36
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
                20                  25                  30

Ser Met Ser Trp Val Arg Gln Ala Pro Gly Lys Gly Leu Glu Trp Val
            35                  40                  45

Ser Ser Ile Ser Ser Ser Ser Tyr Ile Tyr Tyr Ala Asp Ser Val
        50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Phe Leu Gly
225                 230                 235                 240

Gly Pro Cys Val Phe Leu Phe Pro Pro Lys Pro Lys Asp Thr Leu Met
                245                 250                 255
```

```
Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys Gly Gly Gly Gly Ser Gly Gly Gly Gly Ser Gly Gly Gly
            450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
            515                 520                 525

Ser Gly Ser Arg Ser Gly Thr Asp Phe Thr Leu Thr Ile Ser Ser Leu
            530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
                565                 570                 575

Gly Ser Gly Gly Gly Gly Ser Gly Gly Gly Gly Ser Gly Gly Gly Gly
            580                 585                 590

Ser Glu Val Gln Leu Val Glu Ser Gly Gly Gly Leu Val Gln Pro Gly
            595                 600                 605

Gly Ser Leu Arg Leu Ser Cys Ala Ala Ser Gly Phe Asn Ile Lys Asp
            610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                645                 650                 655

Val Lys Gly Arg Phe Thr Ile Ser Ala Asp Thr Ser Lys Asn Thr Ala
            660                 665                 670

Tyr Leu Gln Met Asn Ser Leu Arg Ala Glu Asp Thr Ala Val Tyr Tyr
```

```
              675                 680                 685
Cys Ser Arg Trp Gly Gly Asp Gly Phe Tyr Ala Met Asp Tyr Trp Gly
        690                 695                 700

Gln Gly Thr Leu Val Thr Val Ser Ser
705                 710

<210> SEQ ID NO 37
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Phe Leu Gly
225                 230                 235                 240

Gly Pro Cys Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320
```

-continued

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
        515                 520                 525

Ser Gly Ser Arg Ser Gly Thr Asp Phe Thr Leu Thr Ile Ser Ser Leu
    530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
                565                 570                 575

Gly Ser Gly Gly Gly Gly Ser Gly Gly Gly Gly Ser Gly Gly Gly Gly
            580                 585                 590

Ser Glu Val Gln Leu Val Glu Ser Gly Gly Gly Leu Val Gln Pro Gly
        595                 600                 605

Gly Ser Leu Arg Leu Ser Cys Ala Ala Ser Gly Phe Asn Ile Lys Asp
    610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                645                 650                 655

Val Lys Gly Arg Phe Thr Ile Ser Ala Asp Thr Ser Lys Asn Thr Ala
            660                 665                 670

Tyr Leu Gln Met Asn Ser Leu Arg Ala Glu Asp Thr Ala Val Tyr Tyr
        675                 680                 685

Cys Ser Arg Trp Gly Gly Asp Gly Phe Tyr Ala Met Asp Tyr Trp Gly
    690                 695                 700

Gln Gly Thr Leu Val Thr Val Ser Ser
705                 710

<210> SEQ ID NO 38
<211> LENGTH: 717
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 38

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Lys Thr Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
    290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Thr Phe Gly
                325                 330                 335

Cys Gly Thr Lys Val Glu Ile Lys Gly Gly Gly Gly Ser Gly Gly Gly
            340                 345                 350

Gly Ser Gly Gly Gly Gly Ser Gly Gly Gly Gly Ser Glu Val Gln Leu
        355                 360                 365

Val Glu Ser Gly Gly Gly Leu Val Gln Pro Gly Gly Ser Leu Arg Leu
    370                 375                 380
```

```
Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
            405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
            435                 440                 445

Ser Leu Arg Ala Glu Asp Thr Ala Val Tyr Tyr Cys Ser Arg Trp Gly
        450                 455                 460

Gly Asp Gly Phe Tyr Ala Met Asp Tyr Trp Gly Gln Gly Thr Leu Val
465                 470                 475                 480

Thr Val Ser Ser Gly Gly Gly Gly Ser Gly Gly Gly Gly Ser Gly Cys
            485                 490                 495

Pro Pro Cys Pro Ala Pro Glu Leu Leu Gly Gly Pro Ser Val Phe Leu
            500                 505                 510

Phe Pro Pro Lys Pro Lys Asp Thr Leu Met Ile Ser Arg Thr Pro Glu
        515                 520                 525

Val Thr Cys Val Val Val Asp Val Ser His Glu Asp Pro Glu Val Lys
    530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
                565                 570                 575

Thr Val Leu His Gln Asp Trp Leu Asn Gly Lys Glu Tyr Lys Cys Lys
            580                 585                 590

Val Ser Asn Lys Ala Leu Pro Ala Pro Ile Glu Lys Thr Ile Ser Lys
        595                 600                 605

Ala Lys Gly Gln Pro Arg Glu Pro Gln Val Tyr Thr Leu Pro Pro Ser
    610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
            660                 665                 670

Ser Phe Phe Leu Tyr Ser Lys Leu Thr Val Asp Lys Ser Arg Trp Gln
        675                 680                 685

Gln Gly Asn Val Phe Ser Cys Ser Val Met His Glu Ala Leu His Asn
    690                 695                 700

His Tyr Thr Gln Lys Ser Leu Ser Leu Ser Pro Gly Lys
705                 710                 715

<210> SEQ ID NO 39
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30
```

```
Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
 65              70                  75                      80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Gly Lys Thr Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
            245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
        290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Ser Gly Gly
            340                 345                 350

Gly Ser Gly Gly Gly Gly Ser Gly Gly Gly Gly Ser Glu Val Gln Leu
            355                 360                 365

Val Glu Ser Gly Gly Gly Leu Val Gln Pro Gly Gly Ser Leu Arg Leu
        370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
            435                 440                 445
```

Ser Leu Arg Ala Glu Asp Thr Ala Val Tyr Tyr Cys Ser Arg Trp Gly
    450                 455                 460

Gly Asp Gly Phe Tyr Ala Met Asp Tyr Trp Gly Gln Gly Thr Leu Val
465                 470                 475                 480

Thr Val Ser Ser Gly Gly Gly Ser Gly Gly Gly Gly Ser Cys
            485                 490                 495

Pro Pro Cys Pro Ala Pro Glu Phe Leu Gly Gly Pro Ser Val Phe Leu
            500                 505                 510

Phe Pro Pro Lys Pro Lys Asp Thr Leu Met Ile Ser Arg Thr Pro Glu
            515                 520                 525

Val Thr Cys Val Val Val Asp Val Ser His Glu Asp Pro Glu Val Lys
    530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
            565                 570                 575

Thr Val Leu His Gln Asp Trp Leu Asn Gly Lys Glu Tyr Lys Cys Lys
            580                 585                 590

Val Ser Asn Lys Ala Leu Pro Ala Pro Ile Glu Lys Thr Ile Ser Lys
            595                 600                 605

Ala Lys Gly Gln Pro Arg Glu Pro Gln Val Tyr Thr Leu Pro Pro Ser
    610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
            645                 650                 655

Pro Glu Asn Asn Tyr Lys Thr Thr Pro Pro Val Leu Asp Ser Asp Gly
            660                 665                 670

Ser Phe Phe Leu Tyr Ser Lys Leu Thr Val Asp Lys Ser Arg Trp Gln
            675                 680                 685

Gln Gly Asn Val Phe Ser Cys Ser Val Met His Glu Ala Leu His Asn
    690                 695                 700

His Tyr Thr Gln Lys Ser Leu Ser Leu Ser Pro Gly Lys
705                 710                 715

<210> SEQ ID NO 40
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
210                 215                 220

Gly Lys Thr Gly Gly Gly Gly Ser Gly Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
                260                 265                 270

Tyr Gln Gln Lys Pro Gly Lys Ala Pro Lys Leu Leu Ile Tyr Ser Ala
            275                 280                 285

Ser Phe Leu Tyr Ser Gly Val Pro Ser Arg Phe Ser Gly Ser Arg Ser
            290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Ser Gly Gly Gly Gly
            340                 345                 350

Gly Ser Gly Gly Gly Gly Ser Gly Gly Gly Gly Ser Glu Val Gln Leu
            355                 360                 365

Val Glu Ser Gly Gly Gly Leu Val Gln Pro Gly Gly Ser Leu Arg Leu
370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
                420                 425                 430

Thr Ile Ser Ala Asp Thr Ser Lys Asn Thr Ala Tyr Leu Gln Met Asn
            435                 440                 445

Ser Leu Arg Ala Glu Asp Thr Ala Val Tyr Tyr Cys Ser Arg Trp Gly
            450                 455                 460

Gly Asp Gly Phe Tyr Ala Met Asp Tyr Trp Gly Gln Gly Thr Leu Val
465                 470                 475                 480

Thr Val Ser Ser Ser Gly Gly Gly Ser Gly Gly Gly Gly Ser Cys
                485                 490                 495

Pro Pro Cys Pro Ala Pro Glu Phe Leu Gly Gly Pro Ser Val Phe Leu
            500                 505                 510

Phe Pro Pro Lys Pro Lys Asp Thr Leu Met Ile Ser Arg Thr Pro Glu
            515                 520                 525

Val Thr Cys Val Val Val Asp Val Ser His Glu Asp Pro Glu Val Lys
530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
                565                 570                 575

Thr Val Leu His Gln Asp Trp Leu Asn Gly Lys Glu Tyr Lys Cys Lys
            580                 585                 590

Val Ser Asn Lys Ala Leu Pro Ala Pro Ile Glu Lys Thr Ile Ser Lys
        595                 600                 605

Ala Lys Gly Gln Pro Arg Glu Pro Gln Val Tyr Thr Leu Pro Pro Ser
    610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
            660                 665                 670

Ser Phe Phe Leu Tyr Ser Lys Leu Thr Val Asp Lys Ser Arg Trp Gln
        675                 680                 685

Gln Gly Asn Val Phe Ser Cys Ser Val Met His Glu Ala Leu His Asn
    690                 695                 700

His Tyr Thr Gln Lys Ser Leu Ser Leu Ser Pro Gly Lys
705                 710                 715

<210> SEQ ID NO 41
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

```
Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Val Thr Val
        180                 185                 190

Pro Ser Ser Ser Leu Gly Thr Gln Thr Tyr Ile Cys Asn Val Asn His
    195                 200                 205

Lys Pro Ser Asn Thr Lys Val Asp Lys Arg Val Glu Pro Lys Ser Cys
210                 215                 220

Gly Lys Thr Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
    290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Ser Gly Gly Gly
            340                 345                 350

Gly Ser Gly Gly Gly Ser Gly Gly Gly Ser Glu Val Gln Leu
        355                 360                 365

Val Glu Ser Gly Gly Gly Leu Val Gln Pro Gly Gly Ser Leu Arg Leu
    370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
        435                 440                 445

Ser Leu Arg Ala Glu Asp Thr Ala Val Tyr Tyr Cys Ser Arg Trp Gly
    450                 455                 460

Gly Asp Gly Phe Tyr Ala Met Asp Tyr Trp Gly Gln Gly Thr Leu Val
465                 470                 475                 480

Thr Val Ser Ser Ser Gly Gly Gly Ser Gly Gly Gly Gly Ser Cys
                485                 490                 495

Pro Pro Cys Pro Ala Pro Glu Phe Leu Gly Gly Pro Cys Val Phe Leu
            500                 505                 510

Phe Pro Pro Lys Pro Lys Asp Thr Leu Met Ile Ser Arg Thr Pro Glu
        515                 520                 525

Val Thr Cys Val Val Val Asp Val Ser His Glu Asp Pro Glu Val Lys
    530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
                565                 570                 575
```

```
Thr Val Leu His Gln Asp Trp Leu Asn Gly Lys Glu Tyr Lys Cys Lys
            580                 585                 590

Val Ser Asn Lys Ala Leu Pro Ala Pro Ile Glu Lys Thr Ile Ser Lys
        595                 600                 605

Ala Lys Gly Gln Pro Arg Glu Pro Gln Val Tyr Thr Leu Pro Pro Ser
    610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
            660                 665                 670

Ser Phe Phe Leu Tyr Ser Lys Leu Thr Val Asp Lys Ser Arg Trp Gln
        675                 680                 685

Gln Gly Asn Val Phe Ser Cys Ser Val Met His Glu Ala Leu His Asn
    690                 695                 700

His Tyr Thr Gln Lys Ser Leu Cys Leu Ser Pro Gly Lys
705                 710                 715

<210> SEQ ID NO 42
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Val Phe Phe Arg
            20                  25                  30

Ser Asn Asn Lys Asn Ile Leu Ala Trp Tyr Leu Gln Lys Pro Gly Gln
        35                  40                  45

Pro Pro Gln Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Gly Tyr Asn Tyr Tyr Phe Asp Tyr Trp Gly
            100                 105                 110

Gln Gly Thr Leu Val Thr Val Ser Ser
        115                 120

<210> SEQ ID NO 44
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Val Met Thr Gln Ser Pro Asp Ser Leu Ala Val Ser Leu Gly
1               5                   10                  15

Glu Arg Ala Thr Ile Thr Cys Lys Ser Ser Gln Ser Val Phe Phe Arg
            20                  25                  30

Ser Asn Asn Lys Asn Cys Leu Ala Trp Tyr Gln Gln Arg Pro Gly Gln
        35                  40                  45

Pro Pro Asn Leu Leu Ile Tyr Trp Ala Ser Ser Arg Glu Ser Gly Val
    50                  55                  60

Pro Asp Arg Phe Ser Gly Ser Gly Ser Gly Thr Asp Phe Ala Leu Thr
65                  70                  75                  80

Ile Ser Ser Leu Gln Thr Glu Asp Val Ala Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 45

Ser Tyr Ser Met
1

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Gly Asp Gly Tyr Asn Tyr Tyr Tyr Phe Asp Tyr
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Lys Ser Ser Gln Ser Val Phe Phe Arg Ser Asn Asn Lys Asn Cys Leu
1               5                   10                  15

Ala

<210> SEQ ID NO 48
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Asp Ile Val Met Thr Gln Ser Pro Asp Ser Leu Ala Val Ser Leu Gly
1               5                   10                  15

Glu Arg Ala Thr Ile Thr Cys
            20

<210> SEQ ID NO 49
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Trp Tyr Gln Gln Arg Pro Gly Gln Pro Pro Asn Leu Leu Ile Tyr
1               5                   10                  15

<210> SEQ ID NO 50
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gly Val Pro Asp Arg Phe Ser Gly Ser Gly Ser Gly Thr Asp Phe Ala
1               5                   10                  15
```

```
Leu Thr Ile Ser Ser Leu Gln Thr Glu Asp Val Ala Val Tyr Tyr Cys
             20                  25                  30
```

<210> SEQ ID NO 51
<211> LENGTH: 630
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

```
Thr Gln Val Cys Thr Gly Thr Asp Met Lys Leu Arg Leu Pro Ala Ser
1               5                   10                  15

Pro Glu Thr His Leu Asp Met Leu Arg His Leu Tyr Gln Gly Cys Gln
             20                  25                  30

Val Val Gln Gly Asn Leu Glu Leu Thr Tyr Leu Pro Thr Asn Ala Ser
         35                  40                  45

Leu Ser Phe Leu Gln Asp Ile Gln Glu Val Gln Gly Tyr Val Leu Ile
     50                  55                  60

Ala His Asn Gln Val Arg Gln Val Pro Leu Gln Arg Leu Arg Ile Val
65                  70                  75                  80

Arg Gly Thr Gln Leu Phe Glu Asp Asn Tyr Ala Leu Ala Val Leu Asp
                 85                  90                  95

Asn Gly Asp Pro Leu Asn Asn Thr Thr Pro Val Thr Gly Ala Ser Pro
            100                 105                 110

Gly Gly Leu Arg Glu Leu Gln Leu Arg Ser Leu Thr Glu Ile Leu Lys
        115                 120                 125

Gly Gly Val Leu Ile Gln Arg Asn Pro Gln Leu Cys Tyr Gln Asp Thr
    130                 135                 140

Ile Leu Trp Lys Asp Ile Phe His Lys Asn Asn Gln Leu Ala Leu Thr
145                 150                 155                 160

Leu Ile Asp Thr Asn Arg Ser Arg Ala Cys His Pro Cys Ser Pro Met
                165                 170                 175

Cys Lys Gly Ser Arg Cys Trp Gly Glu Ser Ser Glu Asp Cys Gln Ser
            180                 185                 190

Leu Thr Arg Thr Val Cys Ala Gly Gly Cys Ala Arg Cys Lys Gly Pro
        195                 200                 205

Leu Pro Thr Asp Cys Cys His Glu Gln Cys Ala Ala Gly Cys Thr Gly
    210                 215                 220

Pro Lys His Ser Asp Cys Leu Ala Cys Leu His Phe Asn His Ser Gly
225                 230                 235                 240

Ile Cys Glu Leu His Cys Pro Ala Leu Val Thr Tyr Asn Thr Asp Thr
                245                 250                 255

Phe Glu Ser Met Pro Asn Pro Glu Gly Arg Tyr Thr Phe Gly Ala Ser
            260                 265                 270

Cys Val Thr Ala Cys Pro Tyr Asn Tyr Leu Ser Thr Asp Val Gly Ser
        275                 280                 285

Cys Thr Leu Val Cys Pro Leu His Asn Gln Glu Val Thr Ala Glu Asp
    290                 295                 300

Gly Thr Gln Arg Cys Glu Lys Cys Ser Lys Pro Cys Ala Arg Val Cys
305                 310                 315                 320

Tyr Gly Leu Gly Met Glu His Leu Arg Glu Val Arg Ala Val Thr Ser
                325                 330                 335

Ala Asn Ile Gln Glu Phe Ala Gly Cys Lys Lys Ile Phe Gly Ser Leu
```

```
                340                 345                 350
Ala Phe Leu Pro Glu Ser Phe Asp Gly Asp Pro Ala Ser Asn Thr Ala
            355                 360                 365

Pro Leu Gln Pro Glu Gln Leu Gln Val Phe Glu Thr Leu Glu Glu Ile
        370                 375                 380

Thr Gly Tyr Leu Tyr Ile Ser Ala Trp Pro Asp Ser Leu Pro Asp Leu
385                 390                 395                 400

Ser Val Phe Gln Asn Leu Gln Val Ile Arg Gly Arg Ile Leu His Asn
                405                 410                 415

Gly Ala Tyr Ser Leu Thr Leu Gln Gly Leu Gly Ile Ser Trp Leu Gly
            420                 425                 430

Leu Arg Ser Leu Arg Glu Leu Gly Ser Gly Leu Ala Leu Ile His His
        435                 440                 445

Asn Thr His Leu Cys Phe Val His Thr Val Pro Trp Asp Gln Leu Phe
450                 455                 460

Arg Asn Pro His Gln Ala Leu Leu His Thr Ala Asn Arg Pro Glu Asp
465                 470                 475                 480

Glu Cys Val Gly Glu Gly Leu Ala Cys His Gln Leu Cys Ala Arg Gly
                485                 490                 495

His Cys Trp Gly Pro Gly Pro Thr Gln Cys Val Asn Cys Ser Gln Phe
            500                 505                 510

Leu Arg Gly Gln Glu Cys Val Glu Glu Cys Arg Val Leu Gln Gly Leu
        515                 520                 525

Pro Arg Glu Tyr Val Asn Ala Arg His Cys Leu Pro Cys His Pro Glu
    530                 535                 540

Cys Gln Pro Gln Asn Gly Ser Val Thr Cys Phe Gly Pro Glu Ala Asp
545                 550                 555                 560

Gln Cys Val Ala Cys Ala His Tyr Lys Asp Pro Pro Phe Cys Val Ala
                565                 570                 575

Arg Cys Pro Ser Gly Val Lys Pro Asp Leu Ser Tyr Met Pro Ile Trp
            580                 585                 590

Lys Phe Pro Asp Glu Glu Gly Ala Cys Gln Pro Cys Pro Ile Asn Cys
        595                 600                 605

Thr His Ser Cys Val Asp Leu Asp Asp Lys Gly Cys Pro Ala Glu Gln
    610                 615                 620

Arg Ala Ser Pro Leu Thr
625                 630

<210> SEQ ID NO 52
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Ser Leu Thr Arg Thr Val Cys Ala Gly Gly Cys Ala Arg Cys Lys Gly
1               5                   10                  15

Pro

<210> SEQ ID NO 53
<211> LENGTH: 65
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 53

Leu Pro Cys His Pro Glu Cys Gln Pro Gln Asn Gly Ser Val Thr Cys
1               5                   10                  15

Phe Gly Pro Glu Ala Asp Gln Cys Val Ala Cys Ala His Tyr Lys Asp
            20                  25                  30

Pro Pro Phe Cys Val Ala Arg Cys Pro Ser Gly Val Lys Pro Asp Leu
        35                  40                  45

Ser Tyr Met Pro Ile Trp Lys Phe Pro Asp Glu Glu Gly Ala Cys Gln
    50                  55                  60

Pro
65

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Asp Thr Tyr Ile His
1               5

<210> SEQ ID NO 55
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Arg Ile Tyr Pro Thr Asn Gly Tyr Thr Arg Tyr Ala Asp Ser Val Lys
1               5                   10                  15

Gly

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Trp Gly Gly Asp Gly Phe Tyr Ala Met Asp Tyr
1               5                   10

<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Arg Ala Ser Gln Asp Val Asn Thr Ala Val Ala
1               5                   10

<210> SEQ ID NO 58

-continued

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser Ala Ser Phe Leu Tyr Ser
1               5

<210> SEQ ID NO 59
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Gln Gln His Tyr Thr Thr Pro Pro Thr
1               5

<210> SEQ ID NO 60
<211> LENGTH: 81
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(1)
<223> OTHER INFORMATION: May or may not be present
<220> FEATURE:
<221> NAME/KEY: misc_feature
<222> LOCATION: (2)..(5)
<223> OTHER INFORMATION: This region may encompass 1-4 residues, wherein
      some positions may be absent
<220> FEATURE:
<221> NAME/KEY: misc_feature
<222> LOCATION: (10)..(13)
<223> OTHER INFORMATION: This region may encompass 1-4 residues, wherein
      some positions may be absent
<220> FEATURE:
<221> NAME/KEY: misc_feature
<222> LOCATION: (18)..(21)
<223> OTHER INFORMATION: This region may encompass 1-4 residues, wherein
      some positions may be absent
<220> FEATURE:
<221> NAME/KEY: misc_feature
<222> LOCATION: (26)..(29)
<223> OTHER INFORMATION: This region may encompass 1-4 residues, wherein
      some positions may be absent
<220> FEATURE:
<221> NAME/KEY: misc_feature
<222> LOCATION: (34)..(37)
<223> OTHER INFORMATION: This region may encompass 1-4 residues, wherein
      some positions may be absent
<220> FEATURE:
<221> NAME/KEY: misc_feature
<222> LOCATION: (42)..(45)
<223> OTHER INFORMATION: This region may encompass 1-4 residues, wherein
      some positions may be absent
<220> FEATURE:
<221> NAME/KEY: misc_feature
<222> LOCATION: (50)..(53)
<223> OTHER INFORMATION: This region may encompass 1-4 residues, wherein
      some positions may be absent
<220> FEATURE:
<221> NAME/KEY: misc_feature
<222> LOCATION: (58)..(61)
<223> OTHER INFORMATION: This region may encompass 1-4 residues, wherein
      some positions may be absent
<220> FEATURE:
```

```
<221> NAME/KEY: misc_feature
<222> LOCATION: (66)..(69)
<223> OTHER INFORMATION: This region may encompass 1-4 residues, wherein
      some positions may be absent
<220> FEATURE:
<221> NAME/KEY: misc_feature
<222> LOCATION: (74)..(77)
<223> OTHER INFORMATION: This region may encompass 1-4 residues, wherein
      some positions may be absent
<220> FEATURE:
<221> NAME/KEY: misc_feature
<222> LOCATION: (1)..(81)
<223> OTHER INFORMATION: This sequence may encompass 1-10 (Gly)y-(Ser)4
      repeating units, wherein y is 1-4 and some positions may be absent
<220> FEATURE:
<223> OTHER INFORMATION: See specification as filed for detailed
      description of substitutions and preferred embodiments

<400> SEQUENCE: 60

Ser Gly Gly Gly Gly Ser Ser Ser Gly Gly Gly Gly Ser Ser Ser
1               5                   10                  15

Ser Gly Gly Gly Gly Ser Ser Ser Gly Gly Gly Gly Ser Ser Ser
                20                  25                  30

Ser Gly Gly Gly Gly Ser Ser Ser Gly Gly Gly Gly Ser Ser Ser
            35                  40                  45

Ser Gly Gly Gly Gly Ser Ser Ser Gly Gly Gly Gly Ser Ser Ser
        50                  55                  60

Ser Gly Gly Gly Gly Ser Ser Ser Gly Gly Gly Gly Ser Ser Ser
65                  70                  75                  80

Ser

<210> SEQ ID NO 61
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 61

His His His His His His
1               5

<210> SEQ ID NO 62
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Cys Pro Pro Cys Pro Ala Pro Glu Leu Leu Gly Gly Pro Asp Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
        50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95
```

Lys Val Ser Asn Lys Ala Leu Pro Ala Pro Glu Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 63
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Cys Pro Pro Cys Pro Ala Pro Glu Leu Leu Gly Gly Pro Ser Cys Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220

```
<210> SEQ ID NO 64
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Cys Pro Pro Cys Pro Ala Pro Glu Leu Leu Gly Gly Pro Asp Val Phe
1               5                   10                  15

Leu Phe Pro Pro Lys Pro Lys Asp Thr Leu Met Ile Ser Arg Thr Pro
                20                  25                  30

Glu Val Thr Cys Val Val Val Asp Val Ser His Glu Asp Pro Glu Val
            35                  40                  45

Lys Phe Asn Trp Tyr Val Asp Gly Val Glu Val His Asn Ala Lys Thr
    50                  55                  60

Lys Pro Arg Glu Glu Gln Tyr Asn Ser Thr Tyr Arg Val Val Ser Val
65                  70                  75                  80

Leu Thr Val Leu His Gln Asp Trp Leu Asn Gly Lys Glu Tyr Lys Cys
                85                  90                  95

Lys Val Ser Asn Lys Ala Leu Pro Leu Pro Glu Glu Lys Thr Ile Ser
            100                 105                 110

Lys Ala Lys Gly Gln Pro Arg Glu Pro Gln Val Tyr Thr Leu Pro Pro
        115                 120                 125

Ser Arg Glu Glu Met Thr Lys Asn Gln Val Ser Leu Thr Cys Leu Val
    130                 135                 140

Lys Gly Phe Tyr Pro Ser Asp Ile Ala Val Glu Trp Glu Ser Asn Gly
145                 150                 155                 160

Gln Pro Glu Asn Asn Tyr Lys Thr Thr Pro Pro Val Leu Asp Ser Asp
                165                 170                 175

Gly Ser Phe Phe Leu Tyr Ser Lys Leu Thr Val Asp Lys Ser Arg Trp
            180                 185                 190

Gln Gln Gly Asn Val Phe Ser Cys Ser Val Met His Glu Ala Leu His
        195                 200                 205

Asn His Tyr Thr Gln Lys Ser Leu Ser Leu Ser Pro Gly Lys
    210                 215                 220

<210> SEQ ID NO 65
<211> LENGTH: 223
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Cys Pro Pro Cys Pro Ala Pro Glu Leu Leu Gly Gly Pro Ser Cys Val
1               5                   10                  15

Phe Leu Phe Pro Pro Lys Pro Lys Asp Thr Leu Met Ile Ser Arg Thr
                20                  25                  30

Pro Glu Val Thr Cys Val Val Val Asp Val Ser His Glu Asp Pro Glu
            35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
```

```
                    85                  90                  95
Cys Lys Val Ser Asn Lys Ala Leu Pro Ala Pro Ile Glu Lys Thr Ile
                100                 105                 110
Ser Lys Ala Lys Gly Gln Pro Arg Glu Pro Gln Val Tyr Thr Leu Pro
                115                 120                 125
Pro Ser Arg Glu Glu Met Thr Lys Asn Gln Val Ser Leu Thr Cys Leu
            130                 135                 140
Val Lys Gly Phe Tyr Pro Ser Asp Ile Ala Val Glu Trp Glu Ser Asn
145                 150                 155                 160
Gly Gln Pro Glu Asn Asn Tyr Lys Thr Thr Pro Pro Val Leu Asp Ser
                165                 170                 175
Asp Gly Ser Phe Phe Leu Tyr Ser Lys Leu Thr Val Asp Lys Ser Arg
            180                 185                 190
Trp Gln Gln Gly Asn Val Phe Ser Cys Ser Val Met His Glu Ala Leu
        195                 200                 205
His Asn His Tyr Thr Gln Lys Ser Leu Cys Leu Ser Pro Gly Lys
    210                 215                 220
```

<210> SEQ ID NO 66
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

```
Gln Pro Lys Ala Ala Pro Ser Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Ser Ser Pro Val
        35                  40                  45
Lys Ala Gly Val Glu Thr Thr Thr Pro Ser Lys Gln Ser Asn Asn Lys
    50                  55                  60
Tyr Ala Ala Ser Ser Tyr Leu Ser Leu Thr Pro Glu Gln Trp Lys Ser
65                  70                  75                  80
His Arg Ser Tyr Ser Cys Gln Val Thr His Glu Gly Ser Thr Val Glu
                85                  90                  95
Lys Thr Val Ala Pro Thr Glu Cys
            100
```

<210> SEQ ID NO 67
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Asp Val Asn Thr Ala
            20                  25                  30
Val Ala Trp Tyr Gln Gln Lys Pro Gly Lys Ala Pro Lys Leu Leu Ile
        35                  40                  45
Tyr Ser Ala Ser Phe Leu Tyr Ser Gly Val Pro Ser Arg Phe Ser Gly
```

```
                50              55              60
Ser Arg Ser Gly Thr Asp Phe Thr Leu Thr Ile Ser Ser Leu Gln Pro
65                      70                  75                  80

Glu Asp Phe Ala Thr Tyr Tyr Cys Gln Gln His Tyr Thr Thr Pro Pro
                    85                  90                  95

Thr Phe Gly Cys Gly Thr Lys Val Glu Ile Lys Gly Gly Gly Gly Ser
                100                 105                 110

Gly Gly Gly Gly Ser Gly Gly Gly Ser Gly Gly Gly Gly Ser Glu
            115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
                180                 185                 190

Gly Arg Phe Thr Ile Ser Ala Asp Thr Ser Lys Asn Thr Ala Tyr Leu
            195                 200                 205

Gln Met Asn Ser Leu Arg Ala Glu Asp Thr Ala Val Tyr Tyr Cys Ser
        210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Glu Val Gln Leu Val Glu Ser Gly Gly Gly
                260                 265                 270

Leu Val Lys Pro Gly Gly Ser Leu Arg Leu Ser Cys Ala Ala Ser Gly
            275                 280                 285

Phe Thr Phe Ser Ser Tyr Ser Met Ser Trp Val Arg Gln Ala Pro Gly
        290                 295                 300

Lys Gly Leu Glu Trp Val Ser Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr
        355                 360                 365

Tyr Phe Asp Tyr Trp Gly Gln Gly Thr Leu Val Thr Val Ser Ser Ala
    370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
        435                 440                 445

Ser Ser Val Val Thr Val Pro Ser Ser Ser Leu Gly Thr Gln Thr Tyr
    450                 455                 460

Ile Cys Asn Val Asn His Lys Pro Ser Asn Thr Lys Val Asp Lys Arg
465                 470                 475                 480
```

```
Val Glu Pro Lys Ser Cys Asp Lys Thr His Thr Cys Pro Pro Cys Pro
            485                 490                 495

Ala Pro Glu Leu Leu Gly Gly Pro Ser Val Phe Leu Phe Pro Pro Lys
        500                 505                 510

Pro Lys Asp Thr Leu Met Ile Ser Arg Thr Pro Glu Val Thr Cys Val
        515                 520                 525

Val Val Asp Val Ser His Glu Asp Pro Glu Val Lys Phe Asn Trp Tyr
        530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
            565                 570                 575

Gln Asp Trp Leu Asn Gly Lys Glu Tyr Lys Cys Lys Val Ser Asn Lys
            580                 585                 590

Ala Leu Pro Ala Pro Glu Glu Lys Thr Ile Ser Lys Ala Lys Gly Gln
            595                 600                 605

Pro Arg Glu Pro Gln Val Tyr Thr Leu Pro Pro Ser Arg Glu Glu Met
        610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
            645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
            675                 680                 685

Phe Ser Cys Ser Val Met His Glu Ala Leu His Asn His Tyr Thr Gln
        690                 695                 700

Lys Ser Leu Ser Leu Ser Pro Gly Lys
705                 710

<210> SEQ ID NO 68
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
```

```
            115                 120                 125
Val Gln Leu Val Glu Ser Gly Gly Leu Val Gln Pro Gly Gly Ser
        130                 135                 140
Leu Arg Leu Ser Cys Ala Ala Ser Gly Phe Asn Ile Lys Asp Thr Tyr
145                 150                 155                 160
Ile His Trp Val Arg Gln Ala Pro Gly Lys Cys Leu Glu Trp Val Ala
                165                 170                 175
Arg Ile Tyr Pro Thr Asn Gly Tyr Thr Arg Tyr Ala Asp Ser Val Lys
                180                 185                 190
Gly Arg Phe Thr Ile Ser Ala Asp Thr Ser Lys Asn Thr Ala Tyr Leu
                195                 200                 205
Gln Met Asn Ser Leu Arg Ala Glu Asp Thr Ala Val Tyr Tyr Cys Ser
        210                 215                 220
Arg Trp Gly Gly Asp Gly Phe Tyr Ala Met Asp Tyr Trp Gly Gln Gly
225                 230                 235                 240
Thr Leu Val Thr Val Ser Ser Gly Gly Gly Ser Gly Gly Gly Gly
                245                 250                 255
Ser Gly Gly Gly Gly Ser Glu Val Gln Leu Val Glu Ser Gly Gly Gly
                260                 265                 270
Leu Val Lys Pro Gly Gly Ser Leu Arg Leu Ser Cys Ala Ala Ser Gly
                275                 280                 285
Phe Thr Phe Ser Ser Tyr Ser Met Ser Trp Val Arg Gln Ala Pro Gly
        290                 295                 300
Lys Gly Leu Glu Trp Val Ser Ser Ile Ser Ser Ser Ser Ser Tyr Ile
305                 310                 315                 320
Tyr Tyr Ala Asp Ser Val Lys Gly Arg Phe Thr Ile Ser Arg Asp Asn
                325                 330                 335
Ala Lys Asn Ser Leu Tyr Leu Gln Met Asn Ser Leu Arg Ala Glu Asp
                340                 345                 350
Thr Ala Val Tyr Tyr Cys Ala Arg Gly Gly Asp Ala Tyr Asn Tyr Tyr
                355                 360                 365
Tyr Phe Asp Tyr Trp Gly Gln Gly Thr Leu Val Thr Val Ser Ser Ala
        370                 375                 380
Ser Thr Lys Gly Pro Ser Val Phe Pro Leu Ala Pro Ser Ser Lys Ser
385                 390                 395                 400
Thr Ser Gly Gly Thr Ala Ala Leu Gly Cys Leu Val Lys Asp Tyr Phe
                405                 410                 415
Pro Glu Pro Val Thr Val Ser Trp Asn Ser Gly Ala Leu Thr Ser Gly
                420                 425                 430
Val His Thr Phe Pro Ala Val Leu Gln Ser Ser Gly Leu Tyr Ser Leu
                435                 440                 445
Ser Ser Val Val Thr Val Pro Ser Ser Ser Leu Gly Thr Gln Thr Tyr
        450                 455                 460
Ile Cys Asn Val Asn His Lys Pro Ser Asn Thr Lys Val Asp Lys Arg
465                 470                 475                 480
Val Glu Pro Lys Ser Cys Asp Lys Thr His Thr Cys Pro Pro Cys Pro
                485                 490                 495
Ala Pro Glu Leu Leu Gly Gly Pro Asp Val Phe Leu Phe Pro Pro Lys
                500                 505                 510
Pro Lys Asp Thr Leu Met Ile Ser Arg Thr Pro Glu Val Thr Cys Val
                515                 520                 525
Val Val Asp Val Ser His Glu Asp Pro Glu Val Lys Phe Asn Trp Tyr
        530                 535                 540
```

```
Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
            565                 570                 575

Gln Asp Trp Leu Asn Gly Lys Glu Tyr Lys Cys Lys Val Ser Asn Lys
            580                 585                 590

Ala Leu Pro Ala Pro Glu Glu Lys Thr Ile Ser Lys Ala Lys Gly Gln
            595                 600                 605

Pro Arg Glu Pro Gln Val Tyr Thr Leu Pro Pro Ser Arg Glu Glu Met
            610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
            645                 650                 655

Tyr Lys Thr Thr Pro Pro Val Leu Asp Ser Asp Gly Ser Phe Phe Leu
            660                 665                 670

Tyr Ser Lys Leu Thr Val Asp Lys Ser Arg Trp Gln Gln Gly Asn Val
            675                 680                 685

Phe Ser Cys Ser Val Met His Glu Ala Leu His Asn His Tyr Thr Gln
            690                 695                 700

Lys Ser Leu Ser Leu Ser Pro Gly Lys
705                 710

<210> SEQ ID NO 69
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65              70                  75                  80

Glu Asp Phe Ala Thr Tyr Tyr Cys Gln Gln His Tyr Thr Thr Pro Pro
            85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Leu Val Gln Pro Gly Gly Ser
        130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
            165                 170                 175

Arg Ile Tyr Pro Thr Asn Gly Tyr Thr Arg Tyr Ala Asp Ser Val Lys
```

```
                180                 185                 190
Gly Arg Phe Thr Ile Ser Ala Asp Thr Ser Lys Asn Thr Ala Tyr Leu
                195                 200                 205
Gln Met Asn Ser Leu Arg Ala Glu Asp Thr Ala Val Tyr Tyr Cys Ser
                210                 215                 220
Arg Trp Gly Gly Asp Gly Phe Tyr Ala Met Asp Tyr Trp Gly Gln Gly
225                 230                 235                 240
Thr Leu Val Thr Val Ser Ser Gly Gly Gly Ser Gly Gly Gly Gly
                245                 250                 255
Ser Gly Gly Gly Gly Ser Glu Val Gln Leu Val Glu Ser Gly Gly Gly
                260                 265                 270
Leu Val Lys Pro Gly Gly Ser Leu Arg Leu Ser Cys Ala Ala Ser Gly
                275                 280                 285
Phe Thr Phe Ser Ser Tyr Ser Met Ser Trp Val Arg Gln Ala Pro Gly
                290                 295                 300
Lys Gly Leu Glu Trp Val Ser Ser Ile Ser Ser Ser Ser Ser Tyr Ile
305                 310                 315                 320
Tyr Tyr Ala Asp Ser Val Lys Gly Arg Phe Thr Ile Ser Arg Asp Asn
                325                 330                 335
Ala Lys Asn Ser Leu Tyr Leu Gln Met Asn Ser Leu Arg Ala Glu Asp
                340                 345                 350
Thr Ala Val Tyr Tyr Cys Ala Arg Gly Gly Asp Ala Tyr Asn Tyr Tyr
                355                 360                 365
Tyr Phe Asp Tyr Trp Gly Gln Gly Thr Leu Val Thr Val Ser Ser Ala
                370                 375                 380
Ser Thr Lys Gly Pro Ser Val Phe Pro Leu Ala Pro Ser Ser Lys Ser
385                 390                 395                 400
Thr Ser Gly Gly Thr Ala Ala Leu Gly Cys Leu Val Lys Asp Tyr Phe
                405                 410                 415
Pro Glu Pro Val Thr Val Ser Trp Asn Ser Gly Ala Leu Thr Ser Gly
                420                 425                 430
Val His Thr Phe Pro Ala Val Leu Gln Ser Ser Gly Leu Tyr Ser Leu
                435                 440                 445
Ser Ser Val Val Thr Val Pro Ser Ser Ser Leu Gly Thr Gln Thr Tyr
                450                 455                 460
Ile Cys Asn Val Asn His Lys Pro Ser Asn Thr Lys Val Asp Lys Arg
465                 470                 475                 480
Val Glu Pro Lys Ser Cys Asp Lys Thr His Thr Cys Pro Pro Cys Pro
                485                 490                 495
Ala Pro Glu Leu Leu Gly Gly Pro Ser Cys Val Phe Leu Phe Pro Pro
                500                 505                 510
Lys Pro Lys Asp Thr Leu Met Ile Ser Arg Thr Pro Glu Val Thr Cys
                515                 520                 525
Val Val Val Asp Val Ser His Glu Asp Pro Glu Val Lys Phe Asn Trp
                530                 535                 540
Tyr Val Asp Gly Val Glu Val His Asn Ala Lys Thr Lys Pro Arg Glu
545                 550                 555                 560
Glu Gln Tyr Asn Ser Thr Tyr Arg Val Val Ser Val Leu Thr Val Leu
                565                 570                 575
His Gln Asp Trp Leu Asn Gly Lys Glu Tyr Lys Cys Lys Val Ser Asn
                580                 585                 590
Lys Ala Leu Pro Ala Pro Ile Glu Lys Thr Ile Ser Lys Ala Lys Gly
                595                 600                 605
```

```
Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
                660                 665                 670

Leu Tyr Ser Lys Leu Thr Val Asp Lys Ser Arg Trp Gln Gln Gly Asn
            675                 680                 685

Val Phe Ser Cys Ser Val Met His Glu Ala Leu His Asn His Tyr Thr
    690                 695                 700

Gln Lys Ser Leu Ser Leu Ser Pro Gly Lys
705                 710

<210> SEQ ID NO 70
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Ser Gly Gly Gly Gly Ser Glu
        115                 120                 125

Val Gln Leu Val Glu Ser Gly Gly Leu Val Gln Pro Gly Gly Ser
    130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
```

```
            245                 250                 255
Ser Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
            275                 280                 285

Phe Thr Phe Ser Ser Tyr Ser Met Ser Trp Val Arg Gln Ala Pro Gly
            290                 295                 300

Lys Gly Leu Glu Trp Val Ser Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
            325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr
            355                 360                 365

Tyr Phe Asp Tyr Trp Gly Gln Gly Thr Leu Val Thr Val Ser Ser Ala
            370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                        405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
            435                 440                 445

Ser Ser Val Val Thr Val Pro Ser Ser Ser Leu Gly Thr Gln Thr Tyr
450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
            485                 490                 495

Ala Pro Glu Leu Leu Gly Gly Pro Asp Val Phe Leu Phe Pro Pro Lys
            500                 505                 510

Pro Lys Asp Thr Leu Met Ile Ser Arg Thr Pro Glu Val Thr Cys Val
            515                 520                 525

Val Val Asp Val Ser His Glu Asp Pro Glu Val Lys Phe Asn Trp Tyr
            530                 535                 540

Val Asp Gly Val Glu Val His Asn Ala Lys Thr Lys Pro Arg Glu Glu
545                 550                 555                 560

Gln Tyr Asn Ser Thr Tyr Arg Val Val Ser Val Leu Thr Val Leu His
            565                 570                 575

Gln Asp Trp Leu Asn Gly Lys Glu Tyr Lys Cys Lys Val Ser Asn Lys
            580                 585                 590

Ala Leu Pro Leu Pro Glu Glu Lys Thr Ile Ser Lys Ala Lys Gly Gln
            595                 600                 605

Pro Arg Glu Pro Gln Val Tyr Thr Leu Pro Pro Ser Arg Glu Glu Met
            610                 615                 620

Thr Lys Asn Gln Val Ser Leu Thr Cys Leu Val Lys Gly Phe Tyr Pro
625                 630                 635                 640

Ser Asp Ile Ala Val Glu Trp Glu Ser Asn Gly Gln Pro Glu Asn Asn
            645                 650                 655

Tyr Lys Thr Thr Pro Pro Val Leu Asp Ser Asp Gly Ser Phe Phe Leu
            660                 665                 670
```

Tyr Ser Lys Leu Thr Val Asp Lys Ser Arg Trp Gln Gln Gly Asn Val
        675                 680                 685

Phe Ser Cys Ser Val Met His Glu Ala Leu His Asn His Tyr Thr Gln
    690                 695                 700

Lys Ser Leu Ser Leu Ser Pro Gly Lys
705                 710

<210> SEQ ID NO 71
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Glu Ser Gly Gly Leu Val Gln Pro Gly Gly Ser
130                 135                 140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gly Gly Gly Gly Ser Glu Val Gln Leu Val Glu Ser Gly Gly Gly
            260                 265                 270

Leu Val Lys Pro Gly Gly Ser Leu Arg Leu Ser Cys Ala Ala Ser Gly
        275                 280                 285

Phe Thr Phe Ser Ser Tyr Ser Met Ser Trp Val Arg Gln Ala Pro Gly
    290                 295                 300

Lys Gly Leu Glu Trp Val Ser Ser Ile Ser Ser Ser Ser Ser Tyr Ile

```
            305                 310                 315                 320
Tyr Tyr Ala Asp Ser Val Lys Gly Arg Phe Thr Ile Ser Arg Asp Asn
                325                 330                 335

Ala Lys Asn Ser Leu Tyr Leu Gln Met Asn Ser Leu Arg Ala Glu Asp
                340                 345                 350

Thr Ala Val Tyr Tyr Cys Ala Arg Gly Gly Asp Ala Tyr Asn Tyr Tyr
                355                 360                 365

Tyr Phe Asp Tyr Trp Gly Gln Gly Thr Leu Val Thr Val Ser Ser Ala
                370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
                405                 410                 415

Pro Glu Pro Val Thr Val Ser Trp Asn Ser Gly Ala Leu Thr Ser Gly
                420                 425                 430

Val His Thr Phe Pro Ala Val Leu Gln Ser Ser Gly Leu Tyr Ser Leu
                435                 440                 445

Ser Ser Val Val Thr Val Pro Ser Ser Ser Leu Gly Thr Gln Thr Tyr
                450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
                485                 490                 495

Ala Pro Glu Leu Leu Gly Gly Pro Ser Cys Val Phe Leu Phe Pro Pro
                500                 505                 510

Lys Pro Lys Asp Thr Leu Met Ile Ser Arg Thr Pro Glu Val Thr Cys
                515                 520                 525

Val Val Val Asp Val Ser His Glu Asp Pro Glu Val Lys Phe Asn Trp
                530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
                580                 585                 590

Lys Ala Leu Pro Ala Pro Ile Glu Lys Thr Ile Ser Lys Ala Lys Gly
                595                 600                 605

Gln Pro Arg Glu Pro Gln Val Tyr Thr Leu Pro Pro Ser Arg Glu Glu
                610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
                660                 665                 670

Leu Tyr Ser Lys Leu Thr Val Asp Lys Ser Arg Trp Gln Gln Gly Asn
                675                 680                 685

Val Phe Ser Cys Ser Val Met His Glu Ala Leu His Asn His Tyr Thr
                690                 695                 700

Gln Lys Ser Leu Cys Leu Ser Pro Gly Lys
705                 710

<210> SEQ ID NO 72
```

```
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
```

```
                370                 375                 380
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Gly Gly Gly
    450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
        515                 520                 525

Ser Gly Ser Arg Ser Gly Thr Asp Phe Thr Leu Thr Ile Ser Ser Leu
    530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
                565                 570                 575

Gly Ser Gly Gly Gly Gly Ser Gly Gly Gly Gly Ser Gly Gly Gly Gly
            580                 585                 590

Ser Glu Val Gln Leu Val Glu Ser Gly Gly Gly Leu Val Gln Pro Gly
        595                 600                 605

Gly Ser Leu Arg Leu Ser Cys Ala Ala Ser Gly Phe Asn Ile Lys Asp
    610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                645                 650                 655

Val Lys Gly Arg Phe Thr Ile Ser Ala Asp Thr Ser Lys Asn Thr Ala
            660                 665                 670

Tyr Leu Gln Met Asn Ser Leu Arg Ala Glu Asp Thr Ala Val Tyr Tyr
        675                 680                 685

Cys Ser Arg Trp Gly Gly Asp Gly Phe Tyr Ala Met Asp Tyr Trp Gly
    690                 695                 700

Gln Gly Thr Leu Val Thr Val Ser Ser
705                 710

<210> SEQ ID NO 73
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Ser Tyr
         20                  25                  30
Ser Met Ser Trp Val Arg Gln Ala Pro Gly Lys Gly Leu Glu Trp Val
             35                  40                  45
Ser Ser Ile Ser Ser Ser Ser Tyr Ile Tyr Tyr Ala Asp Ser Val
 50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                 85                  90                  95
Ala Arg Gly Gly Asp Ala Tyr Asn Tyr Tyr Phe Asp Tyr Trp Gly
                100                 105                 110
Gln Gly Thr Leu Val Thr Val Ser Ser Ala Ser Thr Lys Gly Pro Ser
            115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
210                 215                 220
Asp Lys Thr His Thr Cys Pro Pro Cys Pro Ala Pro Glu Leu Leu Gly
225                 230                 235                 240
Gly Pro Asp Val Phe Leu Phe Pro Pro Lys Pro Lys Asp Thr Leu Met
                245                 250                 255
Ile Ser Arg Thr Pro Glu Val Thr Cys Val Val Val Asp Val Ser His
            260                 265                 270
Glu Asp Pro Glu Val Lys Phe Asn Trp Tyr Val Asp Gly Val Glu Val
        275                 280                 285
His Asn Ala Lys Thr Lys Pro Arg Glu Glu Gln Tyr Asn Ser Thr Tyr
290                 295                 300
Arg Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Glu
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Glu Glu Met Thr Lys Asn Gln Val Ser
        355                 360                 365
Leu Thr Cys Leu Val Lys Gly Phe Tyr Pro Ser Asp Ile Ala Val Glu
370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                405                 410                 415
Asp Lys Ser Arg Trp Gln Gln Gly Asn Val Phe Ser Cys Ser Val Met
            420                 425                 430
His Glu Ala Leu His Asn His Tyr Thr Gln Lys Ser Leu Ser Leu Ser
```

```
                435                 440                 445
Pro Gly Lys Gly Gly Gly Ser Gly Gly Gly Ser Gly Gly Gly
    450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
        515                 520                 525

Ser Gly Ser Arg Ser Gly Thr Asp Phe Thr Leu Thr Ile Ser Ser Leu
    530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
                565                 570                 575

Gly Ser Gly Gly Gly Gly Ser Gly Gly Gly Gly Ser Gly Gly Gly Gly
            580                 585                 590

Ser Glu Val Gln Leu Val Glu Ser Gly Gly Gly Leu Val Gln Pro Gly
        595                 600                 605

Gly Ser Leu Arg Leu Ser Cys Ala Ala Ser Gly Phe Asn Ile Lys Asp
    610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                645                 650                 655

Val Lys Gly Arg Phe Thr Ile Ser Ala Asp Thr Ser Lys Asn Thr Ala
            660                 665                 670

Tyr Leu Gln Met Asn Ser Leu Arg Ala Glu Asp Thr Ala Val Tyr Tyr
        675                 680                 685

Cys Ser Arg Trp Gly Gly Asp Gly Phe Tyr Ala Met Asp Tyr Trp Gly
    690                 695                 700

Gln Gly Thr Leu Val Thr Val Ser Ser
705                 710

<210> SEQ ID NO 74
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80
```

```
Leu Gln Met Asn Ser Leu Arg Ala Glu Asp Thr Ala Val Tyr Tyr Cys
                    85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Cys Val Phe Leu Phe Pro Pro Lys Pro Lys Asp Thr Leu
                245                 250                 255

Met Ile Ser Arg Thr Pro Glu Val Thr Cys Val Val Val Asp Val Ser
                260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Lys Gly Gly Gly Ser Gly Gly Gly Ser Gly Gly
    450                 455                 460

Gly Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Gln Asp Val
                485                 490                 495

Asn Thr Ala Val Ala Trp Tyr Gln Gln Lys Pro Gly Lys Ala Pro Lys
```

```
                500             505             510
Leu Leu Ile Tyr Ser Ala Ser Phe Leu Tyr Ser Gly Val Pro Ser Arg
        515             520             525

Phe Ser Gly Ser Arg Ser Gly Thr Asp Phe Thr Leu Thr Ile Ser Ser
    530             535             540

Leu Gln Pro Glu Asp Phe Ala Thr Tyr Tyr Cys Gln Gln His Tyr Thr
545             550             555             560

Thr Pro Pro Thr Phe Gly Cys Gly Thr Lys Val Glu Ile Lys Gly Gly
                565             570             575

Gly Gly Ser Gly Gly Gly Gly Ser Gly Gly Gly Ser Gly Gly Gly
            580             585             590

Gly Ser Glu Val Gln Leu Val Glu Ser Gly Gly Leu Val Gln Pro
        595             600             605

Gly Gly Ser Leu Arg Leu Ser Cys Ala Ala Ser Gly Phe Asn Ile Lys
        610             615             620

Asp Thr Tyr Ile His Trp Val Arg Gln Ala Pro Gly Lys Cys Leu Glu
625             630             635             640

Trp Val Ala Arg Ile Tyr Pro Thr Asn Gly Tyr Thr Arg Tyr Ala Asp
                645             650             655

Ser Val Lys Gly Arg Phe Thr Ile Ser Ala Asp Thr Ser Lys Asn Thr
                660             665             670

Ala Tyr Leu Gln Met Asn Ser Leu Arg Ala Glu Asp Thr Ala Val Tyr
            675             680             685

Tyr Cys Ser Arg Trp Gly Gly Asp Gly Phe Tyr Ala Met Asp Tyr Trp
        690             695             700

Gly Gln Gly Thr Leu Val Thr Val Ser Ser
705             710

<210> SEQ ID NO 75
<211> LENGTH: 713
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
            85                  90                  95

Ala Arg Gly Gly Asp Ala Tyr Asn Tyr Tyr Phe Asp Tyr Trp Gly
        100                 105                 110

Gln Gly Thr Leu Val Thr Val Ser Ser Ala Ser Thr Lys Gly Pro Ser
    115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Asp Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Leu Pro Glu
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys Gly Gly Gly Ser Gly Gly Gly Ser Gly Gly Gly
    450                 455                 460

Gly Ser Asp Ile Gln Met Thr Gln Ser Pro Ser Ser Leu Ser Ala Ser
465                 470                 475                 480

Val Gly Asp Arg Val Thr Ile Thr Cys Arg Ala Ser Gln Asp Val Asn
                485                 490                 495

Thr Ala Val Ala Trp Tyr Gln Gln Lys Pro Gly Lys Ala Pro Lys Leu
            500                 505                 510

Leu Ile Tyr Ser Ala Ser Phe Leu Tyr Ser Gly Val Pro Ser Arg Phe
        515                 520                 525

Ser Gly Ser Arg Ser Gly Thr Asp Phe Thr Leu Thr Ile Ser Ser Leu
    530                 535                 540

Gln Pro Glu Asp Phe Ala Thr Tyr Tyr Cys Gln Gln His Tyr Thr Thr
545                 550                 555                 560

Pro Pro Thr Phe Gly Cys Gly Thr Lys Val Glu Ile Lys Gly Gly Gly
```

```
                          565                 570                 575
Gly Ser Gly Gly Gly Ser Gly Gly Gly Ser Gly Gly Gly
            580                 585                 590

Ser Glu Val Gln Leu Val Glu Ser Gly Gly Leu Val Gln Pro Gly
            595                 600                 605

Gly Ser Leu Arg Leu Ser Cys Ala Ala Ser Gly Phe Asn Ile Lys Asp
            610                 615                 620

Thr Tyr Ile His Trp Val Arg Gln Ala Pro Gly Lys Cys Leu Glu Trp
625                 630                 635                 640

Val Ala Arg Ile Tyr Pro Thr Asn Gly Tyr Thr Arg Tyr Ala Asp Ser
                    645                 650                 655

Val Lys Gly Arg Phe Thr Ile Ser Ala Asp Thr Ser Lys Asn Thr Ala
                    660                 665                 670

Tyr Leu Gln Met Asn Ser Leu Arg Ala Glu Asp Thr Ala Val Tyr Tyr
                    675                 680                 685

Cys Ser Arg Trp Gly Gly Asp Gly Phe Tyr Ala Met Asp Tyr Trp Gly
                    690                 695                 700

Gln Gly Thr Leu Val Thr Val Ser Ser
705                 710

<210> SEQ ID NO 76
<211> LENGTH: 714
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Cys Val Phe Leu Phe Pro Pro Lys Pro Lys Asp Thr Leu
            245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
                275                 280                 285

Val His Asn Ala Lys Thr Lys Pro Arg Glu Glu Gln Tyr Asn Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Glu Glu Met Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Cys Leu
            435                 440                 445

Ser Pro Gly Lys Gly Gly Gly Ser Gly Gly Gly Ser Gly Gly Gly Gly
450                 455                 460

Gly Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Gln Asp Val
                485                 490                 495

Asn Thr Ala Val Ala Trp Tyr Gln Gln Lys Pro Gly Lys Ala Pro Lys
            500                 505                 510

Leu Leu Ile Tyr Ser Ala Ser Phe Leu Tyr Ser Gly Val Pro Ser Arg
            515                 520                 525

Phe Ser Gly Ser Arg Ser Gly Thr Asp Phe Thr Leu Thr Ile Ser Ser
530                 535                 540

Leu Gln Pro Glu Asp Phe Ala Thr Tyr Tyr Cys Gln Gln His Tyr Thr
545                 550                 555                 560

Thr Pro Pro Thr Phe Gly Cys Gly Thr Lys Val Glu Ile Lys Gly Gly
                565                 570                 575

Gly Gly Ser Gly Gly Gly Gly Ser Gly Gly Gly Gly Ser Gly Gly Gly
            580                 585                 590

Gly Ser Glu Val Gln Leu Val Glu Ser Gly Gly Gly Leu Val Gln Pro
            595                 600                 605

Gly Gly Ser Leu Arg Leu Ser Cys Ala Ala Ser Gly Phe Asn Ile Lys
            610                 615                 620

Asp Thr Tyr Ile His Trp Val Arg Gln Ala Pro Gly Lys Cys Leu Glu
```

```
                625                 630                 635                 640
Trp Val Ala Arg Ile Tyr Pro Thr Asn Gly Tyr Thr Arg Tyr Ala Asp
                    645                 650                 655
Ser Val Lys Gly Arg Phe Thr Ile Ser Ala Asp Thr Ser Lys Asn Thr
                660                 665                 670
Ala Tyr Leu Gln Met Asn Ser Leu Arg Ala Glu Asp Thr Ala Val Tyr
            675                 680                 685
Tyr Cys Ser Arg Trp Gly Gly Asp Gly Phe Tyr Ala Met Asp Tyr Trp
        690                 695                 700
Gly Gln Gly Thr Leu Val Thr Val Ser Ser
705                 710

<210> SEQ ID NO 77
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

Glu Val Gln Leu Val Glu Ser Gly Gly Gly Leu Val Lys Pro Gly Gly
1               5                   10                  15
Ser Leu Arg Leu Ser Cys Ala Ala Ser Gly Phe Thr Phe Ser Ser Tyr
            20                  25                  30
Ser Met Ser Trp Val Arg Gln Ala Pro Gly Lys Gly Leu Glu Trp Val
        35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Asp Ala Tyr Asn Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Gly Lys Thr Gly Gly Gly Gly Ser Gly Gly Gly Gly Ser Asp Ile Gln
225                 230                 235                 240
Met Thr Gln Ser Pro Ser Ser Leu Ser Ala Ser Val Gly Asp Arg Val
                245                 250                 255
Thr Ile Thr Cys Arg Ala Ser Gln Asp Val Asn Thr Ala Val Ala Trp
            260                 265                 270
```

```
Tyr Gln Gln Lys Pro Gly Lys Ala Pro Lys Leu Leu Ile Tyr Ser Ala
            275                 280                 285

Ser Phe Leu Tyr Ser Gly Val Pro Ser Arg Phe Ser Gly Ser Arg Ser
        290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Ser Gly Gly Gly
            340                 345                 350

Gly Ser Gly Gly Gly Gly Ser Gly Gly Gly Gly Ser Glu Val Gln Leu
        355                 360                 365

Val Glu Ser Gly Gly Gly Leu Val Gln Pro Gly Gly Ser Leu Arg Leu
370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
        435                 440                 445

Ser Leu Arg Ala Glu Asp Thr Ala Val Tyr Tyr Cys Ser Arg Trp Gly
450                 455                 460

Gly Asp Gly Phe Tyr Ala Met Asp Tyr Trp Gly Gln Gly Thr Leu Val
465                 470                 475                 480

Thr Val Ser Ser Gly Gly Gly Gly Ser Gly Gly Gly Gly Ser Cys
                485                 490                 495

Pro Pro Cys Pro Ala Pro Glu Leu Leu Gly Gly Pro Ser Val Phe Leu
            500                 505                 510

Phe Pro Pro Lys Pro Lys Asp Thr Leu Met Ile Ser Arg Thr Pro Glu
        515                 520                 525

Val Thr Cys Val Val Val Asp Val Ser His Glu Asp Pro Glu Val Lys
530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
                565                 570                 575

Thr Val Leu His Gln Asp Trp Leu Asn Gly Lys Glu Tyr Lys Cys Lys
            580                 585                 590

Val Ser Asn Lys Ala Leu Pro Ala Pro Glu Lys Thr Ile Ser Lys
        595                 600                 605

Ala Lys Gly Gln Pro Arg Glu Pro Gln Val Tyr Thr Leu Pro Pro Ser
610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
            660                 665                 670

Ser Phe Phe Leu Tyr Ser Lys Leu Thr Val Asp Lys Ser Arg Trp Gln
        675                 680                 685

Gln Gly Asn Val Phe Ser Cys Ser Val Met His Glu Ala Leu His Asn
```

```
                690                 695                 700
His Tyr Thr Gln Lys Ser Leu Ser Leu Ser Pro Gly Lys
705                 710                 715

<210> SEQ ID NO 78
<211> LENGTH: 717
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Lys Thr Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
    290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335
```

```
Cys Gly Thr Lys Val Glu Ile Lys Gly Gly Ser Gly Gly
                340                 345                 350

Gly Ser Gly Gly Gly Ser Gly Gly Gly Ser Glu Val Gln Leu
            355                 360                 365

Val Glu Ser Gly Gly Gly Leu Val Gln Pro Gly Gly Ser Leu Arg Leu
370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
                420                 425                 430

Thr Ile Ser Ala Asp Thr Ser Lys Asn Thr Ala Tyr Leu Gln Met Asn
                435                 440                 445

Ser Leu Arg Ala Glu Asp Thr Ala Val Tyr Tyr Cys Ser Arg Trp Gly
    450                 455                 460

Gly Asp Gly Phe Tyr Ala Met Asp Tyr Trp Gly Gln Gly Thr Leu Val
465                 470                 475                 480

Thr Val Ser Ser Ser Gly Gly Gly Ser Gly Gly Gly Gly Ser Cys
                485                 490                 495

Pro Pro Cys Pro Ala Pro Glu Leu Leu Gly Gly Pro Asp Val Phe Leu
                500                 505                 510

Phe Pro Pro Lys Pro Lys Asp Thr Leu Met Ile Ser Arg Thr Pro Glu
                515                 520                 525

Val Thr Cys Val Val Val Asp Val Ser His Glu Asp Pro Glu Val Lys
530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
                565                 570                 575

Thr Val Leu His Gln Asp Trp Leu Asn Gly Lys Glu Tyr Lys Cys Lys
                580                 585                 590

Val Ser Asn Lys Ala Leu Pro Ala Pro Glu Glu Lys Thr Ile Ser Lys
                595                 600                 605

Ala Lys Gly Gln Pro Arg Glu Pro Gln Val Tyr Thr Leu Pro Pro Ser
610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
                645                 650                 655

Pro Glu Asn Asn Tyr Lys Thr Thr Pro Pro Val Leu Asp Ser Asp Gly
                660                 665                 670

Ser Phe Phe Leu Tyr Ser Lys Leu Thr Val Asp Lys Ser Arg Trp Gln
                675                 680                 685

Gln Gly Asn Val Phe Ser Cys Ser Val Met His Glu Ala Leu His Asn
690                 695                 700

His Tyr Thr Gln Lys Ser Leu Ser Leu Ser Pro Gly Lys
705                 710                 715

<210> SEQ ID NO 79
<211> LENGTH: 718
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 79

```
Glu Val Gln Leu Val Glu Ser Gly Gly Gly Leu Val Lys Pro Gly Gly
 1               5                  10                  15
Ser Leu Arg Leu Ser Cys Ala Ala Ser Gly Phe Thr Phe Ser Ser Tyr
            20                  25                  30
Ser Met Ser Trp Val Arg Gln Ala Pro Gly Lys Gly Leu Glu Trp Val
        35                  40                  45
Ser Ser Ile Ser Ser Ser Ser Tyr Ile Tyr Tyr Ala Asp Ser Val
    50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Val Tyr Tyr Cys
                85                  90                  95
Ala Arg Gly Gly Asp Ala Tyr Asn Tyr Tyr Phe Asp Tyr Trp Gly
            100                 105                 110
Gln Gly Thr Leu Val Thr Val Ser Ser Ala Ser Thr Lys Gly Pro Ser
        115                 120                 125
Val Phe Pro Leu Ala Pro Ser Ser Lys Ser Thr Ser Gly Gly Thr Ala
    130                 135                 140
Ala Leu Gly Cys Leu Val Lys Asp Tyr Phe Pro Glu Pro Val Thr Val
145                 150                 155                 160
Ser Trp Asn Ser Gly Ala Leu Thr Ser Gly Val His Thr Phe Pro Ala
                165                 170                 175
Val Leu Gln Ser Ser Gly Leu Tyr Ser Leu Ser Ser Val Val Thr Val
            180                 185                 190
Pro Ser Ser Ser Leu Gly Thr Gln Thr Tyr Ile Cys Asn Val Asn His
        195                 200                 205
Lys Pro Ser Asn Thr Lys Val Asp Lys Arg Val Glu Pro Lys Ser Cys
    210                 215                 220
Gly Lys Thr Gly Gly Gly Gly Ser Gly Gly Gly Ser Asp Ile Gln
225                 230                 235                 240
Met Thr Gln Ser Pro Ser Ser Leu Ser Ala Ser Val Gly Asp Arg Val
                245                 250                 255
Thr Ile Thr Cys Arg Ala Ser Gln Asp Val Asn Thr Ala Val Ala Trp
            260                 265                 270
Tyr Gln Gln Lys Pro Gly Lys Ala Pro Lys Leu Leu Ile Tyr Ser Ala
        275                 280                 285
Ser Phe Leu Tyr Ser Gly Val Pro Ser Arg Phe Ser Gly Ser Arg Ser
    290                 295                 300
Gly Thr Asp Phe Thr Leu Thr Ile Ser Ser Leu Gln Pro Glu Asp Phe
305                 310                 315                 320
Ala Thr Tyr Tyr Cys Gln Gln His Tyr Thr Thr Pro Pro Thr Phe Gly
                325                 330                 335
Cys Gly Thr Lys Val Glu Ile Lys Gly Gly Gly Ser Gly Gly
            340                 345                 350
Gly Ser Gly Gly Gly Gly Ser Gly Gly Gly Gly Ser Glu Val Gln Leu
        355                 360                 365
Val Glu Ser Gly Gly Gly Leu Val Gln Pro Gly Gly Ser Leu Arg Leu
    370                 375                 380
Ser Cys Ala Ala Ser Gly Phe Asn Ile Lys Asp Thr Tyr Ile His Trp
385                 390                 395                 400
```

-continued

```
Val Arg Gln Ala Pro Gly Lys Cys Leu Glu Trp Val Arg Ile Tyr
            405                 410                 415

Pro Thr Asn Gly Tyr Thr Arg Tyr Ala Asp Ser Val Lys Gly Arg Phe
        420                 425                 430

Thr Ile Ser Ala Asp Thr Ser Lys Asn Thr Ala Tyr Leu Gln Met Asn
    435                 440                 445

Ser Leu Arg Ala Glu Asp Thr Ala Val Tyr Tyr Cys Ser Arg Trp Gly
450                 455                 460

Gly Asp Gly Phe Tyr Ala Met Asp Tyr Trp Gly Gln Gly Thr Leu Val
465                 470                 475                 480

Thr Val Ser Ser Gly Gly Gly Gly Ser Gly Gly Gly Gly Ser Cys
            485                 490                 495

Pro Pro Cys Pro Ala Pro Glu Leu Leu Gly Gly Pro Ser Cys Val Phe
            500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
            530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
            565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
            595                 600                 605

Lys Ala Lys Gly Gln Pro Arg Glu Pro Gln Val Tyr Thr Leu Pro Pro
610                 615                 620

Ser Arg Glu Glu Met Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
            645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
            690                 695                 700

Asn His Tyr Thr Gln Lys Ser Leu Ser Leu Ser Pro Gly Lys
705                 710                 715
```

<210> SEQ ID NO 80
<211> LENGTH: 717
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 80

```
Glu Val Gln Leu Val Glu Ser Gly Gly Gly Leu Val Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45
```

```
Ser Ser Ile Ser Ser Ser Ser Tyr Ile Tyr Tyr Ala Asp Ser Val
    50              55              60

Lys Gly Arg Phe Thr Ile Ser Arg Asp Asn Ala Lys Asn Ser Leu Tyr
 65              70              75              80

Leu Gln Met Asn Ser Leu Arg Ala Glu Asp Thr Ala Val Tyr Tyr Cys
            85              90              95

Ala Arg Gly Gly Asp Ala Tyr Asn Tyr Tyr Phe Asp Tyr Trp Gly
        100             105             110

Gln Gly Thr Leu Val Thr Val Ser Ala Ser Thr Lys Gly Pro Ser
        115             120             125

Val Phe Pro Leu Ala Pro Ser Ser Lys Ser Thr Ser Gly Gly Thr Ala
130             135             140

Ala Leu Gly Cys Leu Val Lys Asp Tyr Phe Pro Glu Pro Val Thr Val
145             150             155             160

Ser Trp Asn Ser Gly Ala Leu Thr Ser Gly Val His Thr Phe Pro Ala
                165             170             175

Val Leu Gln Ser Ser Gly Leu Tyr Ser Leu Ser Ser Val Val Thr Val
            180             185             190

Pro Ser Ser Ser Leu Gly Thr Gln Thr Tyr Ile Cys Asn Val Asn His
        195             200             205

Lys Pro Ser Asn Thr Lys Val Asp Lys Arg Val Glu Pro Lys Ser Cys
210             215             220

Gly Lys Thr Gly Gly Gly Gly Ser Gly Gly Gly Ser Asp Ile Gln
225             230             235             240

Met Thr Gln Ser Pro Ser Ser Leu Ser Ala Ser Val Gly Asp Arg Val
                245             250             255

Thr Ile Thr Cys Arg Ala Ser Gln Asp Val Asn Thr Ala Val Ala Trp
            260             265             270

Tyr Gln Gln Lys Pro Gly Lys Ala Pro Lys Leu Leu Ile Tyr Ser Ala
        275             280             285

Ser Phe Leu Tyr Ser Gly Val Pro Ser Arg Phe Ser Gly Ser Arg Ser
        290             295             300

Gly Thr Asp Phe Thr Leu Thr Ile Ser Ser Leu Gln Pro Glu Asp Phe
305             310             315             320

Ala Thr Tyr Tyr Cys Gln Gln His Tyr Thr Thr Pro Pro Thr Phe Gly
                325             330             335

Cys Gly Thr Lys Val Glu Ile Lys Gly Gly Gly Ser Gly Gly Gly
            340             345             350

Gly Ser Gly Gly Gly Ser Gly Gly Gly Ser Glu Val Gln Leu
        355             360             365

Val Glu Ser Gly Gly Gly Leu Val Gln Pro Gly Gly Ser Leu Arg Leu
370             375             380

Ser Cys Ala Ala Ser Gly Phe Asn Ile Lys Asp Thr Tyr Ile His Trp
385             390             395             400

Val Arg Gln Ala Pro Gly Lys Cys Leu Glu Trp Val Ala Arg Ile Tyr
                405             410             415

Pro Thr Asn Gly Tyr Thr Arg Tyr Ala Asp Ser Val Lys Gly Arg Phe
            420             425             430

Thr Ile Ser Ala Asp Thr Ser Lys Asn Thr Ala Tyr Leu Gln Met Asn
        435             440             445

Ser Leu Arg Ala Glu Asp Thr Ala Val Tyr Tyr Cys Ser Arg Trp Gly
450             455             460
```

Gly Asp Gly Phe Tyr Ala Met Asp Tyr Trp Gly Gln Gly Thr Leu Val
465                 470                 475                 480

Thr Val Ser Ser Ser Gly Gly Gly Gly Ser Gly Gly Gly Gly Ser Cys
            485                 490                 495

Pro Pro Cys Pro Ala Pro Glu Leu Leu Gly Gly Pro Asp Val Phe Leu
        500                 505                 510

Phe Pro Pro Lys Pro Lys Asp Thr Leu Met Ile Ser Arg Thr Pro Glu
    515                 520                 525

Val Thr Cys Val Val Val Asp Val Ser His Glu Asp Pro Glu Val Lys
        530                 535                 540

Phe Asn Trp Tyr Val Asp Gly Val Glu Val His Asn Ala Lys Thr Lys
545                 550                 555                 560

Pro Arg Glu Glu Gln Tyr Asn Ser Thr Tyr Arg Val Val Ser Val Leu
            565                 570                 575

Thr Val Leu His Gln Asp Trp Leu Asn Gly Lys Glu Tyr Lys Cys Lys
        580                 585                 590

Val Ser Asn Lys Ala Leu Pro Leu Pro Glu Lys Thr Ile Ser Lys
            595                 600                 605

Ala Lys Gly Gln Pro Arg Glu Pro Gln Val Tyr Thr Leu Pro Pro Ser
610                 615                 620

Arg Glu Glu Met Thr Lys Asn Gln Val Ser Leu Thr Cys Leu Val Lys
625                 630                 635                 640

Gly Phe Tyr Pro Ser Asp Ile Ala Val Glu Trp Glu Ser Asn Gly Gln
            645                 650                 655

Pro Glu Asn Asn Tyr Lys Thr Thr Pro Pro Val Leu Asp Ser Asp Gly
        660                 665                 670

Ser Phe Phe Leu Tyr Ser Lys Leu Thr Val Asp Lys Ser Arg Trp Gln
    675                 680                 685

Gln Gly Asn Val Phe Ser Cys Ser Val Met His Glu Ala Leu His Asn
690                 695                 700

His Tyr Thr Gln Lys Ser Leu Ser Leu Ser Pro Gly Lys
705                 710                 715

<210> SEQ ID NO 81
<211> LENGTH: 718
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Tyr Phe Asp Tyr Trp Gly
            100                 105                 110

-continued

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Lys Thr Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
    290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Gly Ser Gly Gly Gly
            340                 345                 350

Gly Ser Gly Gly Gly Gly Ser Gly Gly Gly Gly Ser Glu Val Gln Leu
        355                 360                 365

Val Glu Ser Gly Gly Gly Leu Val Gln Pro Gly Gly Ser Leu Arg Leu
    370                 375                 380

Ser Cys Ala Ala Ser Gly Phe Asn Ile Lys Asp Thr Tyr Ile His Trp
385                 390                 395                 400

Val Arg Gln Ala Pro Gly Lys Cys Leu Glu Trp Val Ala Arg Ile Tyr
                405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
        435                 440                 445

Ser Leu Arg Ala Glu Asp Thr Ala Val Tyr Tyr Cys Ser Arg Trp Gly
    450                 455                 460

Gly Asp Gly Phe Tyr Ala Met Asp Tyr Trp Gly Gln Gly Thr Leu Val
465                 470                 475                 480

Thr Val Ser Ser Ser Gly Gly Gly Gly Ser Gly Gly Gly Gly Ser Cys
                485                 490                 495

Pro Pro Cys Pro Ala Pro Glu Leu Leu Gly Gly Pro Ser Cys Val Phe
            500                 505                 510

Leu Phe Pro Pro Lys Pro Lys Asp Thr Leu Met Ile Ser Arg Thr Pro
        515                 520                 525

```
Glu Val Thr Cys Val Val Asp Val Ser His Glu Asp Pro Glu Val
            530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Ala Pro Ile Glu Lys Thr Ile Ser
                595                 600                 605

Lys Ala Lys Gly Gln Pro Arg Glu Pro Gln Val Tyr Thr Leu Pro Pro
610                 615                 620

Ser Arg Glu Glu Met Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
                660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
690                 695                 700

Asn His Tyr Thr Gln Lys Ser Leu Cys Leu Ser Pro Gly Lys
705                 710                 715

<210> SEQ ID NO 82
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Val Phe Phe Arg
            20                  25                  30

Ser Asn Asn Lys Asn Ile Leu Ala Trp Tyr Leu Gln Lys Pro Gly Gln
        35                  40                  45

Pro Pro Gln Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Gln Gln
                85                  90                  95

Tyr Phe Gly Ser Pro Phe Thr Phe Gly Pro Gly Thr Lys Val Asp Ile
            100                 105                 110

Lys Gln Pro Lys Ala Ala Pro Ser Val Thr Leu Phe Pro Pro Ser Ser
        115                 120                 125

Glu Glu Leu Gln Ala Asn Lys Ala Thr Leu Val Cys Leu Ile Ser Asp
    130                 135                 140

Phe Tyr Pro Gly Ala Val Thr Val Ala Trp Lys Ala Asp Ser Ser Pro
145                 150                 155                 160

Val Lys Ala Gly Val Glu Thr Thr Thr Pro Ser Lys Gln Ser Asn Asn
                165                 170                 175
```

```
Lys Tyr Ala Ala Ser Ser Tyr Leu Ser Leu Thr Pro Glu Gln Trp Lys
            180                 185                 190

Ser His Arg Ser Tyr Ser Cys Gln Val Thr His Glu Gly Ser Thr Val
        195                 200                 205

Glu Lys Thr Val Ala Pro Thr Glu Cys
    210                 215

<210> SEQ ID NO 83
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Gly Gly Gly Ser Gly Gly Gly Gly Ser
1               5                   10

<210> SEQ ID NO 84
<211> LENGTH: 714
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (500)..(500)
<223> OTHER INFORMATION: Leu or Phe
<220> FEATURE:
<221> NAME/KEY: MOD_RES
<222> LOCATION: (505)..(505)
<223> OTHER INFORMATION: Ser, Asp or Cys
<220> FEATURE:
<221> NAME/KEY: misc_feature
<222> LOCATION: (506)..(506)
<223> OTHER INFORMATION: May or may not be present
<220> FEATURE:
<221> NAME/KEY: MOD_RES
<222> LOCATION: (597)..(597)
<223> OTHER INFORMATION: Ala or Leu
<220> FEATURE:
<221> NAME/KEY: MOD_RES
<222> LOCATION: (599)..(599)
<223> OTHER INFORMATION: Ile or Glu
<220> FEATURE:
<221> NAME/KEY: MOD_RES
<222> LOCATION: (709)..(709)
<223> OTHER INFORMATION: Ser or Cys

<400> SEQUENCE: 84

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Val Glu Ile Lys Gly Gly Gly Gly Ser
            100                 105                 110
```

Gly Gly Gly Gly Ser Gly Gly Gly Ser Gly Gly Gly Ser Glu
            115                 120             125

Val Gln Leu Val Glu Ser Gly Gly Leu Val Gln Pro Gly Gly Ser
        130                 135             140

Leu Arg Leu Ser Cys Ala Ala Ser Gly Phe Asn Ile Lys Asp Thr Tyr
145                 150                 155                 160

Ile His Trp Val Arg Gln Ala Pro Gly Lys Cys Leu Glu Trp Val Ala
                165                 170                 175

Arg Ile Tyr Pro Thr Asn Gly Tyr Thr Arg Tyr Ala Asp Ser Val Lys
            180                 185                 190

Gly Arg Phe Thr Ile Ser Ala Asp Thr Ser Lys Asn Thr Ala Tyr Leu
        195                 200                 205

Gln Met Asn Ser Leu Arg Ala Glu Asp Thr Ala Val Tyr Tyr Cys Ser
    210                 215                 220

Arg Trp Gly Gly Asp Gly Phe Tyr Ala Met Asp Tyr Trp Gly Gln Gly
225                 230                 235                 240

Thr Leu Val Thr Val Ser Ser Gly Gly Gly Ser Gly Gly Gly Gly
            245                 250                 255

Ser Gly Gly Gly Gly Ser Glu Val Gln Leu Val Glu Ser Gly Gly Gly
        260                 265                 270

Leu Val Lys Pro Gly Gly Ser Leu Arg Leu Ser Cys Ala Ala Ser Gly
    275                 280                 285

Phe Thr Phe Ser Ser Tyr Ser Met Ser Trp Val Arg Gln Ala Pro Gly
    290                 295                 300

Lys Gly Leu Glu Trp Val Ser Ser Ile Ser Ser Ser Ser Ser Tyr Ile
305                 310                 315                 320

Tyr Tyr Ala Asp Ser Val Lys Gly Arg Phe Thr Ile Ser Arg Asp Asn
            325                 330                 335

Ala Lys Asn Ser Leu Tyr Leu Gln Met Asn Ser Leu Arg Ala Glu Asp
            340                 345                 350

Thr Ala Val Tyr Tyr Cys Ala Arg Gly Gly Asp Ala Tyr Asn Tyr Tyr
        355                 360                 365

Tyr Phe Asp Tyr Trp Gly Gln Gly Thr Leu Val Thr Val Ser Ser Ala
    370                 375                 380

Ser Thr Lys Gly Pro Ser Val Phe Pro Leu Ala Pro Ser Ser Lys Ser
385                 390                 395                 400

Thr Ser Gly Gly Thr Ala Ala Leu Gly Cys Leu Val Lys Asp Tyr Phe
            405                 410                 415

Pro Glu Pro Val Thr Val Ser Trp Asn Ser Gly Ala Leu Thr Ser Gly
            420                 425                 430

Val His Thr Phe Pro Ala Val Leu Gln Ser Ser Gly Leu Tyr Ser Leu
        435                 440                 445

Ser Ser Val Val Thr Val Pro Ser Ser Ser Leu Gly Thr Gln Thr Tyr
    450                 455                 460

Ile Cys Asn Val Asn His Lys Pro Ser Asn Thr Lys Val Asp Lys Arg
465                 470                 475                 480

Val Glu Pro Lys Ser Cys Asp Lys Thr His Thr Cys Pro Pro Cys Pro
            485                 490                 495

Ala Pro Glu Xaa Leu Gly Gly Pro Xaa Cys Val Phe Leu Phe Pro Pro
            500                 505                 510

Lys Pro Lys Asp Thr Leu Met Ile Ser Arg Thr Pro Glu Val Thr Cys
        515                 520                 525

```
Val Val Val Asp Val Ser His Glu Asp Pro Glu Val Lys Phe Asn Trp
        530                 535                 540

Tyr Val Asp Gly Val Glu Val His Asn Ala Lys Thr Lys Pro Arg Glu
545                 550                 555                 560

Glu Gln Tyr Asn Ser Thr Tyr Arg Val Val Ser Val Leu Thr Val Leu
                565                 570                 575

His Gln Asp Trp Leu Asn Gly Lys Glu Tyr Lys Cys Lys Val Ser Asn
            580                 585                 590

Lys Ala Leu Pro Xaa Pro Xaa Glu Lys Thr Ile Ser Lys Ala Lys Gly
        595                 600                 605

Gln Pro Arg Glu Pro Gln Val Tyr Thr Leu Pro Pro Ser Arg Glu Glu
    610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Val Leu Asp Ser Asp Gly Ser Phe Phe
            660                 665                 670

Leu Tyr Ser Lys Leu Thr Val Asp Lys Ser Arg Trp Gln Gln Gly Asn
        675                 680                 685

Val Phe Ser Cys Ser Val Met His Glu Ala Leu His Asn His Tyr Thr
690                 695                 700

Gln Lys Ser Leu Xaa Leu Ser Pro Gly Lys
705                 710

<210> SEQ ID NO 85
<211> LENGTH: 714
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (238)..(238)
<223> OTHER INFORMATION: Leu or Phe
<220> FEATURE:
<221> NAME/KEY: MOD_RES
<222> LOCATION: (243)..(243)
<223> OTHER INFORMATION: Ser, Asp or Cys
<220> FEATURE:
<221> NAME/KEY: MOD_RES
<222> LOCATION: (244)..(244)
<223> OTHER INFORMATION: May or may not be present
<220> FEATURE:
<221> NAME/KEY: MOD_RES
<222> LOCATION: (335)..(335)
<223> OTHER INFORMATION: Ala or Leu
<220> FEATURE:
<221> NAME/KEY: MOD_RES
<222> LOCATION: (337)..(337)
<223> OTHER INFORMATION: Ile or Glu
<220> FEATURE:
<221> NAME/KEY: MOD_RES
<222> LOCATION: (447)..(447)
<223> OTHER INFORMATION: Ser or Cys

<400> SEQUENCE: 85

Glu Val Gln Leu Val Glu Ser Gly Gly Gly Leu Val Pro Gly Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45
```

```
Ser Ser Ile Ser Ser Ser Ser Tyr Ile Tyr Tyr Ala Asp Ser Val
    50              55                  60
Lys Gly Arg Phe Thr Ile Ser Arg Asp Asn Ala Lys Asn Ser Leu Tyr
 65              70                  75                  80
Leu Gln Met Asn Ser Leu Arg Ala Glu Asp Thr Ala Val Tyr Tyr Cys
                 85                  90                  95
Ala Arg Gly Gly Asp Ala Tyr Asn Tyr Tyr Phe Asp Tyr Trp Gly
                100             105             110
Gln Gly Thr Leu Val Thr Val Ser Ser Ala Ser Thr Lys Gly Pro Ser
            115             120             125
Val Phe Pro Leu Ala Pro Ser Ser Lys Ser Thr Ser Gly Gly Thr Ala
    130             135             140
Ala Leu Gly Cys Leu Val Lys Asp Tyr Phe Pro Glu Pro Val Thr Val
145             150             155             160
Ser Trp Asn Ser Gly Ala Leu Thr Ser Gly Val His Thr Phe Pro Ala
                165             170             175
Val Leu Gln Ser Ser Gly Leu Tyr Ser Leu Ser Ser Val Val Thr Val
                180             185             190
Pro Ser Ser Ser Leu Gly Thr Gln Thr Tyr Ile Cys Asn Val Asn His
            195             200             205
Lys Pro Ser Asn Thr Lys Val Asp Lys Arg Val Glu Pro Lys Ser Cys
210             215             220
Asp Lys Thr His Thr Cys Pro Pro Cys Pro Ala Pro Glu Xaa Leu Gly
225             230             235             240
Gly Pro Xaa Cys Val Phe Leu Phe Pro Pro Lys Pro Lys Asp Thr Leu
                245             250             255
Met Ile Ser Arg Thr Pro Glu Val Thr Cys Val Val Val Asp Val Ser
                260             265             270
His Glu Asp Pro Glu Val Lys Phe Asn Trp Tyr Val Asp Gly Val Glu
            275             280             285
Val His Asn Ala Lys Thr Lys Pro Arg Glu Glu Gln Tyr Asn Ser Thr
    290             295             300
Tyr Arg Val Val Ser Val Leu Thr Val Leu His Gln Asp Trp Leu Asn
305             310             315             320
Gly Lys Glu Tyr Lys Cys Lys Val Ser Asn Lys Ala Leu Pro Xaa Pro
                325             330             335
Xaa Glu Lys Thr Ile Ser Lys Ala Lys Gly Gln Pro Arg Glu Pro Gln
                340             345             350
Val Tyr Thr Leu Pro Pro Ser Arg Glu Glu Met Thr Lys Asn Gln Val
            355             360             365
Ser Leu Thr Cys Leu Val Lys Gly Phe Tyr Pro Ser Asp Ile Ala Val
    370             375             380
Glu Trp Glu Ser Asn Gly Gln Pro Glu Asn Asn Tyr Lys Thr Thr Pro
385             390             395             400
Pro Val Leu Asp Ser Asp Gly Ser Phe Phe Leu Tyr Ser Lys Leu Thr
                405             410             415
Val Asp Lys Ser Arg Trp Gln Gln Gly Asn Val Phe Ser Cys Ser Val
                420             425             430
Met His Glu Ala Leu His Asn His Tyr Thr Gln Lys Ser Leu Xaa Leu
            435             440             445
Ser Pro Gly Lys Gly Gly Gly Ser Gly Gly Gly Ser Gly Gly
    450             455             460
```

Gly Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Gln Asp Val
            485                 490                 495

Asn Thr Ala Val Ala Trp Tyr Gln Gln Lys Pro Gly Lys Ala Pro Lys
        500                 505                 510

Leu Leu Ile Tyr Ser Ala Ser Phe Leu Tyr Ser Gly Val Pro Ser Arg
        515                 520                 525

Phe Ser Gly Ser Arg Ser Gly Thr Asp Phe Thr Leu Thr Ile Ser Ser
    530                 535                 540

Leu Gln Pro Glu Asp Phe Ala Thr Tyr Tyr Cys Gln Gln His Tyr Thr
545                 550                 555                 560

Thr Pro Pro Thr Phe Gly Cys Gly Thr Lys Val Glu Ile Lys Gly Gly
                565                 570                 575

Gly Gly Ser Gly Gly Gly Ser Gly Gly Gly Ser Gly Gly
                580                 585                 590

Gly Ser Glu Val Gln Leu Val Glu Ser Gly Gly Leu Val Gln Pro
    595                 600                 605

Gly Gly Ser Leu Arg Leu Ser Cys Ala Ala Ser Gly Phe Asn Ile Lys
610                 615                 620

Asp Thr Tyr Ile His Trp Val Arg Gln Ala Pro Gly Lys Cys Leu Glu
625                 630                 635                 640

Trp Val Ala Arg Ile Tyr Pro Thr Asn Gly Tyr Thr Arg Tyr Ala Asp
                645                 650                 655

Ser Val Lys Gly Arg Phe Thr Ile Ser Ala Asp Thr Ser Lys Asn Thr
            660                 665                 670

Ala Tyr Leu Gln Met Asn Ser Leu Arg Ala Glu Asp Thr Ala Val Tyr
        675                 680                 685

Tyr Cys Ser Arg Trp Gly Gly Asp Gly Phe Tyr Ala Met Asp Tyr Trp
    690                 695                 700

Gly Gln Gly Thr Leu Val Thr Val Ser Ser
705                 710

<210> SEQ ID NO 86
<211> LENGTH: 718
<212> TYPE: PRT
<213> ORGANISM: Artificial Sequence
<220> FEATURE:
<223> OTHER INFORMATION: Description of Artificial Sequence: Synthetic
      consensus polypeptide
<220> FEATURE:
<221> NAME/KEY: MOD_RES
<222> LOCATION: (504)..(504)
<223> OTHER INFORMATION: Leu or Phe
<220> FEATURE:
<221> NAME/KEY: MOD_RES
<222> LOCATION: (509)..(509)
<223> OTHER INFORMATION: Ser, Asp or Cys
<220> FEATURE:
<221> NAME/KEY: MOD_RES
<222> LOCATION: (510)..(510)
<223> OTHER INFORMATION: May or may not be present
<220> FEATURE:
<221> NAME/KEY: MOD_RES
<222> LOCATION: (601)..(601)
<223> OTHER INFORMATION: Ala or Leu
<220> FEATURE:
<221> NAME/KEY: MOD_RES
<222> LOCATION: (603)..(603)
<223> OTHER INFORMATION: Ile or Glu
<220> FEATURE:
<221> NAME/KEY: MOD_RES
<222> LOCATION: (713)..(713)

<223> OTHER INFORMATION: Ser or Cys

<400> SEQUENCE: 86

```
Glu Val Gln Leu Val Glu Ser Gly Gly Gly Leu Val Lys Pro Gly
1               5                   10                  15

Ser Leu Arg Leu Ser Cys Ala Ala Ser Gly Phe Thr Phe Ser Ser Tyr
            20                  25                  30

Ser Met Ser Trp Val Arg Gln Ala Pro Gly Lys Gly Leu Glu Trp Val
        35                  40                  45

Ser Ser Ile Ser Ser Ser Ser Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Asp Ala Tyr Asn Tyr Tyr Phe Asp Tyr Trp Gly
            100                 105                 110

Gln Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Gly Lys Thr Gly Gly Gly Gly Ser Gly Gly Gly Ser Asp Ile Gln
225                 230                 235                 240

Met Thr Gln Ser Pro Ser Ser Leu Ser Ala Ser Val Gly Asp Arg Val
                245                 250                 255

Thr Ile Thr Cys Arg Ala Ser Gln Asp Val Asn Thr Ala Val Ala Trp
            260                 265                 270

Tyr Gln Gln Lys Pro Gly Lys Ala Pro Lys Leu Leu Ile Tyr Ser Ala
        275                 280                 285

Ser Phe Leu Tyr Ser Gly Val Pro Ser Arg Phe Ser Gly Ser Arg Ser
    290                 295                 300

Gly Thr Asp Phe Thr Leu Thr Ile Ser Ser Leu Gln Pro Glu Asp Phe
305                 310                 315                 320

Ala Thr Tyr Tyr Cys Gln Gln His Tyr Thr Thr Pro Pro Thr Phe Gly
                325                 330                 335

Cys Gly Thr Lys Val Glu Ile Lys Gly Gly Gly Ser Gly Gly Gly
            340                 345                 350

Gly Ser Gly Gly Gly Gly Ser Gly Gly Gly Ser Glu Val Gln Leu
        355                 360                 365

Val Glu Ser Gly Gly Gly Leu Val Gln Pro Gly Gly Ser Leu Arg Leu
    370                 375                 380

Ser Cys Ala Ala Ser Gly Phe Asn Ile Lys Asp Thr Tyr Ile His Trp
385                 390                 395                 400
```

-continued

```
Val Arg Gln Ala Pro Gly Lys Cys Leu Glu Trp Val Arg Ile Tyr
            405                 410                 415

Pro Thr Asn Gly Tyr Thr Arg Tyr Ala Asp Ser Val Lys Gly Arg Phe
            420                 425                 430

Thr Ile Ser Ala Asp Thr Ser Lys Asn Thr Ala Tyr Leu Gln Met Asn
            435                 440                 445

Ser Leu Arg Ala Glu Asp Thr Ala Val Tyr Tyr Cys Ser Arg Trp Gly
    450                 455                 460

Gly Asp Gly Phe Tyr Ala Met Asp Tyr Trp Gly Gln Gly Thr Leu Val
465                 470                 475                 480

Thr Val Ser Ser Ser Gly Gly Gly Ser Gly Gly Gly Gly Ser Cys
                485                 490                 495

Pro Pro Cys Pro Ala Pro Glu Xaa Leu Gly Gly Pro Xaa Cys Val Phe
            500                 505                 510

Leu Phe Pro Pro Lys Pro Lys Asp Thr Leu Met Ile Ser Arg Thr Pro
            515                 520                 525

Glu Val Thr Cys Val Val Val Asp Val Ser His Glu Asp Pro Glu Val
    530                 535                 540

Lys Phe Asn Trp Tyr Val Asp Gly Val Glu Val His Asn Ala Lys Thr
545                 550                 555                 560

Lys Pro Arg Glu Glu Gln Tyr Asn Ser Thr Tyr Arg Val Val Ser Val
                565                 570                 575

Leu Thr Val Leu His Gln Asp Trp Leu Asn Gly Lys Glu Tyr Lys Cys
            580                 585                 590

Lys Val Ser Asn Lys Ala Leu Pro Xaa Pro Xaa Glu Lys Thr Ile Ser
    595                 600                 605

Lys Ala Lys Gly Gln Pro Arg Glu Pro Gln Val Tyr Thr Leu Pro Pro
610                 615                 620

Ser Arg Glu Glu Met Thr Lys Asn Gln Val Ser Leu Thr Cys Leu Val
625                 630                 635                 640

Lys Gly Phe Tyr Pro Ser Asp Ile Ala Val Glu Trp Glu Ser Asn Gly
                645                 650                 655

Gln Pro Glu Asn Asn Tyr Lys Thr Thr Pro Pro Val Leu Asp Ser Asp
            660                 665                 670

Gly Ser Phe Phe Leu Tyr Ser Lys Leu Thr Val Asp Lys Ser Arg Trp
            675                 680                 685

Gln Gln Gly Asn Val Phe Ser Cys Ser Val Met His Glu Ala Leu His
            690                 695                 700

Asn His Tyr Thr Gln Lys Ser Leu Xaa Leu Ser Pro Gly Lys
705                 710                 715
```